US008648092B2

(12) United States Patent
Lee et al.

(10) Patent No.: US 8,648,092 B2
(45) Date of Patent: Feb. 11, 2014

(54) IMIDAZO[1,2-A]PYRIDINE DERIVATIVES: PREPARATION AND PHARMACEUTICAL APPLICATIONS

(75) Inventors: Ken Chi Lik Lee, Singapore (SG); Eric T. Sun, Singapore (SG); Haishan Wang, Singapore (SG)

(73) Assignee: MEI Pharma, San Diego, CA (US)

( * ) Notice: Subject to any disclaimer, the term of this patent is extended or adjusted under 35 U.S.C. 154(b) by 713 days.

(21) Appl. No.: 12/651,052

(22) Filed: Dec. 31, 2009

(65) Prior Publication Data
US 2010/0105721 A1 Apr. 29, 2010

Related U.S. Application Data

(63) Continuation of application No. 11/857,807, filed on Sep. 19, 2007, now Pat. No. 7,666,880, which is a continuation-in-part of application No. PCT/SG2006/000064, filed on Mar. 20, 2006.

(60) Provisional application No. 60/663,265, filed on Mar. 21, 2005, provisional application No. 60/759,544, filed on Jan. 18, 2006, provisional application No. 60/845,748, filed on Sep. 20, 2006.

(51) Int. Cl.
A61K 31/44 (2006.01)
C07D 471/04 (2006.01)

(52) U.S. Cl.
USPC .......................... 514/300; 546/121

(58) Field of Classification Search
USPC .......................... 546/121; 514/300
See application file for complete search history.

(56) References Cited

U.S. PATENT DOCUMENTS

| 6,552,065 B2 | 4/2003 | Remiszewski et al. |
| 7,666,880 B2 | 2/2010 | Lee et al. |
| 2005/0054701 A1 | 3/2005 | Wallace et al. |
| 2005/0239823 A1 | 10/2005 | Oberboersch et al. |

FOREIGN PATENT DOCUMENTS

| EP | 0266890 | 5/1988 |
| EP | 2064211 A1 | 6/2009 |
| WO | WO-99 55705 | 11/1999 |
| WO | WO-99 59587 | 11/1999 |
| WO | WO-01 38322 | 5/2001 |
| WO | WO-03 066579 | 8/2003 |
| WO | WO-2004 021989 | 3/2004 |
| WO | WO-2004082638 | 9/2004 |
| WO | WO-2005/028447 A1 | 3/2005 |
| WO | WO-2005 090358 | 9/2005 |
| WO | WO-2006/101455 | 9/2006 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http://www.cnn/com/2003/HEALTH/conditions/09/24/alzheimers.drug.ap/index.html>.*
Huff, Joel R., Journal of Medicinal Chemistry, vol. 34, No. 8, Aug. 1991, pp. 2305-2314.*
Wade P.A. "Transcriptional control at regulatory checkpoints by histone deacetylases: molecular connections between cancer and chromatin" Hum. Mol. Genet. 10, 693-698(2001).
De Ruijter A.J.M. et al, "Histone deacetylases (HDACs): characterization of the classical HDAC family" Biochem. J., 370, 737-749 (2003).
Richon V.M. et al, "Second generation hybrid polar compounds are potent inducers of transformed cell differentiation" Proc. Natl. Acad. Sci. USA, 93: 5705-5708 (1996).
Richon V.M. et al, "A class of hybrid polar inducers of transformed cell differentiation inhibits histone deacetylases" Proc. Natl. Acad. Sci. USA, 95: 3003-3007 (1998).
Butler L.M. et al, "Suberoylanilide hydroxamic acid, an inhibitor of histone deacetylase, suppresses the growth of prostate cancer cells in vitro and in vivo", Cancer Res. 60, 5165-5170 (2000).
Yoshida M. et al, "Potent and Specific Inhibition of Mammalian Histone Deacetylase Both in Vivo and in Vitro by Trichostatin A" J. Biol. Chem., 265, 17174 (1990).
Kijima M. et al, Trapoxin, an Antitumor Cyclic Tetrapeptide, Is an Irreversible Inhibitor of Mammalian Histone Deacetylase J. Biol. Chem., 268, 22429 (1993).
Remiszewski S.W. et al, "Deacetylase Inhibitors" Patent: US 6,552,065 B2, Apr. 22, 2003.
Bouchain G. et al, "Development of Potential Antitumor Agents. Synthesis and Biological Evaluation of a New Set of Sulfonamide Derivatives as Histone Deacetylase Inhibitors" J. Med. Chem., 46, 820-830 (2003).
Steffan J.S. et al, "Histone deacetylase inhibitors arrest polyglutamine-dependent neurodegeneration in *Dropsophila*" Nature, 413 (6857), 739-43, Oct. 18, 2001.
Schindler et al., "Dissociation between Interleukin-1β mRNA and Protein Synthesis in Human Peripheral Blood Mononuclear Cells" J. Biol. Chem., 265 (18), 10232-10237 (1990).
Carballo et al, "Feedback Inhibition of Macrophage Tumor Necrosis Factor-α Production by Trisxelraprolin" Science 1998; 281: 1001-1005.
J. Taunton et al, "A Mammalian Histone Deacetylase Related to the Yeast Transcriptional Regulator Rpd3p" Science 1996 272: 408.
Blackburn C, et al "Parallel Synthesis of 3-Amino Imidazo [1,2-a] pyridines and pyrazines by a new three-component condensation", Tetrahedron letters, 39(1998) 3635-3688.

(Continued)

Primary Examiner — Rebecca Anderson
(74) Attorney, Agent, or Firm — Wilson Sonsini Goodrich & Rosati

(57) ABSTRACT

The present invention relates to hydroxamate compounds which are inhibitors of histone deacetylase. More particularly, the present invention relates to imidazo[1,2-a]pyridine containing compounds and methods for their preparation. These compounds may be useful as medicaments for the treatment of proliferative disorders as well as other diseases involving, relating to or associated with enzymes having histone deacetylase activities (HDAC).

35 Claims, No Drawings

(56) References Cited

OTHER PUBLICATIONS

Bienayme H, et al "A new Heterocyclic Multicomponent Reaction for the Combinatorial Synthesis of Fused 3-amino imidazoles" Angew. Chem. Int ed., 1998 37(16) 2234-2237.

Gueffier. A, et al "Synthesis of Imidazo [1, 2-a] pyridines as Antiviral agents", Med. Chem. 1998, 41, 5108-5112.

Lombardino, J, "Preparation and New Reactions of Imidazo [1, 2-a] pyridines", J. Org. Chem, 1965, 30 2403.

Trapani, G, "Structure-Activity Relationships and effects on neuroactive steroid synthesis in a series of 2-Phenyl imidazo [1, 2-a] pyridine acetamide Pereripheral Benzodiazepine Receptor Ligands", J. Med. Chem. 2005, 48292-305.

Drummond et al, "Clinical Development of Histone Deacelyal Inhibitors as Anti Cancer agents", Ann. Rev. Pharmaceutical Toxicol. (2005) 45: 495.

Dinarello et al., "Proinflammatory and Anti-Inflammatory Cytokines in Rheumatiois Arthritis—A Primer for Clinicians", $2^{nd}$ Edition, Amgen Inc., 2000.

Marks P.A. et al., Histone deacetylase inhibitors: inducers of differentiation or apoptosis of transformed cells: Journal of the National Cancer Institute, vol. 92, No. 15, Aug. 2, 2000, pp. 1210-1216.

Paris M. et al.: "Histone deacetylase inhibitors: From bench to clinic", Journal of Medicinal Chemistry, vol. 51, No. 5, Mar. 27, 2007, pp. 1505-1529.

Supplementary European Search Report for Appln. No. EP 06717188 dated Sep. 15, 2005.

Riester et al., Biochemical and biophysical research communications, (Nov. 9, 2004) vol. 324, No. 3, pp. 1116-1123.

\* cited by examiner

IMIDAZO[1,2-A]PYRIDINE DERIVATIVES: PREPARATION AND PHARMACEUTICAL APPLICATIONS

RELATION APPLICATIONS

This application is a Continuation of application Ser. No. 11/857,807, filed on Sep. 19, 2007, now U.S. Pat. No. 7,666,880, issued Feb. 23, 2010, which is a continuation-in-part of PCT/SG2006/000064 filed Mar. 20, 2006, which claims benefit of U.S. Provisional Patent Application Nos. 60/663,265 filed Mar. 21, 2005; 60/759,544 filed Jan. 18, 2006; and U.S. Provisional Patent Application No. 60/845,748 filed Sep. 20, 2006, disclosure of which are incorporated herein by reference.

FIELD OF THE INVENTION

The present invention relates to hydroxamate compounds that are inhibitors of histone deacetylase (HDAC). More particularly, the present invention relates to imidazo[1,2-a]pyridine containing compounds and methods for their preparation. These compounds may be useful as medicaments for the treatment of proliferative disorders as well as other diseases involving, relating to or associated with enzymes having histone deacetylase (HDAC) activities.

BACKGROUND OF THE INVENTION

Local chromatin architecture is generally recognized as an important factor in the regulation of gene expression. The architecture of chromatin, a protein-DNA complex, is strongly influenced by post-translational modifications of the histones which are the protein components. Reversible acetylation of histones is a key component in the regulation of gene expression by altering the accessibility of transcription factors to DNA. In general, increased levels of histone acetylation are associated with increased transcriptional activity, whereas decreased levels of acetylation are associated with repression of gene expression [Wade P. A. Hum. Mol. Genet. 10, 693-698 (2001), De Ruijter A. J. M. et al, Biochem. J., 370, 737-749 (2003)]. In normal cells, histone deacetylases (HDACs) and histone acetyl transferase together control the level of acetylation of histones to maintain a balance. Inhibition of HDACs results in the accumulation of acetylated histones, which results in a variety of cell type dependent cellular responses, such as apoptosis, necrosis, differentiation, cell survival, inhibition of proliferation and cytostasis.

Inhibitors of HDAC have been studied for their therapeutic effects on cancer cells. For example, suberoylanilide hydroxamic acid (SAHA) is a potent inducer of differentiation and/or apoptosis in murine erythroleukemia, bladder, and myeloma cell lines [Richon V. M. et al, Proc. Natl. Acad. Sci. USA, 93: 5705-5708 (1996), Richon V. M. et al, Proc. Natl. Acad. Sci. USA, 95: 3003-3007 (1998)]. SAHA has been shown to suppress the growth of prostate cancer cells in vitro and in vivo [Butler L. M. et al, Cancer Res. 60, 5165-5170 (2000)]. Other inhibitors of HDAC that have been widely studied for their anti-cancer activities are trichostatin A (TSA) and trapoxin B [Yoshida M. et al, J. Biol. Chem., 265, 17174 (1990), Kijima M. et al, J. Biol. Chem., 268, 22429 (1993)]. Trichostatin A is a reversible inhibitor of mammalian HDAC. Trapoxin B is a cyclic tetrapeptide, which is an irreversible inhibitor of mammalian HDAC. However, due to the in vivo instability of these compounds they are less desirable as anti-cancer drugs. Recently, other small molecule HDAC inhibitors have become available for clinical evaluation [U.S. Pat. No. 6,552,065]. Additional HDAC inhibiting compounds have been reported in the literature [Bouchain G. et al, J. Med. Chem., 46, 820-830 (2003)] and patents [WO 03/066579A2, WO 01/38322 A1]. The in vivo activity of such inhibitors can be directly monitored by their ability to increase the amount of acetylated histones in the biological sample. HDAC inhibitors have been reported to interfere with neurodegenerative processes, for instance, HDAC inhibitors arrest polyglutamine-dependent neurodegeneration [Nature, 413(6857): 739-43, 18 October, 2001]. In addition, HDAC inhibitors have also been known to inhibit production of cytokines such as TNF, IFN, IL-1 which are known to be implicated in inflammatory diseases and/or immune system disorders. [J. Biol. Chem. 1990; 265(18): 10232-10237; Science, 1998; 281: 1001-1005; Dinarello C. A. and Moldawer L. L. Proinflammatory and anti-inflammatory cytokines in rheumatoid arthritis. A primer for clinicians. $3^{rd}$ Edition, Amergen Inc., 2002].

Nevertheless, there is still a need to provide further HDAC inhibitors that would be expected to have useful, improved pharmaceutical properties in the treatment of diseases such as cancer, neurodegenerative diseases, disorders involving angiogenesis and inflammatory and/or immune system disorders.

SUMMARY OF THE INVENTION

In one aspect the present invention provides a compound of the formula (I):

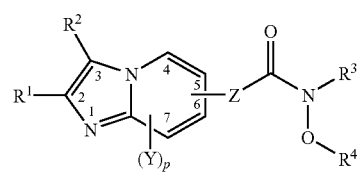

Formula I wherein:
$R^1$ is selected from the group consisting of: H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfonylamino, —COOH, —$OR^5$, —$COOR^5$, —$CONHR^5$, —$NHCOR^5$, —$NHCOOR^5$, —NH-$CONHR^5$, C(=NOH)$R^5$-alkylN$COR^5$, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may optionally be substituted, or $R^1$=L;

$R^2$ is selected from the group consisting of: H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfonylamino, —COOH, —OR$^5$, —COOR$^5$, —CONHR$^5$, —NHCOR$^5$, —NHCOOR$^5$, —NHCONHR$^5$, C(=NOH)R$^5$-alkylNCOR$^5$, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may optionally be substituted, or R$^2$=L;

R$^3$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

R$^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each Y is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalkyl, —COOH—C(O)OR$^6$, —COR$^6$, —SH, —SR$^7$—OR$^7$, acyl and —NR$^8$R$^9$ each of which may be optionally substituted;

each R$^5$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^6$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^7$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^8$ and R$^9$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

p is an integer selected from the group consisting of 0, 1, 2, and 3;

L is selected from the group consisting of:
a) Cy-L$^1$-W—;
b) Cy-L$^1$-W-L$^2$-;
c) Cy—(CH$_2$)$_k$—W—;
d) L$^1$-W-L$^2$-;
e) Cy-L$^1$-;
f) R$^{12}$—W$^1$-L$^1$-W—; and
g) —(CR$^{20}$R$^{21}$)$_m$—(CR$^{22}$R$^{23}$)$_n$—(CR$^{24}$R$^{25}$)$_o$—NR$^{26}$R$^{27}$;

wherein

Cy is selected from the group consisting of C$_1$-C$_{15}$ alkyl, aminoalkyl, heteroalkyl, heterocycloalkyl, cycloalkyl, aryl, aryloxy and heteroaryl, each of which may be optionally substituted;

L$^1$ is selected from the group consisting of a bond, C$_1$-C$_5$ alkyl and C$_2$-C$_5$ alkenyl, each of which may be optionally substituted;

L$^2$ is selected from the group consisting of C$_1$-C$_5$ alkyl and C$_2$-C$_5$ alkenyl, each of which may be optionally substituted;

k is 0, 1, 2, 3, 4 or 5;

W is selected from the group consisting of a bond, —O—, —S—, —S(O)—, —S(O)$_2$—, —N(R$^{10}$)—, —C(O)N(R$^{10}$)—, —SO$_2$N(R$^{11}$)—, —N(R$^{10}$)C(O)—, —N(R$^{10}$)SO$_2$—, —N(R$^{10}$)C(O)N(R$^{11}$)—, —C(O)N(R$^{10}$)C(O)N(R$^{11}$)— and —N(R$^{10}$)C(O)N(R$^{11}$)C(O)—;

W$^1$ is selected from the group consisting of a bond, —O—, —S—, —S(O)—, —S(O)$_2$—, —N(R$^{10}$)—, —C(O)N(R$^{10}$)—, —SO$_2$N(R$^{11}$)—, —N(R$^{10}$)C(O)—, —N(R$^{10}$)SO$_2$—, —N(R$^{10}$)C(O)N(R$^{11}$)—, —C(O)N(R$^{10}$)C(O)N(R$^{11}$)— and —N(R$^{10}$)C(O)N(R$^{11}$)C(O)—;

each R$^{10}$ and R$^{11}$ is independently selected from the group consisting of: H, C$_1$-C$_6$ alkyl, C$_1$-C$_6$ alkenyl, C$_1$-C$_{10}$ heteroalkyl, C$_4$-C$_9$ cycloalkyl, C$_4$-C$_9$ heterocycloalkyl, aryl, heteroaryl, arylalkyl, and heteroarylalkyl and acyl, each of which may be optionally substituted;

each R$^{20}$, R$^{21}$, R$^{22}$, R$^{23}$, R$^{24}$ and R$^{25}$ is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkoxyheteroaryl, alkenyloxy, alkynyloxy, cycloalkyloxy, heterocycloalkyloxy, aryloxy, arylalkyloxy, phenoxy, benzyloxy heteroaryloxy, amino, alkylamino, acylamino, aminoalkyl, arylamino, alkoxycarbonyl, alkylaminocarbonyl, sulfonyl, alkylsulfonyl, aminosulfonyl, arylsulfonyl, arylsulfinyl —COOH, —C(O)OR$^5$, —COR$^5$, —SH, —SR$^5$—, —OR$^6$ and acyl, each of which may be optionally substituted; or R$^{20}$ and R$^{21}$ when taken together may form a group of formula =O or =S, and/or R$^{22}$ and R$^{23}$ when taken together may form a group of formula =O or =S, and/or R$^{24}$ and R$^{25}$ when taken together may form a group of formula =O or =S;

each R$^{26}$ and R$^{27}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^5$, acyl and G, each of which may be optionally substituted, or $R^{26}$ and $R^{27}$ when taken together with the nitrogen atom to which they are attached form a heterocycloalkyl or heteroaryl group, each of which may be optionally substituted;

m, n and o are each integers that are independently selected from the group consisting of 0, 1, 2, 3 and 4;

G is a group of formula:

-$L^3W^3$ wherein $L^3$ is selected from the group consisting of $C_1$-$C_5$ alkyl and $C_2$-$C_5$ alkenyl, each of which may be optionally substituted;

$W^3$ is selected from the group consisting of a —$OR^{12}$, —$SR^{12}$, —$S(O)R^{12}$, —$S(O)_2R^{12}$, —$N(R^{12})_2$—$C(O)N(R^{12})_2$, —$SO_2N(R^{12})_2$, —$NR^{12}C(O)$— —$NR^{12}SO_2R^{12}$, —$NR^{12}C(O)N(R^{12})_2$, —$C(O)NR^{12}C(O)N(R^{12})_2$ and —$N(R^{12})C(O)N(R^{12})C(O)R^{12}$;

each $R^{12}$ is independently selected from the group consisting H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfonylamino, —COOH, —$COR^5$—$COOR^5$, —$CONHR^5$—$NHCOR^5$—$NHCOOR^5$, —$NHCONHR^5$, C(=NOH)$R^5$-alkylN$COR^5$, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may optionally be substituted;

Z is a single bond or is selected from —$CH_2$—, —$CH_2CH_2$—, —CH=CH— and $C_3$-$C_6$ cycloalkyl, each of which may be optionally substituted;

or a pharmaceutically acceptable salt or prodrug thereof.

One suitable genus of hydroxamic compounds are those in which $R^3$ is H:

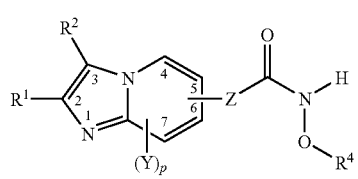

Formula (Ia)

wherein each $R^1$, $R^2$, $R^4$, Y, p and Z are as described above.

Another group of useful compounds are those wherein both $R^3$ and $R^4$ are H:

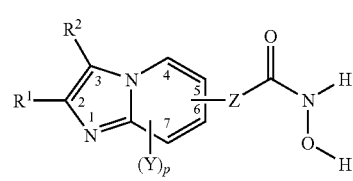

Formula (Ib)

wherein each $R^1$, $R^2$, Y, p and Z are as described above.

As with any group of structurally related compounds which possess a particular utility, certain substitution patterns of the compounds of the Formula (I), (Ia) and (Ib) find particular utility depending upon their end use application.

In certain embodiments $R^1$ is selected from the group consisting of H, —COOH, $C_1$-$C_{10}$alkyl, alkenyl, heteroalkyl, haloalkyl, alkynyl, aryl, cycloalkyl, heterocycloalkyl, heteroaryl, $C_4$-$C_9$ heterocycloalkylalkyl, cycloalkylalkyl, arylalkyl, and heteroarylalkyl, each of which may be optionally substituted.

In another embodiment $R^1$ is selected from the group consisting of: H, hydroxyalkyl, alkyl arylalkyl, aryl, heteroaryl, heteroarylalkyl, alkoxyalkyl, aminoalkyl, and heterocycloalkyl, each of which may be optionally substituted.

In one embodiment $R^1$ is alkyl which may be optionally substituted. In another embodiment $R^1$ is $C_1$-$C_{10}$ alkyl which may be optionally substituted. In another embodiment $R^1$ is $C_1$-$C_6$ alkyl which may be optionally substituted. Examples of specific values of alkyl are methyl, ethyl, propyl, isopropyl, 2-methyl-propyl, 2,2-dimethyl-propyl, butyl, isobutyl, tert-butyl, 2,2-dimethyl butyl; 2-methyl-butyl; 3-methyl-butyl, pentyl, 2,4,4-trimethyl-pentyl, and hexyl, each of which may be optionally substituted.

Accordingly one embodiment of the invention is a compound of formula (II).

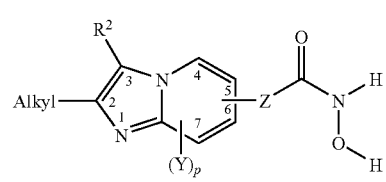

Formula (II)

wherein each $R^2$, Y, p and Z are as defined above for formula (I).

In another embodiment $R^1$ is arylalkyl. The arylalkyl group may be of any suitable type. In general the aryl portion of the arylalkyl group is a monocyclic or bicyclic aryl moiety such as phenyl or naphthyl. The alkyl portion is generally a $C_1$-$C_{10}$ alkyl more generally a $C_1$-$C_6$ alkyl. Examples of specific arylalkyl moieties include 6-phenyl-hexyl, 5-phenyl-pentyl, 4-phenyl-butyl, 3-phenyl-propyl, 2-phenyl-ethyl and phenylmethyl. In each of these groups each of the aryl or the alkyl group may be optionally substituted.

In yet a further embodiment $R^1$ is Ar, wherein Ar is aryl or heteroaryl, each of which may be optionally substituted. In one form the Ar is a monocyclic or bicyclic aryl or a monocyclic or bicyclic heteroaryl.

Accordingly a further embodiment of the invention is a compound of the formula (III).

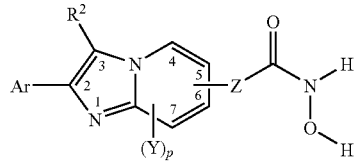

Formula (III)

wherein Ar is aryl or heteroaryl and each $R^2$, Y, p and Z are as defined above for formula (I).

When Ar is aryl, examples of suitable aryl include phenyl, naphthyl, indenyl, anthracenyl and phenanthrenyl.

In one embodiment Ar is phenyl leading to compounds of the formula (IIIa)

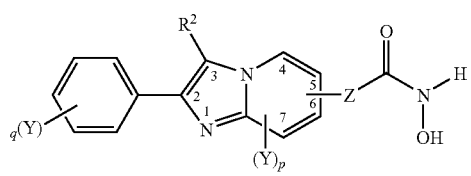

Formula (IIIa)

wherein each $R^2$, Y, p, and Z are as defined above for formula (I) and q is an integer from 0 to 5.

In another embodiment $R^1$ is heteroaryl. Examples of suitable heteroaryl that mat be used include thiophene, benzothiophene, benzofuran, benzimidazole, benzoxazole, benzothiazole, benzisothiazole, naphtho[2,3-b]thiophene, furan, isoindolidine, xantholene, phenoxazine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isoxazole, furazane, phenoxazine, 2-, 3- or 4-pyridyl, 2-, 3-, 4-, 5-, or 8-quinolyl, 1-, 3-, 4-, or 5-isoquinolinyl, 1-, 2-, or 3-indolyl, and 2-, or 3-thienyl.

In another embodiment if $R^1$ is alkyl or heteroalkyl then it is not substituted by a cycloalkyl, aryl, heteroaryl, or heterocycloalkyl moiety.

Specific values of $R^1$ are: H; methyl; carboxyl; (pyridin-2-yl)methyl; (pyridin-3-yl)methyl; ethyl; 2-hydroxy-ethyl; 2-(pyridin-2-yl)ethyl; 2-(pyridin-3-yl)ethyl; 2-phenyl-ethyl; 2-carboxy-ethyl; 2-(morpholin-4-yl)-ethyl; 2-(piperidin-1-yl)-ethyl; 2-(pyrolidin-1-yl)-ethyl; 2-diethylamino-ethyl; propyl; isopropyl 2-methyl-propyl; 2,3-di-hydroxy-propyl; 3-hydroxy-propyl; 3-methoxy-propyl; 3-isopropoxy-propyl; 2,2-dimethyl-propyl; 3-dimethylamino-propyl; 3-dimethylamino-2,2-dimethyl-propyl; 3-(2-oxo-pyrolidin-1-yl)-propyl; 3-(morpholin-4-yl)-propyl; 3-(imidazol-1-yl)-propyl; 3-(4-methyl-piperidin-1-yl)-propyl; 3-(pyrolidin-1-yl)-propyl; butyl; t-butyl, 2-methyl-butyl; 3-methyl-butyl; 2,2-dimethyl-butyl; 4-dimethylamino-butyl; 5-hydroxy-pentyl; allyl; phenyl, 4-fluoro-phenyl; benzyl; 3,4,5-trimethoxybenzyl; norbornyl-1-methyl; bicyclo[3.3.0]octane-3-methyl; pentyl; 2,4,4-trimethyl pentyl; and hexyl.

In certain embodiments $R^2$ is selected from the group consisting of H, halogen, $C_1$-$C_{10}$ alkyl, alkenyl, heteroalkyl, haloalkyl, alkynyl, aryl, cycloalkyl, heterocycloalkyl, heteroaryl, $C_4$-$C_9$ heterocycloalkylalkyl, cycloalkylalkyl, arylalkyl, and heteroarylalkyl each of which may be substituted as previously stated.

In another embodiment $R^2$ is selected from the group consisting of H, alkyl, arylalkyl, aryl, heteroaryl, heteroalkyl, cycloalkyl, each of which may be optionally substituted, or $R^2$ is a group of the formula:

(a) Cy-$L^1$-W—;
(b) $R^{12}$—$W^1$-$L^1$-W—; or
(c) —$(CR^{20}R^{21})_m$—$(CR^{22}R^{23})_n$—$(CR^{24}R^{25})_o$—$NR^{26}R^{27}$;

wherein Cy, $L^1$, W, $W^1$, $R^{12}$, $R^{20}$, $R^{21}$, $R^{22}$, $R^{23}$, $R^{24}$, $R^{25}$, $R^2$, $R^{27}$, m, n and o are as defined above.

In one embodiment $R^2$ is a heteroalkyl group. In one embodiment the heteroalkyl group contains 2 to 10 atoms in the normal chain, more preferably 4 to 6 atoms in the normal chain. In one embodiment the heteroalkyl group contains only one heteroatom in the normal chain, with a nitrogen atom being the preferred heteroatom. In another embodiment the heteroalkyl group contains at least two heteroatoms in the normal chain. In another embodiment there are two heteroatoms in the normal chain, one being a nitrogen atom and the other being selected from the group consisting of O N and S.

In another embodiment $R^2$ is selected from the group consisting of H, hydroxyalkyl, alkyl, alkoxyalkyl, and aminoalkyl each of which may be substituted as previously stated.

In another embodiment if $R^2$ is alkyl or heteroalkyl then it is not substituted by a cycloalkyl, aryl, heteroaryl, or heterocycloalkyl.

Specific values of $R^2$ are: H; methyl; benzylamino-methyl; dibenzylamino-methyl; [2-(4-fluoro-phenyl)-acetylamino]-methyl; [2-(4-methoxy-phenyl)-acetylamino]-methyl; 4-methoxy-benzylamino-methyl; benzyloxy-methyl; phenylacetylamino-methyl; butyl-amino-methyl; methyl-propyl-amino-methyl; (2-dimethylamino-ethyl)-ethyl-amino-methyl; t-butylamino-methyl; 2,2,2-trifluoroethylamino-methyl; (2-hydroxy-ethyl)-propyl-amino-methyl; diethylamino-methyl; butyl-methyl-amino-methyl; butyl-ethyl-amino-methyl; butyl-propyl-amino-methyl; dibutyl-amino-ethyl; ethyl-propyl-amino-ethyl; (ethyl-propyl-amino)-methyl; (cyclopropylmethyl-propyl-amino)-methyl; (sec-butyl-propyl-amino)-methyl; (ethyl-(2-methoxy-ethyl)-amino)-methyl; 2,2-dimethyl-propyl-amino-methyl; cyclopropylmethyl-amino-methyl; cyclopropyl-amino-methyl; (2-(ethyl)-butyl)-amino-methyl; butyl-methyl-amino-methyl; di-propyl-amino-methyl, diethyl-amino-methyl; 1-amino-2-phenyl-ethyl; 2-benzylamino-ethyl; 2-(3-methoxy-phenyl)-ethyl; 2-(pyridin-3-yl)ethyl; 2-(2-phenoxyacetylamino)-ethyl; 2-benzenesulphonylamino-ethyl; 2-phenyl-ethyl; isopropyl; 2-phenyl-propyl; 3-phenyl-propyl; 3-phenoxy-propyl; 3-(1H-indol-3-yl)-propyl; 4-methoxy-phenyl; 4-fluoro-phenyl; 4-benzyloxy-3-methoxy-phenyl; isobutyl; cyclohexyl; octyl; benzyl; pyridin-2-yl; pyridin-4-yl; thiophen-3-yl; (2-methoxy-ethyl)-amine, cyclohexyl-amine, t-butyl-amine, butyl-amine, isopropyl-amine, (4-piperidinyl-phenyl)-amine, 3-(ethylamino)-3-oxopropyl-amine; 3-(2-(dimethylamino)ethylamino)-3-oxopropyl-amine; 3-(3-(dimethylamino)-2,2-dimethyl-propylamino)-3-oxopropyl-amine; 3-(2-(diethylamino)ethylamino)-3-oxopropyl-amine; 3-(butylamino)-3-oxopropyl-amine; 3-(t-butyl-amino)-3-oxopropyl-amine; 3-(2,2,2-trifluoro-ethylamino)-3-oxopropyl-amine; 3-(2-(methoxy)-ethylamino)-3-oxopropyl-amine; 3-(2-(methylsulfanyl)-ethylamino)-3-oxopropyl-amine; 3-(2-(2,2-dimethyl-amino)-N-methyl-ethyl-amine)-3-oxopropyl-amine; 3-(N-(2-hydroxy-ethyl)-propyl-amino)-3-oxopropyl-amine (3,4,5-trimethoxyphenyl)-amine; 3-(prop-2-ynyl-amino)-3-oxopropyl-amine; 3-(2-(1-hydroxymethyl-2-methyl-propylamino)-3-oxopropyl-amine; (3,4-methylenedioxybenzyl)-amine, (3,4-methylenedioxy-phenyl)-amine, benzylsulfanyl; and 2-phenylmethansulfanyl.

In another embodiment $R^2$ is L and thus in one embodiment the compound of the invention is a compound of formula (IV).

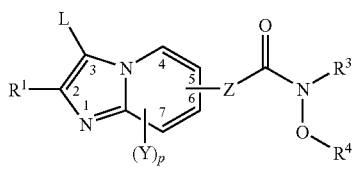

Formula (IV)

wherein each $R^1, R^3, R^4, L, Y, p$ and Z are as defined above for the compounds of formula (I).

In one form of this embodiment $R^3$ is H providing compounds of formula (IVa)

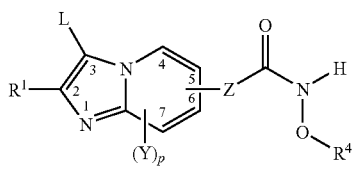

Formula (IVa)

wherein each $R^1, R^4, L, Y, p$ and Z are as defined above for the compounds of formula (I).

In a further form of this embodiment $R^4$ is H providing compounds of formula (IVb).

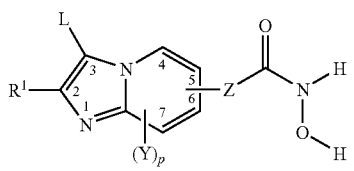

Formula (IVb)

wherein each $R^1, L, Y, p$ and Z are as defined above for the compounds of formula (I).

In the compounds of formula (IV), (IVa) and (IVb) the preferred values of $R^1$ are alkyl cycloalkyl, aryl, arylalkyl and heteroaryl, each of which may be optionally substituted. In one embodiment the compound of the invention is a compound of formula (IVc).

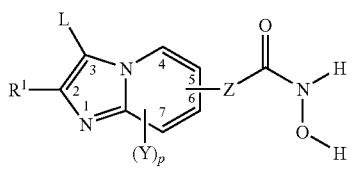

Formula (IVc)

wherein $R^1$ is selected from the group consisting of alkyl cycloalkyl, aryl, arylalkyl and heteroaryl, each of which may be optionally substituted; and each L, Z, Y and p are as defined for compounds of formula I.

In one form of these embodiments $R^1$ is Ar providing a compound of formula (IVd).

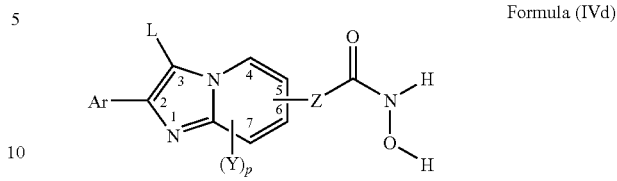

Formula (IVd)

wherein Ar is aryl or heteroaryl and each Y, p, L and Z are as defined above for formula (I).

In a further embodiment Ar is phenyl providing compounds of formula (IVe)

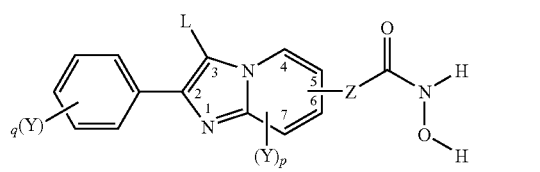

Formula (IVe)

wherein each Y, p, L and Z are as defined above for formula (I) and q is an integer from 0 to 5.

In another embodiment of the compound of formula (IV), $R^1$ is alkyl providing compounds of formula (IVf)

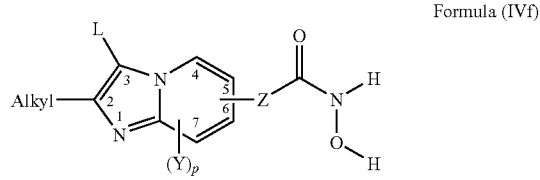

Formula (IVf)

wherein each Y, p, L and Z are as defined above for formula (I).

In the compounds of the invention and in particular the compounds of formula (IV), (IVa), (IVb), (IVc), (IVd), (IVe) and (IVf) there are a number of specific values of L (and hence specific values of $R^2$).

In one embodiment of these compounds L (and hence $R^2$) is selected from the group consisting of:
(a) Cy-$L^1$-W—;
(b) $R^{12}$—$W^1$-$L^1$-W; and
(c) —$(CR^{20}R^{21})_m$—$(CR^{22}R^{23})_n$—$(CR^{24}R^{25})$O—$NR^{26}R^{27}$;
wherein Cy $L^1$, W, $W^1$, $R^{12}$, $R^{20}$, $R^{21}$, $R^{22}$, $R^{23}$, $R^{24}$, $R^{25}$, $R^{26}$, $R^{27}$, m, n and o are as defined above.

In one embodiment $R^2$ is L which is a group of formula:

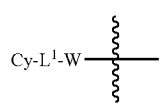

wherein
Cy is selected from the group consisting of $C_1$-$C_{15}$ alkyl, aminoalkyl, heterocycloalkyl, cycloalkyl, aryl, aryloxy and heteroaryl, each of which may be optionally substituted; $L^1$ is selected from the group consisting of a bond, $C_1$-$C_5$ alkyl, and $C_2$-$C_5$ alkenyl, each of which may be optionally substituted;

W is selected from the group consisting of a bond, —O—, —S—, —S(O)—, —S(O)$_2$—, —N(R$^{10}$)—, —C(O)N(R$^{10}$)—, —SO$_2$N(R$^{11}$)—, —N(R$^{10}$)C(O)—, —N(R$^{10}$)SO$_2$— —N(R$^{10}$)C(O)N(R$^{11}$)—, —C(O)N(R$^{10}$)C(O)N(R$^{11}$)— and —N(R$^{10}$)C(O)N(R$^{11}$)C(O)—;

This provides compounds of formula (V):

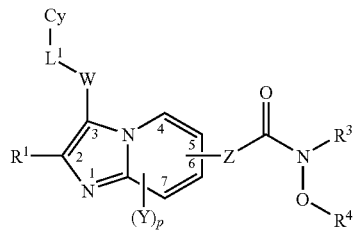

Formula (V)

wherein each R$^1$, R$^3$, R$^4$, Y, p and Z are as defined above for the compounds of formula (I), and W, L$^1$ and Cy are as defined immediately above.

In a further form of this embodiment W is a group of formula

—NR$^{10}$—

In one embodiment W is the group —NH—.

In this form R$^2$ is L which is a group of formula

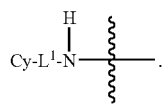

In one form of this embodiment L$^1$ is selected from the group consisting of a bond or methyl.

In one form of this embodiment Cy is aryl, or cycloalkyl, each of which may be substituted. Examples of typical values of Cy include phenyl, cyclopentyl and cyclohexyl. Specific values of Cy include 3,4,5-trimethoxy-phen-1-yl; 3,4-methylenedioxy phenyl-1-yl; 4-piperidin-1-yl-phen-1-yl; and cyclohexyl.

In a further embodiment W is a bond.

In this form R$^2$ is a group of formula

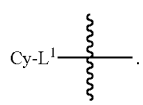

In one form of this embodiment L$^1$ is selected from the group consisting of C$_1$-C$_5$ alkyl and C$_1$-C$_5$ alkenyl, each of which may be optionally substituted.

In one form of this embodiment Cy is selected from C$_1$-C$_{15}$ alkyl, aminoalkyl, heterocycloalkyl, cycloalkyl, aryl, aryloxy or heteroaryl, each of which may be optionally substituted.

In another embodiment of the compounds of the invention R$^2$ is L which is a group of formula:

L$^1$-W-L$^2$- wherein L$^1$ and L$^2$ are the same or different and are independently selected from C$_1$-C$_5$alkyl and C$_2$-C$_5$alkenyl each which may be optionally substituted; and W is selected from the group consisting of a bond, —O—, —S—, —S(O)—, —S(O)$_2$—, —N(R$^{10}$)—, —C(O)N(R$^{10}$)—, —SO$_2$N(R$^{11}$)—, —N(R$^{10}$)C(O)—, —N(R$^{10}$)SO$_2$—, —N(R$^{10}$)C(O)N(R$^{11}$)—, —C(O)N(R$^{10}$)C(O)N(R$^{11}$)— and —N(R$^{10}$)C(O)N(R$^{11}$)C(O);

This provides compounds of formula (VI):

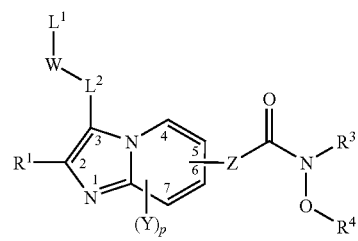

Formula (VI)

wherein each R$^1$, R$^3$R$^4$, Y, p and Z are as defined above for the compounds of formula (I), and W, L$^1$ and L$^2$ are as defined immediately above.

In one form of these embodiments W is a group of formula —N(R$^{10}$)—, such that L is a group of formula:

L$^1$-N(R$^{10}$)-L$^2$-.

In another form of this embodiment R$^{10}$ is selected from H or alkyl. Suitable specific values of R$^{10}$ include H, methyl, ethyl, propyl, isopropyl, butyl, isobutyl, pentyl or hexyl.

In one embodiment L$^2$ is methyl or ethyl, and L$^1$ is H or alkyl. Suitable examples of L$^1$ include H, methyl, ethyl, propyl, isopropyl, butyl, isobutyl, pentyl and hexyl.

In another embodiment of the compounds of the invention the R$^2$ is L which is a group of the formula

R$^{12}$—W$^1$-L$^1$-W— wherein L$^1$ is selected from the group consisting of C$_1$-C$_5$ alkyl, or C$_1$-C$_5$ alkenyl, each of which may be optionally substituted;

W and W$^1$ are each independently selected from the group consisting of a bond, —O—, —S—, —S(O)—, —S(O)$_2$—, —N(R$^{10}$)—, —C(O)N(R$^{10}$)—, —SO$_2$N(R$^{11}$)—, —N(R$^{10}$)C(O)—, —N(R$^{10}$)SO$_2$—N(R$^{10}$)C(O)N(R$^{11}$)—, —C(O)N(R$^{10}$)C(O)N(R$^{11}$)— and —N(R$^{10}$)C(O)N(R$^{11}$)C(O)—;

R$^{12}$ is selected from the group consisting H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^5$—COOR$^5$, —CONHR$^5$, —NHCOR$^5$, —NHCOOR$^5$, —NHCONHR$^5$, C(=NOH)R$^5$-alkylNCOR$^5$, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may optionally be substituted.

This provides compounds of formula (VII):

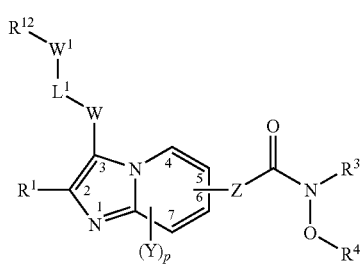

Formula (VII)

wherein each $R^1$, $R^3$, $R^4$, Y, p and Z are as defined above for the compounds of formula (I), and W, $L^1$ and $W^2$ and $R^{12}$ are as defined immediately above.

In one form of this embodiment $W=\!\!=\!\!-N(R^{10})-$ such that $R^2$ is a group of formula:

$$R^{12}-W^1-L^1-N(R^{10})-$$

In one embodiment $R^{10}$ is H such that $R^2$ is a group of formula $$R^{12}-W^1-L^1-NH-$$

In one form $W^1$ is $-N(R^{10})C(O)-$ such that $R^2$ is a group of formula $$R^{12}-N(R^{10})C(O)-L^1-NH-$$

In one embodiment $R^{10}$ is selected from the group consisting of H and alkyl. Specific values of $R^{10}$ include H, methyl, ethyl, propyl and isopropyl.

In another form of this embodiment $W^1$ is —O— such that $R^2$ is a group of formula:

$$R^{12}-O-L^1-NH-$$

In each of these embodiments $L^1$ is $C_1$-$C_5$ alkyl. Specific examples include methyl, ethyl or propyl.

In one embodiment $R^{12}$ is alkyl, heteroalkyl, and alkynyl, each of which may optionally be substituted.

Specific values of $R^{12}$ include methyl, ethyl, 2-(dimethylamino)-ethyl, propyl, isopropyl, butyl, tert-butyl, 2,2,2-trifluoroethyl, 2-methoxy-ethyl, 2-methylsulfanyl-ethyl, 2-propynyl, 2-(diethylamino)-ethyl, 2-cyano-methyl, 2-hydroxyethyl, (3-dimethyl-amino-2,2-dimethyl)-propyl, and 3-methyl-butan1-ol-2-yl.

In another embodiment of the compounds of the invention $R^2$ is L which is a group of formula:

$$-(CR^{20}R^{21})_m-(CR^{22}R^{23})_n-(CR^{24}R^{25})_o-NR^{26}R^{27};$$

wherein
each $R^{20}$, $R^{21}$, $R^{22}$, $R^{23}$, $R^{24}$ and $R^{25}$ is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroaryl heteroalkyl, aryl heteroalkyl, hydroxy, hydroxyalkyl, alkoxy, alkoxyalkyl, alkoxyaryl, alkoxyheteroaryl, alkenyloxy, alkynyloxy, cycloalkyloxy, heterocycloalkyloxy, aryloxy, arylalkyloxy, phenoxy, benzyloxy heteroaryloxy, amino, alkylamino, acylamino, aminoalkyl, arylamino, alkoxycarbonyl, alkylaminocarbonyl, sulfonyl, alkylsulfonyl, aminosulfonyl, arylsulfonyl, arylsulfinyl —COOH, —C(O)OR$^5$, —COR$^5$, —SH, SR$^6$—OR$^6$ and acyl, each of which may be optionally substituted; or $R^{20}$ and $R^{21}$ when taken together may form a group of formula $=\!\!O$ or $=\!\!S$ and/or $R^{22}$ and $R^{23}$ when taken together may form a group of formula $=\!\!O$ or $=\!\!S$ and/or $R^{24}$ and $R^{25}$ when taken together may form a group of formula $=\!\!O$ or $=\!\!S$;

each $R^{26}$ and $R^{27}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, aryl heteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR$^5$ acyl and G, each of which may be optionally substituted, or $R^{26}$ and $R^{27}$ when taken together with the nitrogen atom to which they are attached form a heterocycloalkyl or heteroaryl group, each of which may be optionally substituted;

each m, n and o are each integers independently selected from the group consisting of 0, 1, 2, 3 and 4;

G is a group of formula:

$$-L^3W^3$$

wherein $L^3$ is $C_1$-$C_5$ alkyl or $C_2$-$C_5$ alkenyl, each of which may be optionally substituted;

$W^3$ is selected from the group consisting of —OR$^{12}$, —SR$^{12}$, —S(O)R$^{12}$, —S(O)$_2$R$^{12}$, —N(R$^{12}$)$_2$—C(O)N(R$^{12}$)$_2$, —SO$_2$N(R$^{12}$)$_2$, —NR$^{12}$C(O)—, —NR$^{12}$SO$_2$R$^{12}$, —NR$^{12}$C(O)N(R$^{12}$)$_2$—C(O)NR$^{12}$C(O)N(R$^{12}$)$_2$ and —N(R$^{12}$)C(O)N(R$^{12}$)C(O)R$^{12}$;

This provides compounds of the formula (VIII).

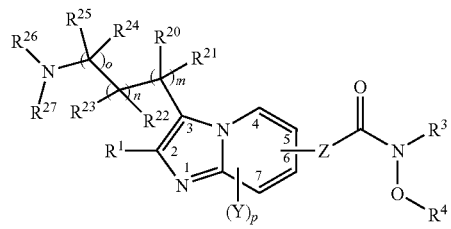

Formula (VIII)

wherein each $R^1$, $R^3$, $R^4$, $R^{20}$, $R^{21}$, $R^{22}$, $R^{23}$, $R^{24}$, $R^{25}$, $R^{26}$, $R^{27}$, Y, Z, m, n, o and p are as defined above for compounds of formula (I).

In one embodiment the compound of formula (VIII) is selected from the group consisting of

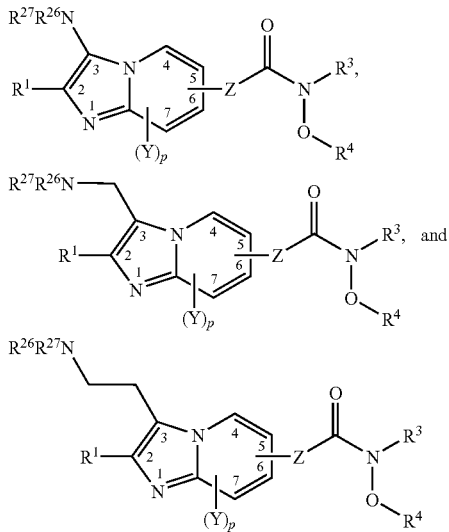

In one specific embodiment of the compounds of formula (VIII) the sum of m+n+o is 0 which provides compounds of formula (VIIIa)

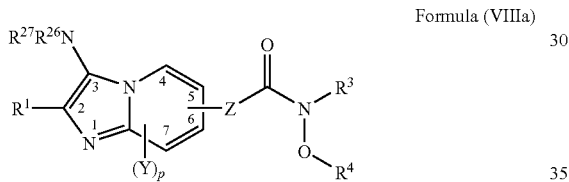

Formula (VIIIa)

wherein each $R^1$, $R^3$, $R^4$, $R^{26}$ and $R^{27}$ Y, p and Z are as defined above for the compounds of formula (I).

In another embodiment the sum of m+n+o is 1 which provides compounds of formula (VIIIb)

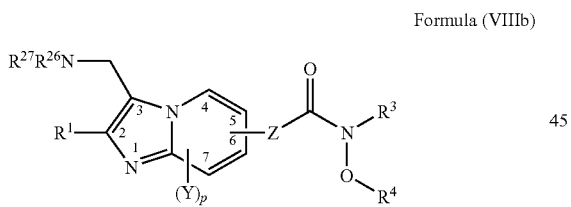

Formula (VIIIb)

wherein each $R^1$, $R^3$, $R^4$, $R^{26}$ and $R^{27}$ Y, p and Z are as defined above for the compounds of formula (I).

In another embodiment the sum of m+n+o is 2 which provides compounds of formula (VIIIc).

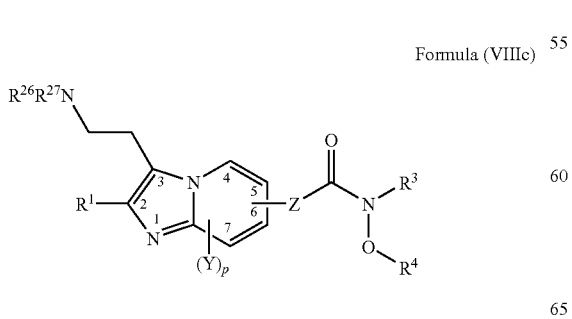

Formula (VIIIc)

wherein each $R^1$, $R^3$, $R^4$, $R^{26}$ and $R^{27}$ Y, p and Z are as defined above for the compounds of formula (I).

In one embodiment of the compounds of formula (VIII) to (VIIIc) $R^{26}$ and $R^{27}$ are independently selected from the group consisting of H, alkyl, hydroxyalkyl, heteroalkyl, cycloalkyl, aryl, arylalkyl, cycloalkylalkyl and G, each of which may be optionally substituted. Examples of specific values of $R^{26}$ and $R^{27}$ include H, methyl, cyclopropyl-methyl, cyclohexyl-methyl, ethyl, 2-methoxy-ethyl, 2-hydroxy-ethyl, 2-cyclopropyl-ethyl, 2,2,2-trifluoroethyl, 2-(dimethylamino)-ethyl, 2-(diethylamino)-ethyl, propyl, isopropyl, cyclopropyl, 1-methyl-propyl, 2-methyl-propyl, 2,2-dimethyl-propyl, butyl, t-butyl, sec-butyl, 2-ethyl-butyl, 2-methyl-butyl, 3-methyl-butyl, 3,3-dimethyl-butyl, pentyl, 2-methyl-pentyl, hexyl, 3,5,5-trimethyl-hexyl, cyclohexyl, heptyl, 3,4,5-trimethoxyphenyl, 3,4-methylenedioxybenzyl, 4-piperidin-1yl-phenyl, and 3,4-methylenedioxyphenyl.

In one embodiment $R^{26}$ is G and $R^{27}$ is H or alkyl.

In one form of this embodiment G is a group of formula:

—(CH$_2$)$_2$—C(O)N(R$^{12}$)$_2$.

In one form of this embodiment each $R^{12}$ is independently selected from the group consisting of H, alkyl, hydroxyalkyl, heteroalkyl, and alkynyl.

In specific embodiments G is selected from the group consisting of:

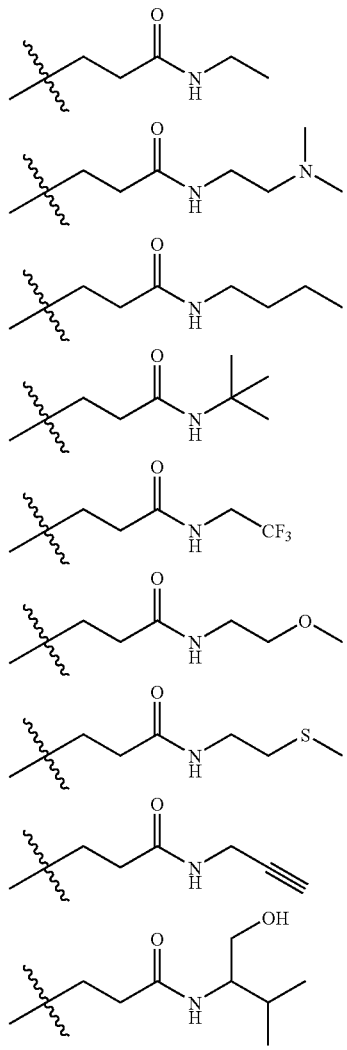

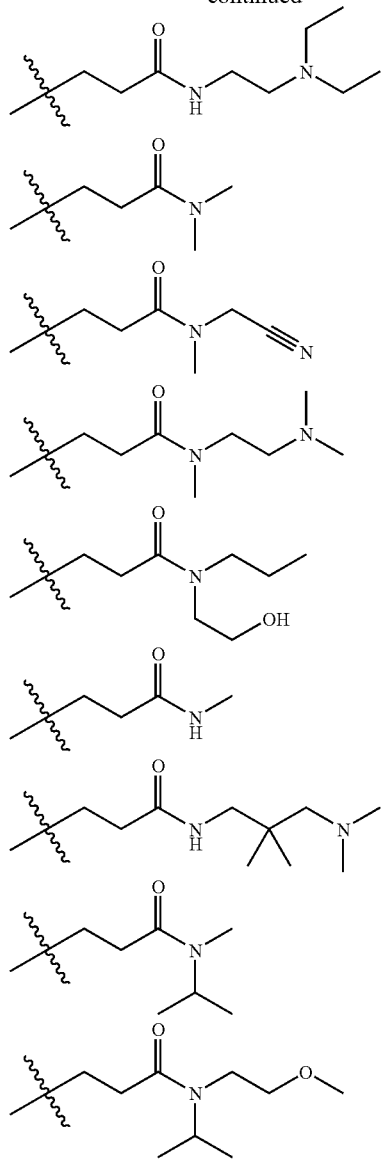

In another embodiment of the compounds of formula (VIII) to (VIIIc) $R^{26}$ and $R^{27}$ when taken together with the nitrogen atom to which they are attached form a heterocycloalkyl group. In one embodiment the heterocycloalkyl group is a $C_5$ or $C_6$ heterocycloalkyl group. Specific values include a piperidinyl, a piperazinyl or a morpholinyl group, each of which may be optionally substituted.

In one embodiment of the compounds of formula (VIII) to (VIIIc), $R^1$ is alkyl aryl, heteroaryl or arylalkyl.

In one embodiment of the compounds of the invention $R^2$ is selected from the group consisting of:

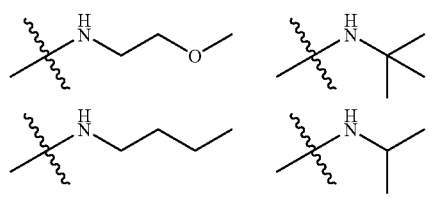

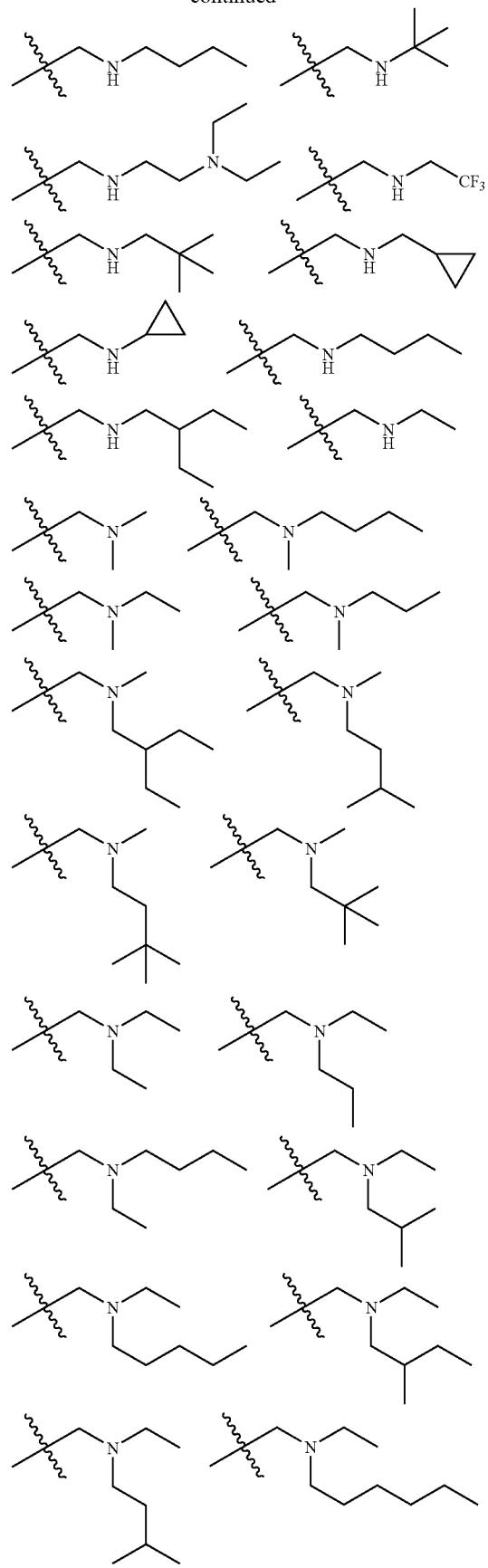

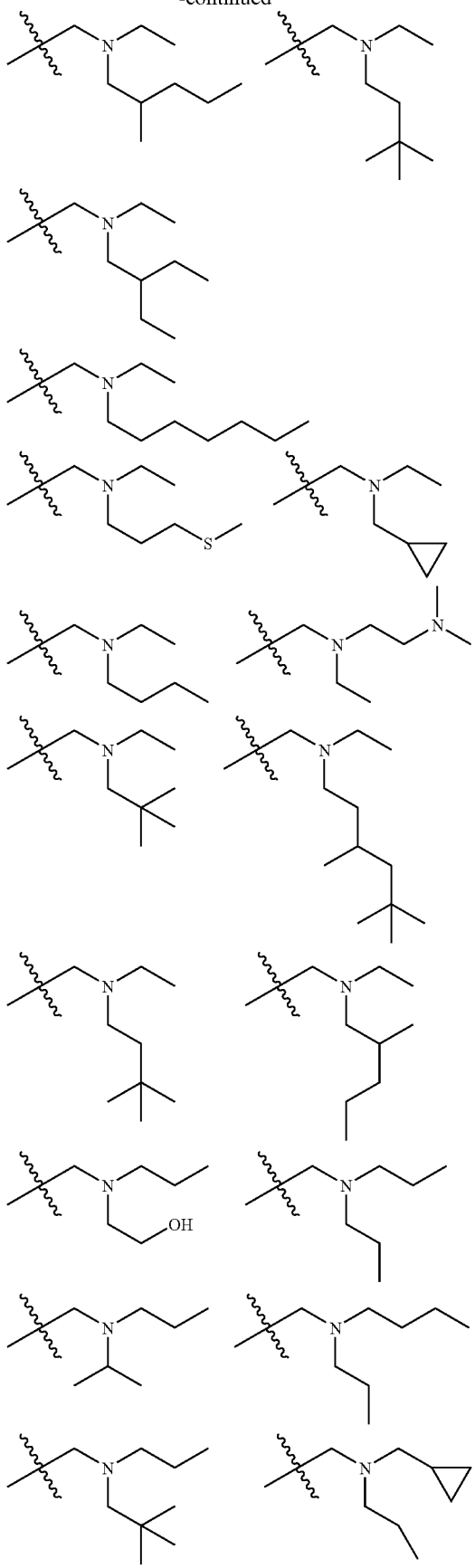

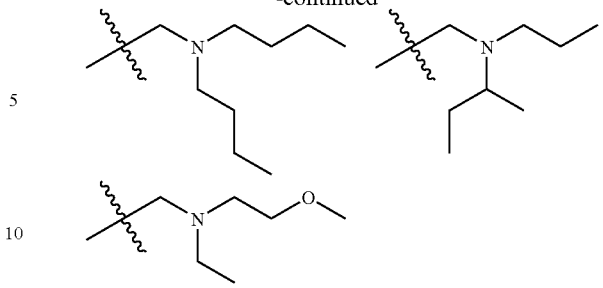

There are a number of specific values of other substituents that are common to the compound of formula (I) to (VIII).

In one embodiment of the compounds of the invention if a group such as $R^1$ or $R^2$ is substituted the substituent may be selected from the group consisting of: halogen, =O, =S, —CN, —NO$_2$, alkyl, alkenyl, methylenedioxy, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)OR$_5$, COOH, SH, and acyl.

In one embodiment Y is at the 4 or 7 positions of the aromatic ring.

In one embodiment p is 0.

In one embodiment $R^3$ is H, $C_1$-$C_6$ alkyl, or acyl. In another embodiment $R^3$ is H or $C_1$-$C_4$ alkyl. In a specific embodiment $R^3$ is H.

In one embodiment $R^4$ is H or $C_1$-$C_4$ alkyl. In a specific embodiment $R^4$ is H.

In one embodiment $R^5$ is $C_1$-$C_4$ alkyl, heteroalkyl, or acyl. In a specific embodiment $R^5$ is methyl.

In one embodiment $R^6$ is $C_1$-$C_4$ alkyl, heteroalkyl or acyl. In a specific embodiment $R^6$ is $C_1$-$C_4$ alkyl.

In one embodiment $R^7$ is $C_1$-$C_4$ alkyl, heteroalkyl or acyl. In a specific embodiment $R^7$ is $C_1$-$C_4$ alkyl.

In one embodiment $R^8$ and $R^9$ are independently selected from the group consisting of H, $C_1$-$C_6$ alkyl, $C_4$-$C_9$cycloalkyl, $C_4$-$C_9$heterocycloalkyl, aryl, heteroaryl, arylalkyl, and heteroarylalkyl.

In one embodiment the Z moiety is a group of formula —CH=CH—. In one form of this embodiment the moiety is in the "E" configuration and is at the 5 or 6 position. In one embodiment the Z moiety is at the 5 position. In another embodiment the Z moiety is at the 6 position.

In addition to compounds of the invention as described above the embodiments disclosed are also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "HDAC inhibiting agents" or "HDAC inhibitors". In certain embodiments the compounds disclosed are used to modify deacetylase activity, in some cases histone deacetylase activity and in some cases HDAC 8, or HDAC 1 activity.

The embodiments disclosed also relate to pharmaceutical compositions each comprising a therapeutically effective amount of a HDAC inhibiting agent of the embodiments described with a pharmaceutically acceptable carrier or diluent for treating cellular proliferative ailments. The term "effective amount" as used herein indicates an amount necessary to administer to a host to achieve a therapeutic result, e.g., inhibition of proliferation of malignant cancer cells, benign tumor cells or other proliferative cells.

The invention also relates to pharmaceutical compositions including a compound of the invention with a pharmaceutically acceptable carrier, diluent or excipient.

In yet a further aspect the present invention provides a method of treatment of a disorder caused by, associated with or accompanied by disruptions of cell proliferation and/or angiogenesis including administration of a therapeutically effective amount of a compound of formula (I). In one embodiment the method includes administration of a compound of formula (Ia), or a compound of formula (Ib).

In one embodiment the disorder is selected from the group consisting of but not limited to cancer (e.g. breast cancer, colon cancer, prostate cancer, pancreatic cancer, leukemias, lymphomas, ovarian cancers, neuroblastomas, melanoma, inflammatory diseases/immune system disorders, angiofibroma, cardiovascular diseases (e.g. restenosis, arteriosclerosis), fibrotic diseases (e.g. liver fibrosis), diabetes, autoimmune diseases, chronic and acute neurodegenerative disease like disruptions of nerval tissue, Huntington's disease and infectious diseases like fungal, bacterial and viral infections. In another embodiment the disorder is a proliferative disorder. The proliferative disorder is preferably cancer. The cancer can include solid tumors or hematologic malignancies.

The invention also provides agents for the treatment of a disorder caused by, associated with or accompanied by disruptions of cell proliferation and/or angiogenesis including a compound of formula (I) as disclosed herein. In one embodiment the agent is an anti-cancer agent. In another embodiment, the agent is an anti-angiogenesis agent. In one embodiment the agent contains a compound of formula (Ia), or a compound of formula (Ib).

In yet a further embodiment the invention provides a method of treatment of a disorder, disease or condition that can be treated by the inhibition of histone deacetylase including administration of a therapeutically effective amount of a compound of formula (I). In one embodiment the method includes administration of a compound of formula (Ia), or a compound of formula (Ib) as described herein.

In one embodiment the disorder is selected from the group consisting of but not limited to Proliferative disorders (e.g. cancer); Neurodegenerative diseases including Huntington's Disease, Polyglutamine diseases, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Pick's disease, Intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, macular myopic degeneration, Rubeotic glaucoma, Interstitial keratitis, Diabetic retinopathy, Peter's anomaly, retinal degeneration, Cellophane Retinopathy; Cogan's Dystrophy; Corneal Dystrophy; Iris Neovascularization (Rubeosis); Neovascularization of the Cornea; Retinopathy of Prematurity; Macular Edema; Macular Hole; Macular Pucker; Marginal Blepharitis, Myopia, nonmalignant growth of the conjunctiva; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease, Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus, allergic contact dermatitis; Disease involving angiogenesis including cancer, psoriasis, rheumatoid arthritis; Psychological disorders including bipolar disease, schizophrenia, depression and dementia; Cardiovascular Diseases including Heart failure, restenosis, cardiac hypertrophy and arteriosclerosis; Fibrotic diseases including liver fibrosis, lung fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania* infection, *Trypanosoma brucei* infection, Toxoplasmosis and coccidiosis, and Haematopoietic disorders including thalassemia, anemia and sickle cell anemia.

The invention also provides agents for the treatment of a disorder, disease or condition that can be treated by the inhibition of histone deacetylase including a compound of formula (I) as disclosed herein. In one embodiment the agent is an anti-cancer agent.

The invention also provides a method for inhibiting cell proliferation including administration of an effective amount of a compound according to formula (I).

The invention also provides agents for inhibiting cell proliferation including a compound of formula (I) as disclosed herein.

In yet an even further aspect the invention provides a method of treatment of a neurodegenerative disorder in a patient including administration of a therapeutically effective amount of a compound of formula (I). In one embodiment the method includes administration of a compound of formula (Ia), or a compound of formula (Ib) as described herein. In one embodiment the neurodegenerative disorder is Huntington's Disease.

The invention also provides agents for the treatment of neurodegenerative disorder including a compound of formula (I) as disclosed herein. In one embodiment the agent is an anti-Huntington's disease agent.

In yet an even further aspect the invention provides a method of treatment of an inflammatory disease and/or immune system disorder in a patient including administration of a therapeutically effective amount of a compound of formula (I). In one embodiment the method includes administration of a compound of formula (Ia), or a compound of formula (Ib) as described herein. In one embodiment the inflammatory disease and/or immune system disorder is rheumatoid arthritis. In another embodiment the inflammatory disease and/or immune system disorder is Systemic Lupus Erythematosus.

The invention also provides agents for the treatment of inflammatory disease and/or immune system disorder including a compound of formula (I) as disclosed herein.

In yet an even further aspect the invention provides a method of treatment of degenerative eye disease in a patient including administration of a therapeutically effective amount of a compound of formula (I). In one embodiment the method includes administration of a compound of formula (Ia), or a compound of formula (Ib). In one embodiment, the eye disease is macular degeneration. In another embodiment, the eye disease is glaucoma. In another embodiment, the eye disease is retinal degeneration.

The invention also provides agents for the treatment of eye disease mediated by HDAC inhibition including a compound of formula (I). In one embodiment, the eye disease is macular degeneration. In another embodiment, the eye disease is glaucoma. In another embodiment, the eye disease is retinal degeneration.

The invention also provides a method of treatment of a proliferative disorder in patient including administration of a therapeutically effective amount of a compound of formula (I).

The invention also provides a method of treatment of cancer in patient including administration of a therapeutically effective amount of a compound of formula (I). In one embodiment the cancer is a hematologic malignancy. In one form of this embodiment the hematologic malignancy is selected from the group consisting of B-cell lymphoma, T-cell lymphoma and leukemia. In another embodiment the cancer is a solid tumor. In one form of this embodiment the solid tumor is selected from the group consisting of breast cancer, lung cancer, ovarian cancer, prostate cancer, head and neck cancer, renal cancer, gastric cancer, colon cancer, pancreatic cancer and brain cancer.

DETAILED DESCRIPTION OF THE EMBODIMENTS

There are disclosed hydroxamate compounds, for example imidazo[1,2-a]pyridine containing hydroxamic acid in one of the substituents, that may be inhibitors of deacetylases, including but not limited to inhibitors of histone deacetylases. The hydroxamate compounds may be suitable for prevention or treatment of a disorder caused by, associated with or accompanied by disruptions of cell proliferation and/or angiogenesis when used either alone or together with a pharmaceutically acceptable carrier, diluent or excipient. An example of such a disorder is cancer.

As used herein the term 'cancer' is a general term intended to encompass the vast number of conditions that are characterised by uncontrolled abnormal growth of cells.

It is anticipated that the compounds of the invention will be useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers, colorectal cancers, advanced colorectal adenocarcinomas, colon cancers, endocrine cancers including adrenocortical carcinoma, pancreatic cancer, pituitary cancer, thyroid cancer, parathyroid cancer, thymus cancer, multiple endocrine neoplasma, gastrointestinal cancers including stomach cancer, esophageal cancer, small intestine cancer, Liver cancer, extra hepatic bile duct cancer, gastrointestinal carcinoid tumour, gall bladder cancer, genitourinary cancers including testicular cancer, penile cancer, prostate cancer, gynecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, myelomas, haematological disorders including myelodysplastic syndromes, myeloproliferative disorders, aplastic anemia, Fanconi anemia, Waldenstroms Macroglobulinemia, lung cancers including small cell lung cancer, non-small cell lung cancer, lymphomas including Hodgkin's disease, non-Hodgkin's lymphoma, cutaneous T-cell lymphoma, peripheral T-cell lymphoma, AIDS related Lymphoma, B-cell lymphoma, Burkitt's lymphoma; eye cancers including retinoblastoma, intraocular melanoma, skin cancers including melanoma, non-melanoma skin cancer, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer.

Exemplary cancers that may be treated by the compounds of the present invention are breast cancer, lung cancer, ovarian cancer, prostate cancer, head and neck cancer, renal cancer (e.g. renal cell carcinoma), gastric cancer, colon cancer, colon cancer, colorectal cancer and brain cancer.

Exemplary cancers that may be treated by compounds of the present invention include but are not limited to B-cell lymphoma (e.g. Burkitt's lymphoma), leukemias (e.g. Acute promyelocytic leukemia), cutaneous T-cell lymphoma (CTCL) and peripheral T-cell lymphoma.

Exemplary cancers that may be treated by compounds of the present invention include solid tumors and hematologic malignancies.

The compounds may also be used in the treatment of a disorder involving, relating to or, associated with dysregulation of histone deacetylase (HDAC).

There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Proliferative disorders (e.g. cancer); Neurodegenerative diseases including Huntington's Disease, Polyglutamine diseases, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Pick's disease, Intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, macular myopic degeneration, Rubeotic glaucoma, Interstitial keratitis, Diabetic retinopathy, Peter's anomaly retinal degeneration, Cellophane Retinopathy; Cogan's Dystrophy; Corneal Dystrophy; Iris Neovascularization (Rubeosis); Neovascularization of the Cornea; Retinopathy of Prematurity; Macular Edema; Macular Hole; Macular Pucker; Marginal Blepharitis, Myopia, nonmalignant growth of the conjunctiva; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease, Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus, allergic contact dermatitis; Disease involving angiogenesis including cancer, psoriasis, rheumatoid arthritis; Psychological disorders including bipolar disease, schizophrenia, depression and dementia; Cardiovascular Diseases including Heart failure, restenosis, cardiac hypertrophy and arteriosclerosis; Fibrotic diseases including liver fibrosis, lung fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania* infection, *Trypanosoma brucei* infection, Toxoplasmosis and coccidiosis, and Haematopoietic disorders including thalassemia, anemia and sickle cell anemia.

As used herein, the term unsubstituted means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. Preferably the substituent groups are one or more groups independently selected from the group consisting of: halogen, $=$O, $=$S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —COR$^6$, —C(O)OR$^6$, CONHR$^6$, NHCOR$^6$, NHCOOR$^6$, NHCONHR$^6$, C($=$NOH)R$^6$, —SH, —SR$^6$, —OR$^6$ and acyl. Substituent groups themselves may be further optionally substituted.

"Halogen" represents chlorine, bromine, fluorine or iodine.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like.

"Alkylamino" includes both monoalkylamino and dialkylamino, unless specified. "Monoalkylamino" means a —NH-Alkyl group, in which alkyl is as defined above. "Dialkylamino" means a —N(alkyl)$_2$ group, in which each alkyl may be the same or different and are each as defined herein for alkyl. The alkyl group is preferably a $C_1$-$C_6$ alkyl group.

"Arylamino" includes both mono-arylamino and di-arylamino unless specified. Mono-arylamino means a group of formula aryl NH— in which aryl is as defined herein, di-arylamino means a group of formula (aryl)$_2$N— where each aryl may be the same or different and each are as defined herein for aryl.

"Acyl" means an alkyl-CO— group in which the alkyl group is as described herein. Examples of acyl include acetyl and benzoyl. The alkyl group is preferably a $C_1$-$C_6$ alkyl group.

"Alkenyl" as group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the chain. The group may contain a plurality of double bonds in the normal chain and the orientation about each is independently E or Z. Exemplary alkenyl groups include, but are not limited to, ethenyl and propenyl.

"Alkoxy" refers to an —O-alkyl group in which alkyl is defined herein. Preferably the alkoxy is a $C_1$-$C_6$alkoxy. Examples include, but are not limited to, methoxy and ethoxy.

"Alkenyloxy" refers to an —O— alkenyl group in which alkenyl is as defined herein. Preferred alkenyloxy groups are $C_1$-$C_6$ alkenyloxy groups.

"Alkynyloxy" refers to an —O-alkynyl group in which alkynyl is as defined herein. Preferred alkynyloxy groups are $C_1$-$C_6$ alkynyloxy groups.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl.

"Alkynyl as a group or part of a group means an aliphatic hydrocarbon group containing a carbon-carbon triple bond and which may be straight or branched preferably having from 2-14 carbon atoms, more preferably 2-12 carbon atoms in the chain, preferably 2-6 carbon atoms in the chain. Exemplary structures include, but are not limited to, ethynyl and propynyl.

"Alkylaminocarbonyl" refers to an alkylamino-C(O)— group in which alkylamino is as defined above.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic system such as cyclohexyl, bicyclic systems such as decalin, and polycyclic systems such as adamantane.

"Cycloalkylalkyl" means a cycloalkyl-alkyl- group in which the cycloalkyl and alkyl moieties are as previously described. Exemplary monocycloalkylalkyl groups include cyclopropylmethyl, cyclopentylmethyl, cyclohexylmethyl and cycloheptylmethyl.

"Heterocycloalkyl" refers to a saturated or partially saturated monocyclic, bicyclic or polycyclic ring containing at least a heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazepane, 1,4-diazepane, 1,4-oxazepine, and 1,4-oxathiapane.

"Heterocycloalkenyl" refers to a heterocycloalkyl as described above but containing at least one double bond.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl.

"Heteroalkyl" refers to a straight- or branched-chain alkyl group preferably having from 2 to 14 carbons, more preferably 2 to 10 atoms in the chain, one or more of which has been replaced by a heteroatom selected from S, O and N. Exemplary heteroalkyls include alkyl ethers, secondary and tertiary alkyl amines, alkyl sulfides, and the like.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl.

"Arylalkenyl" means an aryl-alkenyl- group in which the aryl and alkenyl are as previously described. Exemplary arylalkenyl groups include phenylallyl.

"Arylalkyl" means an aryl-alkyl- group in which the aryl and alkyl moieties are as previously described. Preferred arylalkyl groups contain a $C_{1-5}$ alkyl moiety. Exemplary arylalkyl groups include benzyl, phenethyl and naphthelenemethyl.

"Cycloalkenyl" means an optionally substituted non-aromatic monocyclic or polycyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "heteroaryl" either alone or part of another group refers to groups containing an aromatic ring (preferably a 5 or 6 membered aromatic ring) having 1 or more heteroatoms as ring atoms in the aromatic ring with the remainder of the ring atoms being carbon atoms. Suitable heteroatoms include oxygen, sulfur, and nitrogen. Examples of heteroaryl include thiophene, benzothiophene, benzofuran, benzimidazole, benzoxazole, benzothiazole, benzisothiazole, naphtho[2,3-b]thiophene, furan, isoindolidine, xantholene, phenoxazine, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, phenanthridine, acridine, phenazine, thiazole, isothiazole, phenothiazine, oxazole, isoxazole, furazane, phenoxazine, 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, 2- or 3-thienyl, or the like. More preferred examples include 2- or 3-thienyl, 2-, 3-, or 4-pyridyl, 2- or 3-quinolyl, 1-isoquinolyl, 1- or 2-indolyl, 2-benzothiazolyl, and the like.

"Heteroarylalkyl" means a heteroaryl-alkyl group in which the heteroaryl and alkyl moieties are as previously described. Preferred heteroarylalkyl groups contain a $C_1$ to $C_6$ alkyl moiety. Exemplary heteroarylalkyl groups include pyridylmethyl.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl).

In Formula (I), as well as in Formulae (Ia)-(Ib) defining sub-sets of compounds within Formula (I), there is shown an imidazo[1,2-a]pyridine ring system. Within this ring system, there are substitutable positions at the 4-, 5-, 6-, and 7-ring positions. In each of Formulae (I), (Ia), and (Ib), there is a requirement for attachment of an acidic moiety at one of the ring positions. This acidic moiety may be provided by but is not limited to groups containing, a hydroxamic acid or salt derivatives of such acid which when hydrolyzed would provide the acidic moiety. In some embodiments the acidic moiety may be attached to the ring position through an alkylene group such as —$CH_2$— or —$CH_2CH_2$—, or an alkenyl group such as —CH═CH—. Preferred positions for attachment of the acidic moiety are the 5- and 6-ring positions.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. Some of the compounds of the disclosed embodiments may exist as single stereoisomers, racemates, and/or mixtures of enantiomers and/or diastereomers. All such single stereoisomers, racemates and mixtures thereof are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

In addition to compounds of the Formula (I), the HDAC inhibiting agents of the various embodiments include pharmaceutically acceptable salts, prodrugs, and active metabolites of such compounds, and pharmaceutically acceptable salts of such metabolites.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formula (I) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of formula (I). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula I containing a carboxy group may be convertible by hydrolysis in vivo to the parent molecule. (Examples of ester prodrugs are those described by F. J. Leinweber, Drug Metab. Res., 18:379, 1987).

Preferred HDAC inhibiting agents include those having an $IC_{50}$ value of 10 µM or less.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumors, than to normal cells.

The term "therapeutically effective amount" or "effective amount" is an amount sufficient to effect beneficial or desired results. An effective amount can be administered in one or more administrations. An effective amount is typically sufficient to palliate, ameliorate, stabilize, reverse, slow or delay the progression of the disease state. A therapeutically effective amount can be readily determined by a skilled practitioner by the use of conventional techniques and by observing results obtained in analogous circumstances. In determining the effective amount a number of factors are considered including the species of the patient, its size, age, general health, the specific disease involved, the degree or severity of the disease, the response of the individual patient, the particular compound administered, the mode of administration, the bioavailability of the compound, the dose regimen selected, the use of other medication and other relevant circumstances.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mak Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in a further embodiment the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug (s) that include chemotherapeutic drugs or HDAC inhibitor drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include chemotherapeutic drugs or HDAC inhibitor drugs the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, dragees, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

As discussed above, the compounds of the embodiments disclosed inhibit histone deacetylases. The enzymatic activity of a histone deacetylase can be measured using known methodologies [Yoshida M. et al, J. Biol. Chem., 265, 17174 (1990), J. Taunton et al, Science 1996 272: 408]. In certain embodiments, the histone deacetylase inhibitor interacts with and/or reduces the activity of more than one known histone deacetylase in the cell, which can either be from the same class of histone deacetylase or different class of histone deacetylase. In some other embodiments, the histone deacetylase inhibitor interacts and reduces the activity of predominantly one histone deacetylase, for example HDAC-1, HDAC-2, HDAC-3 or HDAC-8, which belongs to Class I HDAC enzymes [De Ruijter A. J. M. et al, Biochem. J., 370, 737-749 (2003)]. HDACs can also target non-histone substrates to regulate a variety of biological functions implicated in disease pathogenesis. These non-histone substrates include Hsp90, -tubulin, p53, NFkb and HIF1a [Drummond et al., Annu. Rev. Pharmacol. Toxicol. 45:495 (2004)]. Certain preferred histone deacetylase inhibitors are those that interact with, and/or reduce the activity of a histone deacetylase which is involved in tumorigenesis, and these compounds may be useful for treating proliferative diseases. Examples of such cell proliferative diseases or conditions include cancer (include any metastases), psoriasis, and smooth muscle cell proliferative disorders such as restenosis. The inventive compounds may be particularly useful for treating tumors such as breast cancer, colon cancer, lung cancer, ovarian cancer, prostate cancer, head and/or neck cancer, or renal, gastric, pancreatic cancer and brain cancer as well as hematologic malignancies such as lymphoma and leukemias. In addition, the inventive compounds may be useful for treating a proliferative disease that is refractory to the treatment with other chemotherapeutics; and for treating hyperproliferative condition such as leukemias, psoriasis and restenosis. In other embodiments, compounds of this invention can be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

Additionally compounds of the various embodiments disclosed herein may be useful for treating neurodegenerative diseases, and inflammatory diseases and/or immune system disorders.

The disorder is preferably selected from the group consisting of cancer, inflammatory diseases and/or immune system disorders (e.g. rheumatoid arthritis, systemic lupus erythematosus), angiofibroma, cardiovascular diseases, fibrotic diseases, diabetes, autoimmune diseases, chronic and acute neurodegenerative disease like Huntington's disease, Parkinson's disease, disruptions of nerval tissue and infectious diseases like fungal, bacterial and viral infections. In another embodiment the disorder is a proliferative disorder.

The histone deacetylase inhibitors of the invention have significant antiproliferative effects and promote differentiation, cell cycle arrest in the G1 or G2 phase, and induce apoptosis.

Synthesis of Deacetylase Inhibitors

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene and P. G. M. Wuts' Protective Groups in Organic Synthesis, 3rd Edition, John Wiley & Sons, 1999. Alternatively, other reactions disclosed herein or known in the art will be recognized as having applicability for preparing other compounds of the various embodiments.

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. For moisture sensitive reactions, anhydrous solvents like dichloromethane (DCM), dimethylsulfoxide (DMSO), tetrahydrofuran (THF) and N,N-dimethylformamide (DMF) were purchased from Aldrich in SureSeal bottles and used as received. All other solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in iodine chamber. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated.

$^1$H-NMR spectra were recorded on a Bruker instrument operating at 400 MHz, and $^{13}$C-NMR spectra were recorded operating at 100 MHz. NMR spectra were obtained as CDCl$_3$ solutions (reported in ppm), using chloroform as the reference standard (7.25 ppm and 77.00 ppm) or CD$_3$OD (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Mass spectra were obtained using LC/MS either in ESI or APCI. All melting points are uncorrected.

All final products had greater than 90% purity (LC/PDA: Xterra 1S column, 4.6×20 mm 3.5μ column; 2.0 ml/min, gradient 5-95% B over 6 min, Solvent A: H$_2$O with 0.1% TFA; Solvent B: acetonitrile with 0.1% TFA; UV 254 nm), unless indicated otherwise.

The following examples are intended to illustrate the embodiments disclosed and are not to be construed as being limitations thereto. Additional compounds, other than those described below, may be prepared using the following described reaction scheme or appropriate variations or modifications thereof.

Synthesis

Scheme I illustrates the procedure used for preparing compounds of Formula VIIIa, wherein (Y)$_p$ are hydrogens. Specifically, Scheme I illustrates the reaction of 6-membered amino heterocycles (reactant 1,4-bromo-2-amino pyridine) with an aldehyde and an isonitrile to form fused 3-amino imidazo heterocycles [*Tet Lett*, 1998, 39, 3635; *Angew. Chem. Int Ed English*, 1998, 2234]. Other 6-membered amino heterocycles can be used to form fused heterocycles. By analogy, appropriate 5-membered amino heterocycles can be reacted with an appropriate aldehyde and an isonitrile to form 5,5-fused imidazo heterocycles.

As illustrated in Scheme I, an amino heterocycle 4-bromo-2-amino pyridine (I) was reacted with an aldehyde II, and an isonitrile III, in one pot reaction under acid catalyzed condition to furnish a fused imidazo heterocycle bearing secondary amine disposed on the 3-position of the fused ring. The halogen substituent (Y=halogen, p=1) on the fused ring can then be reacted with ethyl acrylate V under Heck conditions to produce an α,β-unsaturated ester which can subsequently be converted to a hydroxamic acid VII.

Scheme I

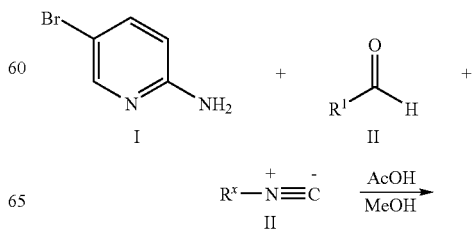

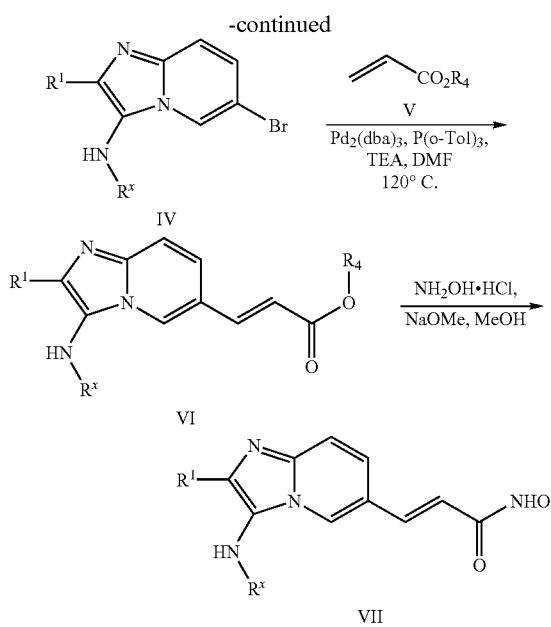

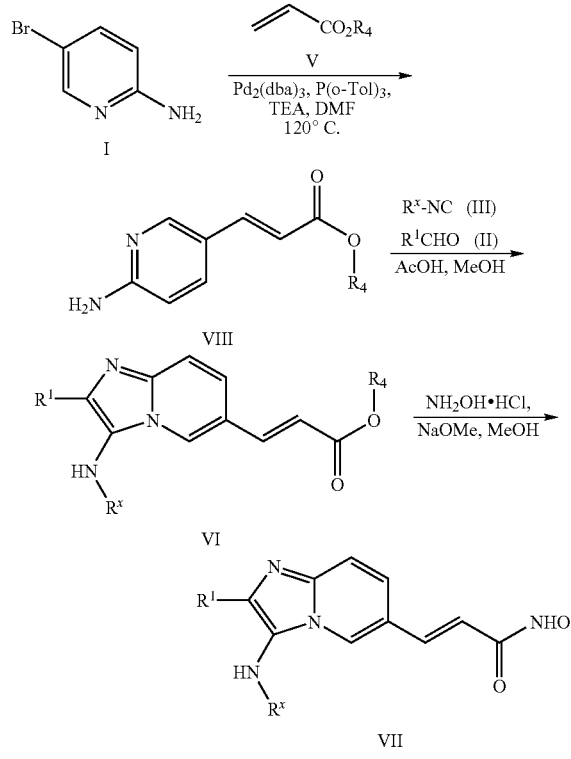

The preparations of 6-substituted alkenoyl hydroxamates are illustrated in Schemes III-XII.

Scheme III illustrates the procedure used for preparing compounds of Formula VIIIa (wherein $(Y)_p$ are hydrogens) in which the hydroxamic acid bearing substituent is at the 6-position. Using 4-cyano-2-amino pyridine as one of the starting materials of the three-component reaction, the imidazopyridine structure could be constructed. Further elaborations by converting the nitrile group to the corresponding aldehyde could be achieved by DIBAL-H reduction. The aldehyde could be reacted with an appropriate Wittig reagent to provide the desired alkenyl ester which could be converted to the desired hydroxamate.

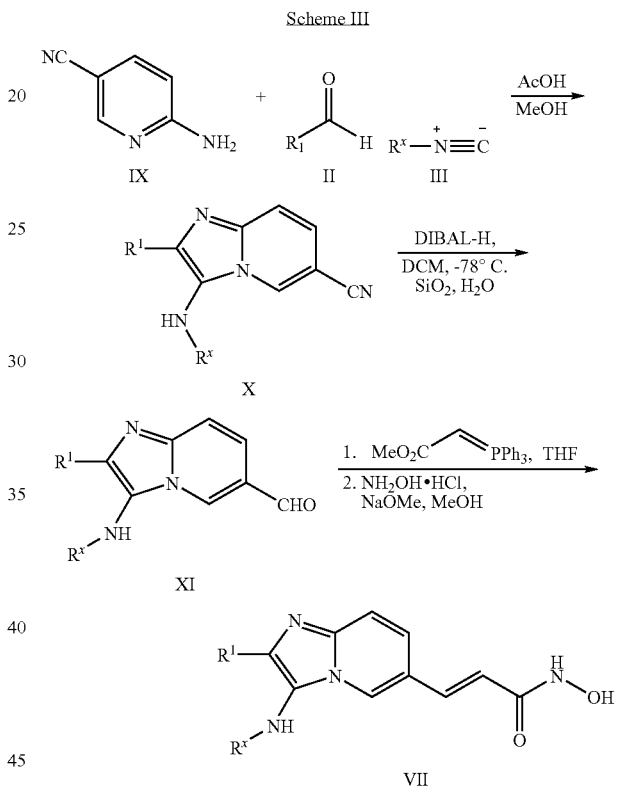

Alternatively, compounds of VII can be prepared by first introducing the α,β-unsaturated ester on amino heterocycle I to form the intermediate VIII. This is followed by a three-component one-pot reaction that fuses VIII, aldehyde II, and isonitrile III to furnish the fused ring VI. The ester VI can be converted to a hydroxamic acid by methods known in the literature. This alternative method of preparation is illustrated in Scheme II.

Scheme IV illustrates yet another procedure to prepare compounds of Formula VIIIa (wherein $(Y)_p$ are hydrogens), by using 4-bromo-2-aminopyridine as the starting material. The synthetic steps are quite similar to those illustrated in Scheme 1. Both schemes utilize Heck reaction to introduce the alkenyl ester functionality which was eventually converted to hydroxamic acid.

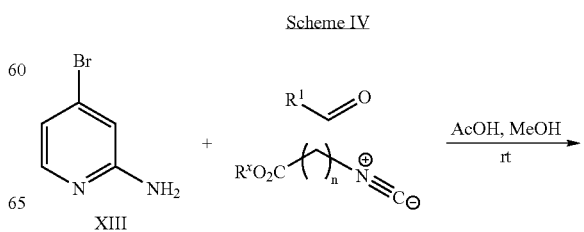

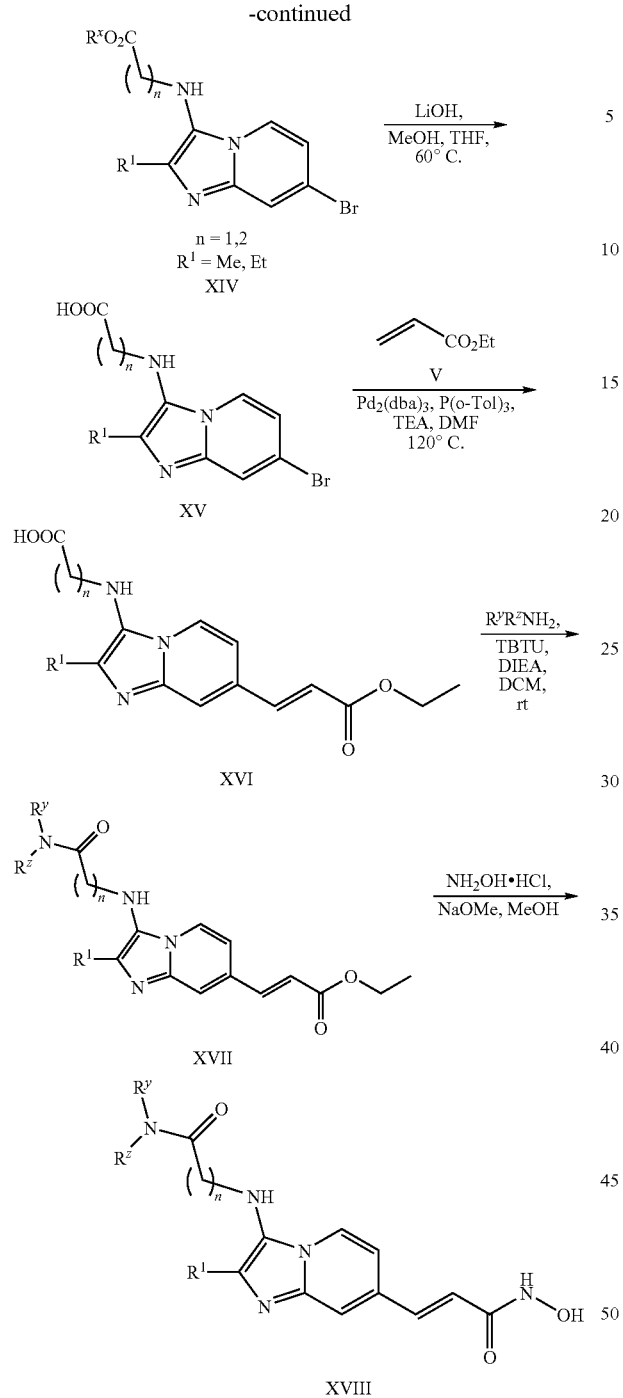
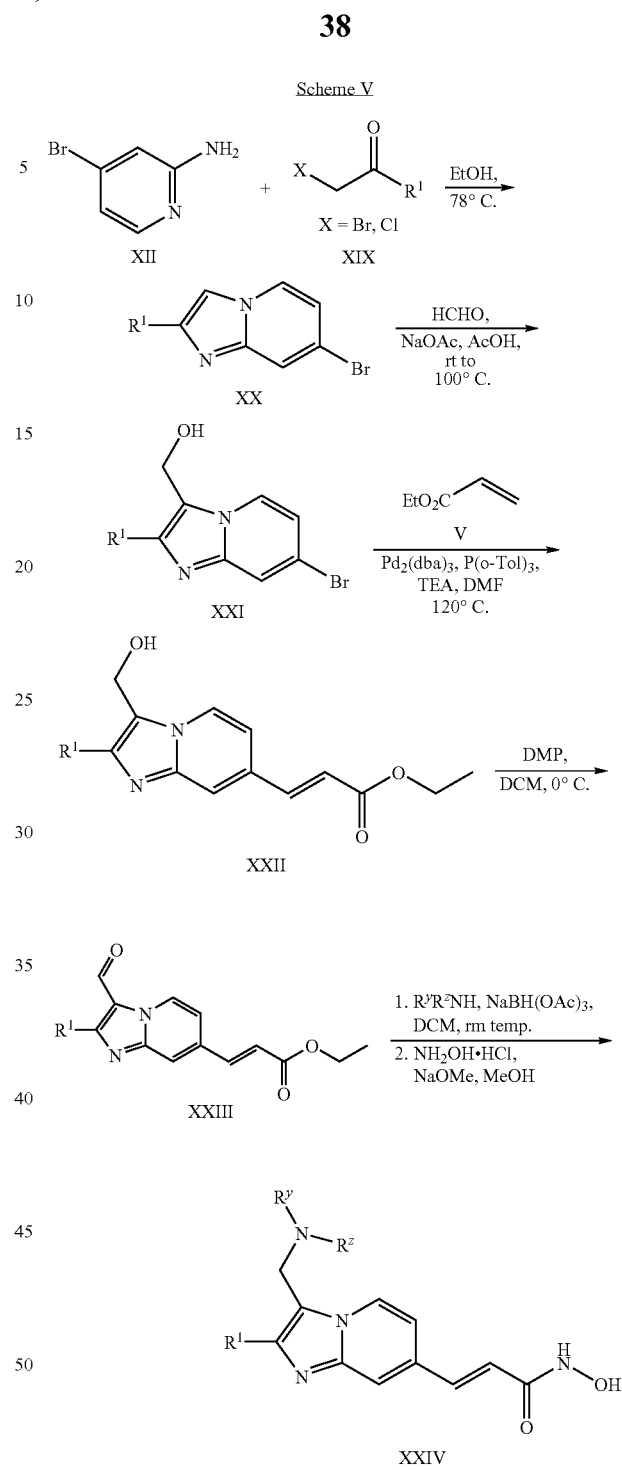

Scheme V illustrates yet another method in preparing compounds of Formula VIIIb, wherein (Y)$_p$ are hydrogens. The imidazopyridine core structure was constructed by a condensation reaction using 4-bromo-2-aminopyridine as one of the starting materials [J. Med. Chem. 1998, 41, 5108]. The methanol group was introduced at the 3 position by reacting with formaldehyde to give the intermediate XX. This intermediate XX was then subjected to Heck reaction condition in which the alkenyl ester was produced. The alcohol group in XXI was then oxidized to the aldehyde which was further converted to an aminoalkyl group under reductive amination conditions using sodium acetoxyborohydride. The hydroxamic acid was formed as described in the previous schemes.

Scheme VI illustrates yet another method in preparing compounds of Formula VIIIb, wherein (Y)$_p$ are hydrogens. The imidazopyridine core structure was constructed by the condensation reaction using 4-bromo-2-aminopyridine as one of the starting material. The alkenyl ester group was introduced at the 6-position by the Heck reaction. This intermediate XXV was then subjected to a Mannich reaction in which the aminoalkyl group was introduced [J. Org. Chem. 1965, 30, 2403]. Without further workups and purifications, the crude material was converted into the hydroxamic acid as described in the previous schemes.

Scheme VI

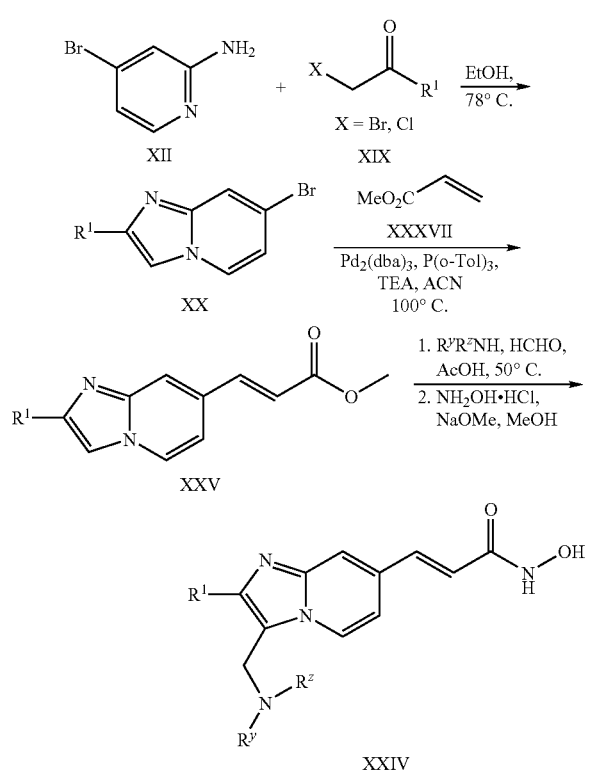

Scheme VII illustrates yet another method of preparing compounds of Formula VIIIb, wherein $(Y)_p$ are hydrogens. The imidazopyridine core structure was constructed by the condensation reaction using 4-cyano-2-aminopyridine as one of the starting material. The alkenyl ester group was introduced at the 6-position by a series of common organic transformations (basic hydrolysis; esterification; DIBAL-H reduction; DMP oxidation and the Wittig reaction). The intermediate XXV was then subjected to a Mannich reaction in which the aminoalkyl group was introduced [*J. Org. Chem.* 1965, 30, 2403]. Without further workups and purifications, the crude material was converted into the hydroxamic acid as described in the previous schemes.

Scheme VII

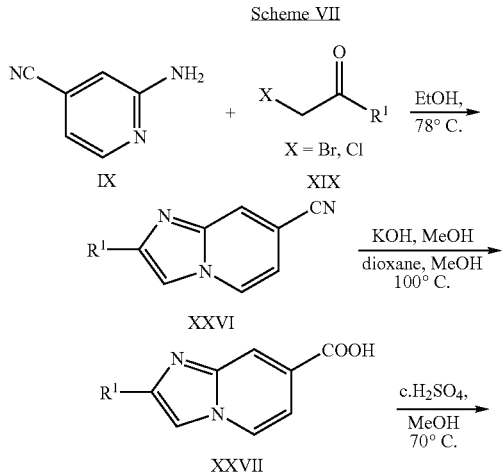

Scheme VIII illustrates yet another method in preparing compounds of Formula VIIIb, wherein $(Y)_p$ are hydrogens. The imidazopyridine core structure was constructed by the condensation reaction using 4-bromo-2-aminopyridine as one of the starting material. The alkenyl ester group was introduced at the 6-position by the Heck reaction. This intermediate XXV was then subjected to a Mannich reaction in which the aminoalkyl group was introduced [*J. Org. Chem.* 1965, 30, 2403]. Without further workups and purifications, the crude material was converted into the hydroxamic acid as described in the previous schemes. After purification by reverse-phase prep-HPLC, the intermediate XXIV was subjected to reductive amination with the appropriate aldehydes to furnish the desired product.

Scheme VIII

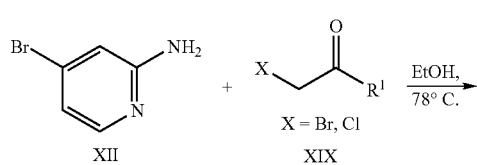

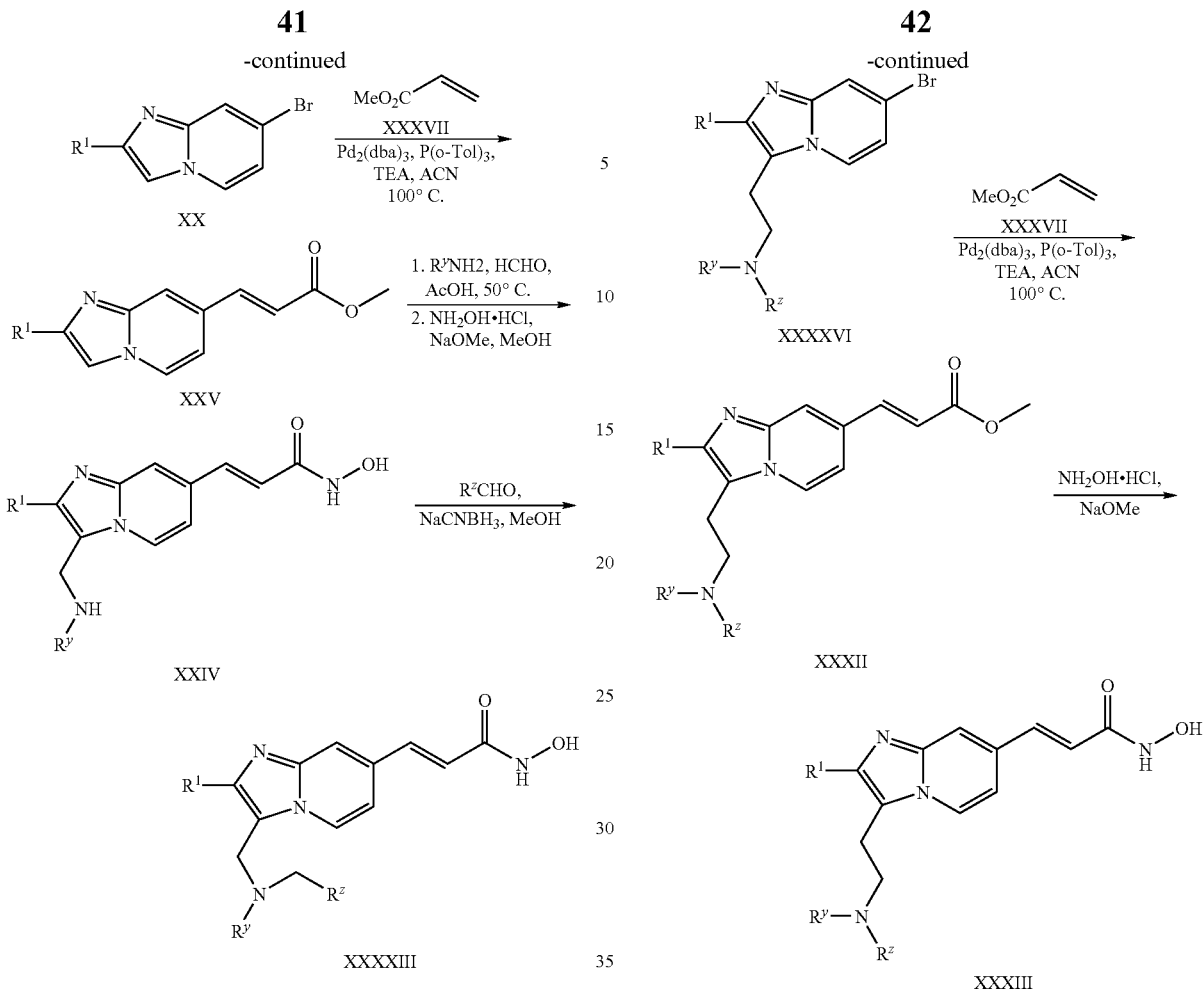

Scheme IX illustrates yet another method of preparing compounds of Formula Ia & Ib. The imidazopyridine core structure was constructed by the condensation reaction using 4-bromo-2-aminopyridine and the appropriate bromoketoamides XXX [J. Med. Chem. 2005, 48, 292]. The amide was reduced to the corresponding amines before introducing the alkenyl ester group at the 6-position by the Heck reaction. The intermediate XXXII was then converted into the hydroxamic acid as described in the previous schemes.

Scheme X illustrates yet another method of preparing compounds of Formula Ia & Ib. The imidazopyridine core structure was constructed by a condensation reaction using 4-bromo-2-aminopyridine as one of the starting materials. The methanol group was introduced at the 3-position by reacting with formaldehyde to give the intermediate XX. This intermediate XX was then subjected to chlorination and subsequent reaction with NaCN to furnish the cyano-intermediate [Eur. Pat. Appl. 266890]. Further reduction with either LiAlH$_4$ or BH$_3$.SMe$_2$ and followed by a reductive amination of the former gave the intermediate XXXVI. The alkenyl ester group was introduced at the 6-position by the Heck reaction. The intermediate XXXII was then converted into the hydroxamic acid as described in the previous schemes.

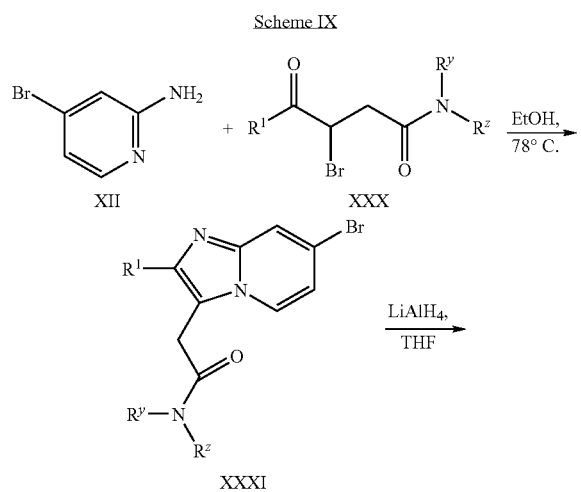

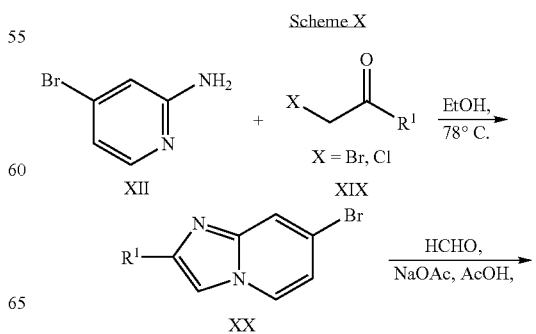

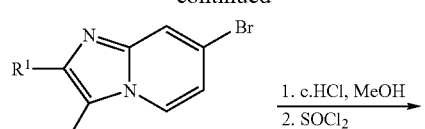
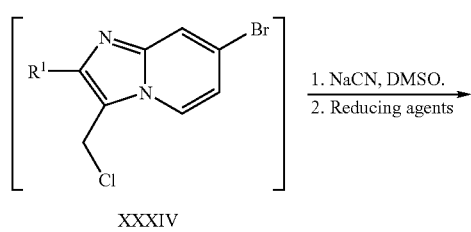
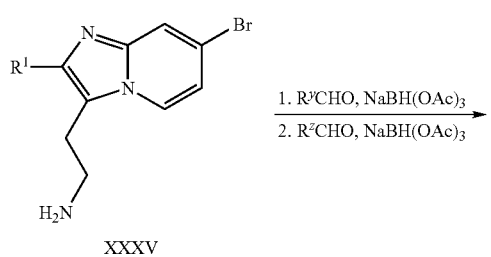
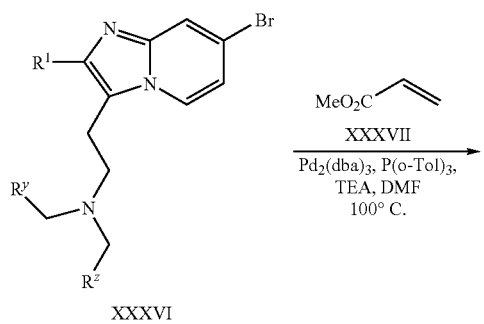
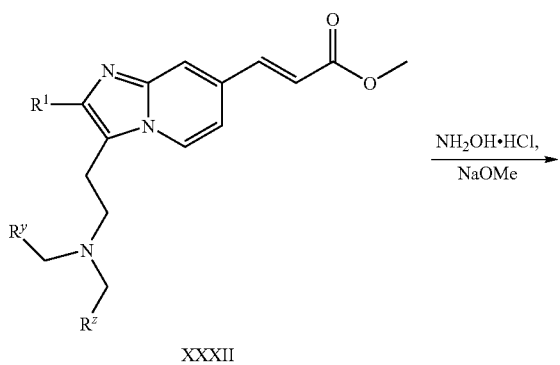
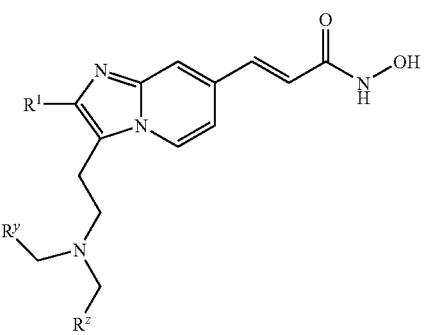

Scheme XI illustrates yet another method of preparing compounds of Formula Ia & Ib. The imidazopyridine core structure was constructed by the condensation reaction using 4-bromo-2-aminopyridine and the appropriate bromoketoamides XXXIX. The alkenyl ester group was introduced at the 6-position by the Heck reaction. Further deprotection and followed by reductive amination provided the intermediate XXXII. The intermediate XXXII was then converted into the hydroxamic acid as described in the previous schemes.

Scheme XI

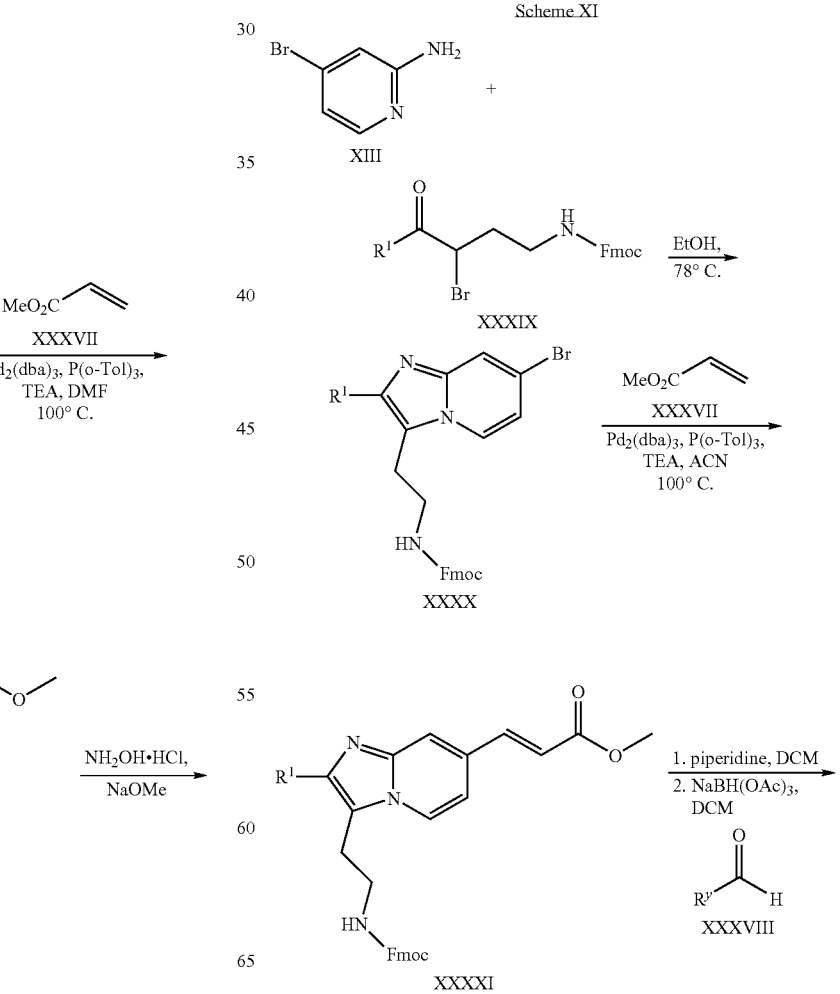

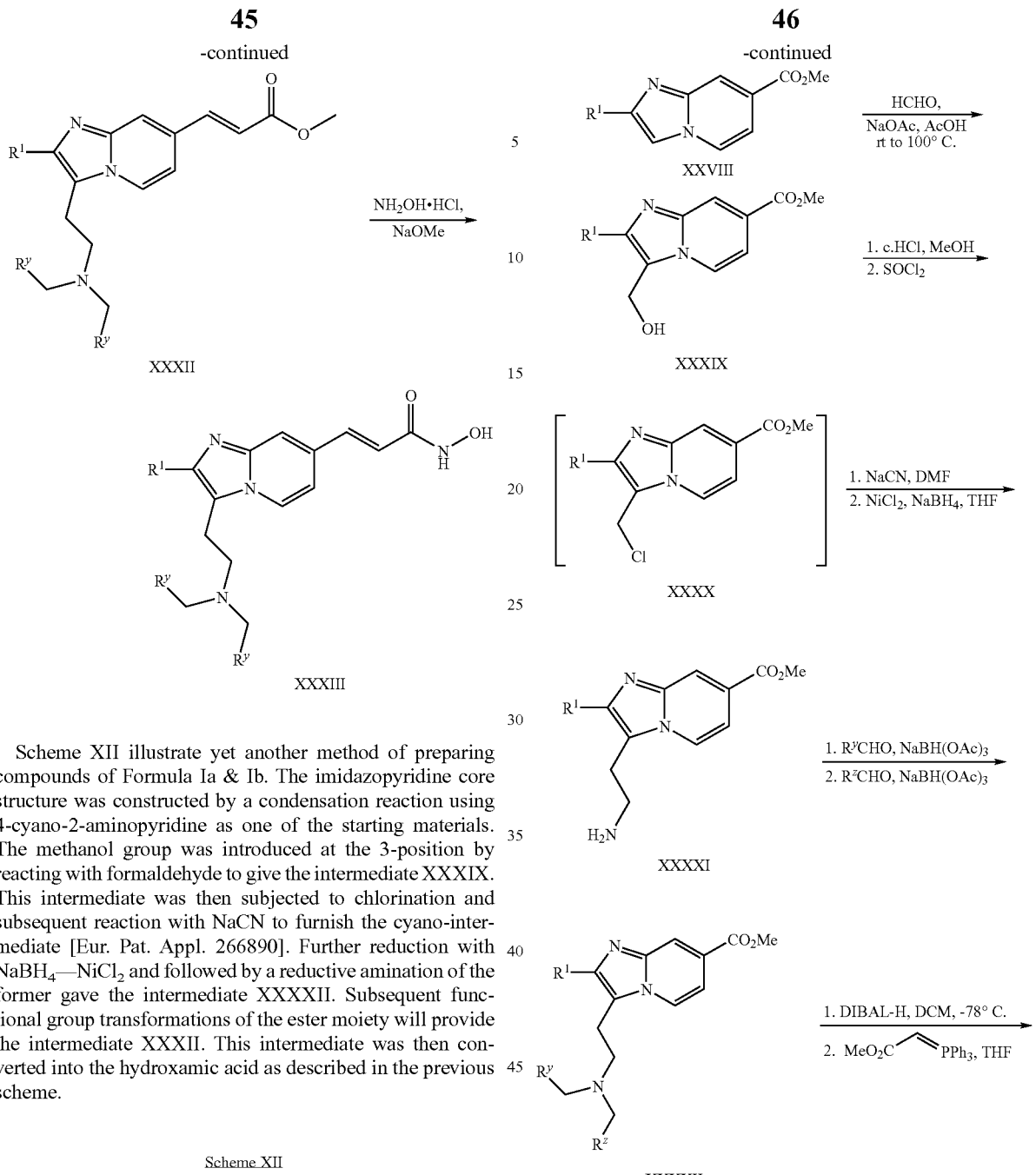

Scheme XII illustrate yet another method of preparing compounds of Formula Ia & Ib. The imidazopyridine core structure was constructed by a condensation reaction using 4-cyano-2-aminopyridine as one of the starting materials. The methanol group was introduced at the 3-position by reacting with formaldehyde to give the intermediate XXXIX. This intermediate was then subjected to chlorination and subsequent reaction with NaCN to furnish the cyano-intermediate [Eur. Pat. Appl. 266890]. Further reduction with NaBH$_4$—NiCl$_2$ and followed by a reductive amination of the former gave the intermediate XXXXII. Subsequent functional group transformations of the ester moiety will provide the intermediate XXXII. This intermediate was then converted into the hydroxamic acid as described in the previous scheme.

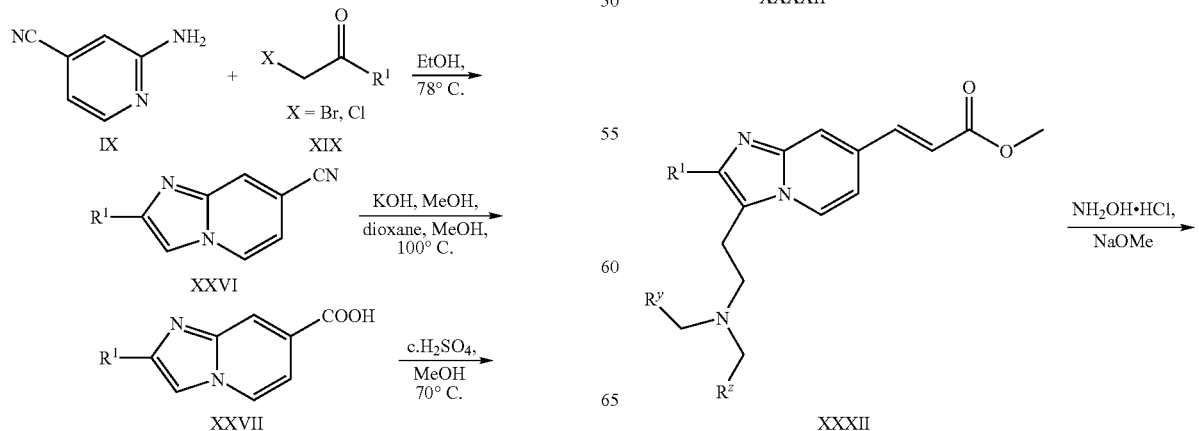

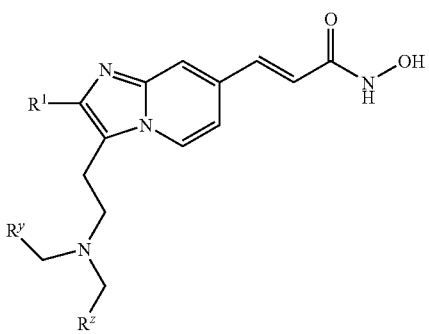

XXXIII

Based on Scheme IX, Scheme X and Scheme XI, and by varying the starting materials used in the synthesis, a wide variety of compounds of Formula Ib (where p=0; Z=CH=CH alkene; $R^2$=—$CH_2CH_2NR^{26}R^{27}$) could be prepared, including, but not limited to, those in Table 1:

TABLE 1

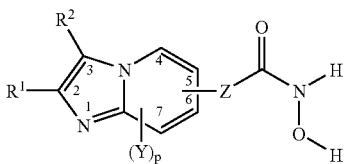

Formula Ib

| Compound No. | $R^1$ | $R^{26}$ | $R^{27}$ |
|---|---|---|---|
| 145 | Ph | —$CH_2CH_3$ | H |
| 146 | Ph | —$CH_2CH_2CH_3$ | H |
| 147 | Ph | —$C(CH_3)_3$ | H |
| 148 | Ph | —$CH_2C(CH_3)_3$ | H |
| 149 | Ph | —$CH_2CH_2CH_3$ | —$CH_2CH_3$ |
| 150 | Ph | —$CH_2CH_2CH_3$ | —$CH_3$ |
| 151 | Ph | —$CH(CH_3)_2$ | —$CH_3$ |
| 152 | 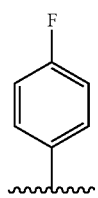 | —$CH_2CH_3$ | H |
| 153 | 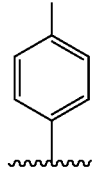 | —$CH_2CH_2CH_3$ | H |
| 154 | 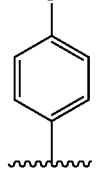 | —$C(CH_3)_3$ | H |

TABLE 1-continued

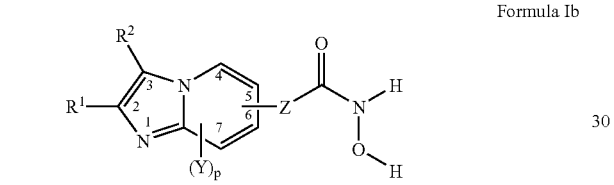

Formula Ib

| Compound No. | $R^1$ | $R^{26}$ | $R^{27}$ |
|---|---|---|---|
| 155 | 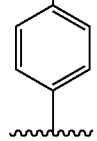 | —$CH_2C(CH_3)_3$ | H |
| 156 | 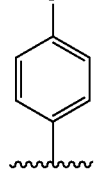 | —$CH_2CH_3$ | —$CH_2CH_3$ |
| 157 | 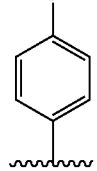 | —$CH_2CH_2CH_3$ | —$CH_3$ |
| 158 | 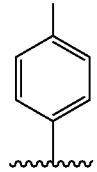 | —$CH(CH_3)_2$ | —$CH_3$ |
| 159 | 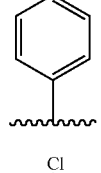 | —$CH_2CH_3$ | H |
| 160 | 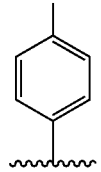 | —$CH_2CH_2CH_3$ | H |
| 161 | 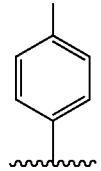 | —$C(CH_3)_3$ | H |

TABLE 1-continued

Formula Ib

| Compound No. | R¹ | R²⁶ | R²⁷ |
|---|---|---|---|
| 162 | 4-Cl-phenyl | —CH₂C(CH₃)₃ | H |
| 163 | 4-Cl-phenyl | —CH₂CH₃ | —CH₂CH₃ |
| 164 | 4-Cl-phenyl | —CH₂CH₂CH₃ | —CH₃ |
| 165 | 4-Cl-phenyl | —CH(CH₃)₂ | —CH₃ |
| 166 | cyclohexyl | —CH₂CH₃ | H |
| 167 | cyclohexyl | —CH₂CH₂CH₃ | H |
| 168 | cyclohexyl | —C(CH₃)₃ | H |
| 169 | cyclohexyl | —CH₂C(CH₃)₃ | H |
| 170 | cyclohexyl | —CH₂CH₃ | —CH₂CH₃ |
| 171 | cyclohexyl | —CH₂CH₂CH₃ | —CH₃ |
| 172 | cyclohexyl | —CH(CH₃)₂ | —CH₃ |
| 173 | cyclohexyl | —C(CH₃)₃ | —CH₃ |
| 174 | 4-pyridyl | —CH₂CH₂CH₃ | H |
| 175 | 4-pyridyl | —C(CH₃)₃ | H |
| 176 | 4-pyridyl | —CH₂C(CH₃)₃ | H |
| 177 | 4-pyridyl | —CH₂CH₃ | —CH₂CH₃ |

TABLE 1-continued

Formula Ib

| Compound No. | R¹ | R²⁶ | R²⁷ |
|---|---|---|---|
| 178 | 4-pyridyl | —CH₂CH₂CH₃ | —CH₃ |
| 179 | 4-pyridyl | —CH(CH₃)₂ | —CH₃ |
| 180 | 2-pyridyl | —CH₂CH₂CH₃ | H |
| 181 | 2-pyridyl | —C(CH₃)₃ | H |
| 182 | 2-pyridyl | —CH₂C(CH₃)₃ | H |
| 183 | 2-pyridyl | —CH₂CH₃ | —CH₂CH₃ |
| 184 | 2-pyridyl | —CH₂CH₂CH₃ | —CH₃ |
| 185 | 2-pyridyl | —CH(CH₃)₂ | —CH₃ |
| 186 | —(CH₂)₃CH₃ | —CH₂CH₃ | —CH₂CH₃ |
| 187 | —(CH₂)₃CH₃ | —CH₂CH₂CH₃ | —CH₃ |
| 188 | —(CH₂)₃CH₃ | —CH(CH₃)₂ | —CH₃ |
| 189 | —(CH₂)₃CH₃ | —C(CH₃)₃ | —CH₃ |
| 190 | —(CH₂)₃CH₃ | —C(CH₃)₃ | —CH₂CH₃ |
| 191 | —(CH₂)₃CH₃ | —CH₂C(CH₃)₃ | H |
| 192 | cyclohexyl | —C(CH₃)₃ | —CH₂CH₃ |
| 193 | cyclopentyl | —CH₂CH₃ | H |
| 194 | cyclopentyl | —CH₂CH₂CH₃ | H |
| 195 | cyclopentyl | —C(CH₃)₃ | H |
| 196 | cyclopentyl | —CH₂C(CH₃)₃ | H |
| 197 | cyclopentyl | —CH₂CH₃ | —CH₂CH₃ |
| 198 | cyclopentyl | —CH₂CH₂CH₃ | —CH₃ |
| 199 | cyclopentyl | —CH(CH₃)₂ | —CH₃ |
| 200 | cyclopentyl | —C(CH₃)₃ | —CH₃ |
| 201 | cyclopentyl | —C(CH₃)₃ | —CH₂CH₃ |

TABLE 1-continued

Formula Ib

[Structure: Imidazo-fused bicyclic core with R², R¹ substituents on positions 3, 2; ring numbered 1-7 with (Y)p; Z linker to C(=O)NH-OH]

| Compound No. | R¹ | R²⁶ | R²⁷ |
|---|---|---|---|
| 202 | —C(CH₃)₃ | —CH₂CH₃ | H |
| 203 | —C(CH₃)₃ | —CH₂CH₂CH₃ | H |
| 204 | —C(CH₃)₃ | —C(CH₃)₃ | H |
| 205 | —C(CH₃)₃ | —CH₂C(CH₃)₃ | H |
| 206 | —C(CH₃)₃ | —CH₂CH₃ | —CH₂CH₃ |
| 207 | —C(CH₃)₃ | —CH₂CH₂CH₃ | —CH₃ |
| 208 | —C(CH₃)₃ | —CH(CH₃)₂ | —CH₃ |
| 209 | —C(CH₃)₃ | —C(CH₃)₃ | —CH₃ |
| 210 | —C(CH₃)₃ | —C(CH₃)₃ | —CH₂CH₃ |
| 211 | —CH₃ | —CH₂CH₃ | H |
| 212 | —CH₃ | —CH₂CH₂CH₃ | H |
| 213 | —CH₃ | —C(CH₃)₃ | H |
| 214 | —CH₃ | —CH₂C(CH₃)₃ | H |
| 215 | —CH₃ | —CH₂CH₃ | —CH₂CH₃ |
| 216 | —CH₃ | —CH₂CH₂CH₃ | —CH₃ |
| 217 | —CH₃ | —CH(CH₃)₂ | —CH₃ |
| 218 | —CH₃ | —C(CH₃)₃ | —CH₃ |
| 219 | —CH₃ | —C(CH₃)₃ | —CH₂CH₃ |
| 220 | 3-pyridyl | —CH₂CH₂CH₃ | H |
| 221 | 3-pyridyl | —C(CH₃)₃ | H |
| 222 | 3-pyridyl | —CH₂C(CH₃)₃ | H |
| 223 | 3-pyridyl | —CH₂CH₃ | —CH₂CH₃ |
| 224 | 3-pyridyl | —CH₂CH₂CH₃ | —CH₃ |
| 225 | 3-pyridyl | —CH(CH₃)₂ | —CH₃ |
| 226 | cyclopropyl | —CH₂CH₃ | H |
| 227 | cyclopropyl | —CH₂CH₂CH₃ | H |
| 228 | cyclopropyl | —C(CH₃)₃ | H |
| 229 | cyclopropyl | —CH₂C(CH₃)₃ | H |
| 230 | cyclopropyl | —CH₂CH₃ | —CH₂CH₃ |
| 231 | cyclopropyl | —CH₂CH₂CH₃ | —CH₃ |
| 232 | cyclopropyl | —CH(CH₃)₂ | —CH₃ |
| 233 | cyclopropyl | —C(CH₃)₃ | —CH₃ |
| 234 | cyclopropyl | —C(CH₃)₃ | —CH₂CH₃ |
| 235 | —(CH₂)₃CH₃ | —CH₂CH₃ | H |
| 236 | —(CH₂)₃CH₃ | —CH₂CH₂CH₃ | H |
| 237 | —(CH₂)₃CH₃ | —C(CH₃)₃ | H |

The following preparation and examples are given to enable those skilled in the art to more clearly understand to practice the subject matter hereof. They should not be considered as limiting the scope of the disclosure, but merely as being illustrative and representative thereof.

Example 1

Preparation of N-Hydroxy-3-[2-phenethyl-3-(3,4,5-trimethoxy-phenylamino)-imidazol[1,2-a]pyridin-6yl]-acrylamide (Compound 1)

Step 1: 3-Component Reaction

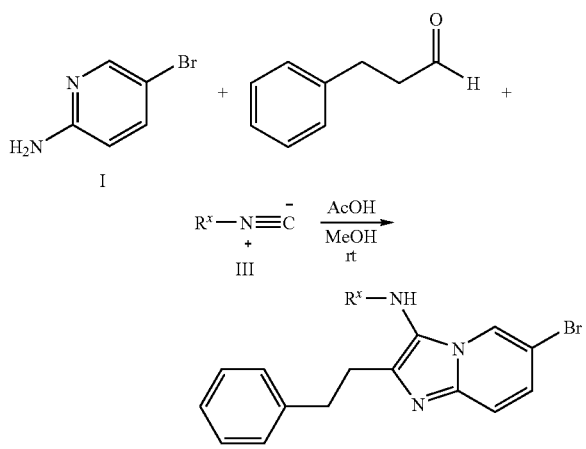

To a solution of the amine (3.04 mmol) in MeOH (10.0 mL) was added the aldehyde (3.04 mmol), the isonitrile (3.04 mmol) and AcOH (6.08 mmol) at room temp. The reaction was stirred overnight. When LCMS had shown the full depletion of the starting material amine, 1M HCl (25 mL) was added till pH ~1 before being concentrated in vacuo. NaHCO₃ (30 mL) was then added and ethyl acetate (4×20 mL) was used to extract the aqueous layer. The combined organic extracts were then washed with NaHCO₃ (2×20 mL) and brine (2×20 mL), before being died in Na₂SO₄. The mixture was then filtered and concentrated in vacuo. The crude product was used immediately for the next step without further purification.

(6-Bromo-2-phenethyl-imidazo[1,2-a]pyridin-3-yl)-(3,4,5-trimethoxy-phenyl)-amine HPLC: 87.5%; $t_R$=2.741 min; LCMS (ESI) m/z 482 [MH]⁺.

Step 2: Heck Reaction

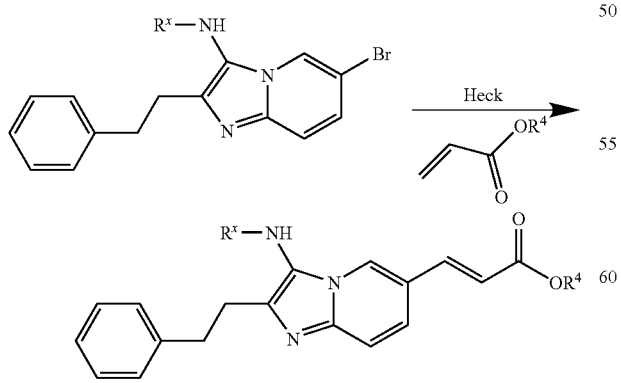

Ethyl acrylate (1.5 equiv) was added into a stirred suspension of the amine (1 equiv), Pd₂(dba)₃ (0.1 equiv), P(o-tol)₃ (0.18 equiv), Et₃N (1.54 equiv) and DMF at room temp. The reaction was heated to reflux at ~120° C. When the starting material had fully depleted (monitored by LCMS), the reaction mixture was diluted with ethyl acetate (20 mL). The organic layer was then washed with NaHCO₃ (2×10 mL) and brine (2×10 mL). The organic layer was dried in Na₂SO₄ before being filtered and concentrated in vacuo. The crude product was purified by flash column chromatography.

3-[2-Phenethyl-3-(3,4,5-trimethoxy-phenylamino)-imidazo[1,2-a]pyridin-6-yl]-acrylic acid ethyl ester $R_f$=0.44 [Hexane:ethyl acetate (1:3)] HPLC: 95.6%; $t_R$=2.532 min; LCMS (ESI) 502 [MH]⁺.

Step 3: Hydroxamic Acid Formation

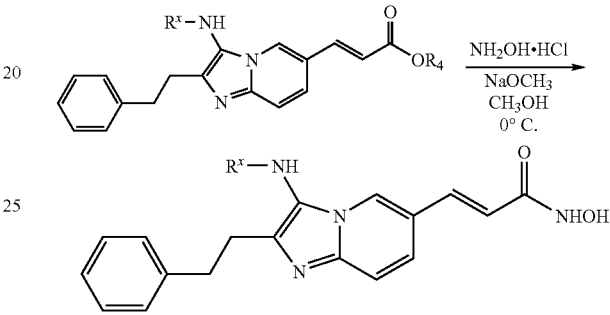

NH₂OH.HCl (10 equiv) was added into a solution of the ester (1 equiv) and MeOH at room temperature. The reaction mixture was cooled to 0° C. before NaOCH₃ (20 equiv; 25% wt solution in MeOH) was introduced. When LCMS had shown the full depletion of the starting material, the reaction mixture was poured into ice-water and extracted with ethyl acetate (4×15 mL). The organic extracts were then washed with NaHCO₃ (2×20 mL) and brine (2×20 mL), before being dried in Na₂SO₄. The mixture was then filtered and concentrated in vacuo. The crude product was purified by reverse phase prep-HPLC.

N-Hydroxy-3-[2-phenethyl-3-(3,4,5-trimethoxy-phenylamino)-imidazo[1,2-a]pyridin-6-yl]-acrylamide (Compound 1)

HPLC: 98.8%; $t_R$=2.847 min; LCMS (ESI) m/z 489 [MH]⁺; ¹H NMR (DMSO-d₆): δ 10.86 (brs, 1H), 8.62 (s, 1H), 8.09 (s, 1H), 8.02 (d, J=9.4 Hz, 1H), 7.94 (d, J=9.4 Hz, 1H), 7.63 (d, J=15.8 Hz, 1H), 7.26-7.23 (m, 2H), 7.18-7.15 (m, 3H), 6.61 (d, J=15.8 Hz, 1H), 3.63 (s, 6H), 3.57 (s, 3H), 2.99 (s, 4H); ¹³C NMR (DMSO-d₆): δ 153.6, 141.3, 140.2, 137.4, 133.4, 132.8, 131.0, 128.4, 128.4, 126.2, 124.5, 124.1, 121.9, 121.7, 113.5, 91.6, 60.0, 55.7, 33.3, 26.1.

Example 2

3-{3-[(Benzo[1,3]-dioxol-5-ylmethyl)-amino]-2-phenethyl-imidazo[1,2-a]pyridin-6-yl}-N-hydroxy-acrylamide (Compound 2)

The titled compound was prepared according to the procedures described in Example 1, by using appropriate starting materials. HPLC: 98.3%; $t_R$=2.368 min; LCMS (ESI) m/z 457 [MH]⁺; ¹H NMR (DMSO-d₆): δ 10.95 (brs, 1H), 8.74 (s, 1H), 8.02 (d, J=9.3 Hz, 1H), 7.88 (d, J=9.33 Hz, 1H), 7.66 (d, J=15.8 Hz, 1H), 7.31-7.27 (m, 2H), 7.22-7.16 (m, 3H), 6.97

(d, J=1.3 Hz, 1H), 6.78 (d, J=7.9 Hz, 1), 6.67-6.63 (m, 2H), 5.93 (s, 2 h), 5.62 (brs, 1H), 3.90 (d, J=7.9 Hz, 2H), 2.87-2.84 (m, 2H), 2.79-2.75 (m, 2H); $^{13}$C NMR (DMSO-d$_6$): 147.2, 146.4, 140.3, 135.8, 133.2, 128.4, 128.1, 127.8, 126.2, 125.0, 124.1, 121.8, 112.4, 109.0, 107.9, 100.8, 50.7, 33.9, 25.5.

Example 3

N-Hydroxy-3-[2-phenethyl-3-(4-piperidin-1-yl-phenylamino)-imidazo[1,2-a]pyridin-6-yl]-acrylamide (Compound 3)

The titled compound was prepared according to the procedures described in Example 1, by using appropriate starting materials. HPLC: 99%; t$_R$=1.604 min; LCMS (ESI) m/z 482 [MH]$^+$; $^1$H NMR (DMSO-d$_6$): δ 8.65 (d, J=10.8 Hz, 2H), 8.09 (d, J=9.4 Hz, 1H), 8.01 (d, J=9.4 Hz, 1H), 7.61 (d, J=15.8 Hz, 1H), 7.45 (d, J=8.5 Hz, 2H), 7.24-7.13 (m, 6H), 6.70-6.62 (m, 3H), 3.45 (brs, 4H), 2.99 (s, 4H), 1.89-1.79 (m, 4H), 1.51 (brs, 2H); $^{13}$C NMR (DMSO-d$_6$): δ 161.8, 140.0, 137.5, 133.2, 132.8, 128.9, 128.4, 128.1, 126.2, 124.7, 124.6, 122.2, 122.0, 121.2, 117.9, 115.0, 114.3, 113.4, 55.9, 33.2, 25.9, 23.4, 20.7.

Example 4

Preparation of 3-[3-(Benzo[1,3]dioxol-5-ylamino)-2-phenethyl-imidazo[1,2a]pyridin-6-yl]-(Compound 4)

Step 1: Heck Reaction

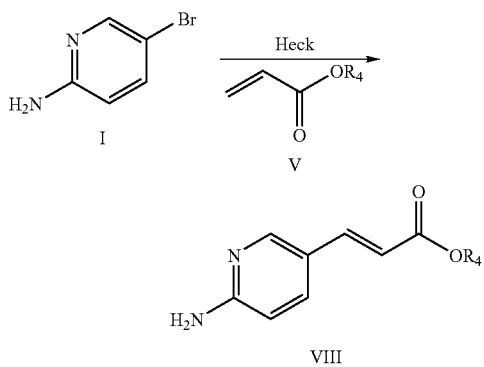

Ethyl acrylate (0.47 mL, 4.33 mmol) was added into a stirred suspension of the amine (0.50 g, 2.89 mmol), Pd$_2$(dba)$_3$ (0.2646 g, 0.289 mmol), P(o-tol)$_3$ (0.1583 g, 0.52 mmol), Et$_3$N (0.62 mL, 4.45 mmol) and CH$_2$Cl$_2$ (12 mL) at room temp. The reaction was heated to reflux at ~80° C. When the starting material had fully depleted (monitored by LCMS), the reaction mixture was diluted with ethyl acetate (20 mL). The organic layer was then washed with NaHCO$_3$ (2×10 mL) and brine (2×10 mL). The organic layer was dried in Na$_2$SO$_4$ before being filtered and concentrated in vacuo. The crude product was purified by reverse phase prep-HPLC and was isolated as a light yellow solid [trifluoroacetic acid (TFA) salt] (75%, 0.63 g).

3-(2-Amino-pyridin-4-yl)-acrylic acid ethyl ester

HPLC: 97.5%; t$_R$=1.114 min; LCMS (ESI) m/z 193 [MH]$^+$; $^1$H NMR (CDCl$_3$): δ 8.36 (brs, 1H), 8.29 (s, 1H), 8.26 (dd, J=2.0, 9.3 Hz, 1H), 7.56 (dd, J=16.0 Hz, 1H), 6.92 (d, J=9.2 Hz, 1H), 6.55 (d, J=16.0 Hz, 1H), 4.17 (q, J=7.1 Hz, 2H), 1.24 (t, J=7.1 Hz, 3H); $^{13}$C NMR (CDCl$_3$): δ 165.9, 155.3, 139.9, 139.5, 139.3, 119.1, 118.1, 117.2, 115.2, 113.1, 60.0, 14.1.

Step 2: 3-Component Reaction

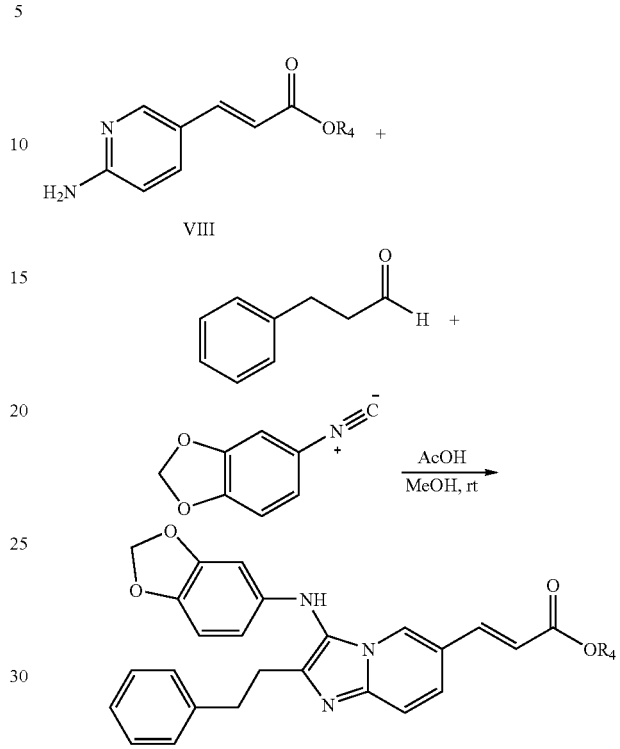

To a solution of the amine (0.48 g, 1.67 mmol) in MeOH (6.0 mL) was added (2) (0.22 mL, 1.67 mmol), (3) (0.27 g, 1.67 mmol) and AcOH (0.19 mL, 3.35 mmol) at room temperature. The reaction was stirred overnight. When LCMS had shown the full depletion of the starting material amine, 1M HCl (15 mL) was added till pH ~1 before being concentrated in vacuo. NaHCO$_3$ (20 mL) was then added and ethyl acetate (3×20 mL) was used to extract the aqueous layer. The combined organic extracts were then washed with brine (2×20 mL), before being died in Na$_2$SO$_4$. The mixture was then filtered and concentrated in vacuo. The crude product was purified by flash column chromatography and the product was isolated as a viscous dark brown oil (72%, 0.55 g).

3-[3-(Benzo[1,3]-dioxol-5-ylamino)-2-phenethyl-imidazo[1,2-a]pyridin-6-yl]-acrylic acid ethyl ester R$_f$=0.33 [Hexane:ethyl acetate (1:1)]; HPLC: 99%; t$_R$=3.057 min; LCMS (ESI) m/z 456 [MH]$^+$; $^1$H NMR (CDCl$_3$): δ 7.79 (s, 1H), 7.54 (s, 1H), 7.51 (d, J=7.2 Hz, 1H), 7.37 (d, J=9.4 Hz, 1H), 7.26-7.21 (m, 2H), 7.08 (dd, J=1.9, 7.9 Hz, 2H), 6.57 (d, J=8.3 Hz, 1H), 6.35 (d, J=15.9 HZ, 1H), 5.89 (d, J=2.3 Hz, 1H), 5.85 (s, 2H), 5.74 (dd, J=2.4, 8.3 Hz, 1H), 4.60 (brs, 1H), 4.23 (q, J=7.1 Hz, 2H), 3.02-2.97 (m, 4H), 1.31 (t, J=7.1 Hz, 3H); $^{13}$C NMR (CDCl$_3$): δ 166.6, 148.6, 142.3, 142.2, 141.7, 141.1, 140.7, 140.2, 128.7, 128.3, 126.0, 124.2, 121.5, 120.8, 120.1, 118.2, 117.5, 108.7, 104.8, 100.9, 95.9, 60.6, 35.4, 29.5, 14.3.

Step 3: Hydroxamic Acid Formation

NH$_2$OH.HCl (0.12 g, 1.7 mmol) was added into a solution of the ester (75.1 mg, 0.17 mmol) and MeOH (5 mL) at room temperature. The reaction mixture was cooled to 0° C. before NaOCH$_3$ (0.78 mL, 3.40 mmol; 25% wt solution in MeOH)

was introduced. When LCMS had shown the full depletion of the starting material, the reaction mixture was poured into ice-water and extracted with ethyl acetate (4×15 mL). The organic extracts were then washed with NaHCO$_3$ (2×20 mL) and brine (2×20 mL), before being dried in Na$_2$SO$_4$. The mixture was then filtered and concentrated in vacuo. The crude product was purified by reverse phase prep-HPLC and was isolated as a light yellow solid [trifluoroacetic acid (TFA) salt] (62%, 67.1 mg).

3-[3-(Benzo[1,3]-dioxol-5-ylamino)-2-phenethyl-imidazo[1,2-a]pyridin-6-yl]-N-hydroxy-acrylamide (Compound 4)

HPLC: 99%; $t_R$=2.332 min; LCMS (ESI) m/z 443 [MH]$^+$; $^1$H NMR (CDCl$_3$): δ 8.55 (s, 1H), 8.02-7.96 (m, 2H), 7.91 (d, J=9.3 Hz, 1H), 7.62 (d, J=15.8 Hz, 1H), 7.26-7.13 (m, 7H), 6.68 (d, J=8.3 Hz, 1H), 6.58 (d, J=15.8 Hz, 1H), 6.29 (d, J=2.1 Hz, 1H), 5.98 (dd, J=2.2, 8.3 Hz, 1H), 5.89 (s, 2H), 2.97 (s, 4H); $^{13}$C NMR (CDCl$_3$): δ 148.0, 140.5, 140.2, 140.0, 129.1, 128.9, 128.6, 128.4, 128.1, 126.2, 124.4, 122.4, 121.6, 108.6, 105.3, 100.6, 99.4, 96.5, 33.4, 26.1.

Example 5

N-Hydroxy-3-[3-(2-methoxy-ethylamino)-2-phenethyl-imidazo[1,2-a]pyridin-6-yl]-acrylamide (Compound 5)

The titled compound was prepared according to the procedures described in Example 1, by using appropriate starting materials. HPLC: 99%; $t_R$=1.806 min; LCMS (ESI) m/z 381 [MH]$^+$; $^1$H NMR (DMSO-d$_6$): δ 10.95 (brs, 1H), 8.82 (s, 1H), 8.02 (d, J=9.4 Hz, 1H), 7.88 (d, J=9.3 Hz, 1H), 7.65 (d, J=15.8 Hz, 1H), 7.32-7.15 (m, 5H), 6.65 (d, J=15.8 Hz, 1H), 5.19 (brs, 1H), 3.35 (t, J=5.3 Hz, 2H), 3.21 (s, 3H), 3.07-3.06 (m, 2H), 3.02-2.99 (m, 4H).

Example 6

3-(3-Cyclohexylamino-2-phenethyl-imidazo[1,2-a]pyridin-6-yl)-N-hydroxy-acrylamide (Compound 6)

The titled compound was prepared according to the procedures described in Example 1, by using appropriate starting materials. HPLC: 99%; $t_R$=1.806 min; LCMS (ESI) m/z 405 [MH]$^+$; $^1$H NMR (DMSO-d$_6$): δ 10.94 (brs, 1H), 8.80 (s, 1H), 8.01 (d, J=9.5 Hz, 1H), 7.88 (d, J=9.3 Hz, 1H), 7.75 (d, J=15.8 Hz, 1H), 7.32-7.19 (m, 5H), 6.64 (d, J=15.9 Hz, 1H), 4.97 (brs, 1H), 3.10-2.99 (m, 4H), 2.73 (brs, 1H), 1.79-1.76 (m, 2H), 1.66-1.65 (m, 2H), 1.20-1.10 (m, 6H); $^{13}$C NMR (DMSO-d$_6$): δ 140.4, 135.7, 133.4, 128.7, 128.6, 128.4, 128.2, 127.5, 126.2, 124.9, 124.1, 121.8, 118.5, 115.5, 112.4, 109.5, 71.4, 57.9, 46.8, 40.1, 39.9, 39.7, 39.5, 39.3, 39.1, 38.9, 33.9, 25.6.

Example 7

N-Hydroxy-3-[2-isopropyl-3-(2-methoxy-ethylamino)-imidazo[1,2-a]pyridin-6-yl]-acrylamide (Compound 7)

The titled compound was prepared according to the procedures described in Example 1, by using appropriate starting materials. HPLC: 97.3%; $t_R$=1.164 min; LCMS (ESI) m/z 319 [MH]$^+$; $^1$H NMR (DMSO-d$_6$): δ 10.95 (brs, 1H), 8.84 (s, 1H), 8.02 (d, J=9.3 Hz, 1H), 7.85 (d, J=9.3 Hz, 1H), 7.67 (d, J=15.8 Hz, 1H), 6.65 (d, J=15.8 Hz, 1H), 5.25 (brs, 1H), 3.43 (t, J=5.4 Hz, 2H), 3.39-3.27 (m, 1H), 3.23 (s, 3H), 3.15 (t, J=5.2 Hz, 2H), 1.32 (d, J=7.0 Hz, 6H).

Example 8

3-[2-(2,2-Dimethyl-propyl)-3-(2-methoxy-ethylamino)-imidazo[1,2-a]pyridin-6-yl]-N-hydroxy-acrylamide (Compound 8)

The titled compound was prepared according to the procedures described in Example 1, by using appropriate starting materials. HPLC: 99%; $t_R$=1.601 min; LCMS (ESI) m/z 347 [MH]$^+$; $^1$H NMR (DMSO-d$_6$): δ 8.88 (s, 1H), 8.04 (d, J=9.4 Hz, 1H), 7.87 (d, J=9.3 Hz, 1H), 7.67 (d, J=15.8 Hz, 1H), 6.67 (d, J=15.8 Hz, 1H), 5.07 (brs, 1H), 3.48 (t, J=5.3 Hz, 2H), 3.27 (s, 3H), 3.18 (t, J=5.2 Hz, 2H), 2.72 (s, 2H), 0.99 (s, 9H).

Example 9

N-Hydroxy-3-[3-(2-methoxy-ethylamino)-2-pentyl-imidazo[1,2-a]pyridin-6-yl]-acrylamide (Compound 9)

The titled compound was prepared according to the procedures described in Example 1, by using appropriate starting materials. HPLC: 99%; $t_R$=1.787 min; LCMS (ESI) m/z 347 [MH]$^+$; $^1$H NMR (CD$_3$OD): δ 8.77 (s, 1H), 8.04 (d, J=9.3 Hz, 1H), 7.71 (d, J=9.3 Hz, 1H), 7.62 (d, J=15.8 Hz, 1H), 6.61 (d, J=15.8 Hz, 1H), 3.46 (t, J=5.1 Hz, 2H), 3.29 (s, 3H), 3.19 (t, J=5.1 Hz, 2H), 1.37-1.23 (m, 6H), 0.90-0.86 (m, 3H).

Example 10

3-[6-(2-Hydroxycarbamoyl-vinyl)-3-(2-methoxy-ethylamino)-imidazo[1,2-a]pyridin-2-yl]-propionic acid (Compound 10)

The titled compound was prepared according to the procedures described in Example 1, by using appropriate starting materials. HPLC: 99%; $t_R$=1.524 min; LCMS (ESI) m/z 350 [MH]$^+$; $^1$H NMR (DMSO-d$_6$): δ 10.91 (s, 1H), 8.81 (s, 1H), 7.96 (d, J=9.5 Hz, 1H), 7.77 (d, J=9.3 Hz, 1H), 7.65 (d, J=15.7 Hz, 1H), 7.26 (s, 1H), 6.61 (d, J=15.8 Hz, 1H), 5.31 (brs, 1 h), 4.32 (d, J=5.6 Hz, 2H), 3.38-3.32 (masked peaks).

Example 11

3-[2-Ethyl-3-(2-methoxy-ethylamino)-imidazo[1,2-a]pyridin-6-yl]-N-hydroxy-acrylamide (Compound 11)

The titled compound was prepared according to the procedures described in Example 1, by using appropriate starting materials. HPLC: 87%; $t_R$=0.936 min; LCMS (ESI) m/z 305 [MH]$^+$; $^1$H NMR (DMSO-d$_6$): δ 8.85 (s, 1H), 8.04 (dd, J=1.1, 9.4 Hz, 1H), 7.88 (d, J=9.3 Hz, 1H), 7.66 (d, J=15.9 Hz, 1H), 6.67 (d, J=15.8 Hz, 1H), 3.43 (t, J=5.3 Hz, 2H), 3.23 (s, 3H), 3.16 (t, J=5.2 Hz, 2H), 2.82 (q, J=7.6 Hz, 2H), 1.28 (t, J=7.6 Hz, 3H).

Example 12

3-tert-Butylamino-6-(2-hydroxycarbamoyl-vinyl)-imidazo[1,2-a]pyridine-2-carboxylic acid (Compound 12)

The titled compound was prepared according to the procedures described in Example 1, by using appropriate starting materials. HPLC: 99%; $t_R$=1.752 min; LCMS (ESI) m/z 274 [MH—COOH]$^+$; $^1$H NMR (CD$_3$OD): δ 8.84 (s, 1H), 8.09 (dd, J=1.5, 9.5 Hz, 1H), 7.83 (d, J=16.0 Hz, 1H), 7.76 (d, J=9.4 Hz, 1H), 7.55 (s, 1H), 6.74 (d, J=16.0 Hz, 1H), 1.32 (s, 9H).

Example 13

3-(2-Butyl-3-butylamino-imidazo[1,2-a]pyridin-6-yl)-N-hydroxy-acrylamide (Compound 13)

The titled compound was prepared according to the procedures described in Example 1, by using appropriate starting materials. HPLC: 99%; $t_R$=2.136 min; LCMS (ESI) m/z 331 [MH]$^+$; $^1$H NMR (DMSO-d$_6$): δ 10.94 (brs, 1H), 8.82 (s, 1H), 8.01 (dd, J=0.9, 8.4 Hz, 1H), 7.85 (d, J=9.3 Hz, 1H), 7.69 (d, J=15.8 Hz, 1H), 6.65 (d, J=15.8 Hz, 1H), 5.13 (brs, 1H), 2.99 (t, J=7.2 Hz, 2H), 2.79 (t, J=7.5 Hz, 2H), 1.71-1.63 (m, 1H), 1.56-1.49 (m, 2H), 1.42-1.32 (m, 4H), 0.94-0.88 (m, 6H); $^{13}$C NMR (DMSO-d$_6$): 161.9, 135.5, 133.4, 128.8, 128.5, 127.4, 124.9, 124.3, 121.9, 118.4, 112.3, 47.2, 32.0, 30.3, 23.1, 21.7, 19.5, 13.8, 13.6.

Example 14

N-Hydroxy-3-(2-isopropyl-3-isopropylamino-imidazo[1,2-a]pyridin-6-yl)-acrylamide (Compound 14)

The titled compound was prepared according to the procedures described in Example 1, by using appropriate starting materials. HPLC: 99.2%; $t_R$=1.432 min; LCMS (ESI) m/z 303 [MH]$^+$; $^1$H NMR (DMSO-d$_6$): δ 8.86 (s, 1H), 8.05 (dd, J=1.0, 9.4 Hz, 1H), 7.90 (d, J=9.3 Hz, 1H), 7.75 (d, J=15.8 Hz, 1H), 6.68 (d, J=15.9 Hz, 1H), 3.38-2.27 (m, 2H), 1.32 (d, J=7.0 Hz, 6H), 1.13 (d, J=6.3 Hz, 6H); $^{13}$C NMR (DMSO-d$_6$): 161.9, 136.2, 134.0, 133.5, 128.8, 126.2, 125.3, 124.5, 121.9, 121.1, 112.3, 48.3, 23.7, 22.8, 21.5.

Example 15

(E)-N-hydroxy-3-(3-(2-methoxyethylamino)-2-(2,4,4-trimethylpentyl)imidazo[1,2-a]pyridin-6-yl)acrylamide (Compound 15)

The titled compound was prepared according to the procedures described in Example 1, by using appropriate starting materials. HPLC: 99%; $t_R$=2.281 min; LCMS (ESI) m/z 389 [MH]$^+$.

Example 16

(E)-N-hydroxy-3-(3-(2-methoxyethylamino)-2-(2,4,4-trimethylpentyl)imidazo[1,2-a]pyridin-8-yl)acrylamide (Compound 16)

The titled compound was prepared according to the procedures described in Scheme III by using appropriate starting materials. HPLC: 99%; $t_R$=2.272 min; LCMS (ESI) m/z 389 [MH]$^+$.

Example 17

Preparation of (E)-N-hydroxy-3-(3-(2-methoxyethylamino)-2-pentylimidazo[1,2-a]pyridin-7-yl)acrylamide (Compound 17)

Step 1: Multi-Component Reaction

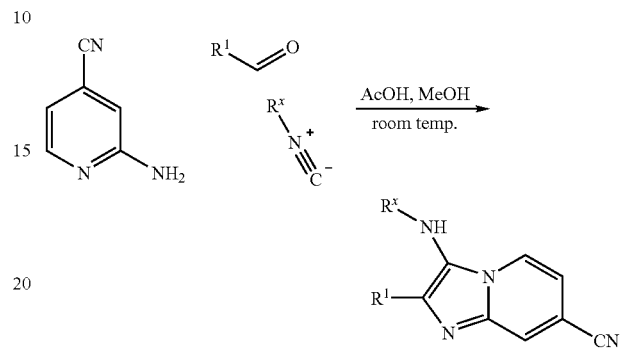

To a solution of 4-cyano-2-aminopyridine (0.27 mg, 2.24 mmol) in MeOH (7.45 mL) was added the aldehyde (2.24 mmol), the isonitrile (2.24 mmol) and AcOH (260 μL, 4.48 mmol) at room temp. The reaction was stirred overnight and monitored by LCMS/TLC. When the reaction has completed, 1N hydrochloric acid was added till pH ~1. The mixture was then evaporated. Saturated sodium bicarbonate solution was then added and ethyl acetate was used to extract. The combined organic extracts were then washed with brine, before drying in anhydrous sodium sulfate. The mixture was then filtered and concentrated. The crude product was used immediately without further purification (Tetrahedron Letters, 1998, 39, 3635).

Step 2: Reduction of Nitrile

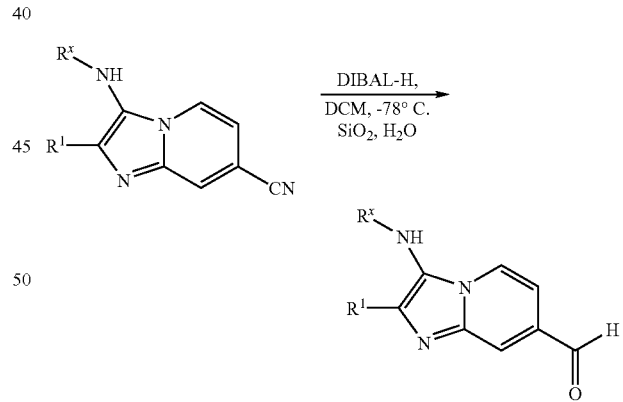

DIBAL-H (1.70 mL, 1.70 mmol) was added slowly into a stirred pre-dried solution of the nitrile (0.33 g, 1.13 mmol) and DCM (5 mL) at −78° C. and the reaction was allowed to warm up to 40° C. over 1 h. Hydrolysis was effected by slowly adding a homogenous mixture of silica gel and water. After stirring for 1 h at 0° C., anhydrous potassium carbonate and magnesium sulfate solids were added, the solids were filtered off and rinsed thoroughly with DCM. The solvents were evaporated and the crude product was purified by flash column chromatography (European Journal of Organic Chemistry, 1999, 2609-2621).

Step 3: Wittig Reaction

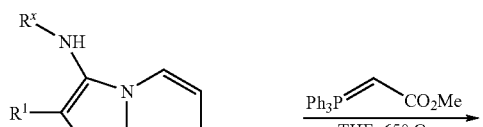

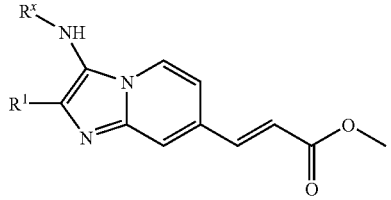

The Wittig reagent (0.12 g, 0.37 mmol) was added slowly into a stirred solution of the aldehyde (0.11 g, 0.37 mmol) and THF (4 mL) and the reaction was allowed to warm up to 65° C. overnight. When LCMS has indicated the completion of the reaction, the reaction mixture was concentrated and purified by flash column chromatography.

Step 4: Hydroxamic Acid Formation

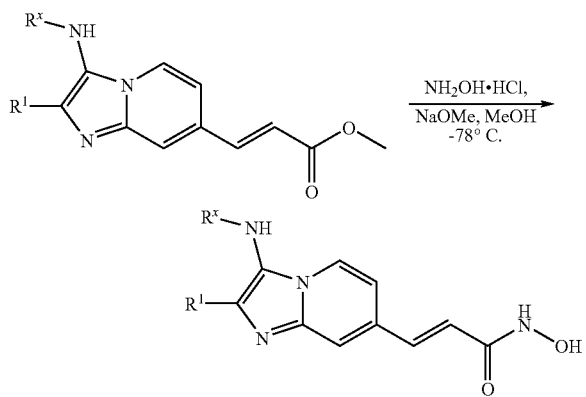

To a stirred solution of the ester (27.6 mg, 0.08 mmol), NH$_2$OH.HCl (55.4 mg, 0.80 mmol), MeOH (159 µL) at −78° C. was added NaOMe (365 µL, 1.60 mmol). The mixture was then allowed to warm up to room temperature. The reaction was monitored by LCMS. After the completion of the reaction, the mixture was cooled to −78° C. before 1N hydrochloric acid was added slowly to solubilize the mixture. Small amounts of H$_2$O and MeOH were added if necessary to dissolve the mixture. The crude was purified immediately by reverse phase prep-HPLC.

(E)-N-hydroxy-3-(3-(2-methoxyethylamino)-2-pentylimidazo[1,2-a]pyridin-7-yl)acrylamide (Compound 17)

HPLC: 98.9%; t$_R$=1.697 min; LCMS (ESI) m/z 347 [MH]$^+$; $^1$H NMR (CD$_3$OD): δ 8.60 (d, J=7.2 Hz, 1H), 7.82 (s, 1H), 7.67 (d, J=15.7 Hz, 1H), 7.62 (dd, J=7.4, 1.4 Hz, 1H), 6.76 (d, J=15.7 Hz, 1H), 3.51 (t, J=4.8 Hz, 2H), 3.36 (s, 3H), 3.25 (t, J=5.1 Hz, 2H), 2.88 (d, J=7.7 Hz, 2H), 1.80-1.75 (m, 2H), 1.45-1.38 (m, 4H), 0.97 (t, J=7.0 Hz, 3H); $^{13}$C NMR (CD$_3$OD): 140.1, 137.8, 137.2, 130.8, 130.3, 126.6, 124.8, 114.9, 113.3, 111.9, 73.2, 59.2, 59.0, 32.6, 29.4, 24.8, 23.4, 14.2.

Example 18

Preparation of (E)-3-(3-(3-(ethylamino)-3-oxopropylamino)-2-hexylimidazo[1,2-a]pyridin-6-yl)-N-hydroxyacrylamide (Compound 18)

Step 1: Ester Hydrolysis

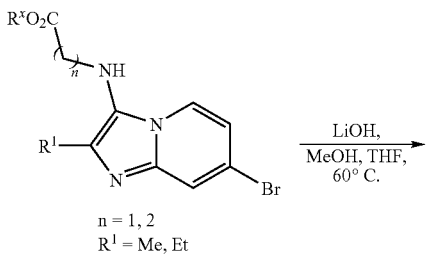

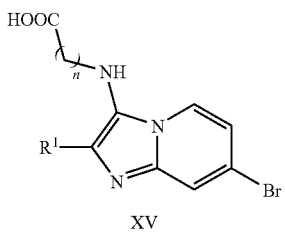

To a stirred solution of the ester (0.39 g, 1.06 mmol), MeOH (1.6 mL) and THF (8.4 mL) was added LiOH (45.7 mg, 1.9 mmol) and the reaction was stirred at 65° C. for 4 h. When the reaction is completed, the reaction mixture was evaporated. The crude product was used immediately without further purification.

Step 2: Acylation

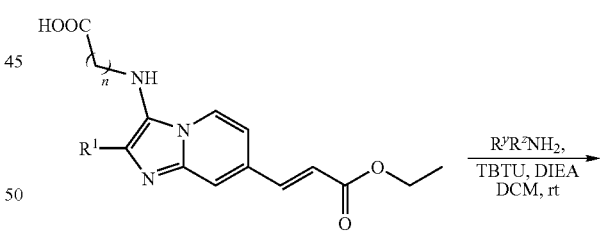

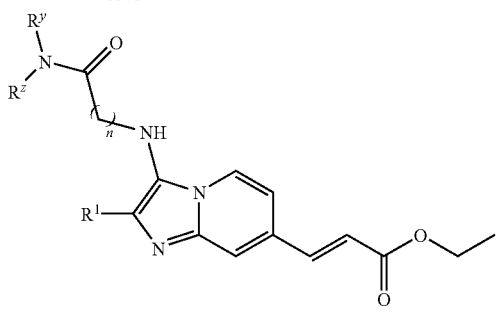

To a solution of the acid (40.0 mg, 0.103 mmol), DCM (2.0 mL) and DIEA (25.6 µL, 0.155 mmol) at room temperature was added TBTU (49.7 mg, 0.155 mmol). After stirring for ~0.5 h, the amine (0.155 mmol) was added. When the starting material has fully depleted, ethyl acetate (20 mL) was added to dilute the mixture. The organic contents were washed with saturated sodium bicarbonate solution and brine, before drying in anhydrous sodium sulfate. The mixture was then filtered and concentrated in vacuo. The crude product was used immediately without further purification.

For subsequent hydroxamic acid formation, please refer to Step 4 from Example 17.

(E)-3-(3-(3-(ethylamino)-3-oxopropylamino)-2-hexylimidazo[1,2a]pyridin-6-yl)-N-hydroxyacrylamide (Compound 18)

HPLC: 96.3%; $t_R$=1.845 min; LCMS (ESI) m/z 402 [MH]$^+$; $^1$H NMR (CD$_3$OD): δ 8.75 (s, 1H), 8.00 (d, J=9.19 Hz, 1H), 7.67 (d, J=9.3 Hz, 1H), 7.61 (d, J=15.8 Hz, 1H), 6.61 (d, J=15.7 Hz, 1H), 3.27-3.24 (m, 2H), 3.10 (q, J=7.3 Hz, 2H), 2.78 (t, J=7.7 Hz, 2H), 2.39 (t, J=6.0 Hz, 2H), 1.71-1.63 (m, 2H), 1.34-1.31 (masked peaks), 1.29-1.25 (masked peaks), 1.01 (t, J=7.3 Hz, 3H), 0.82 (t, J=7.1 Hz, 3H); $^{13}$C NMR (CD$_3$OD): δ 173.8, 162.5, 137.6, 131.1, 130.3, 130.0, 126.6, 126.3, 122.5, 112.9, 45.2, 37.3, 35.3, 32.6, 30.1, 29.7, 24.9, 23.6, 14.8, 14.4.

Example 19

(E)-3-(3-(3-(2-(dimethylamino)ethylamino)-3-oxo-propylamino)-2-hexylimidazo[1,2-a]pyridin-6-yl)-N-hydroxyacrylamide (Compound 19)

The titled compound was prepared according to the procedures described in Example 18 by using appropriate starting materials. HPLC: 99%; $t_R$=1.494 min; LCMS (ESI) m/z 445 [MH]$^+$; $^1$H NMR (CD$_3$OD): δ 8.96 (s, 1H), 8.11 (d, J=9.0 Hz, 1H), 7.81 (d, J=12.1 Hz, 1H), 7.70 (d, J=15.8 Hz, 1H), 6.71 (d, J=15.8 Hz, 1H), 3.62 (t, J=5.9 Hz, 2H), 3.35 (t, J=6.6 Hz, 2H), 2.96 (s, 6H), 2.86 (t, J=7.8 Hz, 2H), 2.59 (t, J=6.1 Hz, 2H), 1.8-1.72 (m, 2H), 1.43-1.4 (m, 2H), 1.37-1.34 (m, 4H), 0.91 (t, J=4.6 Hz, 3H); $^{13}$C NMR (CD$_3$OD): δ 175.4, 165.0, 163.0, 137.6, 135.7, 130.8, 130.2, 130.0, 126.8, 126.5, 122.5, 112.9, 58.6, 44.8, 43.9, 36.8, 35.8, 32.6, 30.0, 29.8, 24.8, 23.6, 14.3.

Example 20

3-{3-[2-(2-Dimethylamino-ethylcarbamoyl)-ethylamino]-2-hexyl-imidazo[1,2-a]pyridin-7-yl}-N-hydroxy-acrylamide (Compound 20)

The titled compound was prepared according to the procedures described in Example 18 by using appropriate starting materials. HPLC: 97.6%; $t_R$=1.524 min; LCMS (ESI) m/z 445 [MH]$^+$; $^1$H NMR (CD$_3$OD): δ 8.66 (d, J=7.1 Hz, 1H), 7.86 (s, 1H), 7.69-7.64 (m, 2H), 6.79 (d, J=15.8 Hz, 1H), 3.59 (t, J=5.9 Hz, 2H), 3.36-3.32 (m, 2H), 3.28-3.25 (m, 2H), 2.94 (s, 6H), 2.89 (t, J=7.8 Hz, 2H), 2.58 (t, J=6.4 Hz, 2H), 1.81-1.74 (m, 2H), 1.44-1.31 (m, 6H), 0.92 (t, J=6.9 Hz, 3H); $^{13}$C NMR (CD$_3$OD): δ 175.1, 164.5, 140.3, 137.9, 137.1, 130.5, 130.0, 126.3, 125.0, 115.2, 111.8, 58.4, 44.9, 43.8, 37.1, 35.7, 32.6, 30.1, 29.8, 24.9, 23.6, 14.3.

Example 21

3-[3-(2-Butylcarbamoyl-ethylamino)-2-hexyl-imidazo[1,2-a]pyridin-7-yl]-N-hydroxy-acrylamide (Compound 21)

The titled compound was prepared according to the procedures described in Example 18 by using appropriate starting materials. HPLC: 99%; $t_R$=2.301 min; LCMS (ESI) m/z 430 [MH]$^+$; $^1$H NMR (CD$_3$OD): δ 8.65 (d, J=7.2 Hz, 1H), 7.83 (s, 1H), 7.70-7.64 (m, 2H), 6.77 (d, J=15.7 Hz, 1H), 3.33-3.33 (m, 2H), 3.19-3.16 (m, 2H), 2.89-2.86 (m, 2H), 2.49 (t, J=6.2 Hz, 2H), 1.81-1.73 (m, 2H), 1.51-1.33 (m, 12H), 0.95-0.90 (m, 6H).

Example 22

3-[3-(2-tert-Butylcarbamoyl-ethylamino)-2-hexyl-imidazo[1,2-a]pyridin-7-yl]-N-hydroxy-acrylamide (Compound 22)

The titled compound was prepared according to the procedures described in Example 18 by using appropriate starting materials. HPLC: 99%; $t_R$=2.331 min; LCMS (ESI) m/z 430 [MH]$^+$.

Example 23

3-{2-Hexyl-3-[2-(2,2,2-trifluoro-ethylcarbamoyl)-ethylamino]-imidazo[1,2-a]pyridin-7-yl}-N-hydroxy-acrylamide (Compound 23)

The titled compound was prepared according to the procedures described in Example 18 by using appropriate starting materials. HPLC: 99%; $t_R$=2.228 min; LCMS (ESI) m/z 456 [MH]$^+$; $^1$H NMR (CD$_3$OD): δ 8.64 (d, J=7.0 Hz, 1H), 7.85 (s, 1H), 7.69-7.63 (m, 2H), 6.79 (d, J=15.7 Hz, 1H), 5.48 (s, 2H), 3.98-3.91 (m, 2H), 3.41-3.33 (m, 2H), 2.93-2.81 (m, 2H), 1.78-1.73 (m, 2H), 1.44-1.30 (m, 6H), 0.92 (t, J=6.9 Hz, 3H); $^{13}$C NMR (CD$_3$OD): δ 174.5, 164.5, 140.2, 137.9, 137.1, 130.6, 129.9, 126.3, 124.9, 121.3, 115.0, 111.9, 54.8, 44.8, 36.9, 32.6, 30.0, 29.7, 24.9, 23.6, 14.3.

Example 24

3-{2-Hexyl-3-[2-(2-methoxy-ethylcarbamoyl)-ethylamino]-imidazo[1,2-a]pyridin-7-yl}-N-hydroxy-acrylamide (Compound 24)

The titled compound was prepared according to the procedures described in Example 18 by using appropriate starting materials. HPLC: 99%; $t_R$=1.875 min; LCMS (ESI) m/z 432.13 [MH]$^+$; $^1$H NMR (CD$_3$OD): δ 8.64 (d, J=7.1 Hz, 1H), 7.85 (s, 1H), 7.69-7.63 (m, 2H), 6.78 (d, J=15.7 Hz, 1H), 3.46 (t, J=5.4 Hz, 2H), 3.39-3.34 (m, 2H), 2.88 (t, J=7.6 Hz, 2H), 2.51 (t, J=6.1 Hz, 2H), 1.81-1.73 (m, 2H), 1.44-1.30 (m, 6H), 0.92 (t, J=6.9 Hz, 3H); $^{13}$C NMR (CD$_3$OD): δ 174.1, 164.5, 140.2, 137.9, 137.2, 130.6, 130.0, 126.4, 124.9, 115.0, 111.9, 71.9, 58.9, 45.1, 40.3, 37.2, 32.6, 30.1, 29.8, 24.9, 23.6, 14.4.

Example 25

3-{2-Hexyl-3-[2-(2-methylsulfanyl-ethylcarbamoyl)-ethylamino]-imidazo[1,2-a]pyridin-7-yl}-N-hydroxy-acrylamide (Compound 25)

The titled compound was prepared according to the procedures described in Example 18 by using appropriate starting materials. HPLC: 98.07%; $t_R$=2.109 min; LCMS (ESI) m/z 448.07 [MH]$^+$; $^1$H NMR (CD$_3$OD): δ 8.64 (d, J=7.1 Hz, 1H), 7.85 (s, 1H), 7.69-7.63 (m, 2H), 6.78 (d, J=15.7 Hz, 1H), 3.46 (t, J=5.4 Hz, 2H), 3.39-3.34 (m, 2H), 2.88 (t, J=7.6 Hz, 2H), 2.51 (t, J=6.1 Hz, 2H), 1.81-1.73 (m, 2H), 1.44-1.30 (m, 6H), 0.92 (t, J=6.9 Hz, 3H); $^{13}$C NMR (CD$_3$OD): δ 174.1, 164.5, 140.2, 137.9, 137.2, 130.6, 130.0, 126.4, 124.9, 115.0, 111.9, 71.9, 58.9, 45.1, 40.3, 37.2, 32.6, 30.1, 29.8, 24.9, 23.6, 14.4.

Example 26

3-[2-Hexyl-3-(2-prop-2-ynylcarbamoyl-ethylamino)-imidazo[1,2-a]pyridin-7-yl]-N-hydroxy-acrylamide (Compound 26)

The titled compound was prepared according to the procedures described in Example 18 by using appropriate starting materials. HPLC: 99.08%; $t_R$=1.985 min; LCMS (ESI) m/z 412 [MH]$^+$; $^1$H NMR (CD$_3$OD): δ 8.65 (d, J=7.1 Hz, 1H), 7.84 (s, 1H), 7.69-7.64 (m, 2H), 6.78 (d, J=15.7 Hz, 1H), 5.49 (s, 2H), 3.96 (d, J=2.5 Hz, 2H), 3.38-3.34 (m, 2H), 2.88 (t, J=7.6 Hz, 2H), 2.51 (t, J=6.0 Hz, 2H), 1.81-1.73 (m, 2H), 1.45-1.30 (m, 6H), 0.92 (t, J=6.9 Hz, 3H); $^{13}$C NMR (CD$_3$OD): δ 173.6, 164.5, 140.3, 137.9, 137.1, 130.6, 129.9, 126.4, 124.9, 115.1, 111.9, 80.6, 72.3, 44.9, 37.1, 132.6, 30.1, 29.7, 29.4, 24.9, 23.6, 14.4.

Example 27

3-{2-Hexyl-3-[2-(1-hydroxymethyl-2-methyl-propylcarbamoyl)-ethylamino]-imidazo[1,2-a]pyridin-7-yl}-N-hydroxy-acrylamide (Example 27)

The titled compound was prepared according to the procedures described in Example 18 by using appropriate starting materials. HPLC: 90.50%; $t_R$=2.049 min; LCMS (ESI) m/z 460 [MH]$^+$; $^1$H NMR (CD$_3$OD): δ 8.68 (d, J=7.1 Hz, 1H), 7.84 (s, 1H), 7.70-7.63 (m, 2H), 6.78 (d, J=15.3 Hz, 1H), 3.79-3.74 (m, 1H), 3.64 (dd, J=4.4, 11.2 Hz, 1H), 3.55 (dd, J=6.7, 11.2 Hz, 1H), 3.36-3.34 (m, 2H), 2.89 (t, J=7.7 Hz, 2H), 2.57 (t, J=6.7 Hz, 2H), 1.91-1.83 (m, 1H), 1.81-1.74 (m, 2H), 1.45-1.29 (m, 6H), 0.98-0.90 (m, 9H).

Example 28

3-{3-[2-(2-Diethylamino-ethylcarbamoyl)-ethylamino]-2-hexyl-imidazo[1,2-a]pyridin-7-yl}-N-hydroxy-acrylamide (Compound 28)

The titled compound was prepared according to the procedures described in Example 18 by using appropriate starting materials. HPLC: 99%; $t_R$=1.622 min; LCMS (ESI) m/z 473 [MH]$^+$.

Example 29

3-[3-(2-Ethylcarbamoyl-ethylamino)-2-hexyl-imidazo[1,2-a]pyridin-7-yl]-N-hydroxy-acrylamide (Compound 29)

The titled compound was prepared according to the procedures described in Example 18 by using appropriate starting materials. HPLC: 91.98%; $t_R$=1.926 min; LCMS (ESI) m/z 402 [MH]$^+$; $^1$H NMR (CD$_3$OD): δ 8.48 (d, J=7.2 Hz, 1H), 7.70 (s, 1H), 7.64 (d, J=15.5 Hz, 1H), 7.45 (d, J=7.8 Hz, 1H), 6.67 (d, J=15.8 Hz, 1H), 3.68-3.35 (m, 2H), 3.27-3.25 (m, 2H), 2.83 (t, J=7.4 Hz, 2H), 2.46 (t, J=6.2 Hz, 2H), 1.78-1.74 (m, 1H), 1.42-1.33 (m, 2H), 1.12 (t, J=7.3 Hz, 3H), 0.93-0.91 (m, 3H).

Example 30

3-[3-(2-Dimethylcarbamoyl-ethylamino)-2-hexyl-imidazo[1,2-a]pyridin-7-yl]-N-hydroxy-acrylamide (Compound 30)

The titled compound was prepared according to the procedures described in Example 18 by using appropriate starting materials. HPLC: 99% $t_R$=1.990 min; LCMS (ESI) m/z 402 [MH]$^+$; $^1$H NMR (CD$_3$OD): δ 8.71 (d, J=7.5 Hz, 1H), 7.83 (s, 1H), 7.73 (d, J=19.0 Hz, 1H), 7.66 (d, J=6.4 Hz, 1H), 6.77 (d, J=15.6 Hz, 1H), 3.27-3.25 (m, 2H), 3.10 (d, J=2.6 Hz, 3H), 2.97 (d, J=2.8 Hz, 3H), 2.88 (t, J=7.4 Hz, 2H), 2.71 (t, J=5.9 Hz, 2H), 1.77 (brs, 2H), 1.38-1.30 (m, 6H), 0.92 (t, J=6.8 Hz, 3H).

Example 31

3-{3-[2-(Cyanomethyl-methyl-carbamoyl)-ethylamino]-2-hexyl-imidazo[1,2-a]pyridin-7-yl}-N-hydroxy-acrylamide (Compound 31)

The titled compound was prepared according to the procedures described in Example 18 by using appropriate starting materials. HPLC: 99% $t_R$=1.958 min; LCMS (ESI) m/z 430 [MH]$^+$; $^1$H NMR (CD$_3$OD): δ 8.56 (d, J=7.6 Hz, 1H), 7.78 (s, 1H), 7.69 (d, J=16.2 Hz, 1H), 7.61 (d, J=7.6 Hz, 1H), 6.73 (d, J=16.0 Hz, 1H), 3.43-3.43 (m, 2H), 3.07-3.07 (m, 2H), 2.82 (t, J=7.6 Hz, 2H), 2.46 (t, J=6.3 Hz, 2H), 1.72 (t, J=7.3 Hz, 2H), 1.31-1.23 (m, 6H), 0.94-0.82 (m, 3H).

Example 32

3-(3-{2-[(2-Dimethylamino-ethyl)-methyl-carbamoyl]-ethylamino}-2-hexyl-imidazo[1,2a]pyridin-7-yl)-N-hydroxy-acrylamide (Compound 32)

The titled compound was prepared according to the procedures described in Example 18 by using appropriate starting materials. HPLC: 99%; $t_R$=1.631 min; LCMS (ESI) m/z 459 [MH]$^+$; $^1$H NMR (CD$_3$OD): δ 8.64 (d, J=6.5 Hz, 1H), 7.88 (s, 1H), 7.66 (d, J=15.7 Hz, 1H), 7.54 (d, J=6.2 Hz, 1H), 6.73 (d, J=15.7 Hz, 1H), 3.79 (brs, 2H), 3.37-3.35 (m, 2H), 3.27-3.25 (m, 2H), 3.12 (s, 3H), 2.96 (s, 6H), 2.86 (t, J=7.5 Hz, 2H), 2.76 (brs, 2H), 1.79-1.74 (m, 2H), 1.43-1.30 (m, 6H), 0.92 (t, J=7.2 Hz, 3H).

Example 33

3-(2-Hexyl-3-{2-[(2-hydroxy-ethyl)-propyl-carbamoyl]-ethylamino}-imidazo[1,2-a]pyridin-7-yl)-N-hydroxy-acrylamide (Example 33)

The titled compound was prepared according to the procedures described in Example 18 by using appropriate starting materials. HPLC: 99%; $t_R$=2.137 min; LCMS (ESI) m/z 460 [MH]$^+$; $^1$H NMR (CD$_3$OD): δ 8.69 (d, J=7.2 Hz, 1H), 7.80 (s, 1H), 7.68 (d, J=15.2 Hz, 1H), 7.62 (d, J=7.5 Hz, 1H), 6.76 (d, J=15.8 Hz, 1H), 3.73-3.68 (m, 2H), 3.51 (t, J=6.00 Hz, 2H), 3.41-3.38 (m, 2H), 3.34-3.33 (masked peaks), 2.87 (t, J=7.69 Hz, 2H), 2.77 (t, J=5.9 Hz, 1H), 2.74 (t, J=5.8 Hz, 1H), 1.77 (t, J=5.1 Hz, 2H), 1.70-1.64 (m, 1H), 1.62-1.56 (m, 1H), 1.45-1.30 (m, 6H), 0.98-0.89 (m, 6H).

Example 34

N-Hydroxy-3-(2-phenyl-imidazo[1,2-a]pyridin-7-yl)-acrylamide (Compound 34)

The titled compound was prepared according to the procedures described in Scheme V and Example 38 by using appropriate starting materials. HPLC: 99%; $t_R$=1.345 min; LCMS (ESI) m/z 280 [MH]$^+$; $^1$H NMR (CD$_3$OD): δ 8.72 (d, J=7.1 Hz, 1H), 8.54 (s, 1H), 7.96 (s, 1H), 7.91-7.89 (m, 2H), 7.72-7.65 (m, 2H), 7.61-7.53 (m, 3H), 6.80 (d, J=15.7 Hz, 1H); $^{13}$C NMR (CD$_3$OD): δ 164.4, 142.6, 140.9, 139.6, 137.1, 131.7, 130.7, 129.9, 128.2, 127.5, 125.2, 115.8, 112.7, 112.5.

Example 35

3-{3-[2-(3-Dimethylamino-2,2-dimethyl-propylcarbamoyl)-ethylamino]-2-hexyl-imidazo[1,2-a]pyridin-7-yl}-N-hydroxy-acrylamide (Compound 35)

The titled compound was prepared according to the procedures described in Example 18 by using appropriate starting materials. HPLC: 99%; $t_R$=1.666 min; LCMS (ESI) m/z 487 [MH]$^+$; $^1$H NMR (CD$_3$OD): δ 8.67 (d, J=7.2 Hz, 1H), 7.87 (s, 1H), 7.70-7.64 (m, 2H), 6.78 (d, J=15.8 Hz, 1H), 3.38-3.35 (m, 2H), 3.22 (s, 1H), 3.02 (s, 1H), 2.96 (s, 1H), 2.91-2.87 (m, 2H), 2.62 (t, J=6.45 Hz, 2H), 1.81-1.74 (m, 2H), 1.45-1.35 (m, 6H), 1.10 (s, 1H), 0.92 (t, J=6.9 Hz, 3H); $^{13}$C NMR (CD$_3$OD): δ 173.3, 138.3, 135.1, 128.5, 128.0, 124.3, 113.3, 109.8, 64.9, 45.4, 45.1, 43.1, 35.0, 34.9, 30.6, 28.1, 27.8, 22.9, 22.7, 21.6, 12.4.

Example 36

3-[2-Hexyl-3-(2-methylcarbamoyl-ethylamino)-imidazo[1,2-a]pyridin-7-yl]-N-hydroxy-acrylamide (Compound 36)

The titled compound was prepared according to the procedures described in Example 18 by using appropriate starting materials. HPLC: 99%; $t_R$=1.800 min; LCMS (ESI) m/z 388 [MH]$^+$; $^1$H NMR (CD$_3$OD): δ 8.68 (d, J=7.2 Hz, 1H), 7.83 (s, 1H), 7.70-7.65 (m, 2H), 6.78 (d, J=15.8 Hz, 1H), 3.36-3.34 (m, 2H), 3.22 (s, 1H), 2.98 (t, J=7.6 Hz, 2H), 2.96 (s, 1H), 2.91-2.87 (m, 2H), 2.62 (t, J=6.5 Hz, 2H), 2.49 (t, J=6.2 Hz, 2H), 1.81-1.73 (m, 2H), 1.45-1.36 (m, 6H), 0.94 (t, J=6.9 Hz, 3H); $^{13}$C NMR (CD$_3$OD): δ 172.5, 124.4, 113.0, 110.0, 35.1, 30.6, 28.1, 27.8, 24.3, 22.9, 21.6, 12.4.

Example 37

3-{2-Hexyl-3-[2-(isopropyl-methyl-carbamoyl)-ethylamino]-imidazo[1,2-a]pyridin-7-yl}-N-hydroxy-acrylamide (Compound 37)

The titled compound was prepared according to the procedures described in Example 18 by using appropriate starting materials. HPLC: 99%; $t_R$=2.301 min; LCMS (ESI) m/z 430 [MH]$^+$; $^1$H NMR (CD$_3$OD): δ 8.74 (d, J=7.1 Hz, 1H), 7.83 (s, 1H), 7.70-7.65 (m, 2H), 6.78 (d, J=16.9 Hz, 1H), 4.24-4.22 (m, 1H), 3.37-3.34 (m, 2H), 2.91 (s, 3H), 2.88 (t, J=7.9 Hz, 2H), 2.76 (dt, J=6.4 Hz, 28.2 Hz, 2H), 1.81-1.74 (m, 2H), 1.45-1.29 (m, 6H), 1.24 (d, J=6.6 Hz, 1H), 1.13 (d, J=6.8 Hz, 1H), 0.92 (t, J=6.9 Hz, 3H); $^{13}$C NMR (CD$_3$OD): δ 124.5, 122.9, 109.9, 30.6, 28.1, 27.8, 21.6, 18.4, 17.6, 12.4.

Example 38

3-(2-Hexyl-3-{2-[isopropyl-(2-methoxy-ethyl)-carbamoyl]-ethylamino}-imidazo[1,2-a]pyridin-7-yl)-N-hydroxy-acrylamide (Compound 38)

The titled compound was prepared according to the procedures described in Example 18 by using appropriate starting materials. HPLC: 99%; $t_R$=2.381 min; LCMS (ESI) m/z 474 [MH]$^+$; $^1$H NMR (CD$_3$OD): δ 8.70 (dd. J=13.6, 72 Hz, 1H), 7.84 (s, 1H), 7.70-7.65 (m, 2H), 6.78 (d, J=15.7 Hz, 1H), 3.53 (s, 3H), 3.49-3.43 (m, 2H), 3.37-3.33 (m, 4H), 2.88 (t, J=7.6 Hz, 2H), 2.76 (dt, J=6.0, 2.4 Hz, 2H), 1.81-1.74 (m, 2H), 1.45-1.36 (m, 6H), 1.24 (d, J=6.7 Hz, 3H), 1.21 (d, J=6.9 Hz, 3H), 0.92 (t, J=7.0 Hz, 3H).

Example 39

Preparation of 3-(3-Butylaminomethyl-2-phenyl-imidazo[1,2-a]pyridin-7-yl)-N-hydroxy-acrylamide (Compound 39)

Step 1: Condensation reaction

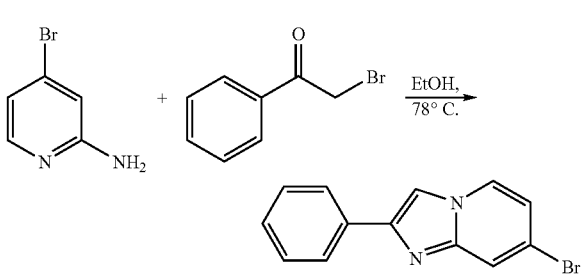

To a stirred solution of the amino-pyridine (0.10 g, 0.578 mmol) and EtOH (1.4 mL) was added the ketone (0.14 g, 0.6934 mmol) and the mixture was then stirred at 78° C. for 4 h. When the reaction has completed, the contents were evaporated. Saturated sodium carbonate solution was added and ethyl acetate was used to extract the aqueous layer. The combined organic extracts were then washed with water and followed by brine, before drying in anhydrous sodium sulfate. The contents were then filtered and concentrated. The crude product was used immediately without further purification (Journal of Medicinal Chemistry, 1998, 41(25), 5108).

Step 2: Hydroxymethylation

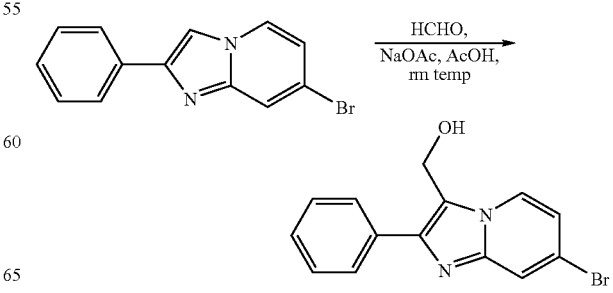

To a stirred solution of the aryl-bromide (179 mg, 0.656 mmol), HCHO (315 µL, 4.20 mmol) and AcOH (572 µL) was added NaOAc (203 mg, 2.47 mmol). When the reaction has completed, the contents were evaporated. Saturated sodium carbonate solution was added and ethyl acetate was used to extract the aqueous layer. The combined organic extracts were then washed with water and followed by brine, before drying in anhydrous sodium sulfate. The contents were then filtered and concentrated. The crude product was used immediately without further purification (Journal of Medicinal Chemistry, 1998, 41(25), 5108).

Step 3: Heck Reaction

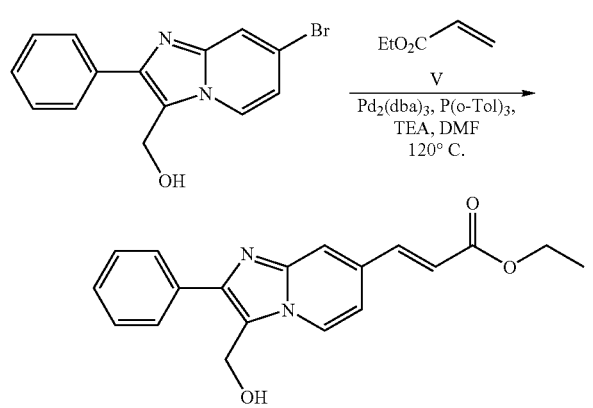

Ethyl acrylate (1.5 equiv) was added into a stirred suspension of the amine (1 equiv), Pd$_2$(dba)$_3$ (0.03 equiv), P(o-tol)$_3$ (0.08 equiv), Et$_3$N (2.0 equiv) and DMF at room temp. The reaction was heated to reflux at ~120° C. When the starting material had fully depleted (monitored by LCMS), the reaction mixture was diluted with ethyl acetate (20 mL). The organic layer was then washed with NaHCO$_3$ (2×10 mL) and brine (2×10 mL). The organic layer was dried in Na$_2$SO$_4$ before being filtered and concentrated in vacuo. The crude product was purified by flash column chromatography.

Step 4: Oxidation

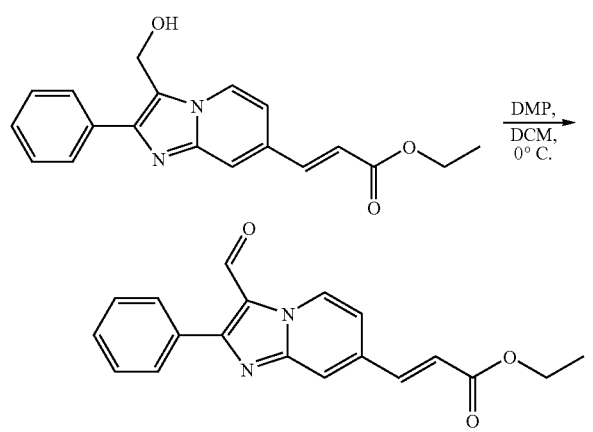

To a stirred solution of the alcohol (162 mg, 0.50 mmol) in DCM (25 mL) at 0° C. was added DMP (319 mg, 0.75 mmol). When the reaction has completed, a solution of saturated sodium bicarbonate and saturated sodium sulfate (1:1 mixture) was added. DCM was used to extract the aqueous layer. The combined organic extracts were dried in anhydrous sodium sulfate before being filtered and concentrated. The crude product was purified by flash column chromatography.

Step 5: Reductive Amination

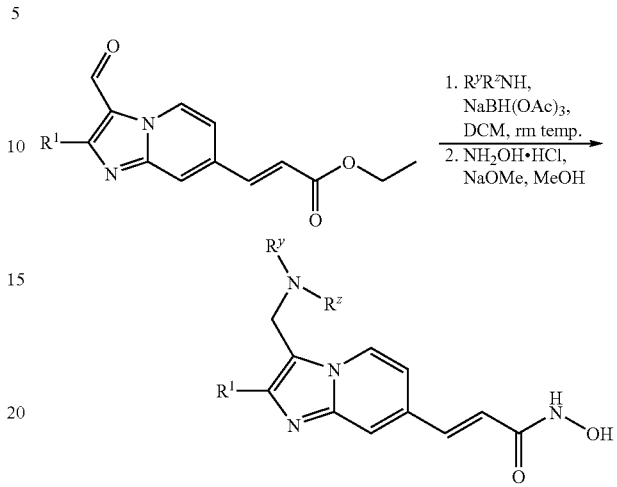

To a stirred solution of the aldehyde (43.9 mg, 0.137 mmol) and amine (0.821 mmol) in DCM (10 mL) was added NaBH(OAc)$_3$ (120 mg, 0.548 mmol). When the reaction has completed, the contents were diluted with DCM. The organic contents were washed with saturated sodium bicarbonate, water and brine, before drying in anhydrous sodium sulfate. The contents were then filtered and concentrated. The crude product was used immediately without further purification.

For subsequent hydroxamic acid formation, please refer to Step 4 from Example 17.

3-(3-Butylaminomethyl-2-phenyl-imidazo[1,2-a]pyridin-7-yl)-N-hydroxy-acrylamide (Compound 39)

The titled compound was prepared according to the procedures described in Example 39 by using appropriate starting materials. HPLC: 99%; t$_R$=1.000 min; LCMS (ESI) 365 [MH]$^+$; $^1$H NMR (CD$_3$OD): δ 8.76 (d, J=6.7 Hz, 1H), 7.88 (s, 1H), 7.81-7.79 (m, 2H), 7.64-7.52 (m, 5H), 6.71 (d, J=15.7 Hz, 1H), 4.92 (masked peaks, 2H), 2.93 (t, J=8.0 Hz, 2H), 1.57-1.51 (m, 2H), 1.29-1.24 (m, 2H), 0.87 (t, J=7.3 Hz, 3H); $^{13}$C NMR (100.5 MHz, d$_4$-MeOD): δ 164.9, 146.8, 137.9, 137.8, 131.9, 131.0, 130.5, 130.1, 127.2, 123.2, 115.8, 114.3, 113.6, 39.8, 28.8, 20.8, 13.7.

Example 40

N-Hydroxy-3-{3-[(methyl-propyl-amino)-methyl]-2-phenyl-imidazo[1,2-a]pyridin-7-yl}-acrylamide (Compound 40)

The titled compound was prepared according to the procedures described in Example 39 by using appropriate starting materials. HPLC: 99%; t$_R$=0.630 min; LCMS (ESI) m/z 365 [MH]$^+$; $^1$H NMR (CD$_3$OD): δ 8.81 (d, J=7.0 Hz, 1H), 7.96 (s, 1H), 7.81-7.79 (m, 2H), 7.69-7.56 (m, 5H), 6.73 (d, J=15.7 Hz, 1H), 5.03 (s, 2H), 2.96-2.94 (m, 2H), 2.69 (s, 3H), 1.61-1.57 (m, 2H), 0.79 (t, J=7.3 Hz, 3H); $^{13}$C NMR (CD$_3$OD): δ 164.9, 147.2, 145.6, 138.3, 137.8, 131.7, 131.3, 130.7, 130.2, 127.3, 123.6, 115.6, 113.9, 113.5, 58.3, 40.2, 18.4, 10.9.

Example 41

N-Hydroxy-3-(2-methyl-imidazo[1,2-a]pyridin-7-yl)-acrylamide (Compound 41)

The titled compound was prepared according to the procedures described in Example 39 by using appropriate starting materials. HPLC: 99%; $t_R$=0.348 min; m/z 218 [MH]$^+$; $^1$H NMR (CD$_3$OD): δ 8.57 (d, J=7.1 Hz, 1H), 7.86 (s, 1H), 7.82 (s, 1H), 7.58 (d, J=15.8 Hz, 1H), 7.54 (d, J=1.5 Hz, 1H), 6.68 (d, J=15.8 Hz, 1H), 2.46 (d, J=0.9 Hz, 3H).

Example 42

Preparation of 3-(3-Butylaminomethyl-2-methyl-imidazo[1,2-a]pyridin-7-yl)-N-hydroxy-acrylamide (Compound 42))

Step 1: Condensation Reaction

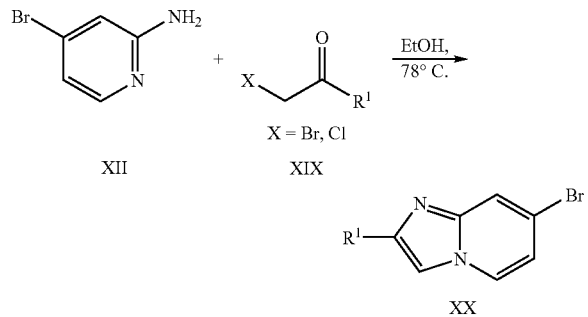

To a stirred solution of the amino-pyridine XII (0.10 g, 0.578 mmol) and EtOH (1.4 mL) was added the ketone XIX (0.14 g, 0.6934 mmol) and the mixture was then stirred at 78° C. for 4 h. When the reaction has completed, the contents were evaporated. Saturated sodium carbonate solution was added and ethyl acetate was used to extract the aqueous layer. The combined organic extracts were then washed with water and followed by brine, before drying in anhydrous sodium sulfate. The contents were then filtered and concentrated. The crude product was used immediately without further purification (Journal of Medicinal Chemistry, 1998, 41(25), 5108).

Step 2: Heck Reaction

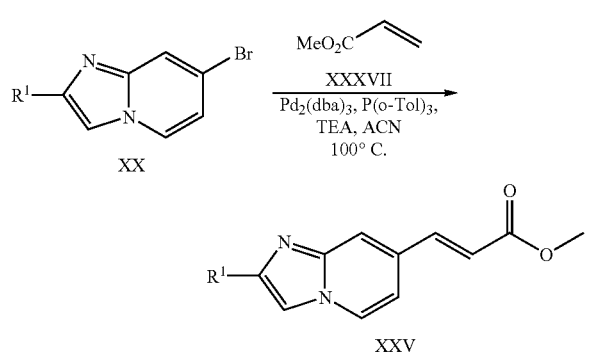

Methyl acrylate (1.5 equiv) was added into a stirred suspension of XX (1 equiv), Pd$_2$(dba)$_3$ (0.02 equiv), P(o-Tol)$_3$ (0.05 equiv), Et$_3$N (2.0 equiv) and CH$_3$CN at room temperature. The reaction was heated to reflux at ~100° C. When the starting material had fully depleted (monitored by LCMS), the reaction mixture was diluted with ethyl acetate. The organic layer was then washed with NaHCO$_3$ and brine. The organic layer was dried in Na$_2$SO$_4$ before being filtered and concentrated in vacuo. The crude product was purified by flash column chromatography.

Step 3: Mannich Reaction and Hydroxamic Acid Formation

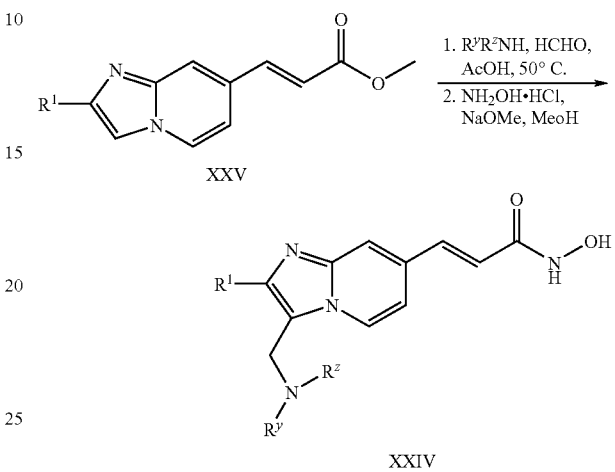

The amine (3.0 equiv) was added slowly into a stirred solution of the imidazol[1,2-α]pyridinyl methyl ester XXV (1.0 equiv), formaldehyde solution (3.0 equiv) and AcOH (20 equiv) and the mixture was heated up to 50° C. When the starting material has fully depleted (monitored by LCMS), the crude product was used immediately for the next step.

To a stirred solution of the crude material from the Mannich reaction and NH$_2$OH.HCl (20 equiv) was added NaOMe (40 equiv) at −78° C. The reaction mixture was allowed to warm up slowly to room temperature. When the reaction is completed, the mixture was cooled to 0° C. before using 1M HCl to quench the reaction. Small amounts of MeOH and H$_2$O were added to solubilize the mixture. The crude product was purified by reverse phase prep-HPLC.

3-(3-Butylaminomethyl-2-methyl-imidazo[1,2-a]pyridin-7-yl)-N-hydroxy-acrylamide (Compound 42)

HPLC: 99%; $t_R$=0.332 min; LCMS (ESI) m/z 303 [MH]$^+$; $^1$H NMR (CD$_3$OD): δ 8.74 (dd, J=7.1, 7.2 Hz, 1H), 7.93 (d, J=14.6, 1H), 7.72-7.61 (m, 2H), 6.80 (d, J=15.6 Hz, 1H), 5.03 (s, 2H), 2.62 (s, 3H), 2.57 (s, 3H), 1.80-1.70 (m, 2H), 1.47 (q, J=7.5 Hz, 2H), 1.01 (t, J=3.0 Hz, 2H).

Example 43

3-{2-tert-Butyl-3-[(2-diethylamino-ethylamino)-methyl]-imidazo[1,2-a]pyridin-7-yl}-N-hydroxy-acrylamide (Compound 43)

The titled compound was prepared according to the procedures described in Example 42 by using appropriate starting materials. HPLC: 99%; $t_R$=0.628 min; LCMS (ESI) m/z 388 [MH]$^+$; $^1$H NMR (CD$_3$OD): δ 8.84 (d, J=7.2 Hz, 1H), 7.91 (s, 1H), 7.70-7.67 (m, 2H), 6.82 (d, J=15.7 Hz, 1H), 4.44 (s, 2H), 3.34-3.33 (m, 4H), 3.27-3.20 (m, 4H) 1.58 (s, 9H), 1.31 (t, J=7.3 Hz, 6H).

Example 44

3-(3-{[(2-Dimethylamino-ethyl)-ethyl-amino]-methyl}-2-phenyl-imidazo[1,2-a]pyridin-7-yl)-N-hydroxy-acrylamide (Compound 44)

The titled compound was prepared according to the procedures described in Example 42 by using appropriate starting materials. HPLC: 98.14%; $t_R$=1.216 min; LCMS (ESI) m/z 408 [MH]$^+$; $^1$H NMR (CD$_3$OD): δ 8.86 (d, J=7.1 Hz, 1H), 8.03 (s, 1H), 7.80-7.75 (m, 3H), 7.71-7.64 (m, 4H), 6.86 (d, J=15.7 Hz, 1H), 5.09 (masked peaks), 3.27 (t, J=6.6 Hz, 2H), 2.90 (t, J=6.6 Hz, 2H), 2.79 (s, 6H), 1.04 (t, J=7.1 Hz, 3H); $^{13}$C NMR (CD$_3$OD): δ 164.3, 141.6, 137.9, 136.8, 132.0, 130.7, 130.4, 130.0, 129.1, 128.6, 127.6, 125.8, 120.9, 116.0, 112.2, 55.3, 52.9, 48.3, 47.4, 46.9, 43.9, 9.8.

Example 45

3-[3-(tert-Butylamino-methyl)-2-phenyl-imidazo[1,2-a]pyridin-7-yl]-N-hydroxy-acrylamide (Compound 45)

The titled compound was prepared according to the procedures described in Example 42 by using appropriate starting materials. HPLC: 98.86%; $t_R$=0.881 min; LCMS (ESI) m/z 365 [MH]$^+$; $^1$H NMR (CD$_3$OD): δ 8.82 (s, 1H), 7.96 (s, 1H), 7.82 (d, J=6.1 Hz, 2H), 7.66-7.59 (m, 5H), 6.74 (d, J=15.7 Hz, 1H), 4.90 (masked peaks), 1.41 (s, 9H); $^{13}$C NMR (CD$_3$OD): δ 164.5, 143.8, 143.5, 140.0, 137.3, 131.8, 131.5, 130.6, 130.3, 129.5, 127.7, 124.5, 119.3, 116.4, 114.9, 114.2, 59.7, 34.4, 25.6.

Example 46

N-Hydroxy-3-{2-phenyl-3-[(2,2,2-trifluoro-ethylamino)-methyl]-imidazo[1,2-a]pyridin-7-yl}-acrylamide (Compound 46)

The titled compound was prepared according to the procedures described in Example 42 by using appropriate starting materials. HPLC: 92.99%; $t_R$=1.889 min; LCMS (ESI) m/z 391 [MH]$^+$; $^1$H NMR (CD$_3$OD): δ 8.92 (d, J=7.2 Hz, 1H), 8.02 (s, 1H), 7.78-7.76 (m, 3H), 7.71 (d, J=15.7 Hz, 1H), 7.65-7.63 (m, 3H), 6.86 (d, J=15.7 Hz, 1H), 4.92 (masked peaks), 4.43 (s, 2H); $^{13}$C NMR (CD$_3$OD): δ 164.3, 141.6, 141.4, 136.8, 136.6, 131.9, 130.6, 130.1, 129.1, 128.7, 127.7, 125.9, 122.5, 119.1, 116.2, 115.7, 111.9, 49.9 (masked peaks), 42.1.

Example 47

3-{3-[(2-Diethylamino-ethylamino)-methyl]-2-phenyl-imidazo[1,2a]pyridin-7-yl}-N-hydroxy-acrylamide (Compound 47)

The titled compound was prepared according to the procedures described in Example 42 by using appropriate starting materials. HPLC: 97.82%; $t_R$=0.680 min; LCMS (ESI) m/z 408 [MH]$^+$; $^1$H NMR (CD$_3$OD): δ 9.09 (d, J=6.3 Hz, 1H), 8.05 (s, 1H), 7.86-7.83 (m, 2H), 7.73 (d, J=6.3 Hz, 1H), 7.67-7.66 (m, 3H), 7.56 (d, J=15.7 Hz, 1H), 6.80 (d, J=15.7 Hz, 1H), 5.01 (s, 2H), 3.51-3.50 (m, 4H), 3.21 (t, J=7.2 Hz, 4H), 1.28 (t, J=7.2 Hz, 6H); $^{13}$C NMR (CD$_3$OD): δ 164.3, 142.3, 141.3, 140.3, 136.9, 132.1, 130.8, 130.3, 129.3, 128.8, 125.3, 122.2, 120.2, 116.4, 115.8, 112.7, 49.1, 43.5, 40.8, 8.9.

Example 48

N-Hydroxy-3-(3-{[(2-hydroxy-ethyl)-propyl-amino]-methyl}-2-phenyl-imidazo[1,2-a]pyridin-7-yl)-acrylamide (Compound 48)

The titled compound was prepared according to the procedures described in Example 42 by using appropriate starting materials. HPLC: 99%; $t_R$=0.758 min; LCMS (ESI) m/z 395 [MH]$^+$; $^1$H NMR (CD$_3$OD): δ 8.83 (d, J=7.1 Hz, 1H), 7.85 (s, 1H), 7.79 (d, J=6.7 Hz, 2H), 7.65-7.59 (m, 3H), 7.56 (d, J=15.7 Hz, 1H), 7.49 (d, J=6.9 Hz, 1H), 6.70 (d, J=15.7 Hz, 1H), 5.10 (s, 2H), 3.98 (t, J=4.8 Hz, 2H), 3.50-3.43 (m, 2H), 2.78-2.74 (m, 2H), 1.43-1.39 (m, 2H), 1.35 (t, J=7.3 Hz, 3H), 0.52 (t, J=7.2 Hz, 3H); $^{13}$C NMR (CD$_3$OD): δ 164.8, 146.3, 145.0, 138.7, 137.7, 131.4, 131.1, 130.7, 130.4, 128.0, 123.8, 115.1, 114.4, 113.9, 57.4, 55.8, 55.5, 45.6, 35.1, 17.1, 10.8, 9.3.

Example 49

3-(2-tert-Butyl-3-butylaminomethyl-imidazo[1,2-a]pyridin-7-yl)-N-hydroxy-acrylamide (Compound 49)

The titled compound was prepared according to the procedures described in Example 42 by using appropriate starting materials. HPLC: 94.10%; $t_R$=0.706 min; LCMS (ESI) m/z 345 [MH]$^+$; $^1$H NMR (CD$_3$OD): δ 8.38 (d, J=11.9 Hz, 1H), 7.61 (s, 1H), 7.54 (d, J=15.8, 1H), 7.21 (d, J=7.2, 1H), 6.55 (d, J=15.7 Hz, 1H), 4.84 (masked peaks), 3.20-3.12 (m, 2H), 1.73-1.65 (m, 2H), 1.47 (s, 9H), 1.44-1.38 (m, 2H), 0.95 (t, J=7.3 Hz, 3H).

Example 50

3-{2-tert-Butyl-3-[(methyl-propyl-amino)-methyl]-imidazo[1,2-a]pyridin-7-yl}-N-hydroxy-acrylamide (Compound 50)

The titled compound was prepared according to the procedures described in Example 42 by using appropriate starting materials. HPLC: 99%; $t_R$=0.499 min; LCMS (ESI) m/z 345 [MH]$^+$.

Example 51

3-(3-Diethylaminomethyl-2-phenyl-imidazo[1,2-a]pyridin-7-yl)-N-hydroxy-acrylamide (Compound 51)

The titled compound was prepared according to the procedures described in Example 42 by using appropriate starting materials. HPLC: 99.16%; $t_R$=0.708 min; LCMS (ESI) m/z 365 [MH]$^+$; $^1$H NMR (CD$_3$OD): δ 8.88 (d, J=6.1 Hz, 1H), 8.02 (s, 1H), 7.83 (d, J=3.5 Hz, 2H), 7.71-7.69 (m, 4H), 7.61 (d, J=15.7 Hz, 1H), 7.68 (d, J=15.7 Hz, 1H), 5.04 (masked peaks), 3.16-3.15 (m, 4H), 1.12 (t, J=7.1 Hz, 6H); $^{13}$C NMR (CD$_3$OD): δ 164.7, 145.9, 144.7, 139.4, 137.5, 131.7, 130.8, 130.5, 127.8, 124.2, 116.4, 114.8, 114.6, 113.9, 47.5, 44.6, 8.3.

Example 52

3-{3-[(Ethyl-propyl-amino)-methyl]-2-phenyl-imidazo[1,2-a]pyridin-7-yl}-N-hydroxy-acrylamide (Compound 52)

The titled compound was prepared according to the procedures described in Example 42 by using appropriate starting materials. HPLC: 99%; $t_R$=1.808 min; LCMS (ESI) m/z 379 [MH]$^+$; $^1$H NMR (CD$_3$OD): δ 8.88 (s, 1H), 8.02 (s, 1H), 7.84 (s, 1H), 7.70-7.69 (m, 4H), 7.61 (d, J=15.7 Hz, 1H), 6.81 (d, J=15.7 Hz, 1H), 5.06 (masked peaks), 3.19 (d, J=6.1 Hz, 2H), 2.96 (brs, 2H), 1.55 (brs, 2H), 1.15 (t. J=6.5 Hz, 3H), 0.72 (t. J=7.1 Hz, 3H); $^{13}$C NMR (CD$_3$OD): δ 164.9, 148.4, 146.1, 138.1, 137.4, 132.4, 131.1, 130.6, 130.3, 127.2, 122.9, 116.3, 113.3, 53.8, 45.4, 17.5, 10.9, 8.6.

Example 53

3-{3-[(Cyclopropylmethyl-propyl-amino)-methyl]-2-phenyl-imidazo[1,2a]pyridin-7-yl}-N-hydroxy-acrylamide (Compound 53)

The titled compound was prepared according to the procedures described in Example 42 by using appropriate starting materials. HPLC: 99%; $t_R$=1.136 min; LCMS (ESI) m/z 405 [MH]$^+$; $^1$H NMR (CD$_3$OD): δ 8.79 (d, J=7.0 Hz, 1H), 8.01 (s, 1H), 7.84-7.82 (m, 2H), 7.72-7.65 (m, 5H), 6.81 (d, J=15.7 Hz, 1H), 5.11 (s, 2H), 3.07 (d, J=7.1 Hz, 2H), 2.97-2.93 (m, 2H), 1.49-1.47 (m, 2H), 1.07 (brs, 1H), 0.73 (d, J=7.6 Hz, 2H), 0.65 (t, J=7.2 Hz, 3H), 0.39 (d, J=4.9 Hz, 2H); $^{13}$C NMR (CD$_3$OD): δ 164.6, 145.4, 144.5, 139.7, 137.4, 131.8, 130.9, 130.4, 127.7, 124.5, 114.7, 114.6, 114.1, 58.7, 54.7, 44.9, 17.4, 10.9, 6.5, 5.0.

Example 54

3-{3-[(sec-Butyl-propyl-amino)-methyl]-2-phenyl-imidazo[1,2-a]pyridin-7-yl}-N-hydroxy-acrylamide (Compound 54)

The titled compound was prepared according to the procedures described in Example 42 by using appropriate starting materials. HPLC: 91.38%; $t_R$=1.190 min; LCMS (ESI) m/z 407 [MH]$^+$; $^1$H NMR (CD$_3$OD): δ 8.66 (d, J=6.8 Hz, 1H), 7.98 (s, 1H), 7.83-7.78 (m, 2H), 7.68-7.64 (m, 6H), 6.79 (d, J=15.7 Hz, 1H), 5.01 (masked peaks), 3.23-3.20 (m, 1H), 2.90 (d, J=7.9 Hz, 2H), 1.72 (brs, 3H), 1.59-1.55 (m, 1H), 1.17 (brs, 3H), 0.84 (t, J=7.2 Hz, 3H), 0.73 (brs, 3H); $^{13}$C NMR (CD$_3$OD): 164.9, 137.9, 137.6, 137.1, 132.4, 131.8, 131.1, 130.7, 130.4, 130.0, 128.3, 127.1, 123.2, 116.1, 113.4, 61.6, 52.8, 24.7, 19.8, 13.0, 11.3, 10.8.

Example 55

3-[3-(2,6-Dimethyl-morpholin-4-ylmethyl)-2-phenyl-imidazo[1,2-a]pyridin-7-yl]-N-hydroxy-acrylamide (Compound 55)

The titled compound was prepared according to the procedures described in Example 42 by using appropriate starting materials. HPLC: 98.36%; $t_R$=1.332 min; LCMS (ESI) m/z 407 [MH]$^+$; $^1$H NMR (CD$_3$OD): δ 9.02 (d, J=7.2 Hz, 1H), 8.02 (s, 1H), 7.83-7.76 (m, 3H), 7.71 (d, J=15.8 Hz, 1H), 7.68-7.60 (m, 3H), 6.85 (d, J=15.7 Hz, 1H), 4.31 (d, J=2.5 Hz, 2H), 4.03-4.00 (m, 2H), 2.73 (d, J=8.7 Hz, 2H), 2.40-2.39 (m, 2H), 1.15 (d, J=6.5 Hz, 6H); $^{13}$C NMR (CD$_3$OD): δ 164.4, 159.2, 141.9, 141.3, 138.3, 136.9, 131.9, 130.6, 130.3, 129.3, 128.1, 125.6, 120.3, 117.5, 115.5, 114.6, 112.3, 67.7, 58.8, 51.1, 18.1.

Example 56

3-(3-{[Ethyl-(2-methoxy-ethyl)-amino]-methyl}-2-phenyl-imidazo[1,2-a]pyridin-7-yl)-N-hydroxy-acrylamide (Compound 56)

The titled compound was prepared according to the procedures described in Example 42 by using appropriate starting materials. HPLC: 99.02%; $t_R$=1.289 min; LCMS (ESI) m/z 395 [MH]$^+$; $^1$H NMR (CD$_3$OD): δ 8.82 (d, J=6.4 Hz, 1H), 8.04 (s, 1H), 7.83-7.74 (m, 3H), 7.64 (d, J=15.7 Hz, 1H), 7.70-7.69 (m, 3H), 6.84 (d, J=15.7 Hz, 1H), 5.14 (s, 2H), 3.78 (t, J=4.3 Hz, 2H), 3.47 (s, 3H), 3.42 (brs, 2H), 3.04 (d, J=6.8 Hz, 2H), 1.00 (t, J=7.0 Hz, 3H); $^{13}$C NMR (CD$_3$OD): δ 164.7, 145.9, 144.8, 138.9, 137.6, 131.5, 130.8, 130.7, 130.4, 127.8, 124.0, 114.9, 114.6, 114.5, 114.1, 67.8, 59.3, 25.6, 8.4.

Example 57

3-[3-(4-Ethyl-piperazin-1-ylmethyl)-2-phenyl-imidazo[1,2-a]pyridin-7-yl]-N-hydroxy-acrylamide (Compound 57)

The titled compound was prepared according to the procedures described in Example 42 by using appropriate starting materials. HPLC: 99%; $t_R$=0.899 min; LCMS (ESI) m/z 406 [MH]$^+$; $^1$H NMR (CD$_3$OD): δ 8.95 (d, J=7.1 Hz, 1H), 8.04 (s, 1H), 7.78-7.59 (m, 7H), 6.88 (d, J=15.7 Hz, 1H), 4.20 (s, 2H), 3.52 (d, J=11.6 Hz, 2H), 3.21-3.04 (m, 6H), 2.49 (t, J=11.0 Hz, 2H), 1.31 (t, J=7.3 Hz, 3H); $^{13}$C NMR (CD$_3$OD): δ 164.4, 142.2, 141.0, 138.6, 137.0, 131.8, 130.6, 130.3, 129.3, 128.3, 125.5, 120.1, 115.5, 112.5, 52.9, 52.6, 50.4, 50.1, 9.5.

Example 58

3-[3-(4-Benzyl-piperidin-1-ylmethyl)-2-phenyl-imidazo[1,2-a]pyridin-7-yl]-N-hydroxy-acrylamide (Compound 58)

The titled compound was prepared according to the procedures described in Example 42 by using appropriate starting materials. HPLC: 97.12%; $t_R$=1.941 min; LCMS (ESI) m/z 467 [MH]$^+$; $^1$H NMR (CD$_3$OD): δ 8.86 (s, 1H), 7.92 (s, 1H), 7.78 (d, J=6.2 Hz, 2H), 7.64-7.59 (m, 5H), 7.25-7.21 (m, 2H), 7.17-7.13 (m, 1H), 7.09-7.02 (m, 2H), 6.75 (d, J=15.6 Hz, 1H), 4.99 (s, 2H), 3.45-3.43 (m, 2H), 2.87-2.79 (m, 2H), 2.49 (d, J=6.8 Hz, 2H), 1.72-1.68 (m, 3H), 1.40-1.37 (m, 2H); $^{13}$C NMR (CD$_3$OD): δ 164.9, 147.3, 145.6, 140.3, 138.2, 137.9, 131.7, 131.2, 130.6, 130.2, 130.1, 129.4, 127.5, 123.4, 115.6, 113.8, 113.2, 53.7, 42.6, 36.2, 33.9, 29.9.

Example 59

3-{3-[(2,2-Dimethyl-propylamino)-methyl]-2-phenyl-imidazo[1,2-a]pyridin-7-yl}-N-hydroxy-acrylamide (Compound 59)

The titled compound was prepared according to the procedures described in Example 42 by using appropriate starting materials. HPLC: 98.57%; $t_R$=1.196 min; LCMS (ESI) m/z 379 [MH]$^+$; $^1$H NMR (CD$_3$OD): δ 8.90 (s, 1H), 7.98 (s, 1H), 7.80 (d, J=6.8 Hz, 2H), 7.66-7.67 (m, 5H), 6.80 (d, J=15.7 Hz, 1H), 5.04 (s, 2H), 2.76 (s, 2H), 0.93 (s, 9H);

Example 60

N-Hydroxy-3-(2-phenyl-3-pyrrolidin-1-ylmethyl-imidazo[1,2-a]pyridin-7-yl)-acrylamide (Compound 60)

The titled compound was prepared according to the procedures described in Example 42 by using appropriate starting materials. HPLC: 98.79%; $t_R$=0.513 min; LCMS (ESI) m/z 363 [MH]$^+$; $^1$H NMR (DMSO-d$_6$): δ 8.92 (d, J=7.2 Hz, 1H), 7.97 (s, 1H), 7.84 (d, J=7.2 Hz, 2H), 7.49-7.61 (m, 4H), 7.45

(d, J=7.2 Hz, 1H), 6.76 (d, J=16.0 Hz, 1H), 5.09 (s, 2H), 3.38 (brs, 2H), 2.89 (brs, 2H), 1.79 (brs, 4H).

Example 61

3-{3-[(Cyclopropylmethyl-amino)-methyl]-2-phenyl-imidazo[1,2-a]pyridin-7-yl}-N-hydroxy-acrylamide (Compound 61)

The titled compound was prepared according to the procedures described in Example 42 by using appropriate starting materials. HPLC: 97.36%; $t_R$=0.846 min; LCMS (ESI) m/z 363 [MH]$^+$; $^1$H NMR (CD$_3$OD): δ 8.84 (d, J=6.4 Hz, 1H), 7.94 (s, 1H), 7.82 (d, J=6.4 Hz, 2H), 7.58-7.66 (m, 5H), 6.76 (d, J=15.7 Hz, 1H), 4.94 (masked peaks), 2.95 (d, J=7.4 Hz, 2H), 1.02-1.06 (m, 1H), 0.63-0.68 (m, 2H), 0.33-0.37 (m, 2H).

Example 62

3-(3-Cyclopropylaminomethyl-2-phenyl-imidazo[1,2-a]pyridin-7-yl)-N-hydroxy-acrylamide (Compound 62)

The titled compound was prepared according to the procedures described in Example 42 by using appropriate starting materials. HPLC: 94.09%; $t_R$=0.595 min; LCMS (ESI) m/z 349 [MH]$^+$; $^1$H NMR (CD$_3$OD): δ 8.87 (s, 1H), 8.03 (s, 1H), 7.82 (d, J=7.04 Hz, 2H), 7.65-7.68 (m, 5H), 6.79 (d, J=15.6 Hz, 1H), 5.04 (s, 2H), 2.62-2.63 (q, 1H), 0.78 (s, 2H), 0.64 (d, J=6.5 Hz, 2H).

Example 63

3-[3-Butylaminomethyl-2-(4-fluoro-phenyl)-imidazo[1,2-a]pyridin-7-yl]-N-hydroxy-acrylamide (Compound 63)

The titled compound was prepared according to the procedures described in Example 42 by using appropriate starting materials. HPLC: 99%; $t_R$=1.151 min; LCMS (ESI) m/z 383 [MH]$^+$; $^1$H NMR (CD$_3$OD): δ 8.77 (d, J=7.1 Hz, 1H), 7.89 (s, 1H), 7.85-7.82 (m, 2H), 7.62 (d, J=15.7 Hz, 1H), 7.54 (d, J=7.0 Hz, 1H), 7.40-7.35 (m, 3H), 6.72 (d, J=15.8 Hz, 1H), 4.91 (masked peaks), 3.00-2.96 (m, 2H), 1.62-1.54 (m, 2H), 1.33-1.27 (m, 2H), 0.90 (t, J=7.3 Hz, 3H);

Example 64

3-[3-(tert-Butylamino-methyl)-2-(4-fluoro-phenyl)-imidazo[1,2-a]pyridin-7-yl]-N-hydroxy-acrylamide (Compound 64)

The titled compound was prepared according to the procedures described in Example 42 by using appropriate starting materials. HPLC: 95.45%; $t_R$=0.887 min; LCMS (ESI) m/z 383 [MH]$^+$; $^1$H NMR (CD$_3$OD): δ 8.69 (brs, 1H), 7.87-7.83 (m, 4H), 7.60-7.54 (m, 2H), 7.38-7.34 (m, 2H), 6.62 (d, J=15.6 Hz, 1H), 4.92 (masked peaks), 1.42 (s, 9H);

Example 65

3-[3-(tert-Butylamino-methyl)-2-phenyl-imidazo[1,2-a]pyridin-6-yl]-N-hydroxy-acrylamide (Compound 65)

The titled compound was prepared according to the procedures described in Example 42 by using appropriate starting materials. HPLC: 99.67%; $t_R$=0.667 min; LCMS (ESI) m/z 365 [MH]$^+$; $^1$H NMR (CD$_3$OD): δ 8.71 (s, 1H), 7.79 (d, J=7.6 Hz, 3H), 7.68 (d, J=15.2 Hz, 2H), 7.59-7.55 (m, 3H), 7.52 (d, J=7.2 Hz, 1H), 6.57 (d, J=14.0 Hz, 1H), 4.84 (Masked peak, 2H), 1.41 (s, 9H).

Example 66

3-(3-Butylaminomethyl-2-phenyl-imidazo[1,2-a]pyridin-6-yl)-N-hydroxy-acrylamide (Compound 66)

The titled compound was prepared according to the procedures described in Example 42 by using appropriate starting materials. HPLC: 99.07%; $t_R$=0.979 min; LCMS (ESI) m/z 365 [MH]$^+$; $^1$H NMR (CD$_3$OD): δ 8.85 (s, 1H), 7.78 (d, J=7.1 Hz, 3H), 7.68 (d, J=8.7 Hz, 2H), 7.58-7.53 (m, 3H), 7.51 (d, J=7.3 Hz, 1H), 6.55 (d, J=13.4 Hz, 1H), 4.86 (Masked peak, 2H), 2.94 (brs, 2H), 1.56 (brs, 2H), 1.26 (q, J=7.0 Hz, 2H), 0.87 (t, J=7.2 Hz, 3H).

Example 67

3-[2-tert-Butyl-3-[(2,2-dimethyl-propylamino)-methyl]-imidazo[1,2-a]pyridin-7-yl]-N-hydroxy-acrylamide (Compound 67)

The titled compound was prepared according to the procedures described in Example 42 by using appropriate starting materials. HPLC: 85.65%; $t_R$=0.821 min; LCMS (ESI) m/z 359 [MH]$^+$.

Example 68

3-{2-tert-Butyl-3-[(1-ethyl-propylamino)-methyl]-imidazo[1,2-a]pyridin-7-yl}-N-hydroxy-acrylamide (Compound 68)

The titled compound was prepared according to the procedures described in Example 42 by using appropriate starting materials. HPLC: 86.52%; $t_R$=0.654 min; LCMS (ESI) m/z 359 [MH]$^+$; $^1$H NMR (CD$_3$OD): δ 8.86 (d, J=7.2 Hz, 1H), 7.91 (s, 1H), 7.76 (d, J=7.0 Hz, 1H), 7.65 (d, J=15.8 Hz, 1H), 6.81 (d, J=15.7 Hz, 1H), 4.88 (s, 2H), 1.91-1.87 (m, 4H), 1.58 (s, 9H) 1.05 (t, J=7.5 Hz, 6H).

Example 69

3-[2-tert-Butyl-3-(tert-butylamino-methyl)-imidazo[1,2-a]pyridin-7-yl]-N-hydroxy-acrylamide (Compound 69)

The titled compound was prepared according to the procedures described in Example 42 by using appropriate starting materials. HPLC: 94.13%; $t_R$=0.541 min; LCMS (ESI) m/z 345.07 [MH]$^+$; $^1$H NMR (CD$_3$OD): δ 8.71 (d, J=7.2 Hz, 1H), 7.89 (s, 1H), 7.71 (d, J=6.0 Hz, 1H), 7.64 (d, J=6.0 Hz, 1H), 6.79 (d, J=15.7 Hz, 1H), 4.88-4.73 (m, 2H), 1.59 (s, 9H), 1.57 (s, 9H).

Example 70

3-(tert-Butylamino-methyl)-2-phenyl-imidazo[1,2-a]pyridine-7-carboxylic acid hydroxyamide (Compound 70)

The titled compound was prepared according to the procedures described in Example 42 by using appropriate starting materials. HPLC: 95.08%; $t_R$=0.427 min; LC-MS (ESI) m/z 339 [MH]$^+$; $^1$H NMR (CD$_3$OD) δ 1.29 (s, 9H), 4.78 (masked peaks, 2H), 7.51 (m, 4H), 7.68 (m, 2H), 8.05 (s, 1H), 8.69 (1H, d, J=7.04); $^{13}$C NMR (CD$_3$OD) δ 23.6, 32.7, 57.6, 111.9, 112.8, 113.4, 114.3, 125.3, 129.3, 132.6, 142.4, 144.4, 160.0, 160.3, 162.0.

Example 71

3-{3-[(Butyl-methyl-amino)-methyl]-2-phenyl-imidazo[1,2-a]pyridin-7-yl}-N-hydroxy-acrylamide (Compound 71)

The titled compound was prepared according to the procedures described in Example 42 by using appropriate starting materials. HPLC: 99%; $t_R$=0.932 min; LCMS (ESI) m/z 379 [MH]$^+$; $^1$H NMR (CD$_3$OD): δ 8.87 (d, J=7.2 Hz, 1H), 7.93 (s, 1H), 7.81 (dd, J=1.8, 8.0 Hz, 2H), 7.69-7.57 (m, 5H), 6.74 (d, J=15.8 Hz, 1H), 5.06 (s, 2H), 2.99 (t, J=7.8 Hz, 2H), 2.74 (s, 3H), 1.56-1.52 (m, 2H), 1.18-1.13 (m, 2H), 0.83 (t, J=7.3 Hz, 3H); $^{13}$C NMR (CD$_3$OD): δ 164.7, 145.7, 144.7, 139.5, 137.4, 131.7, 130.8, 130.5, 130.3, 127.8, 124.3, 114.8, 114.6, 113.9, 56.6, 47.9, 40.3, 26.7, 20.8, 13.7.

Example 72

3-(2-Butyl-3-butylaminomethyl-imidazo[1,2-a]pyridin-7-yl)-N-hydroxy-acrylamide (Compound 72)

The titled compound was prepared according to the procedures described in Example 42 by using appropriate starting materials. HPLC: 99.9%; $t_R$=0.891 min; LCMS (ESI) m/z 345 [MH]$^+$.

Example 73

3-[2-Butyl-3-(tert-butylamino-methyl)-imidazo[1,2-a]pyridin-7-yl]-N-hydroxy-acrylamide (Compound 73)

The titled compound was prepared according to the procedures described in Example 42 by using appropriate starting materials. HPLC: 98.53%; $t_R$=0.673 min; LCMS (ESI) m/z 345 [MH]$^+$; $^1$H NMR (CD$_3$OD): δ 8.86 (d, J=6.8 Hz, 1H), 7.99 (s, 1H), 7.78 (d, J=6.8 Hz, 1H), 7.56 (d, J=15.7 Hz, 1H), 6.76 (d, J=15.7 Hz, 1H), 4.87 (masked peaks, 2H), 3.05 (t, J=7.9 Hz, 2H), 1.80-1.88 (m, 2H), 1.49-1.67 (m, 11H), 1.04 (t, J=7.3 Hz, 3H).

Example 74

3-(2-Butyl-3-dipropylaminomethyl-imidazo[1,2-a]pyridin-7-yl)-N-hydroxy-acrylamide (compound 74)

The titled compound was prepared according to the procedures described in Example 42 by using appropriate starting materials. HPLC: 99%; $t_R$=1.169 min; LCMS (ESI) m/z 373 [MH]$^+$.

Example 75

3-(2-Butyl-3-diethylaminomethyl-imidazo[1,2-a]pyridin-7-yl)-N-hydroxy-acrylamide (compound 75)

The titled compound was prepared according to the procedures described in Example 42 by using appropriate starting materials. HPLC: 99%; $t_R$=0.537 min; LCMS (ESI) m/z 345 [MH]$^+$.

Example 76

3-{2-Butyl-3-[(butyl-methyl-amino)-methyl]-imidazo[1,2-a]pyridin-7-yl}-N-hydroxy-acrylamide (compound 76)

The titled compound was prepared according to the procedures described in Example 42 by using appropriate starting materials. HPLC: 99%; $t_R$=1.154 min; LCMS (ESI) m/z 359 [MH]$^+$.

Example 77

3-{2-Butyl-3-[(butyl-ethyl-amino)-methyl]-imidazo[1,2-a]pyridin-7-yl}-N-hydroxy-acrylamide (compound 77)

The titled compound was prepared according to the procedures described in Example 42 by using appropriate starting materials. HPLC: 99%; $t_R$=1.248 min; LCMS (ESI) m/z 373 [MH]$^+$.

Example 78

3-{2-Butyl-3-[(butyl-propyl-amino)-methyl]-imidazo[1,2-a]pyridin-7-yl}-N-hydroxy-acrylamide (compound 78)

The titled compound was prepared according to the procedures described in Example 42 by using appropriate starting materials. HPLC: 99%; $t_R$=1.429 min; LCMS (ESI) m/z 387 [MH]$^+$.

Example 79

3-Diethylaminomethyl-2-phenyl-imidazo[1,2-a]pyridine-7-carboxylic acid hydroxyamide (compound 79)

The titled compound was prepared according to the procedures described in Example 42 by using appropriate starting materials. HPLC: 99%; $t_R$=0.540 min; LC-MS (ESI) m/z 339 [MH]$^+$; $^1$H NMR (CD$_3$OD) δ 1.00 (m, 6H), 3.03 (m, 2H), 5.00 (s, 2H), 7.51-7.61 (m, 4H), 7.72 (m, 2H), 8.07 (s, 1H), 8.84 (1H, d, J=7.04).

Example 80

3-(2-tert-Butyl-3-diethylaminomethyl-imidazo[1,2-a]pyridin-7-yl)-N-hydroxy-acrylamide (compound 80)

The titled compound was prepared according to the procedures described in Example 42 by using appropriate starting materials. HPLC: 99%; $t_R$=0.652 min; LCMS (ESI) m/z 345 [MH]$^+$.

Example 81

3-(3-Dibutylaminomethyl-2-methyl-imidazo[1,2-a]pyridin-7-yl)-N-hydroxy-acrylamide (compound 81)

The titled compound was prepared according to the procedures described in Example 42 by using appropriate starting materials. HPLC: 98.00%; $t_R$=0.964 min; LCMS (ESI) m/z 359 [MH]$^+$; $^1$H NMR (CD$_3$OD): δ 8.73 (s, 1H), 7.96 (s, 1H), 7.67-7.62 (m, 2H), 6.79 (d, J=15.8 Hz, 1H), 4.91 (masked peaks, 2H), 3.26 (t, J=1.6 Hz, 4H), 2.65 (s, 3H), 1.83-1.77 (m, 4H), 1.46-1.38 (m, 4H), 1.04 (t, J=8.0 Hz, 6H).

Example 82

3-{2-tert-Butyl-3-[(ethyl-propyl-amino)-methyl]-imidazo[1,2-a]pyridin-7-yl}-N hydroxy-acrylamide (compound 82)

The titled compound was prepared according to the procedures described in Example 42 by using appropriate starting materials. HPLC: 99%; $t_R$=0.631 min; LCMS (ESI) m/z 359 [MH]$^+$.

Example 83

3-(2-Butyl-3-dimethylaminomethyl-imidazo[1,2-a]pyridin-7-yl)-N-hydroxy-acrylamide (compound 83)

The titled compound was prepared according to the procedures described in Example 42 by using appropriate starting materials. HPLC: 99%; $t_R$=0.477 min; LCMS (ESI) m/z 317 [MH]$^+$.

Example 84

3-(2-tert-Butyl-3-ethylaminomethyl-imidazo[1,2-a]pyridin-7-yl)-N-hydroxy-acrylamide (compound 84)

The titled compound was prepared according to the procedures described in Example 42 by using appropriate starting materials. HPLC: 99%; $t_R$=0.379 min; LCMS (ESI) m/z 317 [MH]$^+$.

Example 85

Preparation of 3-{2-tert-Butyl-3-[(butyl-ethylamino)-methyl]-imidazo[1,2-a]pyridin-7-yl}-N-hydroxy-acrylamide (Compound 85)

The intermediate XXIV was prepared according to the 3-steps procedure described in Example 42 by using appropriate starting materials. XXIV was then subjected to reductive amination described below.

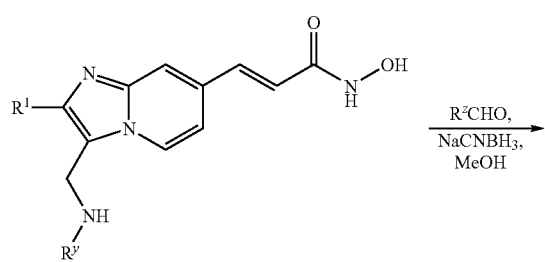

XXIV

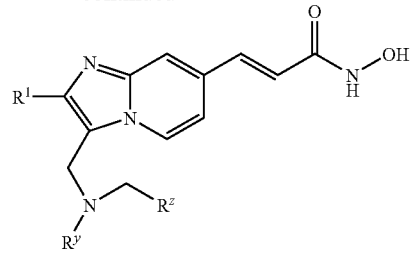

XXXXIII

To a stirred solution of the amine XXIV (1.0 equiv.), R$^Z$CHO (2.0 equiv.) and MeOH was added NaCNBH$_3$ (3.0 equiv.) and the mixture was then stirred at room temperature for 2 h. When the reaction has completed, the contents were purified by reverse phase prep-HPLC immediately.

3-{2-tert-Butyl-3-[(butyl-ethyl-amino)-methyl]-imidazo[1,2-a]pyridin-7-yl}-N-hydroxy-acrylamide (Compound 85)

HPLC: 99%; $t_R$=0.976 min; LCMS (ESI) m/z 373 [MH]$^+$.

Example 86

3-{2-tert-Butyl-3-[(ethyl-isobutyl-amino)-methyl]-imidazo[1,2-a]pyridin-7-yl}-N-hydroxy-acrylamide (compound 86)

The titled compound was prepared according to the procedures described in Example 85 by using appropriate starting materials. HPLC: 99%; $t_R$=1.159 min; LCMS (ESI) m/z 373 [MH]$^+$.

Example 87

3-{2-tert-Butyl-3-[(ethyl-pentyl-amino)-methyl]-imidazo[1,2-a]pyridin-7-yl}-N-hydroxy-acrylamide (compound 87)

The titled compound was prepared according to the procedures described in Example 85 by using appropriate starting materials. HPLC: 99%; $t_R$=1.337 min; LCMS (ESI) m/z 387 [MH]$^+$.

Example 88

3-(2-tert-Butyl-3-{[ethyl-(2-methyl-butyl)-amino]-methyl}-imidazo[1,2-a]pyridin-7-yl)-N-hydroxy-acrylamide (compound 88)

The titled compound was prepared according to the procedures described in Example 85 by using appropriate starting materials. HPLC: 99%; $t_R$=1.446 min; LCMS (ESI) m/z 387 [MH]$^+$.

Example 89

3-(2-tert-Butyl-3-{[ethyl-(3-methyl-butyl)-amino]-methyl}-imidazo[1,2-a]pyridin-7-yl)-N-hydroxy-acrylamide (compound 89)

The titled compound was prepared according to the procedures described in Example 85 by using appropriate starting materials. HPLC: 99%; $t_R$=0.275 min; LCMS (ESI) m/z 387 [MH]$^+$.

Example 90

3-{2-tert-Butyl-3-[(ethyl-hexyl-amino)-methyl]-imidazo[1,2-a]pyridin-7-yl}-N-hydroxy-acrylamide (compound 90)

The titled compound was prepared according to the procedures described in Example 85 by using appropriate starting materials. HPLC: 99%; $t_R$=1.647 min; LCMS (ESI) m/z 401 [MH]$^+$.

Example 91

3-(2-tert-Butyl-3-{[ethyl-(2-methyl-pentyl)-amino]-methyl}-imidazo[1,2-a]pyridin-7-yl)-N-hydroxy-acrylamide (compound 91)

The titled compound was prepared according to the procedures described in Example 85 by using appropriate starting materials. HPLC: 99%; $t_R$=1.752 min; LCMS (ESI) m/z 401 [MH]$^+$.

Example 92

3-(2-tert-Butyl-3-{[(3,3-dimethyl-butyl)-ethyl-amino]-methyl}-imidazo[1,2a]pyridin-7-yl)-N-hydroxy-acrylamide (compound 92)

The titled compound was prepared according to the procedures described in Example 85 by using appropriate starting materials. HPLC: 99%; $t_R$=1.503 min; LCMS (ESI) m/z 400 [MH]$^+$.

Example 93

3-(2-tert-Butyl-3-{[ethyl-(2-ethyl-butyl)-amino]-methyl}-imidazo[1,2-a]pyridin-7-yl)-N-hydroxy-acrylamide (compound 93)

The titled compound was prepared according to the procedures described in Example 85 by using appropriate starting materials. HPLC: 99%; $t_R$=1.692 min; LCMS (ESI) m/z 401 [MH]$^+$.

Example 94

3-{2-tert-Butyl-3-[(ethyl-heptyl-amino)-methyl]-imidazo[1,2-a]pyridin-7-yl}-N-hydroxy-acrylamide (compound 94)

The titled compound was prepared according to the procedures described in Example 85 by using appropriate starting materials. HPLC: 99%; $t_R$=1.943 min; LCMS (ESI) m/z 415 [MH]$^+$.

Example 95

3-(2-tert-Butyl-3-{[ethyl-(3-methylsulfanyl-propyl)-amino]-methyl}-imidazo[1,2-a]pyridin-7-yl)-N-hydroxy-acrylamide (compound 95)

The titled compound was prepared according to the procedures described in Example 85 by using appropriate starting materials. HPLC: 99%; $t_R$=1.133 min; LCMS (ESI) m/z 405 [MH]$^+$.

Example 96

3-(2-tert-Butyl-3-{[ethyl-(tetrahydro-furan-3-ylmethyl)-amino]-methyl}-imidazo[1,2-a]pyridin-7-yl)-N-hydroxy-acrylamide (compound 96)

The titled compound was prepared according to the procedures described in Example 85 by using appropriate starting materials. HPLC: 99%; $t_R$=1.049 min; LCMS (ESI) m/z 401 [MH]$^+$.

Example 97

3-{2-tert-Butyl-3-[(cyclopropylmethyl-ethyl-amino)-methyl]-imidazo[1,2-a]pyridin-7-yl}-N-hydroxy-acrylamide (compound 97)

The titled compound was prepared according to the procedures described in Example 85 by using appropriate starting materials. HPLC: 99%; $t_R$=0.695 min; LCMS (ESI) m/z 371 [MH]$^+$.

Example 98

3-{2-tert-Butyl-3-[(cyclohexylmethyl-ethyl-amino)-methyl]-imidazo[1,2-a]pyridin-7-yl}-N-hydroxy-acrylamide (compound 98)

The titled compound was prepared according to the procedures described in Example 85 by using appropriate starting materials. HPLC: 99%; $t_R$=1.699 min; LCMS (ESI) m/z 413 [MH]$^+$.

Example 99

3-{3-[(Butyl-ethyl-amino)-methyl]-2-methyl-imidazo[1,2-a]pyridin-7-yl}-N-hydroxy-acrylamide (compound 99)

The titled compound was prepared according to the procedures described in Example 85 by using appropriate starting materials. HPLC: 99%; $t_R$=0.412 min; LCMS (ESI) m/z 331 [MH]$^+$; $^1$H NMR (CD$_3$OD): δ 8.67 (d, J=7.0 Hz, 1H), 7.91 (s, 1H), 7.65 (d, J=15.6 Hz, 1H), 7.60 (d, J=7.2 Hz, 1H), 6.76 (d, J=16.0 Hz, 1H), 4.95 (masked peaks, 2H), 3.36-3.37 (m, 2H), 3.25 (masked peaks, 2H), 2.63 (s, 3H), 1.83-1.75 (m, 2H), 1.47-1.38 (m, 5H), 1.01 (t, J=7.4 Hz, 3H).

Example 100

3-{3-[(Ethyl-propyl-amino)-methyl]-2-methyl-imidazo[1,2-a]pyridin-7-yl}-N-hydroxy-acrylamide (compound 100)

The titled compound was prepared according to the procedures described in Example 85 by using appropriate starting materials. HPLC: 97.28%; $t_R$=0.316 min; LCMS (ESI) m/z 317 [MH]$^+$; $^1$H NMR (CD$_3$OD): δ 8.72 (d, J=6.8 Hz, 1H), 7.94 (s, 1H), 7.68-7.61 (m, 2H), 6.80 (d, J=15.6 Hz, 1H), 4.95 (masked peaks, 2H), 3.64-3.60 (m, 2H), 3.27-3.25 (m, 2H), 2.64 (s, 3H), 1.85-1.82 (m, 2H), 1.38 (t, J=7.4 Hz, 3H), 1.03 (t, J=7.3 Hz, 3H).

Example 101

3-(3-{[Ethyl-(2-ethyl-butyl)-amino]-methyl}-2-methyl-imidazo[1,2-a]pyridin-7-yl)-N-hydroxy-acrylamide (compound 101)

The titled compound was prepared according to the procedures described in Example 85 by using appropriate starting materials. HPLC: 99%; $t_R$=0.963 min; LCMS (ESI) m/z 359 [MH]$^+$; $^1$H NMR (CD$_3$OD): δ 8.70 (d, J=7.2 Hz, 1H), 7.92 (s, 1H), 7.69-7.64 (m, 2H), 6.78 (d, J=15.8 Hz, 1H), 4.61 (brs, 2H), 3.14-3.12 (m, 2H), 2.91-2.86 (m, 2H), 2.60 (s, 3H), 1.68 (brs, 1H), 1.42-1.35 (m, 7H), 0.86 (t, J=7.2 Hz, 3H).

Example 102

3-{2-tert-Butyl-3-[(isopropyl-propyl-amino)-methyl]-imidazo[1,2-a]pyridin-7-yl}-N-hydroxy-acrylamide (compound 102)

The titled compound was prepared according to the procedures described in Example 42 by using appropriate starting materials. HPLC: 95.11%; $t_R$=0.756 min; LCMS (ESI) m/z 373 [MH]$^+$; $^1$H NMR (CD$_3$OD): δ 8.81 (s, 1H), 8.02 (s, 1H), 7.91 (s, 1H), 7.59 (d, J=15.9 Hz, 1H), 6.79 (d, J=15.7 Hz, 1H), 5.04-4.76 (m, 2H), 3.91 (s, 1H), 1.86-1.28 (m, 19H), 0.83 (s, 3H).

Example 103

3-(3-Diethylaminomethyl-2-phenyl-imidazo[1,2a]pyridin-6-yl)-N-hydroxy-acrylamide (compound 103)

The titled compound was prepared according to the procedures described in Example 42 by using appropriate starting materials. HPLC: 99%; $t_R$=0.735 min; LCMS (ESI) m/z 365 [MH]$^+$; $^1$H NMR (CD$_3$OD): δ 8.99 (s, 1H), 8.01 (d, J=9.3 Hz, 1H), 7.84-7.62 (m, 7H), 6.50 (s, 1H), 5.02 (s, 2H), 3.17 (brs, 4H), 1.12 (t, J=9.3 Hz, 6H).

Example 104

3-(2-tert-Butyl-3-{[(2,2-dimethyl-propyl)-methyl-amino]-methyl}-imidazo[1,2-a]pyridin-7-yl)-N-hydroxy-acrylamide (compound 104)

The titled compound was prepared according to the procedures described in Example 85 by using appropriate starting materials. HPLC: 99%; $t_R$=1.318 min; LCMS (ESI) m/z 373 [MH]$^+$; $^1$H NMR (CD$_3$OD): δ 8.82 (d, J=6.9 Hz, 1H), 7.83 (s, 1H), 7.65 (d, J=6.9 Hz, 1H), 7.59 (d, J=15.8 Hz, 1H), 6.75 (d, J=15.7 Hz, 1H), 4.85-4.70 (m, 2H), 4.26 (s, 2H), 2.56-2.46 (m, 3H), 1.49 (s, 9H), 0.71 (s, 9H).

Example 105

3-(3-{[Ethyl-(2,2,2-trifluoro-ethyl)-amino]-methyl}-2-phenyl-imidazo [1,2-a]pyridin-7-yl)-N-hydroxy-acrylamide (compound 105)

The titled compound was prepared according to the procedures described in Example 85 by using appropriate starting materials. HPLC: 99%; $t_R$=2.386 min; LCMS (ESI) m/z 419 [MH]$^+$.

Example 106

3-{2-tert-Butyl-3-[(butyl-methyl-amino)-methyl]-imidazo[1,2-a]pyridin-7-yl}-N-hydroxy-acrylamide (compound 106)

The titled compound was prepared according to the procedures described in Example 85 by using appropriate starting materials. HPLC: 99%; $t_R$=0.841 min; LCMS (ESI) m/z 359 [MH]$^+$; $^1$H NMR (CD$_3$OD): δ 8.78 (d, J=7.2 Hz, 1H), 7.87 (s, 1H), 7.65-7.61 (m, 3H), 6.76 (d, J=15.9 Hz, 1H), 4.89-4.74 (m, 2H), 2.74 (s, 3H), 2.60 (s, 2H), 1.54 (s, 9H), 1.34 (m, 2H), 0.93 (t, J=7.5 Hz, 3H).

Example 107

3-(2-tert-Butyl-3-{[(2-ethyl-butyl)-methyl-amino]-methyl}-imidazo[1,2-a]pyridin-7-yl)-N-hydroxy-acrylamide (compound 107)

The titled compound was prepared according to the procedures described in Example 85 by using appropriate starting materials. HPLC: 99%; $t_R$=1.454 min; LCMS (ESI) m/z 387 [MH]$^+$; $^1$H NMR (CD$_3$OD): δ 8.78 (d, J=7.3 Hz, 1H), 7.86 (s, 1H), 7.66-7.62 (m, 2H), 6.77 (d, J=15.7 Hz, 1H), 4.89-4.74 (m, 2H), 4.41 (s, 2H), 2.60 (s, 2H), 2.49 (s, 3H) 1.53 (s, 9H), 1.32-1.20 (m, 4H), 0.75 (t, J=7.5 Hz, 6H).

Example 108

3-(2-tert-Butyl-3-{[methyl-(3-methyl-butyl)-amino]-methyl}-imidazo[1,2-a]pyridin-7-yl)-N-hydroxy-acrylamide (compound 108)

The titled compound was prepared according to the procedures described in Example 85 by using appropriate starting materials. HPLC: 99%; $t_R$=1.141 min; LCMS (ESI) m/z 373 [MH]$^+$.

Example 109

3-(2-tert-Butyl-3-{[(3,3-dimethyl-butyl)-methyl-amino]-methyl}-imidazo[1,2-a]pyridin-7-yl)-N-hydroxy-acrylamide (compound 109)

The titled compound was prepared according to the procedures described in Example 85 by using appropriate starting materials. HPLC: 99%; $t_R$=1.360 min; LCMS (ESI) m/z 387 [MH]$^+$.

Example 110

3-(3-{[(2,2-Dimethyl-propyl)-propyl-amino]-methyl}-2-methyl-imidazo[1,2a]pyridin-7-yl)-N-hydroxy-acrylamide (compound 110)

The titled compound was prepared according to the procedures described in Example 85 by using appropriate starting materials. HPLC: 99%; $t_R$=0.816 min; LCMS (ESI) m/z 359 [MH]$^+$; $^1$H NMR (CD$_3$OD): δ 8.71 (d, J=7.2 Hz, 1H), 7.99 (s, 1H), 7.72-7.65 (m, 2H), 6.80 (d, J=15.7 Hz, 1H), 4.90

(masked peaks, 2H), 2.73 (brs, 2H), 2.59 (s, 3H), 2.43 (brs, 2H), 1.76-1.74 (m, 2H), 0.95 (t, J=7.2 Hz, 3H), 0.72 (s, 9H).

Example 111

3-(3-{[(2,2-Dimethyl-propyl)-ethyl-amino]-methyl}-2-methyl-imidazo[1,2a]pyridin-7-yl)-N-hydroxy-acrylamide (compound 111)

The titled compound was prepared according to the procedures described in Example 85 by using appropriate starting materials. HPLC: 99%; $t_R$=0.623 min; LCMS (ESI) m/z 345 [MH]$^+$; $^1$H NMR (CD$_3$OD): δ 8.72 (d, J=7.2 Hz, 1H), 7.94 (s, 1H), 7.66-7.71 (m, 2H), 6.80 (d, J=15.7 Hz, 1H), 4.84 (masked peaks, 2H), 4.28 (brs, 2H), 2.96 (brs, 2H), 2.61 (s, 3H), 1.30 (t, J=4 Hz, 3H), 0.79 (s, 9H).

Example 112

3-{2-Butyl-3-[(ethyl-isobutyl-amino)-methyl]-imidazo[1,2-a]pyridin-7-yl}-N-hydroxy-acrylamide (compound 112)

The titled compound was prepared according to the procedures described in Example 85 by using appropriate starting materials. HPLC: 99%; $t_R$=1.078 min; LCMS (ESI) m/z 373 [MH]$^+$; $^1$H NMR (CD$_3$OD): δ 8.64 (d, J=7.2 Hz, 1H), 7.85 (s, 1H), 7.63-7.57 (m, 2H), 6.72 (d, J=15.7 Hz, 1H), 4.47 (brs, 2H), 3.00 (brs, 2H), 2.89 (t, J=8.1 Hz, 2H), 1.95 (brs, 1H) 1.74 (q, J=7.6 Hz, 2H), 1.41 (q, J=7.6 Hz, 2H), 1.25-1.23 (m, 3H), 0.96-0.87 (m, 9H).

Example 113

3-(2-Butyl-3-{[ethyl-(2-methyl-pentyl)-amino]-methyl}-imidazo[1,2-a]pyridin-7-yl)-N-hydroxy-acrylamide (compound 113)

The titled compound was prepared according to the procedures described in Example 85 by using appropriate starting materials. HPLC: 99%; $t_R$=1.338 min; LCMS (ESI) m/z 387 [MH]$^+$; $^1$H NMR (CD$_3$OD): δ 8.61 (d, J=7.1 Hz, 1H), 7.83 (s, 1H), 7.63-7.55 (m, 2H), 6.72 (d, J=15.8 Hz, 1H), 4.91-4.66 (masked peaks, 2H), 2.95 (brs, 2H), 2.88 (t, J=8.1 Hz, 2H), 1.73 (q, J=7.5 Hz, 4H), 1.43-1.36 (m, 4H), 1.23 (masked peaks, 3H), 1.10-1.00 (m, 1H), 0.92 (t, J=7.3 Hz, 3H), 0.82-0.77 (m, 6H).

Example 114

3-(2-Butyl-3-{[ethyl-(3-methyl-butyl)-amino]-methyl}-imidazo[1,2-a]pyridin-7-yl)-N-hydroxy-acrylamide (compound 114)

The titled compound was prepared according to the procedures described in Example 85 by using appropriate starting materials. HPLC: 99%; $t_R$=1.428 min; LCMS (ESI) m/z 387 [MH]$^+$; $^1$H NMR (CD$_3$OD): δ 8.58 (d, J=7.1 Hz, 1H), 7.82 (s, 1H), 7.60 (d, J=15.7 Hz, 1H), 7.51 (d, J=6.0 Hz, 1H), 6.69 (d, J=15.7 Hz, 1H), 4.83-4.71 (masked peaks, 2H), 3.30-3.19 (m, 4H), 3.20-3.00 (m, 2H), 2.89 (t, J=7.8 Hz, 1H) 1.90-1.70 (m, 2H), 1.61-1.50 (m, 3H), 1.43 (q, J=7.6 Hz, 2H), 1.32 (t, J=7.2 Hz, 3H), 0.97-0.90 (m, 9H).

Example 115

3-(2-Butyl-3-{[(2,2-dimethyl-propyl)-ethyl-amino]-methyl}-imidazo[1,2-a]pyridin-7-yl)-N-hydroxy-acrylamide (compound 115)

The titled compound was prepared according to the procedures described in Example 85 by using appropriate starting materials. HPLC: 90.41%; $t_R$=1.344 min; LCMS (ESI) m/z 387 [MH]$^+$; $^1$H NMR (CD$_3$OD): δ 8.80-8.60 (m, 1H), 7.90 (s, 1H), 7.80-7.65 (m, 2H), 6.73 (d, J=15.7 Hz, 1H), 4.88-4.73 (masked peaks, 2H), 3.98 (brs, 2H), 2.90 (t, J=7.8 Hz, 2H), 2.75 (brs, 2H), 1.73 (q, J=7.4 Hz, 2H), 1.41 (q, J=7.6 Hz, 2H), 1.20 (m, 3H), 0.95 (t, J=7.4 Hz, 3H), 0.61 (brs, 9H).

Example 116

3-(2-Butyl-3-{[ethyl-(2-methyl-pentyl)-amino]-methyl}-imidazo[1,2-a]pyridin-7-yl)-N-hydroxy-acrylamide (compound 116)

The titled compound was prepared according to the procedures described in Example 85 by using appropriate starting materials. HPLC: 99%; $t_R$=1.638 min; LCMS (ESI) m/z 401 [MH]$^+$; $^1$H NMR (CD$_3$OD): δ 8.70 (d, J=7.3 Hz, 1H), 7.89 (s, 1H), 7.68-7.57 (m, 2H), 6.72 (d, J=15.7 Hz, 1H), 4.40 (s, 2H), 3.10-3.00 (m, 2H), 2.89 (t, J=7.5 Hz, 2H), 2.40-2.80 (m, 2H), 1.73 (q, J=7.8 Hz, 2H), 1.42 (q, J=7.6 Hz, 2H), 1.27-1.23 (m, 7H), 0.93 (t, J=7.4 Hz, 4H), 0.84-0.77 (m, 6H).

Example 117

3-(2-Butyl-3-{[(3,3-dimethyl-butyl)-ethyl-amino]-methyl}-imidazo[1,2-a]pyridin-7-yl)-N-hydroxy-acrylamide (compound 117)

The titled compound was prepared according to the procedures described in Example 85 by using appropriate starting materials. HPLC: 99%; $t_R$=1.630 min; LCMS (ESI) m/z 401 [MH]$^+$; $^1$H NMR (CD$_3$OD): δ 8.71 (d, J=7.8 Hz, 1H), 7.91 (s, 1H), 7.67-7.58 (m, 2H), 6.73 (d, J=15.7 Hz, 1H), 4.89-4.74 (masked peaks, 2H), 2.93 (t, J=7.7 Hz, 2H), 1.77 (m, 2H), 1.68 (m, 2H), 1.44 (q, J=7.6 Hz, 2H), 1.33 (t, J=7.2 Hz, 2H), 0.99-0.89 (m, 12H).

Example 118

3-(2-Butyl-3-{[ethyl-(2-ethyl-butyl)-amino]-methyl}-imidazo[1,2-a]pyridin-7-yl)-N-hydroxy-acrylamide (compound 118)

The titled compound was prepared according to the procedures described in Example 85 by using appropriate starting materials. HPLC: 96.23%; $t_R$=1.586 min; LCMS (ESI) m/z 401 [MH]$^+$; $^1$H NMR (CD$_3$OD): δ 8.64 (d, J=7.2 Hz, 1H), 7.90 (s, 1H), 7.64-7.55 (m, 2H), 6.73 (d, J=15.7 Hz, 1H), 4.36 (brs, 2H), 2.89 (t, J=7.5 Hz, 2H), 1.73 (q, J=7.8 Hz, 2H), 1.41 (q, J=7.6 Hz, 2H), 1.30-1.25 (m, 4H), 0.95 (t, J=7.4 Hz, 3H), 0.75-0.72 (m, 6H).

Example 119

3-(2-Butyl-3-{[ethyl-(3,55-trimethyl-hexyl)-amino]-methyl}-imidazo[1,2-a]pyridin-7-yl)-N-hydroxy-acrylamide (compound 119)

The titled compound was prepared according to the procedures described in Example 85 by using appropriate starting materials. HPLC: 96.82%; $t_R$=2.298 min; LCMS (ESI) m/z 443 [MH]$^+$; $^1$H NMR (CD$_3$OD): δ 8.72 (d, J=7.6 Hz, 1H), 7.90 (s, 1H), 7.62-7.53 (m, 2H), 6.72 (d, J=15.7 Hz, 1H), 4.84-4.74 (masked peaks, 2H), 2.92 (m, 2H), 1.80-1.60 (m, 4H), 1.60-1.50 (m, 2H), 1.44 (q, J=7.6 Hz, 2H), 1.36 (t, J=7.2 Hz, 3H), 0.96-0.88 (m, 5H), 0.84 (s, 9H).

Example 120

3-{3-[(Butyl-ethylamino)-methyl]-2-phenyl-imidazo[1,2-a]pyridin-7-yl}-N-hydroxy-acrylamide (compound 120)

The titled compound was prepared according to the procedures described in Example 85 by using appropriate starting materials. HPLC: 99%; $t_R$=1.237 min; LCMS (ESI) m/z 393 [MH]$^+$.

Example 121

3-(3-{[Ethyl-(3-methyl-butyl)-amino]-methyl}-2-phenyl-imidazo[1,2-a]pyridin-7-yl)-N-hydroxy-acrylamide (compound 121)

The titled compound was prepared according to the procedures described in Example 85 by using appropriate starting materials. HPLC: 99%; $t_R$=1.434 min; LCMS (ESI) m/z 407 [MH]$^+$.

Example 122

3-(3-{[(3,3-Dimethyl-butyl)-ethyl-amino]-methyl}-2-phenyl-imidazo[1,2-a]pyridin-7-yl)-N-hydroxy-acrylamide (compound 122)

The titled compound was prepared according to the procedures described in Example 85 by using appropriate starting materials. HPLC: 99%; $t_R$=1.646 min; LCMS (ESI) m/z 421 [MH]$^+$.

Example 123

3-[3-(tert-Butylamino-methyl)-2-propyl-imidazo[1,2-a]pyridin-7-yl]-N-hydroxy-acrylamide (compound 123)

The titled compound was prepared according to the procedures described in Example 42 by using appropriate starting materials. HPLC: 99%; LC-MS (ESI) m/z 331 [MH]$^+$; $^1$H NMR (CD$_3$OD) δ 8.71 (d, J=7.1 Hz, 1H), 7.97 (s, 1H), 7.73 (d, J=6.8 Hz, 1H), 7.63 (d, J=15.7 Hz, 1H), 6.78 (d, J=15.7 Hz, 1H), 4.78 (s, 2H), 2.98 (t, 2H), 1.90-1.84 (m, 2H), 1.59 (brs, 9H), 1.10 (t, 3H).

Example 124

3-(3-{[Ethyl-(3-methyl-butyl)-amino]-methyl}-2-methyl-imidazo[1,2a]pyridin-7-yl)-N-hydroxy-acrylamide (compound 124)

The titled compound was prepared according to the procedures described in Example 85 by using appropriate starting materials. HPLC: 99%; $t_R$=0.622 min; LCMS (ESI) m/z 345 [MH]$^+$; $^1$H NMR (CD$_3$OD): δ 8.72 (brs, 1H), 7.92 (s, 1H), 7.70-7.60 (m, 2H), 6.78 (d, J=14.5 Hz, 1H), 4.84 (masked peaks, 2H), 3.30-3.24 (m, 4H), 2.61 (s, 3H), 1.66-1.59 (m, 3H), 1.37-1.24 (m, 3H), 0.95-0.90 (m, 6H).

Example 125

3-(3-{[(3,3-Dimethyl-butyl)-ethyl-amino]-methyl}-2-methyl-imidazo[1,2-a]pyridin-7-yl)-N-hydroxy-acrylamide (compound 125)

The titled compound was prepared according to the procedures described in Example 85 by using appropriate starting materials. HPLC: 94.31%; $t_R$=1.176 min; LCMS (ESI) m/z 359 [MH]$^+$; $^1$H NMR (CD$_3$OD): δ 8.66 (brs, 1H), 7.90 (s, 1H), 7.69-7.62 (m, 2H), 6.77 (d, J=15.7 Hz, 1H), 4.75 (masked peaks, 2H), 3.27-3.20 (m, 4H), 2.56 (d, J=1.0 Hz, 3H), 1.63-1.62 (m, 2H), 1.32-1.24 (m, 3H), 0.91 (s, 9H).

Example 126

3-(3-{[Ethyl-(3-methyl-butyl)-amino]-methyl}-2-propyl-imidazo[1,2-a]pyridin-7-yl)-N-hydroxy-acrylamide (compound 126)

The titled compound was prepared according to the procedures described in Example 85 by using appropriate starting materials. HPLC: 95.68%; LCMS (ESI) m/z 373 [MH]$^+$; $^1$H NMR (CD$_3$OD) δ 8.70 (d, J=7.3 Hz, 1H), 7.92 (s, 1H), 7.68 (d, J=15.7 Hz, 1H), 7.63 (dd, J=1.4, 7.2 Hz, 1H), 6.78 (d, J=15.7 Hz, 1H), 2.95 (t, 2H), 1.94-1.82 (m, 2H), 1.70-1.62 (brs, 3H), 1.39 (t, 3H), 1.08 (t, 3H), 0.98 (t, 9H).

Example 127

3-(3-{[(3,3-Dimethyl-butyl)-ethyl-amino]-methyl}-2-propyl-imidazo[1,2-a]pyridin-7-yl)-N-hydroxy-acrylamide (compound 127)

The titled compound was prepared according to the procedures described in Example 85 by using appropriate starting materials. HPLC: 95.13%; LCMS (ESI) m/z 387 [MH]$^+$; $^1$H NMR (CD$_3$OD) δ 8.71 (d, J=7.1 Hz, 1H), 7.92 (s, 1H), 7.68 (d, J=15.7 Hz, 1H), 7.63 (dd, J=7.3 Hz, 1H), 6.78 (d, J=15.7 Hz, 1H), 2.96 (t, 2H), 1.91-1.85 (m, 2H), 1.73-1.69 (m, 2H), 1.38 (t, 3H), 1.08 (t, 3H), 0.99 (t, 10H).

Example 128

3-[3-(tert-Butylamino-methyl)-2-pentyl-imidazo[1,2-a]pyridin-7-yl]-N-hydroxy-acrylamide (compound 128)

The titled compound was prepared according to the procedures described in Example 42 by using appropriate starting materials. HPLC: 89.81%; $t_R$=1.192 min; LCMS (ESI) m/z 359 [MH]$^+$; $^1$H NMR (CD$_3$OD): δ 8.56 (brs, 1H), 7.86 (s, 1H), 7.61-7.57 (m, 2H), 6.69 (d, J=15.8 Hz, 1H), 4.70 (s, 2H), 2.90 (t, J=8.1 Hz, 2H), 1.77 (brs, 2H), 1.51 (s, 9H), 1.42-1.35 (m, 4H), 0.90 (t, J=7.2 Hz, 3H).

Example 129

3-{3-[(Butyl-ethyl-amino)-methyl]-2-pentyl-imidazo[1,2-a]pyridin-7-yl}-N-hydroxy-acrylamide (compound 129)

The titled compound was prepared according to the procedures described in Example 85 by using appropriate starting materials. HPLC: 95.63%; $t_R$=1.451 min; LCMS (ESI) m/z 387 [MH]⁺; ¹H NMR (CD₃OD): δ 8.60 (d, J=7.2 Hz, 1H), 7.83 (s, 1H), 7.65-7.53 (m, 2H), 6.69 (d, J=15.7 Hz, 1H), 4.87-4.72 (masked peaks, 2H), 3.18-3.00 (m, 2H), 2.88 (t, J=8.0 Hz, 2H), 1.76-1.60 (m, 5H), 1.37-1.29 (m, 10H), 0.94-0.86 (m, 6H).

Example 130

3-(3-{[Ethyl-(3-methyl-butyl)-amino]-methyl}-2-pentyl-imidazo[1,2-a]pyridin-7-yl)-N-hydroxy-acrylamide (compound 130)

The titled compound was prepared according to the procedures described in Example 85 by using appropriate starting materials. HPLC: 94.84%; $t_R$=1.681 min; LCMS (ESI) m/z 401 [MH]⁺; ¹H NMR (CD₃OD): δ 8.61 (d, J=7.3 Hz, 1H), 7.84 (s, 1H), 7.62 (d, J=8.2 Hz, 2H), 6.72 (d, J=15.7 Hz, 1H), 3.20-3.19 (m, 2H), 2.90 (t, J=8.0 Hz, 2H), 1.80-1.77 (m, 2H), 1.63-1.55 (m, 2H), 1.39-1.37 (m, 4H), 1.33 (t, J=7.2 Hz, 4H), 0.95-0.88 (m, 9H).

Example 131

3-(3-{[(3,3-Dimethyl-butyl)-ethyl-amino]-methyl}-2-pentyl-imidazo[1,2a]pyridin-7-yl)-N-hydroxy-acrylamide (compound 131)

The titled compound was prepared according to the procedures described in Example 85 by using appropriate starting materials. HPLC: 94.41%; $t_R$=1.871 min; LCMS (ESI) m/z 415 [MH]⁺; ¹H NMR (CD₃OD): δ 8.62 (d, J=7.2 Hz, 1H), 7.87 (s, 1H), 7.61 (d, J=15.8 Hz, 1H), 7.55 (d, J=7.1 Hz, 1H), 6.74 (d, J=15.9 Hz, 1H), 4.84-4.74 (masked peaks, 2H), 3.21-3.19 (m, 2H), 2.91 (t, J=7.8 Hz, 2H), 1.88-1.77 (m, 2H), 1.66-1.62 (m, 4H), 1.49-1.30 (m, 7H), 1.03-0.85 (m, 12H).

Example 132

3-{3-[(Butyl-ethylamino)-methyl]-2-propyl-imidazo[1,2-a]pyridin-7-yl}-N-hydroxy-acrylamide (compound 132)

The titled compound was prepared according to the procedures described in Example 85 by using appropriate starting materials. HPLC: 96.93%; LCMS (ESI) m/z 359 [MH]⁺; ¹H NMR (CD₃OD) δ 8.71 (d, J=7.2 Hz, 1H), 7.93 (s, 1H), 7.67 (d, J=15.7 Hz, 1H), 7.63 (brs, 1H), 6.79 (d, J=15.7 Hz, 1H), 3.24-3.22 (m, 2H), 2.96 (t, 2H), 1.90-1.84 (m, 2H), 1.82-1.72 (m, 3H), 1.55-1.30 (m, 8H), 1.08 (t, 3H), 1.02-0.96 (m, 5H).

Example 133

3-[3-(tert-Butylamino-methyl)-2-isobutyl-imidazo[1,2-a]pyridin-7-yl]-N-hydroxy-acrylamide (compound 133)

The titled compound was prepared according to the procedures described in Example 42 by using appropriate starting materials. HPLC: 99%; $t_R$=0.716 min; LCMS (ESI) m/z 345 [MH]⁺; ¹H NMR (CD₃OD): δ 8.64 (d, J=7.0 Hz, 1H), 7.93 (s, 1H), 7.58-7.67 (m, 2H), 6.73 (d, J=15.8 Hz, 1H), 4.74 (s, 2H), 2.86 (d, J=7.3 Hz, 2H), 2.17-2.21 (m, 1H), 1.58 (s, 9H), 1.04 (d, J=6.6 Hz, 6H).

Example 134

3-{3-[(Butyl-ethyl-amino)-methyl]-2-isobutyl-imidazo[1,2-a]pyridin-7-yl}-N-hydroxy-acrylamide (compound 134)

The titled compound was prepared according to the procedures described in Example 85 by using appropriate starting materials. HPLC: 99%; $t_R$=0.934 min; LCMS (ESI) m/z 373 [MH]⁺; ¹H NMR (CD₃OD): δ 8.73 (s, 1H), 7.96 (s, 1H), 7.63-7.68 (m, 2H), 6.80 (d, J=15.7 Hz, 1H), 4.87 (masked peaks, 2H), 3.31 (masked peaks, 4H), 2.88 (d, J=7.1 Hz, 2H), 2.19-2.28 (m, 1H), 1.79 (brs, 2H), 1.34-1.51 (m, 5H), 0.98-1.10 (m, 9H).

Example 135

3-(3-{[Ethyl-(3-methyl-butyl)-amino]-methyl}-2-isobutyl-imidazo[1,2-a]pyridin-7-yl)-N-hydroxy-acrylamide (compound 135)

The titled compound was prepared according to the procedures described in Example 85 by using appropriate starting materials. HPLC: 99%; $t_R$=1.264 min; LCMS (ESI) m/z 387 [MH]⁺; ¹H NMR (CD₃OD): δ 8.74 (d, J=7.1 Hz, 1H), 7.95 (s, 1H), 7.63-7.67 (m, 2H), 6.80 (d, J=15.7 Hz, 1H), 4.87 (masked peaks, 2H), 3.31 (masked peaks, 4H), 2.88 (d, J=7.4 Hz, 2H), 2.19-2.26 (m, 1H), 1.65-1.72 (m, 3H), 1.39 (t, J=7.2 Hz, 3H), 0.93-0.97 (m, 12H).

Example 136

3-(3-{[(3,3-Dimethyl-butyl)-ethyl-amino]-methyl}-2-isobutyl-imidazo[1,2-a]pyridin-7-yl)-N-hydroxy-acrylamide (compound 136)

The titled compound was prepared according to the procedures described in Example 85 by using appropriate starting materials. HPLC: 99%; $t_R$=1.479 min; LCMS (ESI) m/z 401 [MH]⁺; ¹H NMR (CD₃OD): δ 8.74 (d, J=5.0 Hz, 1H), 7.95 (s, 1H), 7.64-7.68 (m, 2H), 6.79 (d, J=15.8 Hz, 1H), 4.87 (masked peaks, 2H), 3.31 (masked peaks, 4H), 2.88 (d, J=7.2 Hz, 2H), 2.21-2.24 (m, 1H), 1.74 (brs, 2H), 1.38 (t, J=6.9 Hz, 3H), 0.95-1.10 (m, 15H).

Example 137

3-[3-(tert-Butylamino-methyl)-2-ethyl-imidazo[1,2-a]pyridin-7-yl]-N-hydroxy-acrylamide (compound 137)

The titled compound was prepared according to the procedures described in Example 42 by using appropriate starting materials. HPLC: 99%; $t_R$=1.264 min; LCMS (ESI) m/z 317 [MH]⁺; ¹H NMR (CD₃OD): δ 8.64 (d, J=6.9 Hz, 1H), 7.94 (s, 1H), 7.66 (d, J=6.8 Hz, 1H), 7.61 (d, J=15.7 Hz, 1H), 6.73 (d, J=15.2 Hz, 1H), 4.78 (s, 2H), 3.00 (q, J=7.6 Hz, 2H), 1.58 (s, 9H), 1.44 (t, J=7.5 Hz, 3H).

Example 138

3-{3-[(Butyl-ethyl-amino)-methyl]-2-ethyl-imidazo[1,2-a]pyridin-7-yl}-N-hydroxy-acrylamide (compound 138)

The titled compound was prepared according to the procedures described in Example 85 by using appropriate starting materials. HPLC: 99%; $t_R$=0.405 min; LCMS (ESI) m/z 345 [MH]$^+$; $^1$H NMR (CD$_3$OD): δ 8.64 (d, J=7.2 Hz, 1H), 7.88 (s, 1H), 7.67 (d, J=15.7 Hz, 1H), 7.57 (d, J=7.0 Hz, 1H), 6.76 (d, J=16.2 Hz, 1H), 4.87 (masked peaks, 2H), 3.31 (masked peaks, 4H), 2.99 (q, J=7.5 Hz, 2H), 1.70-1.82 (m, 2H), 1.34-1.47 (m, 8H), 1.00 (t, J=7.3 Hz, 3H).

Example 139

3-(2-Ethyl-3-{[ethyl-(3-methyl-butyl)-amino]-methyl}-imidazo[1,2-a]pyridin-7-yl)-N-hydroxy-acrylamide (compound 139)

The titled compound was prepared according to the procedures described in Example 85 by using appropriate starting materials. HPLC: 99%; $t_R$=0.728 min; LCMS (ESI) m/z 359 [MH]$^+$; $^1$H NMR (CD$_3$OD): δ 8.70 (d, J=6.0 Hz, 1H), 7.92 (s, 1H), 7.61-7.67 (m, 2H), 6.78 (d, J=14.0 Hz, 1H), 4.87 (masked peaks, 2H), 3.31 (masked peaks, 4H), 3.01 (q, J=7.4 Hz, 2H), 1.60-1.70 (m, 3H), 1.38-1.46 (m, 6H), 0.98 (d, J=5.8 Hz, 6H).

Example 140

3-[3-(tert-Butylamino-methyl)-2-(3-methyl-butyl)-imidazo[1,2-a]pyridin-7-yl]-N-hydroxy-acrylamide (compound 140)

The titled compound was prepared according to the procedures described in Example 42 by using appropriate starting materials. HPLC: 99%; $t_R$=1.075 min; LCMS (ESI) m/z 359 [MH]$^+$ $^1$H NMR (CD$_3$OD): δ 8.65 (brs, 1H), 7.92 (s, 1H), 7.60-7.64 (m, 2H), 6.75 (d, J=14.0 Hz, 1H), 4.87 (masked peaks, 2H), 2.97 (brs, 2H), 1.73 (brs, 3H), 1.58 (s, 9H), 1.03 (d, J=5.8 Hz, 6H).

Example 141

3-[3-[(Butyl-ethyl-amino)-methyl]-2-(3-methyl-butyl)-imidazo[1,2a]pyridin-7-yl)-N-hydroxy-acrylamide (compound 141)

The titled compound was prepared according to the procedures described in Example 85 by using appropriate starting materials. HPLC: 99%; $t_R$=1.315 min; LCMS (ESI) m/z 387 [MH]$^+$; $^1$H NMR (CD$_3$OD): δ 8.69 (d, J=5.4 Hz, 1H), 7.91 (s, 1H), 7.61-7.65 (m, 2H), 6.77 (d, J=15.8 Hz, 1H), 4.87 (masked peaks, 2H), 3.31 (masked peaks, 4H), 2.97 (t, J=7.6 Hz, 2H), 1.70-1.83 (m, 5H), 1.36-1.48 (m, 5H), 0.96-1.09 (m, 9H).

Example 142

3-[3-{[Ethyl-(3-methyl-butyl)-amino]-methyl}-2-(3-methyl-butyl)-imidazo[1,2-a]pyridin-7-yl]-N-hydroxy-acrylamide (compound 142)

The titled compound was prepared according to the procedures described in Example 85 by using appropriate starting materials. HPLC: 99%; $t_R$=1.551 min; LCMS (ESI) m/z 401 [MH]$^+$; $^1$H NMR (CD$_3$OD): δ 8.68 (d, J=5.9 Hz, 1H), 7.90 (s, 1H), 7.59-7.63 (m, 2H), 6.78 (d, J=15.7 Hz, 1H), 4.87 (masked peaks, 2H), 3.31 (masked peaks, 4H), 2.97 (t, J=7.5 Hz, 2H), 1.69-1.78 (m, 6H), 1.40 (t, J=7.0 Hz, 3H), 0.93-1.04 (m, 12H).

Example 143

3-[3-{[(3,3-Dimethyl-butyl)-ethyl-amino]-methyl}-2-(3-methyl-butyl)-imidazo[1,2-a]pyridin-7-yl]-N-hydroxy-acrylamide (compound 143)

The titled compound was prepared according to the procedures described in Example 85 by using appropriate starting materials. HPLC: 99%; $t_R$=1.719 min; LCMS (ESI) m/z 415 [MH]$^+$; $^1$H NMR (CD$_3$OD): δ 8.70 (d, J=7.1 Hz, 1H), 7.91 (s, 1H), 7.60-7.65 (m, 2H), 6.77 (d, J=15.8 Hz, 1H), 4.87 (masked peaks, 2H), 3.31 (masked peaks, 4H), 2.98 (t, J=7.8 Hz, 2H), 1.70-1.78 (m, 5H), 1.40 (t, J=7.2 Hz, 3H), 1.00-1.05 (m, 15H).

Example 144

Preparation of 3-[3-(2-Diethylamino-ethyl)-2-phenyl-imidazo[1,2-a]pyridin-7-yl]-N-hydroxy-acrylamide (compound 144)

The intermediate XX was prepared according to the 2-steps procedure described in Example 39 by using appropriate starting materials. XX was then subjected to chlorination described below.

Step 1: Chlorination

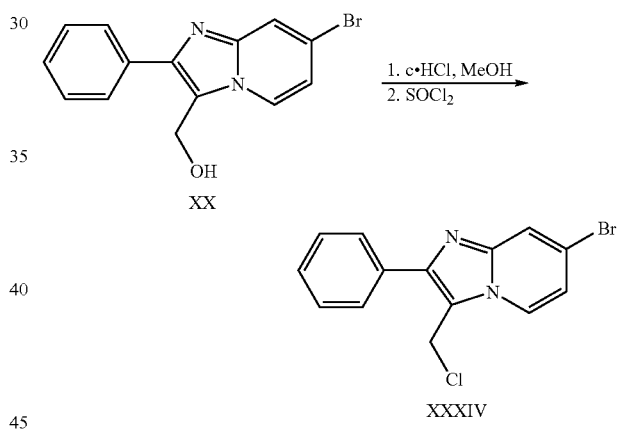

To a stirred solution of the alcohol XX (1.0 equiv.) in MeOH was added concentrated HCl (3 equiv.). Excess diethyl ether was then added and the solid formed was filtered and washed thoroughly by the former. The crude solid was dispersed in SOCl$_2$ and the solution was stirred at room temperature for 3 h. The mixture was then concentrated in vacuo and the residue obtained was washed with ethanol/ether solution. The solid obtained was dried under vacuum. The crude solid XXXIV was then used immediately for the next step.

Step 2: Cyanation and Cyano-Reduction

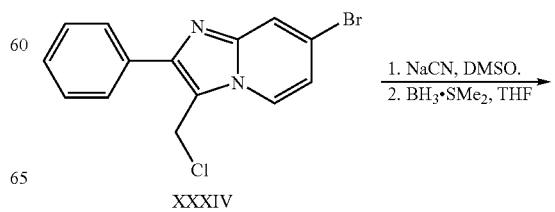

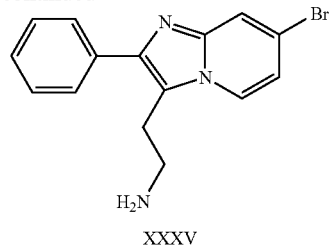

XXXV

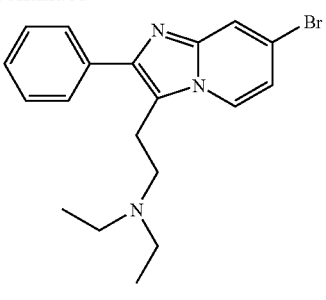

XXXVI

The crude solid XXXIV (1.0 equiv.) was dispersed in dry DMSO and this solution was added slowly to another stirred solution of NaCN (4.0 equiv.) in dry DMSO at 0° C. The temperature was brought up to room temperature slowly and the mixture was stirred for another 3 h. After the conclusion of the reaction, the solution was added into 3% NaHCO$_3$ aqueous solution. The mixture was extracted with ethyl acetate. After washing with water and brine, the organic contents were dried in anhydrous Na$_2$SO$_4$. The mixture was then filtered and concentrated. The crude product was then dispersed in dry THF before adding BH$_3$.SMe$_2$ (6.0 equiv.) at room temperature. The mixture was stirred for 5 h before being quenched with MeOH at 0° C. after the conclusion of the reaction. The mixture was then evaporated and subsequently, 1.0 N HCl was added till pH ~2.0 and the mixture was extracted with ethyl acetate. The aqueous layer was then basified with 1.0 N NaOH till pH ~8.0 and extracted with ethyl acetate. The combined organic layers were washed with brine and dried over anhydrous Na$_2$SO$_4$. The mixture was then filtered and concentrated. The crude solid XXXV was then used immediately for the next step.

Step 3: Reductive Amination

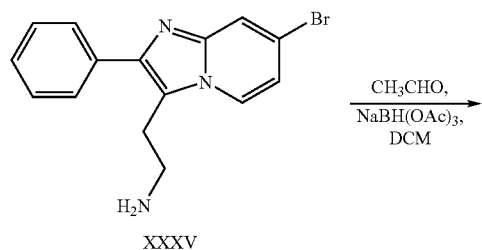

To a stirred suspension of XXXV (1.0 equiv.) in DCM was added NaBH(OAc)$_3$ (3.0 equiv.) and acetaldehyde (5.0 equiv.) at room temperature. The mixture was allowed to stir for 3 h. After the conclusion of the reaction, 1.0 N HCl was added till pH ~2 and the solvent was evaporated before extracting with ethyl acetate. The aqueous layer was then basified with 1.0 N NaOH till pH ~8.0 and extracted with ethyl acetate. The combined organic layers were washed with brine, dried over anhydrous Na$_2$SO$_4$, filtered and concentrated in vacuo. The crude product was purified by flash column chromatography.

For subsequent Heck reaction and hydroxamic acid formation, please refer to Step 2 from Example 42 and Step 4 from Example 17 respectively.

3-[3-(2-Diethylamino-ethyl)-2-phenyl-imidazo[1,2-a]pyridin-7-yl]-N-hydroxy-acrylamide (compound 144)

HPLC: 99.59%; t$_R$=0.462 min; LCMS (ESI) m/z 379 [MH]$^+$; $^1$H NMR (CD$_3$OD): δ 8.75 (s, 1H), 7.94 (s, 1H), 7.58-7.81 (m, 7H), 6.78 (d, J=15.8 Hz, 1H), 3.71 (t, J=7.9 Hz, 2H), 3.46 (t, J=83 Hz, 2H), 3.25 (masked peaks, 4H), 1.26 (t, J=7.2 Hz, 6H). The following compounds (Table 2) are some representative examples prepared by methods disclosed or analogous to those disclosed in above Examples 1-144:

TABLE 2

| Compound No. | Structure | m/z [MH]$^+$ |
|---|---|---|
| 1 | ![structure] | 489 |

TABLE 2-continued

| Compound No. | Structure | m/z [MH]+ |
|---|---|---|
| 2 | 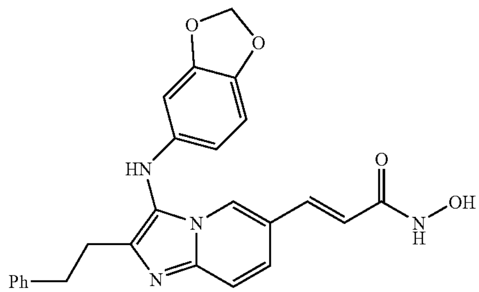 [SMILES: O=C(/C=C/c1ccc2nc(CCc3ccccc3)c(Nc3ccc4c(c3)OCO4)n2c1)NO] | 457 |
| 3 | 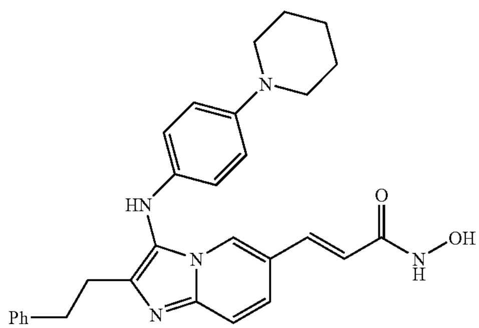 [SMILES: O=C(/C=C/c1ccc2nc(CCc3ccccc3)c(Nc3ccc(N4CCCCC4)cc3)n2c1)NO] | 482 |
| 4 | 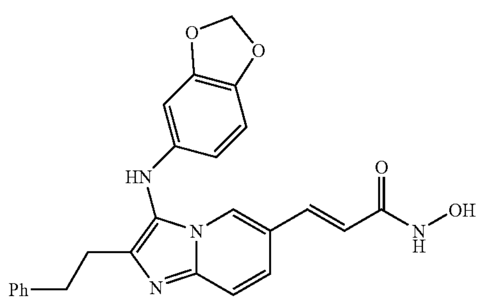 [SMILES: O=C(/C=C/c1ccc2nc(CCc3ccccc3)c(Nc3ccc4c(c3)OCO4)n2c1)NO] | 443 |
| 5 | 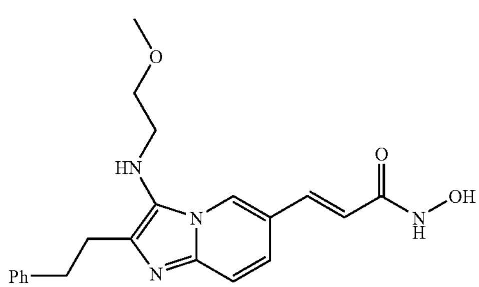 [SMILES: COCCNc1c(CCc2ccccc2)nc2ccc(/C=C/C(=O)NO)cn12] | 381 |
| 6 | 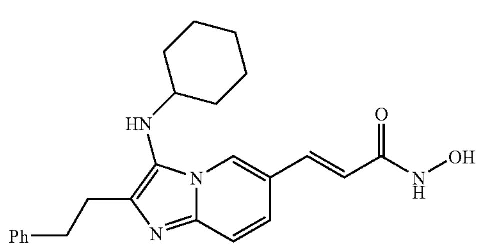 [SMILES: O=C(/C=C/c1ccc2nc(CCc3ccccc3)c(NC3CCCCC3)n2c1)NO] | 405 |

TABLE 2-continued

| Compound No. | Structure | m/z [MH]+ |
|---|---|---|
| 7 | 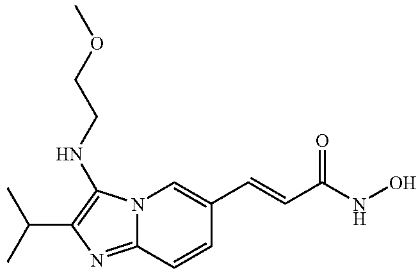 [SMILES: COCCNc1c(C(C)C)nc2ccc(/C=C/C(=O)NO)cn12] | 319 |
| 8 | 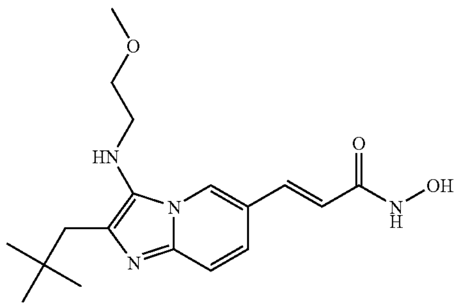 [SMILES: COCCNc1c(CC(C)(C)C)nc2ccc(/C=C/C(=O)NO)cn12] | 347 |
| 9 | 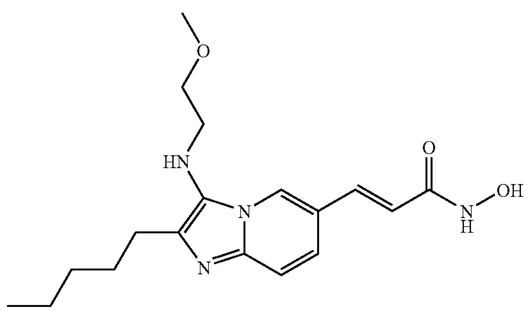 [SMILES: CCCCCc1nc2ccc(/C=C/C(=O)NO)cn2c1NCCOC] | 347 |
| 10 | 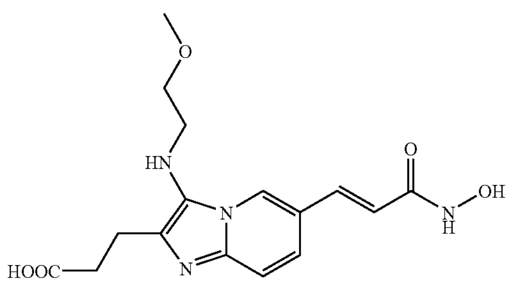 [SMILES: COCCNc1c(CCC(=O)O)nc2ccc(/C=C/C(=O)NO)cn12] | 350 |
| 11 | 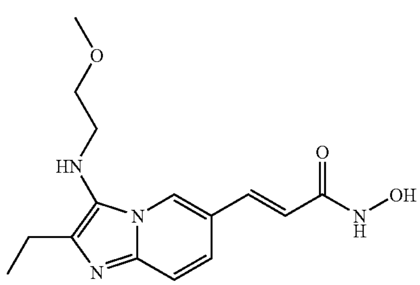 [SMILES: CCc1nc2ccc(/C=C/C(=O)NO)cn2c1NCCOC] | 305 |

TABLE 2-continued

| Compound No. | Structure | m/z [MH]+ |
|---|---|---|
| 12 | 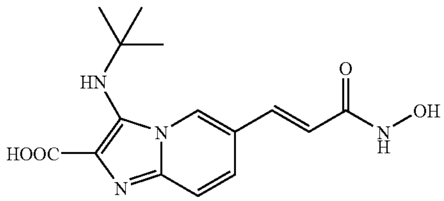 [SMILES: CC(C)(C)Nc1c(C(=O)O)nc2ccc(/C=C/C(=O)NO)cn12] | 274 (M − COOH]+ |
| 13 | 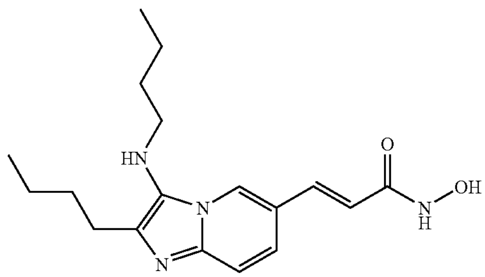 [SMILES: CCCCNc1c(CCCC)nc2ccc(/C=C/C(=O)NO)cn12] | 331 |
| 14 | 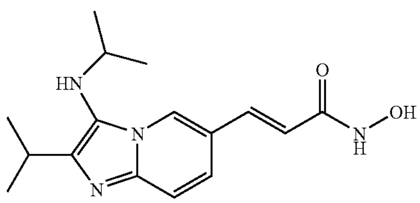 [SMILES: CC(C)Nc1c(C(C)C)nc2ccc(/C=C/C(=O)NO)cn12] | 303 |
| 15 | 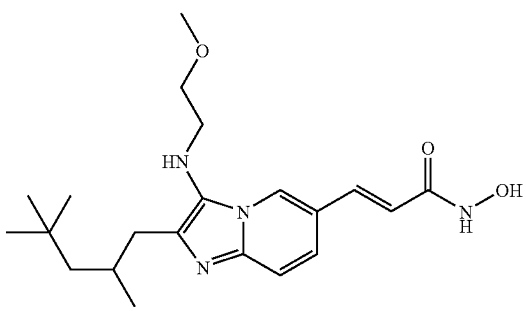 [SMILES: COCCNc1c(CC(C)CC(C)(C)C)nc2ccc(/C=C/C(=O)NO)cn12] | 389 |
| 16 | 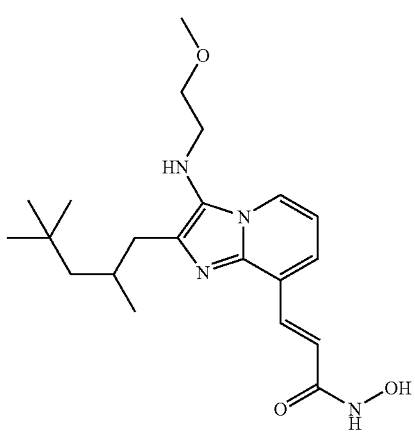 [SMILES: COCCNc1c(CC(C)CC(C)(C)C)nc2c(/C=C/C(=O)NO)cccn12] | 389 |

TABLE 2-continued
| Compound No. | Structure | m/z [MH]+ |
|---|---|---|
| 17 | 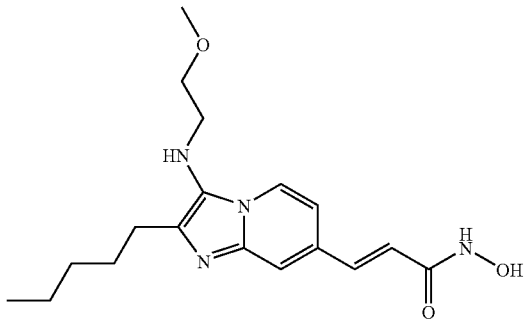 [SMILES: CCCCCc1nc2cc(/C=C/C(=O)NO)ccn2c1NCCOC] | 347 |
| 18 | 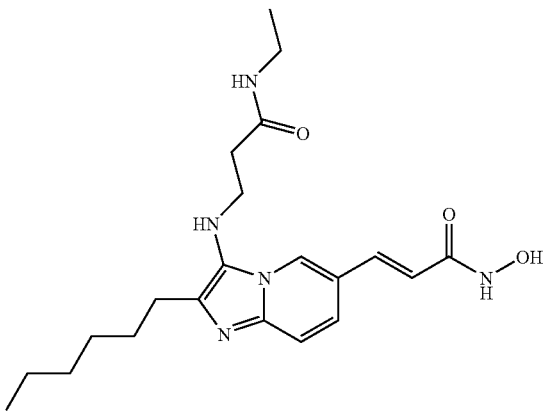 [SMILES: CCCCCCc1nc2ccc(/C=C/C(=O)NO)cn2c1NCCC(=O)NCC] | 402 |
| 19 | 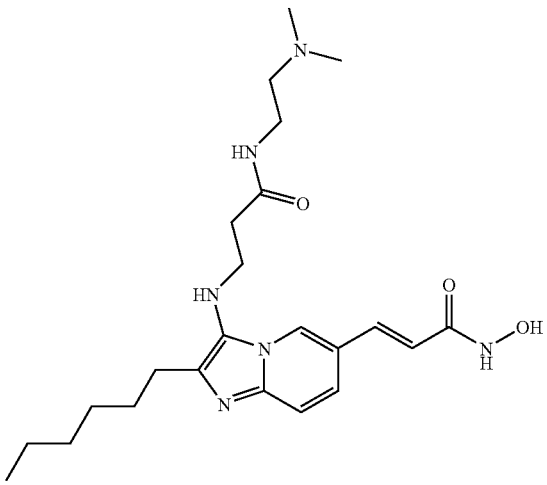 [SMILES: CCCCCCc1nc2ccc(/C=C/C(=O)NO)cn2c1NCCC(=O)NCCN(C)C] | 445 |

TABLE 2-continued
| Compound No. | Structure | m/z [MH]+ |
|---|---|---|
| 20 | 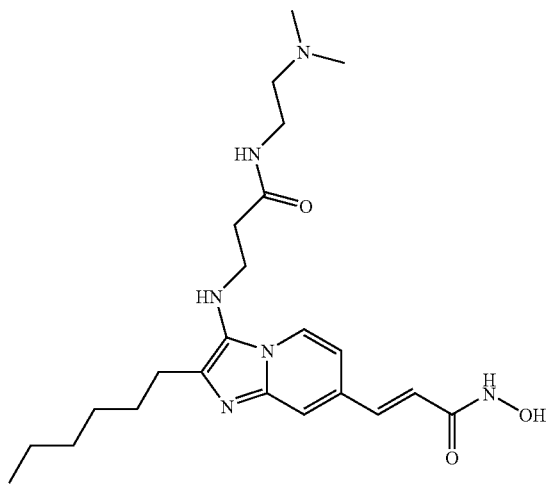 [SMILES: CCCCCCc1nc2cc(/C=C/C(=O)NO)ccn2c1NCCC(=O)NCCN(C)C] | 445 |
| 21 | 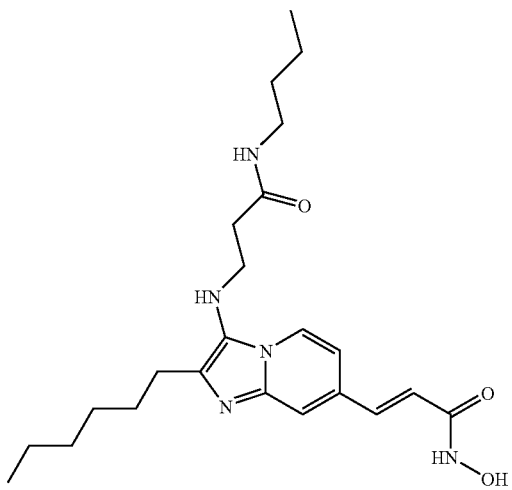 [SMILES: CCCCCCc1nc2cc(/C=C/C(=O)NO)ccn2c1NCCC(=O)NCCCC] | 430 |
| 22 | 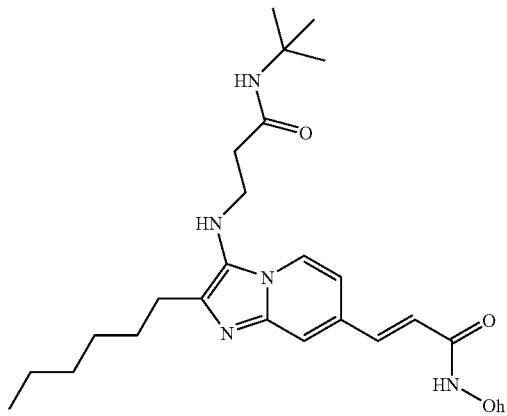 | 430 |

TABLE 2-continued
| Compound No. | Structure | m/z [MH]+ |
|---|---|---|
| 23 | 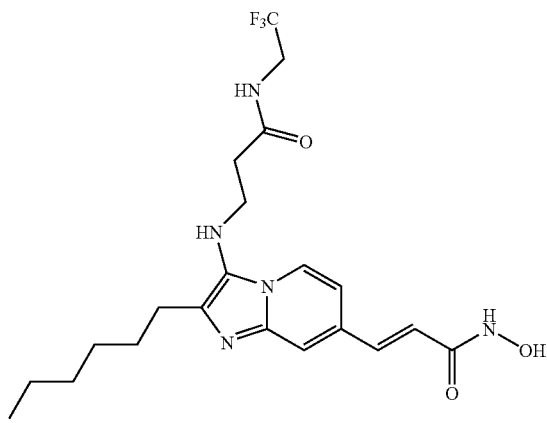 [SMILES: CCCCCCc1nc2cc(/C=C/C(=O)NO)ccn2c1NCCC(=O)NCC(F)(F)F] | 456 |
| 24 | 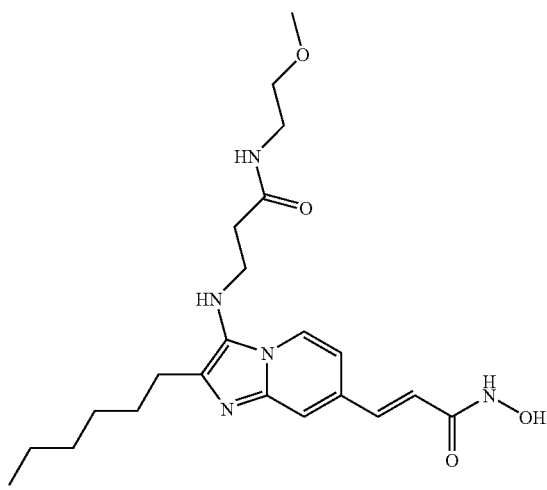 | 432 |
| 25 | 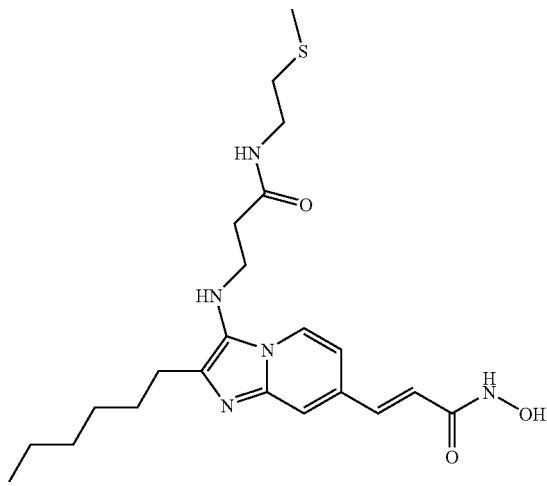 | 448 |

TABLE 2-continued

| Compound No. | Structure | m/z [MH]+ |
|---|---|---|
| 26 | 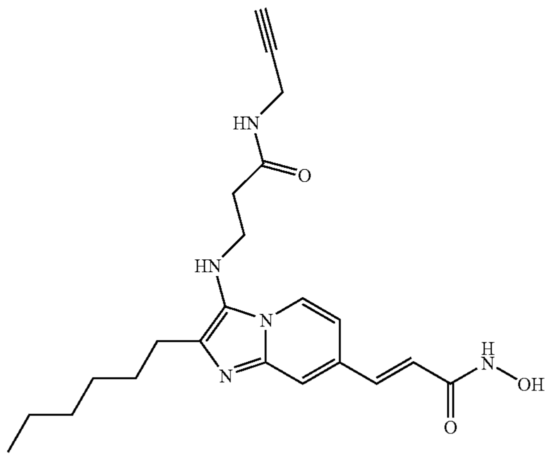 [SMILES: C#CCNC(=O)CCNc1c(CCCCCC)nc2cc(/C=C/C(=O)NO)ccn12] | 412 |
| 27 | 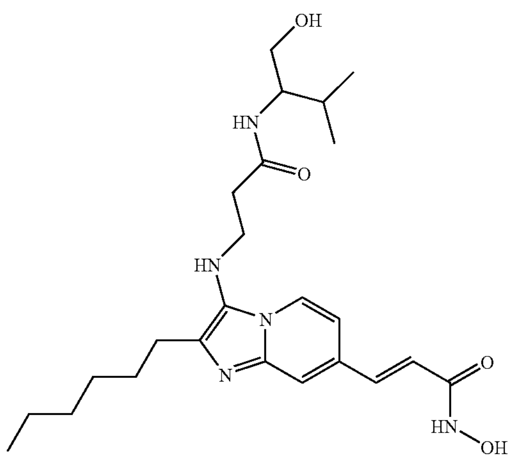 [SMILES: CCCCCCc1nc2cc(/C=C/C(=O)NO)ccn2c1NCCC(=O)NC(CO)C(C)C] | 460 |
| 28 | 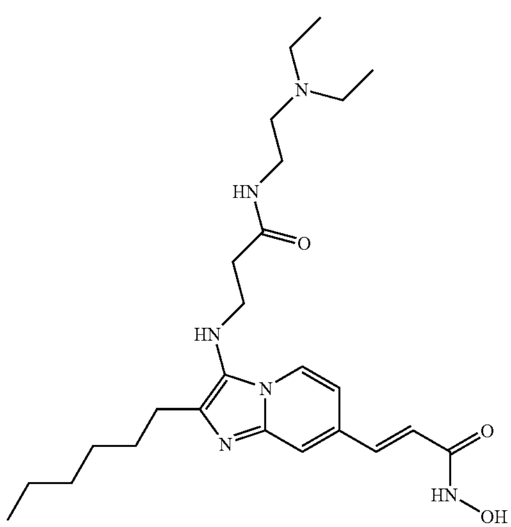 [SMILES: CCCCCCc1nc2cc(/C=C/C(=O)NO)ccn2c1NCCC(=O)NCCN(CC)CC] | 473 |

TABLE 2-continued
| Compound No. | Structure | m/z [MH]+ |
|---|---|---|
| 29 | 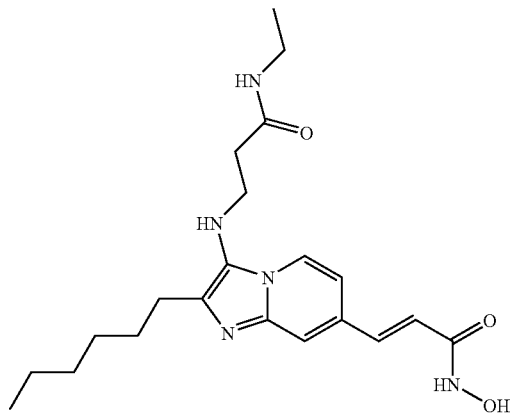 [SMILES: CCCCCCc1nc2cc(/C=C/C(=O)NO)ccn2c1NCCC(=O)NCC] | 402 |
| 30 | 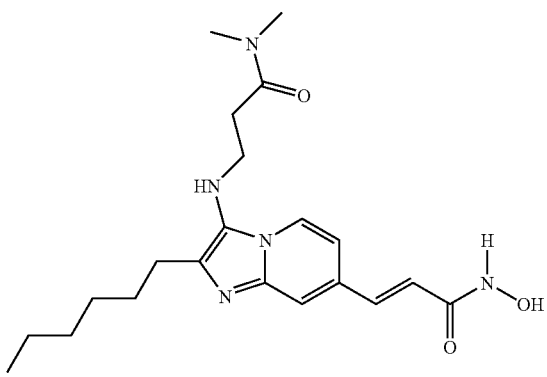 [SMILES: CCCCCCc1nc2cc(/C=C/C(=O)NO)ccn2c1NCCC(=O)N(C)C] | 402 |
| 31 | 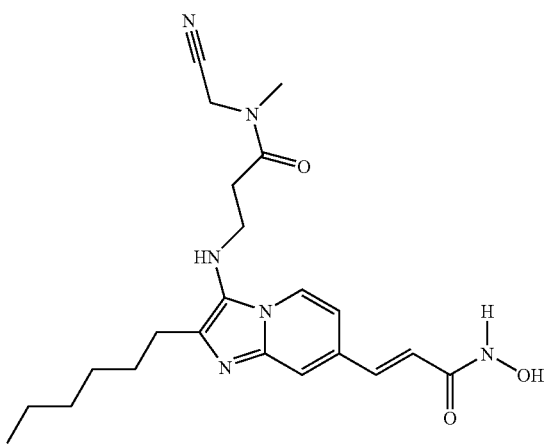 [SMILES: CCCCCCc1nc2cc(/C=C/C(=O)NO)ccn2c1NCCC(=O)N(C)CC#N] | 430 |

TABLE 2-continued

| Compound No. | Structure | m/z [MH]+ |
|---|---|---|
| 32 | 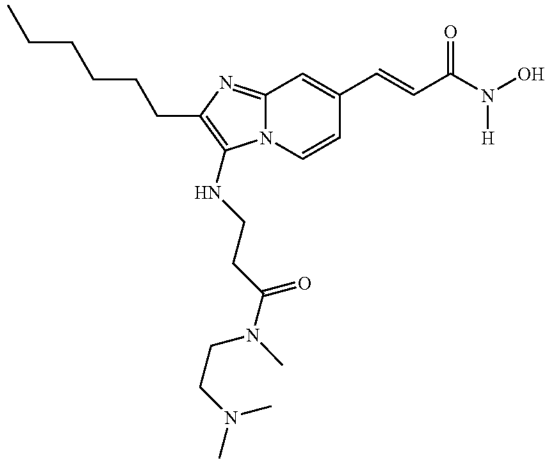 [SMILES: CCCCCCc1nc2cc(/C=C/C(=O)NO)ccn2c1NCCC(=O)N(C)CCN(C)C] | 459 |
| 33 | 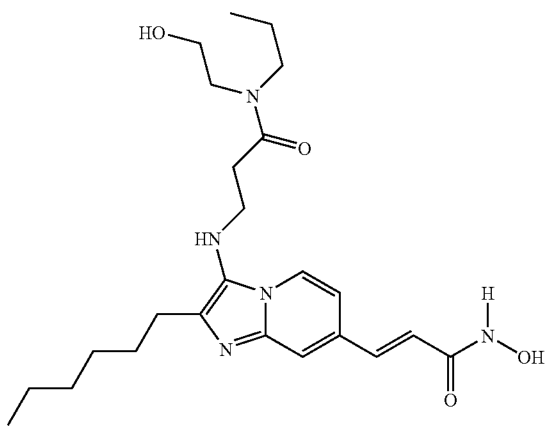 [SMILES: CCCCCCc1nc2cc(/C=C/C(=O)NO)ccn2c1NCCC(=O)N(CCC)CCO] | 460 |
| 34 | 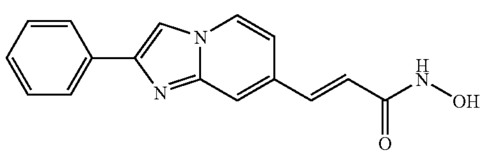 [SMILES: O=C(/C=C/c1ccn2cc(-c3ccccc3)nc2c1)NO] | 280 |
| 35 | 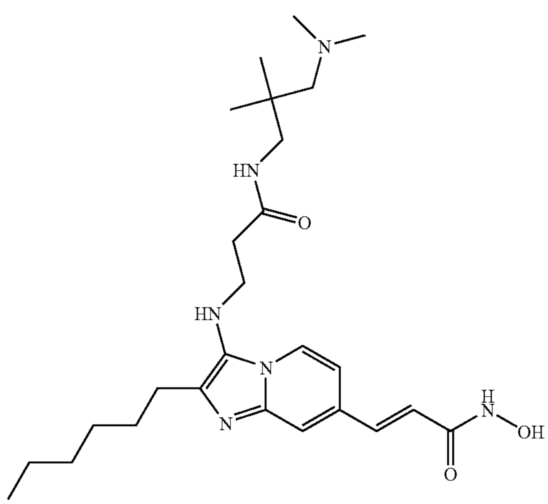 [SMILES: CCCCCCc1nc2cc(/C=C/C(=O)NO)ccn2c1NCCC(=O)NCC(C)(C)CN(C)C] | 487 |

TABLE 2-continued

| Compound No. | Structure | m/z [MH]+ |
|---|---|---|
| 36 | 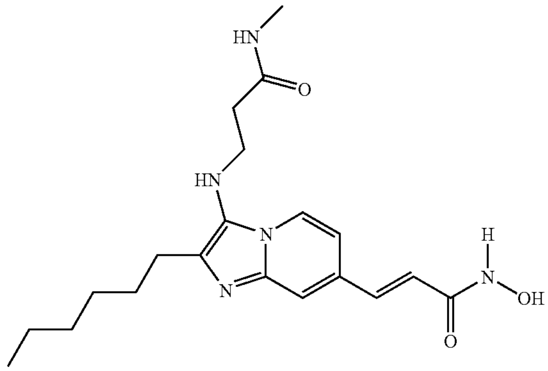 [SMILES: CCCCCCc1nc2cc(/C=C/C(=O)NO)ccn2c1NCCC(=O)NC] | 388 |
| 37 | 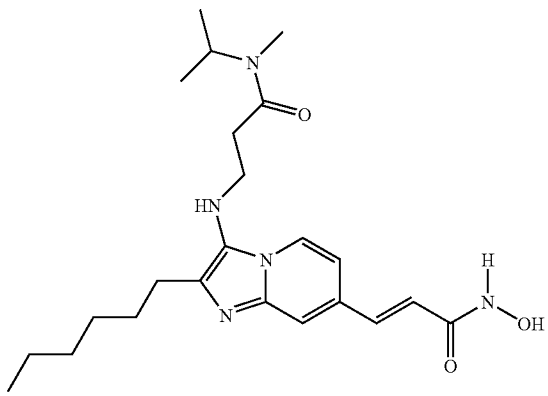 [SMILES: CCCCCCc1nc2cc(/C=C/C(=O)NO)ccn2c1NCCC(=O)N(C)C(C)C] | 430 |
| 38 | 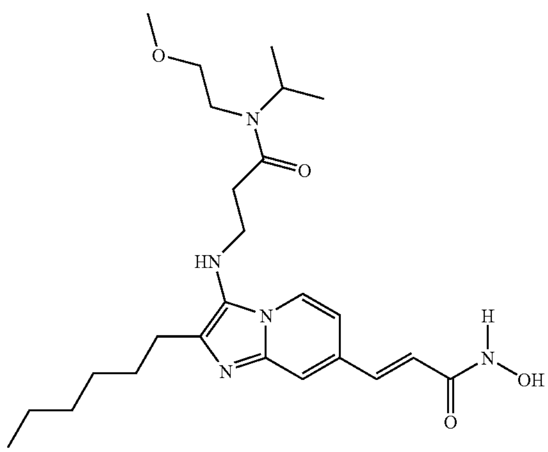 [SMILES: CCCCCCc1nc2cc(/C=C/C(=O)NO)ccn2c1NCCC(=O)N(CCOC)C(C)C] | 474 |
| 39 | 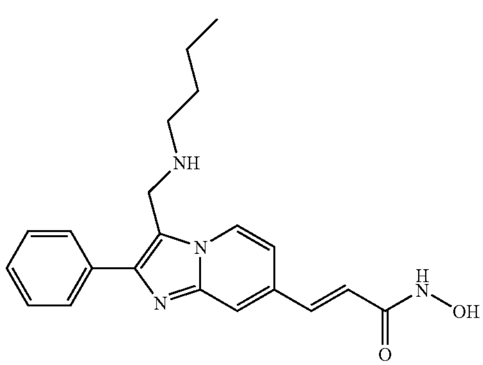 [SMILES: CCCCNCc1c(-c2ccccc2)nc2cc(/C=C/C(=O)NO)ccn12] | 365 |

TABLE 2-continued

| Compound No. | Structure | m/z [MH]+ |
|---|---|---|
| 40 | 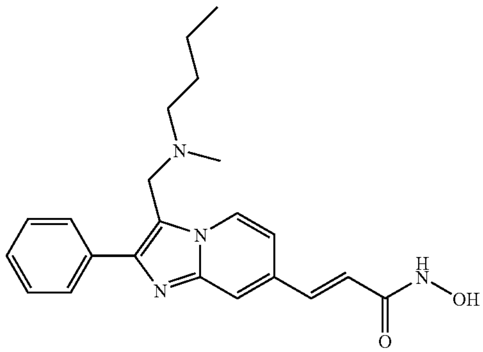 [SMILES: CCCCN(C)Cc1c(-c2ccccc2)nc2cc(/C=C/C(=O)NO)ccn12] | 365 |
| 41 | 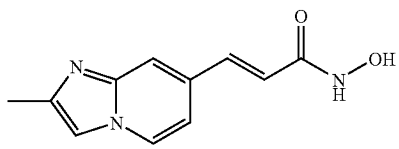 [SMILES: Cc1cn2ccc(/C=C/C(=O)NO)cc2n1] | 218 |
| 42 | 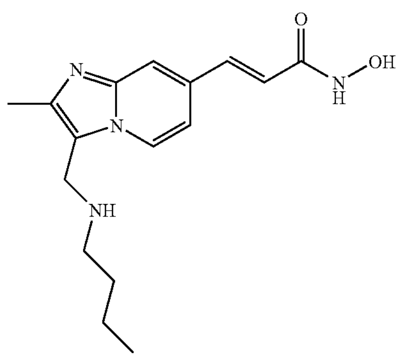 [SMILES: CCCCNCc1c(C)nc2cc(/C=C/C(=O)NO)ccn12] | 303 |
| 43 | 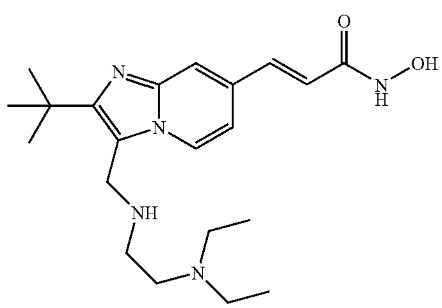 [SMILES: CCN(CC)CCNCc1c(C(C)(C)C)nc2cc(/C=C/C(=O)NO)ccn12] | 388 |
| 44 | 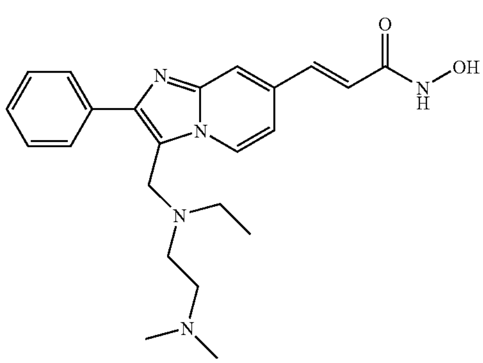 [SMILES: CCN(CCN(C)C)Cc1c(-c2ccccc2)nc2cc(/C=C/C(=O)NO)ccn12] | 408 |

TABLE 2-continued

| Compound No. | Structure | m/z [MH]+ |
|---|---|---|
| 45 | 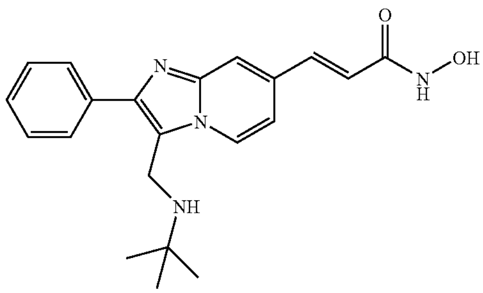 [SMILES: CC(C)(C)NCc1c(-c2ccccc2)nc2cc(/C=C/C(=O)NO)ccn12] | 365 |
| 46 | 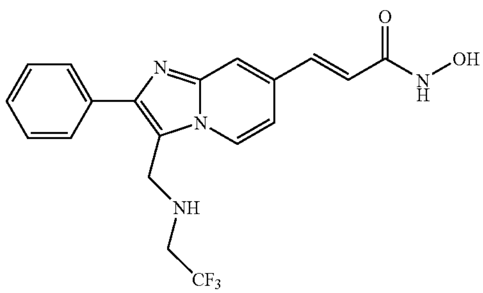 [SMILES: O=C(/C=C/c1ccn2c(CNCC(F)(F)F)c(-c3ccccc3)nc2c1)NO] | 391 |
| 47 | 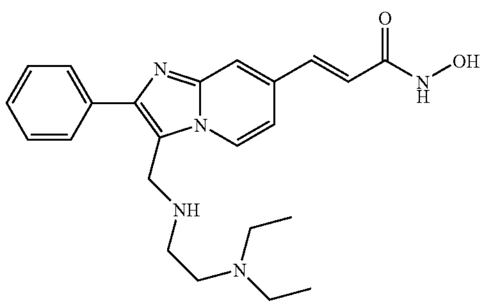 [SMILES: CCN(CC)CCNCc1c(-c2ccccc2)nc2cc(/C=C/C(=O)NO)ccn12] | 408 |
| 48 | 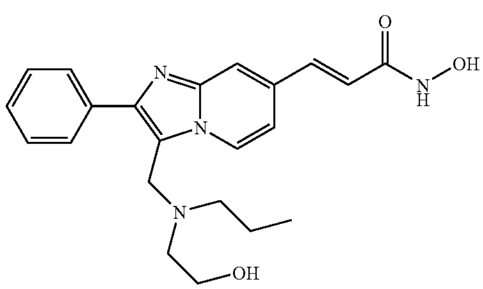 [SMILES: CCCN(CCO)Cc1c(-c2ccccc2)nc2cc(/C=C/C(=O)NO)ccn12] | 395 |
| 49 | 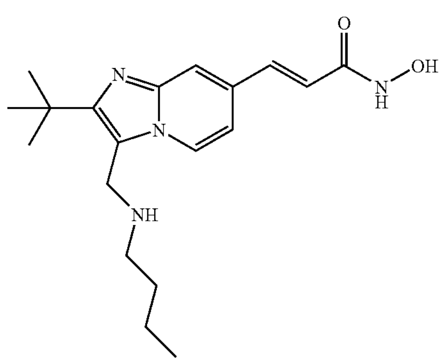 [SMILES: CCCCNCc1c(C(C)(C)C)nc2cc(/C=C/C(=O)NO)ccn12] | 345 |

TABLE 2-continued

| Compound No. | Structure | m/z [MH]+ |
|---|---|---|
| 50 | 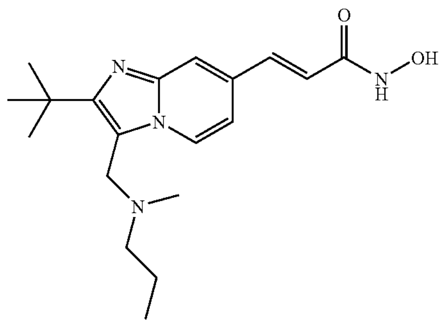 [SMILES: CCCN(C)Cc1c(C(C)(C)C)nc2cc(/C=C/C(=O)NO)ccn12] | 345 |
| 51 | 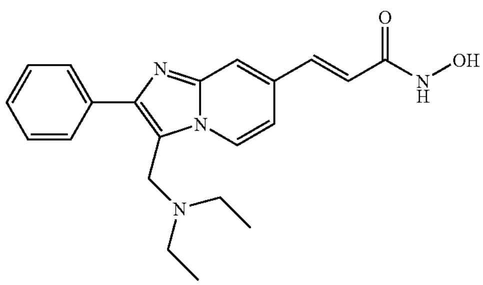 [SMILES: CCN(CC)Cc1c(-c2ccccc2)nc2cc(/C=C/C(=O)NO)ccn12] | 365 |
| 52 | 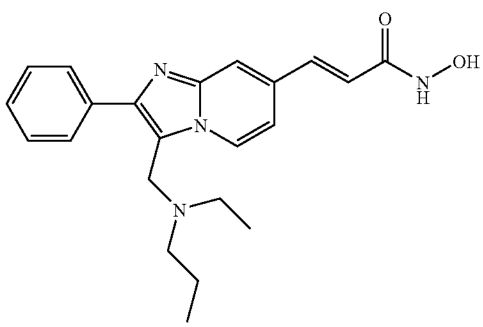 [SMILES: CCCN(CC)Cc1c(-c2ccccc2)nc2cc(/C=C/C(=O)NO)ccn12] | 379 |
| 53 | 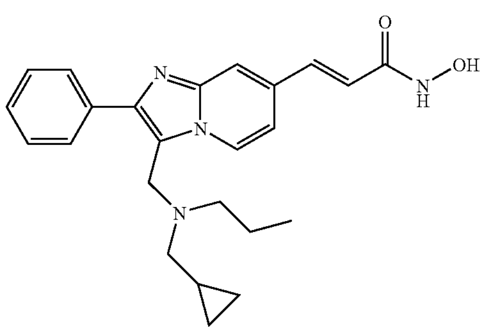 [SMILES: CCCN(Cc1c(-c2ccccc2)nc2cc(/C=C/C(=O)NO)ccn12)CC1CC1] | 405 |
| 54 | 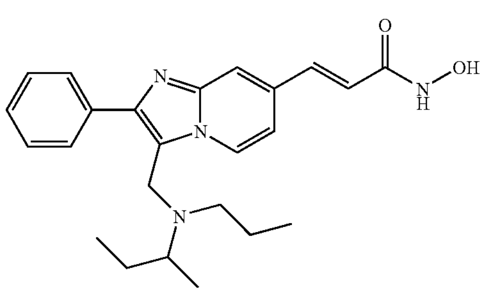 [SMILES: CCCN(Cc1c(-c2ccccc2)nc2cc(/C=C/C(=O)NO)ccn12)C(C)CC] | 407 |

TABLE 2-continued

| Compound No. | Structure | m/z [MH]+ |
|---|---|---|
| 55 | 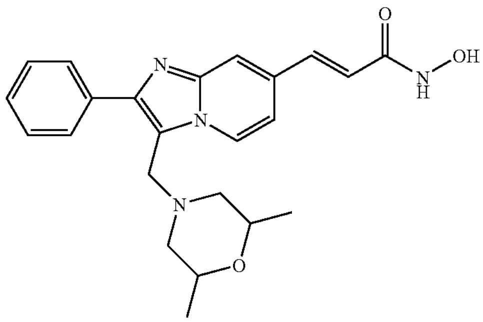 [SMILES: CC1CN(Cc2c(-c3ccccc3)nc3cc(/C=C/C(=O)NO)ccn23)CC(C)O1] | 407 |
| 56 | 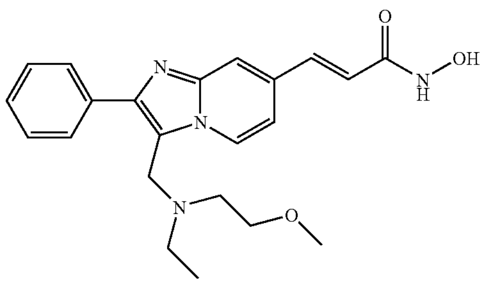 [SMILES: CCN(CCOC)Cc1c(-c2ccccc2)nc2cc(/C=C/C(=O)NO)ccn12] | 395 |
| 57 | 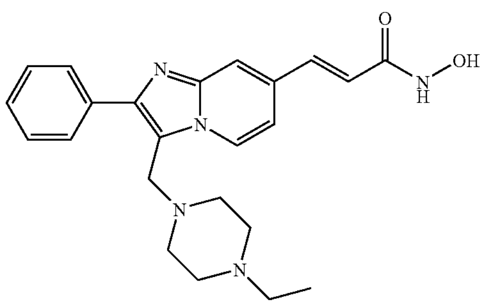 [SMILES: CCN1CCN(Cc2c(-c3ccccc3)nc3cc(/C=C/C(=O)NO)ccn23)CC1] | 406 |
| 58 | 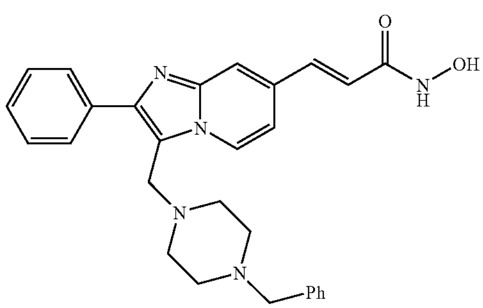 | 467 |
| 59 | 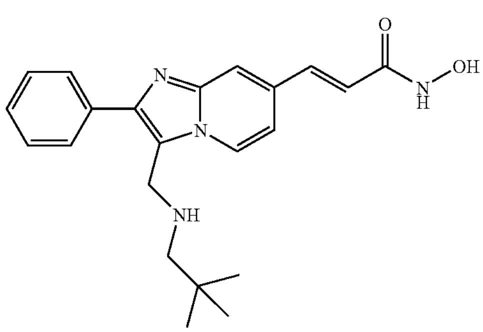 [SMILES: CC(C)(C)CNCc1c(-c2ccccc2)nc2cc(/C=C/C(=O)NO)ccn12] | 379 |

TABLE 2-continued
| Compound No. | Structure | m/z [MH]+ |
|---|---|---|
| 60 | 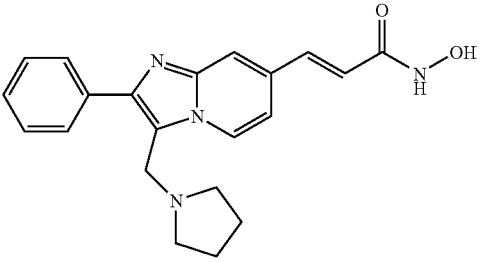 [SMILES: O=C(/C=C/c1ccn2c(CN3CCCC3)c(-c3ccccc3)nc2c1)NO] | 363 |
| 61 | 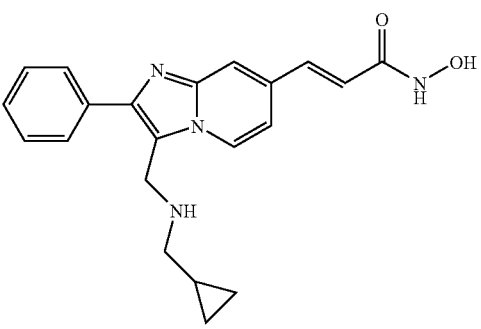 [SMILES: O=C(/C=C/c1ccn2c(CNCC3CC3)c(-c3ccccc3)nc2c1)NO] | 363 |
| 62 | 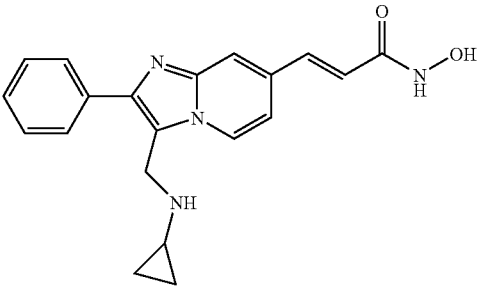 [SMILES: O=C(/C=C/c1ccn2c(CNC3CC3)c(-c3ccccc3)nc2c1)NO] | 349 |
| 63 | 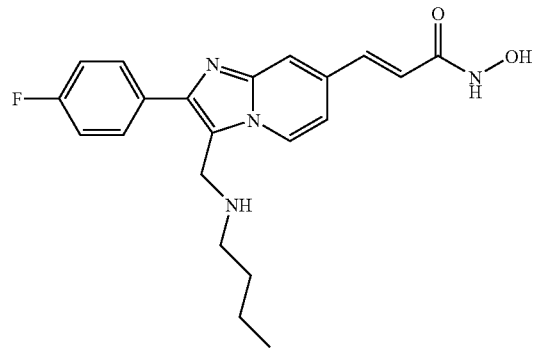 [SMILES: CCCCNCc1c(-c2ccc(F)cc2)nc2cc(/C=C/C(=O)NO)ccn12] | 383 |
| 64 | 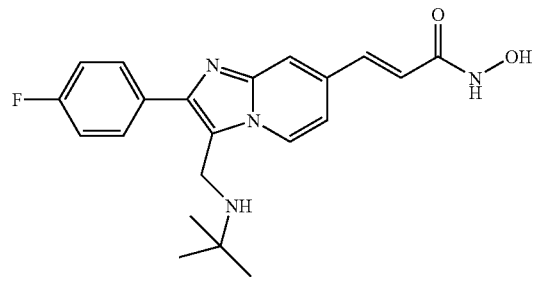 [SMILES: CC(C)(C)NCc1c(-c2ccc(F)cc2)nc2cc(/C=C/C(=O)NO)ccn12] | 383 |

TABLE 2-continued

| Compound No. | Structure | m/z [MH]+ |
|---|---|---|
| 65 | 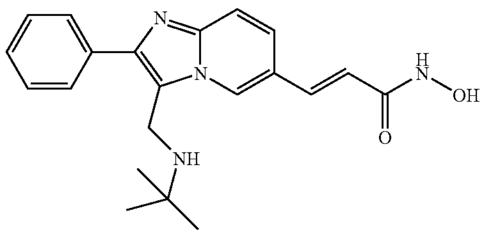 [SMILES: CC(C)(C)NCc1c(-c2ccccc2)nc2ccc(/C=C/C(=O)NO)cn12] | 364 |
| 66 | 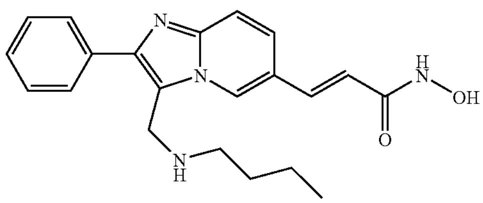 [SMILES: CCCCNCc1c(-c2ccccc2)nc2ccc(/C=C/C(=O)NO)cn12] | 364 |
| 67 | 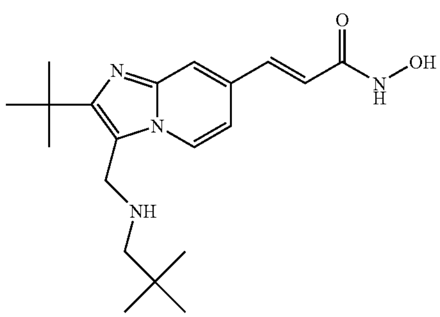 [SMILES: CC(C)(C)CNCc1c(C(C)(C)C)nc2cc(/C=C/C(=O)NO)ccn12] | 358 |
| 68 | 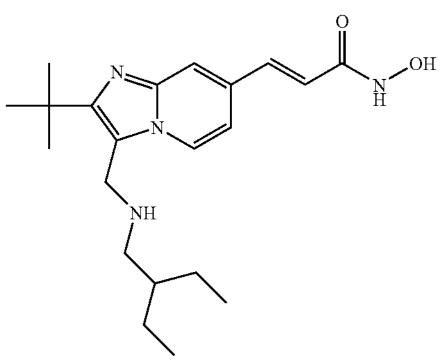 [SMILES: CCC(CC)CNCc1c(C(C)(C)C)nc2cc(/C=C/C(=O)NO)ccn12] | 358 |
| 69 | 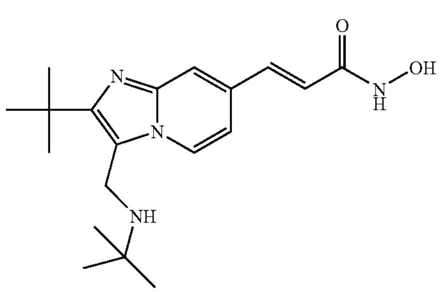 [SMILES: CC(C)(C)NCc1c(C(C)(C)C)nc2cc(/C=C/C(=O)NO)ccn12] | 344 |

TABLE 2-continued
| Compound No. | Structure | m/z [MH]+ |
|---|---|---|
| 70 | 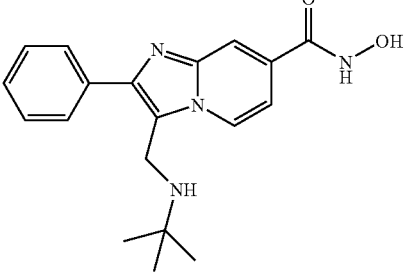 | 338 |
| 71 | 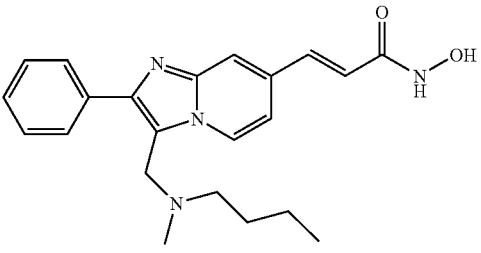 [SMILES: CCCCN(C)Cc1c(-c2ccccc2)nc2cc(/C=C/C(=O)NO)ccn12] | 378 |
| 72 | 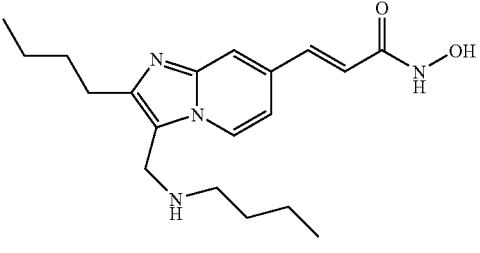 [SMILES: CCCCNCc1c(CCCC)nc2cc(/C=C/C(=O)NO)ccn12] | 344 |
| 73 | 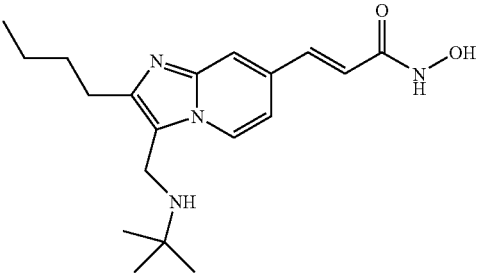 [SMILES: CCCCc1nc2cc(/C=C/C(=O)NO)ccn2c1CNC(C)(C)C] | 344 |
| 74 | 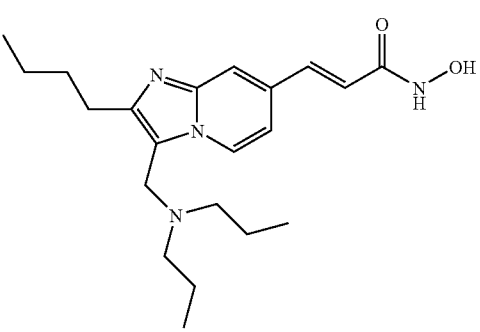 [SMILES: CCCCc1nc2cc(/C=C/C(=O)NO)ccn2c1CN(CCC)CCC] | 372 |

TABLE 2-continued

| Compound No. | Structure | m/z [MH]+ |
|---|---|---|
| 75 | 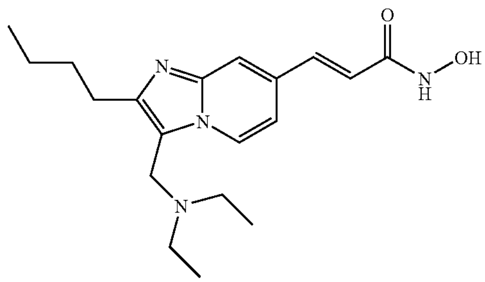 [SMILES: CCCCc1nc2cc(/C=C/C(=O)NO)ccn2c1CN(CC)CC] | 344 |
| 76 | 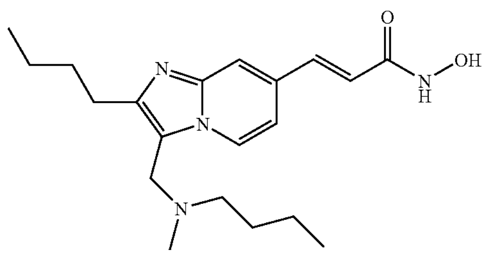 [SMILES: CCCCc1nc2cc(/C=C/C(=O)NO)ccn2c1CN(C)CCCC] | 358 |
| 77 | 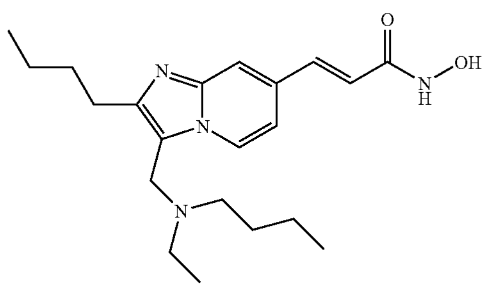 [SMILES: CCCCc1nc2cc(/C=C/C(=O)NO)ccn2c1CN(CC)CCCC] | 372 |
| 78 | 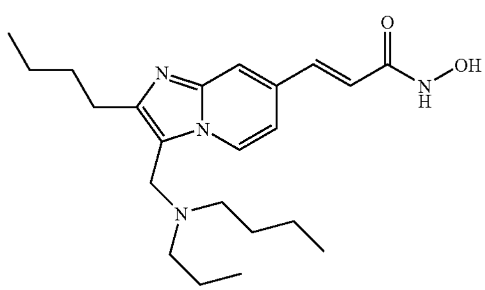 [SMILES: CCCCc1nc2cc(/C=C/C(=O)NO)ccn2c1CN(CCC)CCCC] | 386 |
| 79 | 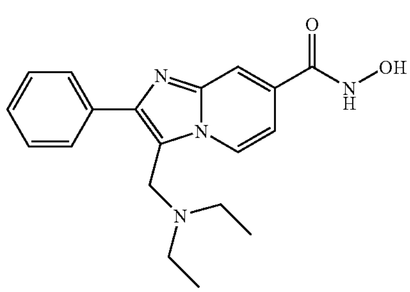 [SMILES: CCN(CC)Cc1c(-c2ccccc2)nc2cc(C(=O)NO)ccn12] | 338 |

TABLE 2-continued
| Compound No. | Structure | m/z [MH]+ |
|---|---|---|
| 80 | 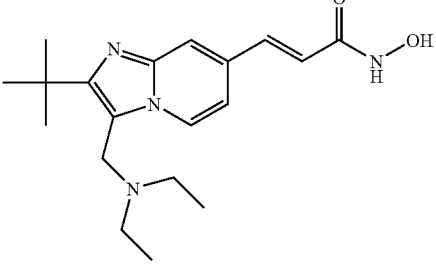 | 344 |
| 81 | 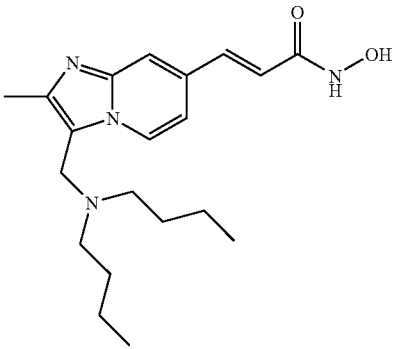 [SMILES: CCCCN(CCCC)Cc1c(C)nc2cc(/C=C/C(=O)NO)ccn12] | 358 |
| 82 | 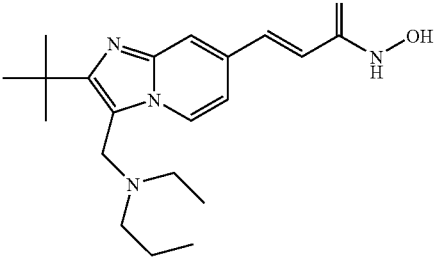 | 358 |
| 83 | 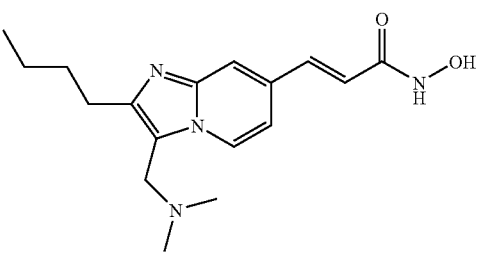 [SMILES: CCCCc1nc2cc(/C=C/C(=O)NO)ccn2c1CN(C)C] | 316 |
| 84 | 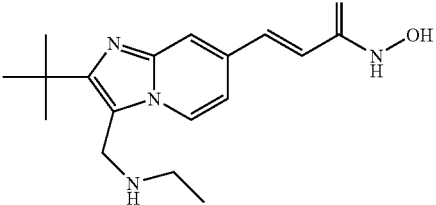 | 316 |

TABLE 2-continued
| Compound No. | Structure | m/z [MH]+ |
|---|---|---|
| 85 | 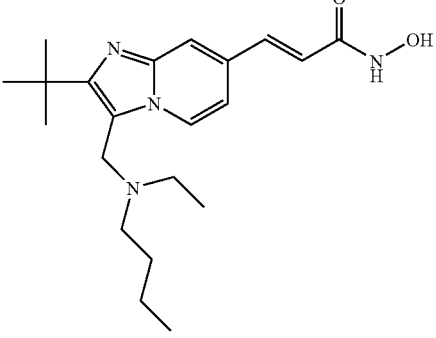 | 373 |
| 86 | 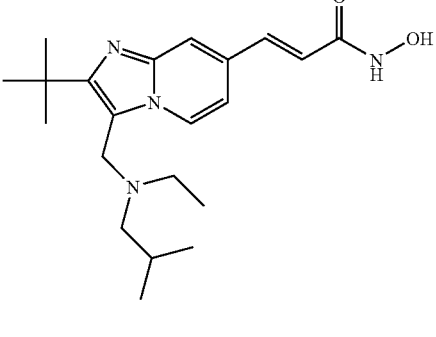 | 373 |
| 87 | 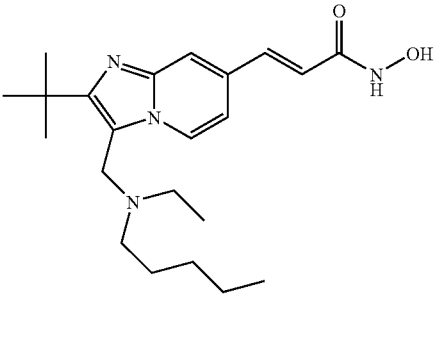 [SMILES: CCCCCN(CC)Cc1c(C(C)(C)C)nc2cc(/C=C/C(=O)NO)ccn12] | 387 |
| 88 | 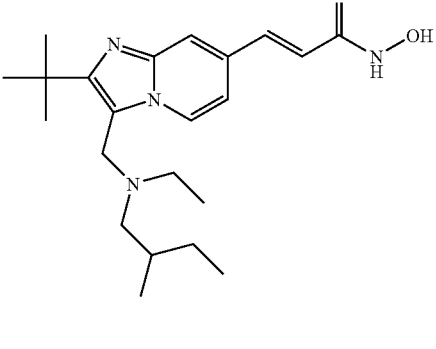 | 387 |

TABLE 2-continued

| Compound No. | Structure | m/z [MH]+ |
|---|---|---|
| 89 | 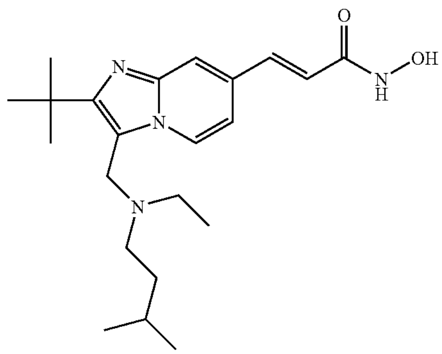 [SMILES: CCN(CCC(C)C)Cc1c(C(C)(C)C)nc2cc(/C=C/C(=O)NO)ccn12] | 387 |
| 90 | 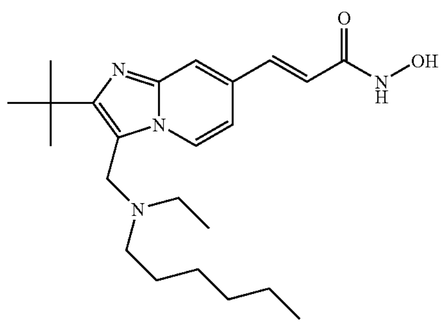 [SMILES: CCCCCCN(CC)Cc1c(C(C)(C)C)nc2cc(/C=C/C(=O)NO)ccn12] | 401 |
| 91 | 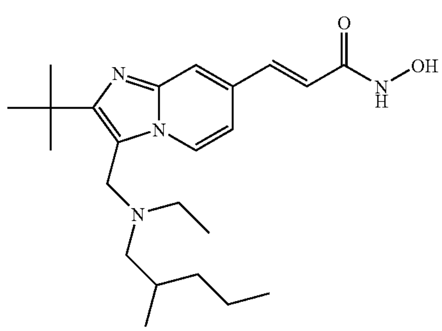 [SMILES: CCCC(C)CN(CC)Cc1c(C(C)(C)C)nc2cc(/C=C/C(=O)NO)ccn12] | 401 |
| 92 | 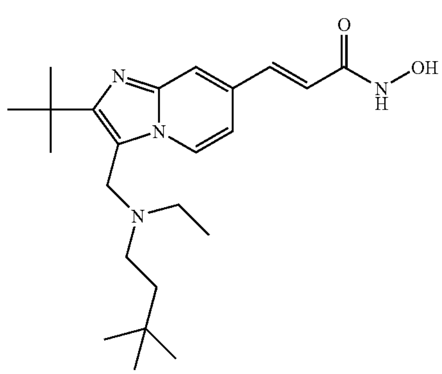 [SMILES: CCN(CCC(C)(C)C)Cc1c(C(C)(C)C)nc2cc(/C=C/C(=O)NO)ccn12] | 401 |

TABLE 2-continued

| Compound No. | Structure | m/z [MH]+ |
|---|---|---|
| 93 | 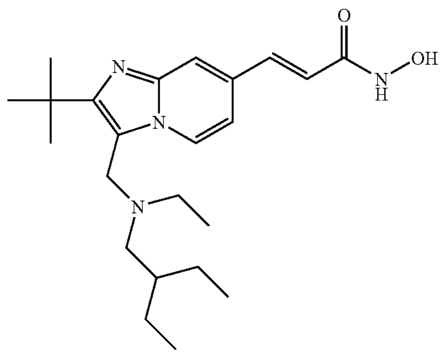 [SMILES: CCC(CC)CN(CC)Cc1c(C(C)(C)C)nc2cc(/C=C/C(=O)NO)ccn12] | 401 |
| 94 | 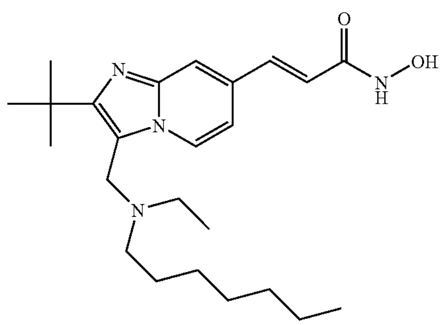 [SMILES: CCCCCCCN(CC)Cc1c(C(C)(C)C)nc2cc(/C=C/C(=O)NO)ccn12] | 415 |
| 95 | 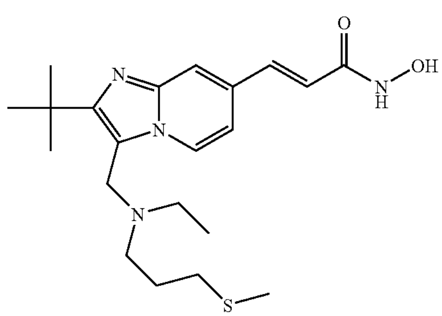 [SMILES: CCN(CCCSC)Cc1c(C(C)(C)C)nc2cc(/C=C/C(=O)NO)ccn12] | 405 |
| 96 | 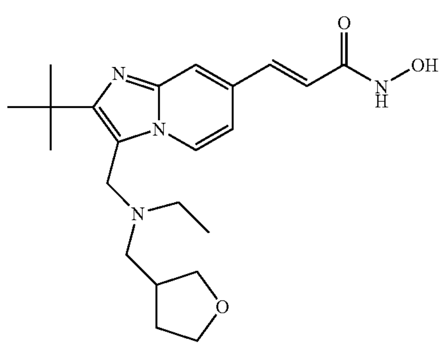 [SMILES: CCN(Cc1c(C(C)(C)C)nc2cc(/C=C/C(=O)NO)ccn12)CC1CCOC1] | 401 |

TABLE 2-continued
| Compound No. | Structure | m/z [MH]+ |
|---|---|---|
| 97 | 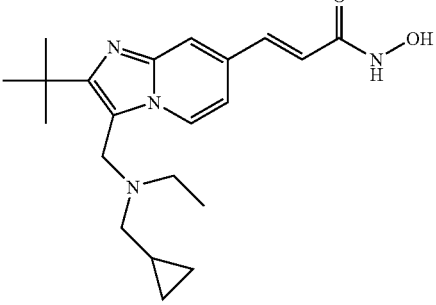 | 370 |
| 98 | 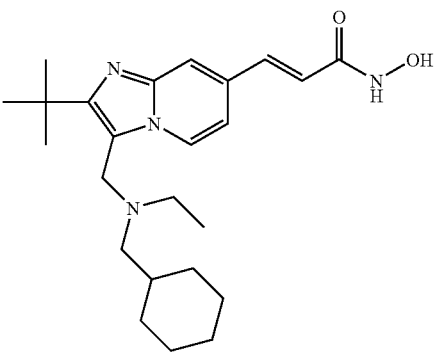 [SMILES: CCN(Cc1c(C(C)(C)C)nc2cc(/C=C/C(=O)NO)ccn12)CC1CCCCC1] | 413 |
| 99 | 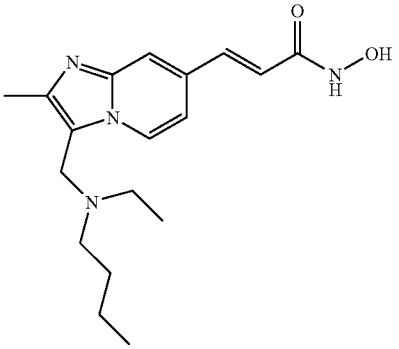 [SMILES: CCCCN(CC)Cc1c(C)nc2cc(/C=C/C(=O)NO)ccn12] | 330 |
| 100 | 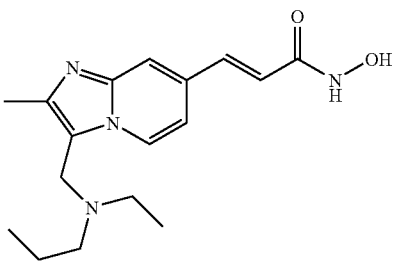 [SMILES: CCCN(CC)Cc1c(C)nc2cc(/C=C/C(=O)NO)ccn12] | 316 |

TABLE 2-continued

| Compound No. | Structure | m/z [MH]+ |
|---|---|---|
| 101 | 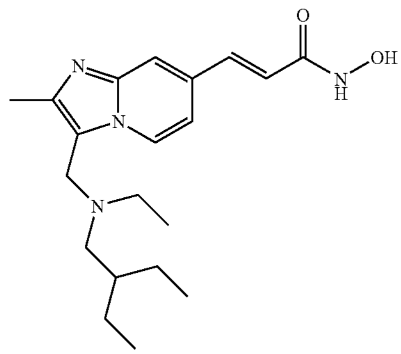 [SMILES: CCC(CC)CN(CC)Cc1c(C)nc2cc(/C=C/C(=O)NO)ccn12] | 358 |
| 102 | 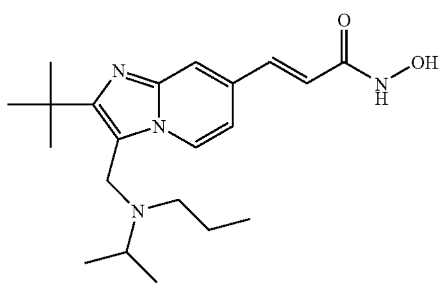 [SMILES: CCCN(Cc1c(C(C)(C)C)nc2cc(/C=C/C(=O)NO)ccn12)C(C)C] | 373 |
| 103 | 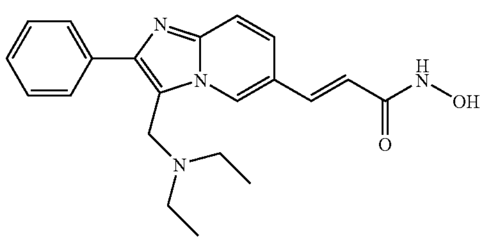 [SMILES: CCN(CC)Cc1c(-c2ccccc2)nc2ccc(/C=C/C(=O)NO)cn12] | 364 |
| 104 | 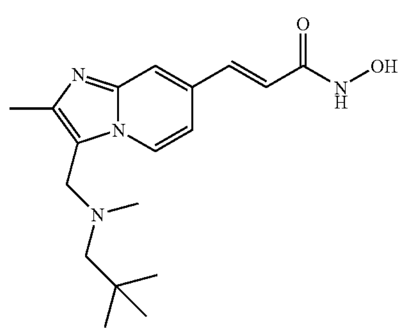 [SMILES: Cc1nc2cc(/C=C/C(=O)NO)ccn2c1CN(C)CC(C)(C)C] | 373 |
| 105 | 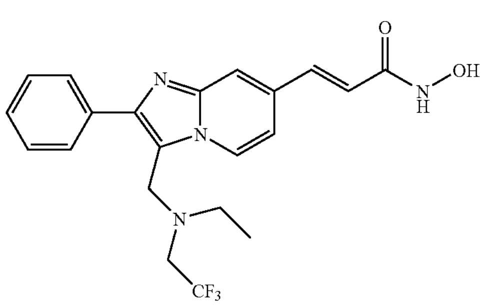 [SMILES: CCN(Cc1c(-c2ccccc2)nc2cc(/C=C/C(=O)NO)ccn12)CC(F)(F)F] | 418 |

TABLE 2-continued

| Compound No. | Structure | m/z [MH]+ |
|---|---|---|
| 106 | 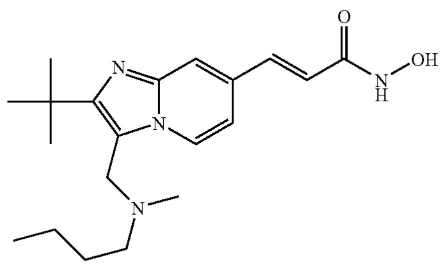 [SMILES: CCCCN(C)Cc1c(C(C)(C)C)nc2cc(/C=C/C(=O)NO)ccn12] | 358 |
| 107 | 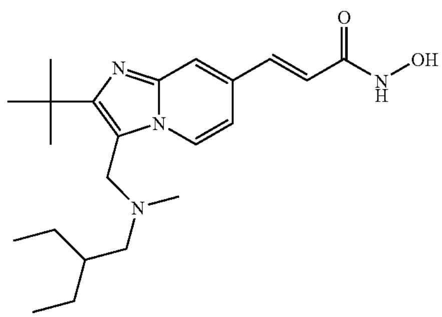 [SMILES: CCC(CC)CN(C)Cc1c(C(C)(C)C)nc2cc(/C=C/C(=O)NO)ccn12] | 387 |
| 108 | 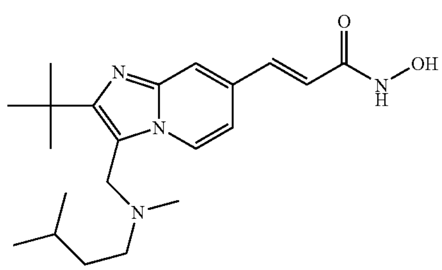 [SMILES: CC(C)CCN(C)Cc1c(C(C)(C)C)nc2cc(/C=C/C(=O)NO)ccn12] | 373 |
| 109 | 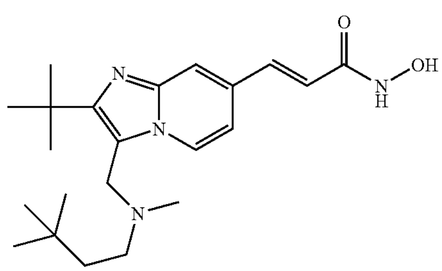 | 387 |
| 110 | 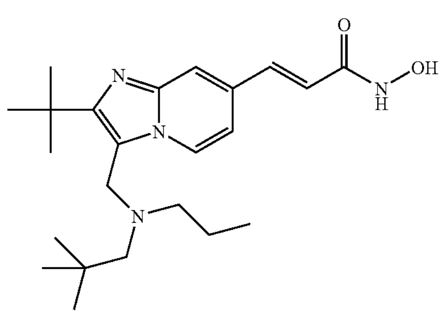 [SMILES: CCCN(Cc1c(C(C)(C)C)nc2cc(/C=C/C(=O)NO)ccn12)CC(C)(C)C] | 358 |

TABLE 2-continued

| Compound No. | Structure | m/z [MH]+ |
|---|---|---|
| 111 | 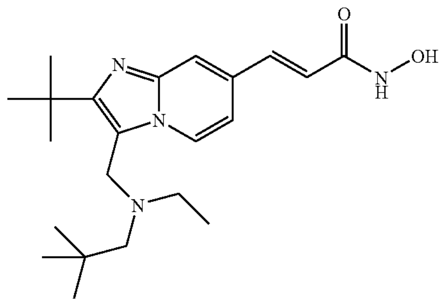 [SMILES: CCN(Cc1c(C(C)(C)C)nc2cc(/C=C/C(=O)NO)ccn12)CC(C)(C)C] | 344 |
| 112 | 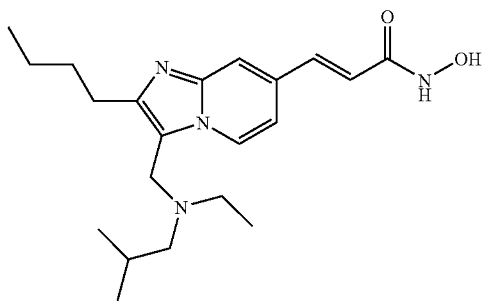 [SMILES: CCCCc1nc2cc(/C=C/C(=O)NO)ccn2c1CN(CC)CC(C)C] | 373 |
| 113 | 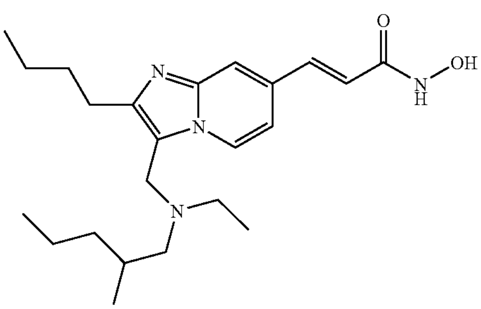 [SMILES: CCCCc1nc2cc(/C=C/C(=O)NO)ccn2c1CN(CC)CC(C)CCC] | 387 |
| 114 | 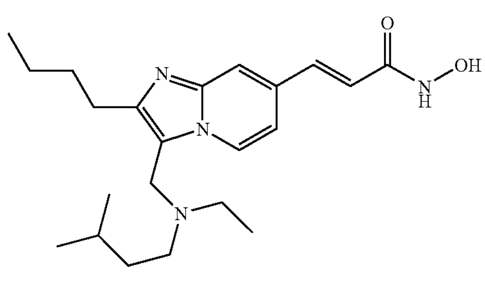 [SMILES: CCCCc1nc2cc(/C=C/C(=O)NO)ccn2c1CN(CC)CCC(C)C] | 387 |
| 115 | 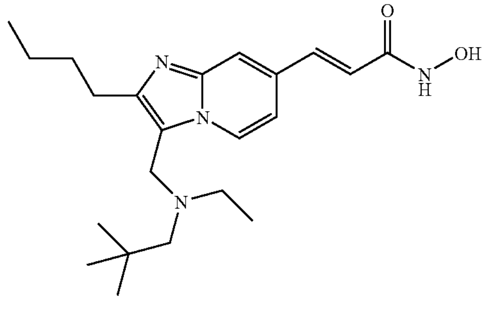 [SMILES: CCCCc1nc2cc(/C=C/C(=O)NO)ccn2c1CN(CC)CC(C)(C)C] | 387 |

TABLE 2-continued

| Compound No. | Structure | m/z [MH]+ |
|---|---|---|
| 116 | 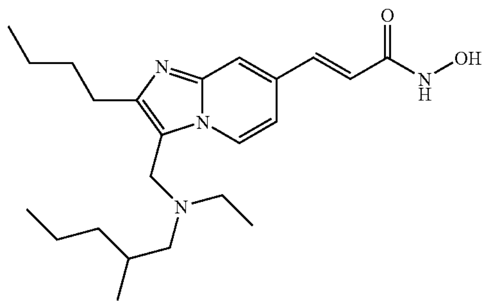 [SMILES: CCCCc1nc2cc(/C=C/C(=O)NO)ccn2c1CN(CC)CC(C)CCC] | 401 |
| 117 | 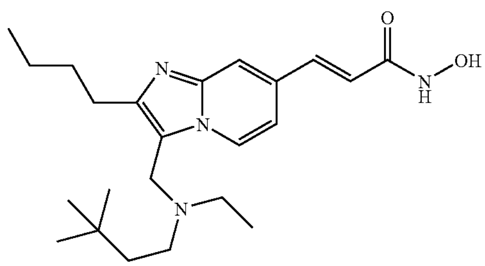 [SMILES: CCCCc1nc2cc(/C=C/C(=O)NO)ccn2c1CN(CC)CCC(C)(C)C] | 401 |
| 118 | 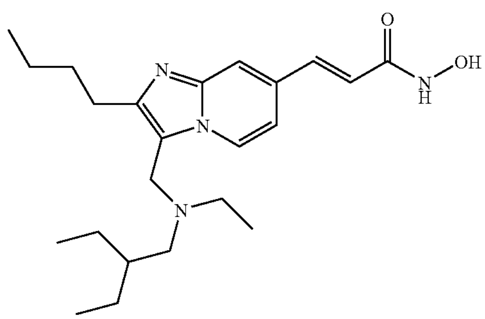 [SMILES: CCCCc1nc2cc(/C=C/C(=O)NO)ccn2c1CN(CC)CC(CC)CC] | 401 |
| 119 | 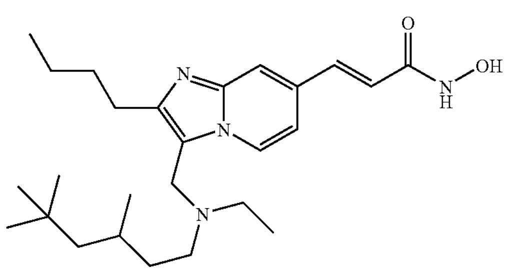 [SMILES: CCCCc1nc2cc(/C=C/C(=O)NO)ccn2c1CN(CC)CCC(C)CC(C)(C)C] | 443 |
| 120 | 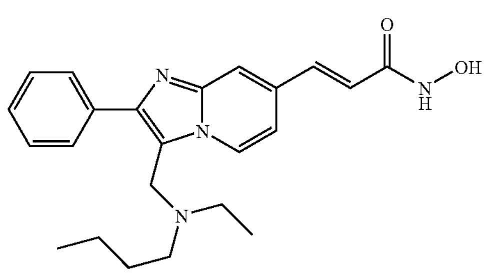 [SMILES: CCCCN(CC)Cc1c(-c2ccccc2)nc2cc(/C=C/C(=O)NO)ccn12] | 393 |

TABLE 2-continued

| Compound No. | Structure | m/z [MH]+ |
|---|---|---|
| 121 | 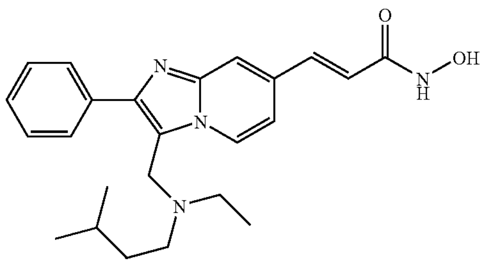 [SMILES: CCN(CCC(C)C)Cc1c(-c2ccccc2)nc2cc(/C=C/C(=O)NO)ccn12] | 407 |
| 122 | 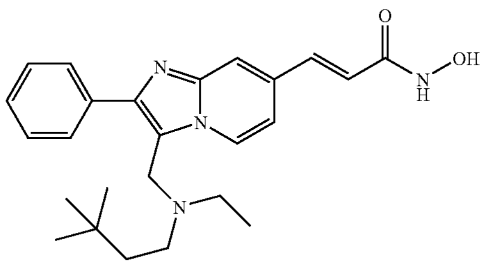 [SMILES: CCN(CCC(C)(C)C)Cc1c(-c2ccccc2)nc2cc(/C=C/C(=O)NO)ccn12] | 421 |
| 123 | 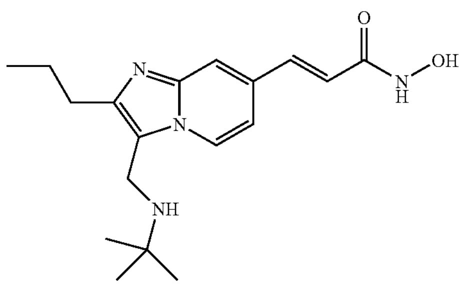 [SMILES: CCCc1nc2cc(/C=C/C(=O)NO)ccn2c1CNC(C)(C)C] | 330 |
| 124 | 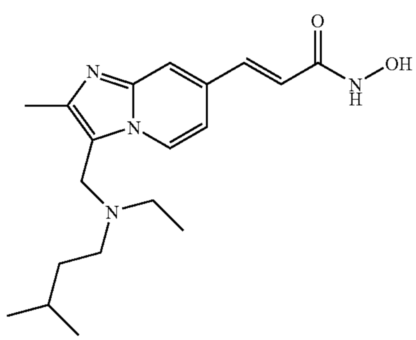 [SMILES: CCN(CCC(C)C)Cc1c(C)nc2cc(/C=C/C(=O)NO)ccn12] | 344 |
| 125 | 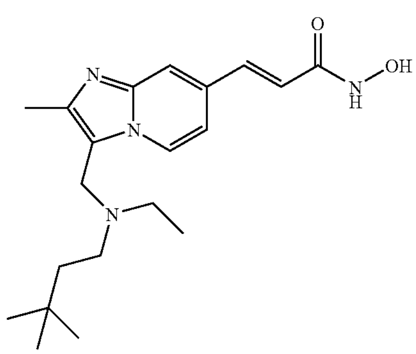 [SMILES: CCN(CCC(C)(C)C)Cc1c(C)nc2cc(/C=C/C(=O)NO)ccn12] | 358 |

TABLE 2-continued

| Compound No. | Structure | m/z [MH]+ |
|---|---|---|
| 126 | 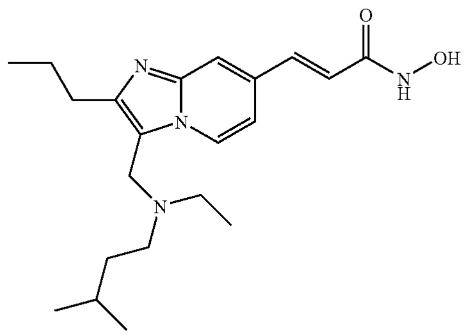 [SMILES: CCCc1nc2cc(/C=C/C(=O)NO)ccn2c1CN(CC)CCC(C)C] | 373 |
| 127 | 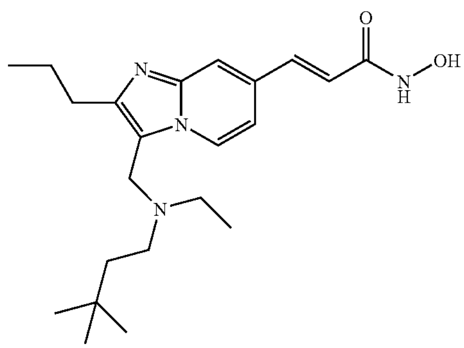 [SMILES: CCCc1nc2cc(/C=C/C(=O)NO)ccn2c1CN(CC)CCC(C)(C)C] | 387 |
| 128 | 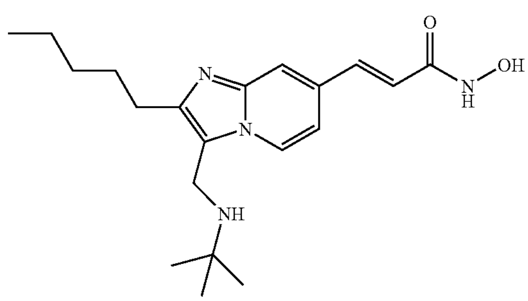 [SMILES: CCCCCc1nc2cc(/C=C/C(=O)NO)ccn2c1CNC(C)(C)C] | 358 |
| 129 | 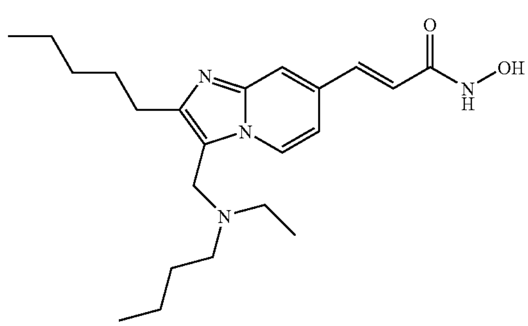 [SMILES: CCCCCc1nc2cc(/C=C/C(=O)NO)ccn2c1CN(CC)CCCC] | 387 |

TABLE 2-continued

| Compound No. | Structure | m/z [MH]+ |
| --- | --- | --- |
| 130 | 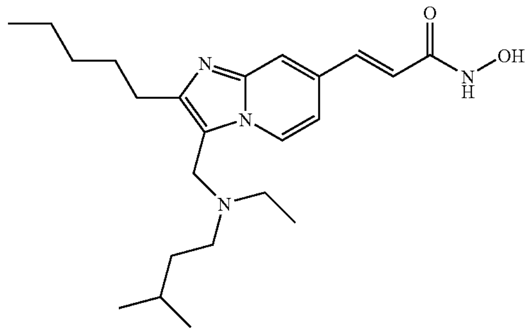 [SMILES: CCCCCc1nc2cc(/C=C/C(=O)NO)ccn2c1CN(CC)CCC(C)C] | 401 |
| 131 | 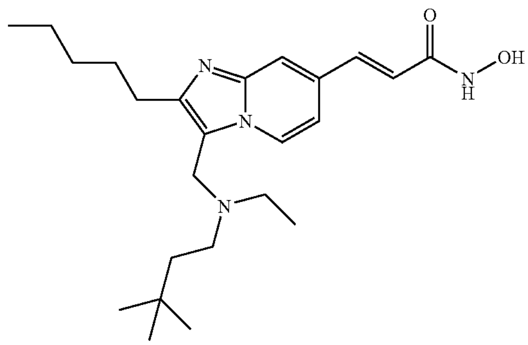 [SMILES: CCCCCc1nc2cc(/C=C/C(=O)NO)ccn2c1CN(CC)CCC(C)(C)C] | 415 |
| 132 | 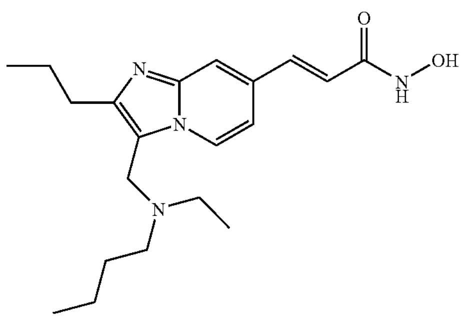 | 358 |
| 133 | 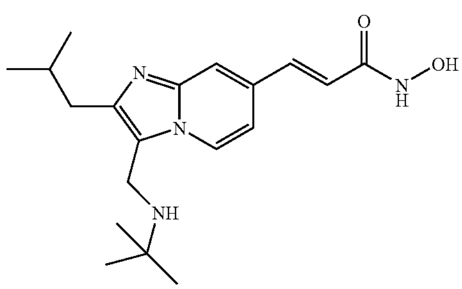 [SMILES: CC(C)Cc1nc2cc(/C=C/C(=O)NO)ccn2c1CNC(C)(C)C] | 344 |
| 134 | 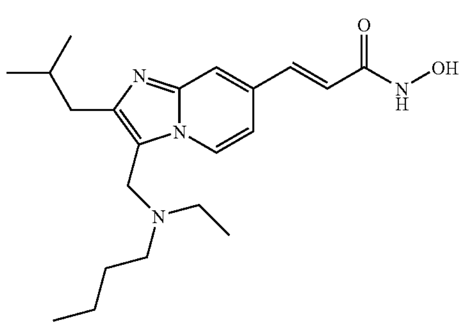 [SMILES: CCCCN(CC)Cc1c(CC(C)C)nc2cc(/C=C/C(=O)NO)ccn12] | 373 |

TABLE 2-continued
| Compound No. | Structure | m/z [MH]+ |
|---|---|---|
| 135 | 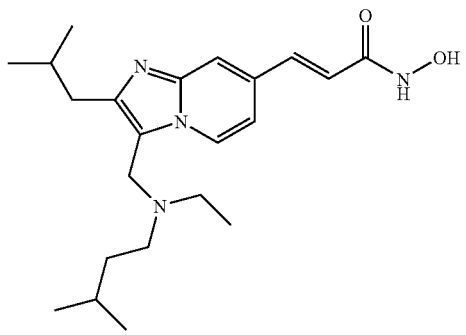 [SMILES: CCN(CCC(C)C)Cc1c(CC(C)C)nc2cc(/C=C/C(=O)NO)ccn12] | 387 |
| 136 | 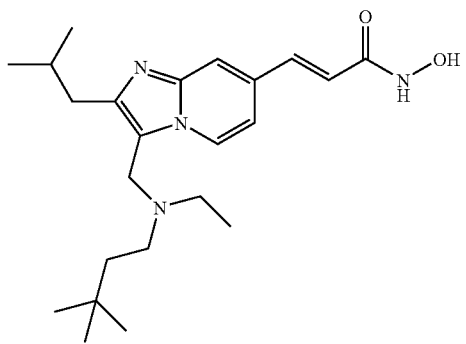 [SMILES: CCN(CCC(C)(C)C)Cc1c(CC(C)C)nc2cc(/C=C/C(=O)NO)ccn12] | 401 |
| 137 | 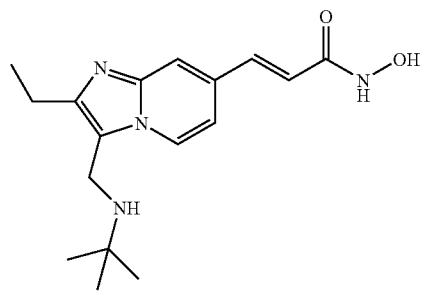 [SMILES: CCc1nc2cc(/C=C/C(=O)NO)ccn2c1CNC(C)(C)C] | 316 |
| 138 | 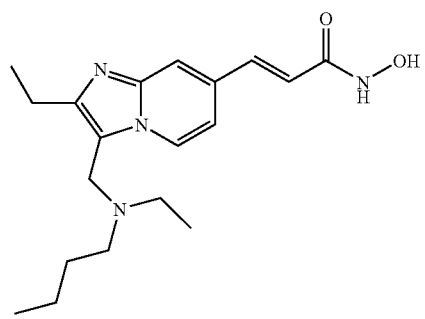 [SMILES: CCCCN(CC)Cc1c(CC)nc2cc(/C=C/C(=O)NO)ccn12] | 344 |

TABLE 2-continued
| Compound No. | Structure | m/z [MH]+ |
|---|---|---|
| 139 | 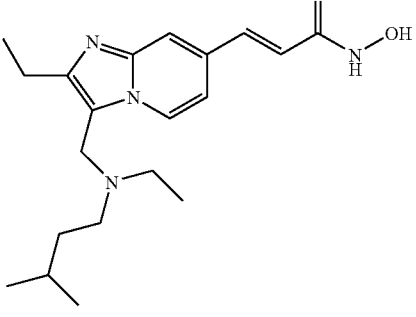 | 358 |
| 140 | 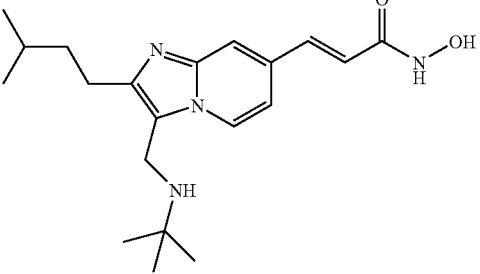 | 358 |
| 141 | 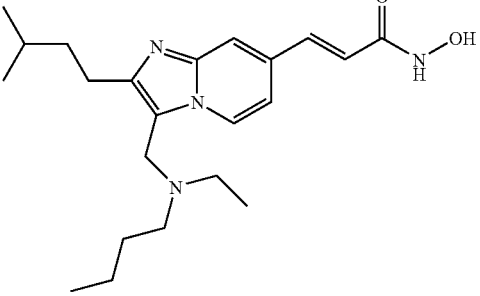 | 387 |
| 142 | 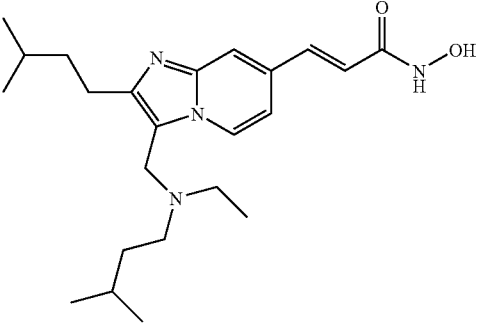 [SMILES: CCN(CCC(C)C)Cc1c(CCC(C)C)nc2cc(/C=C/C(=O)NO)ccn12] | 401 |

TABLE 2-continued

| Compound No. | Structure | m/z [MH]+ |
|---|---|---|
| 143 | 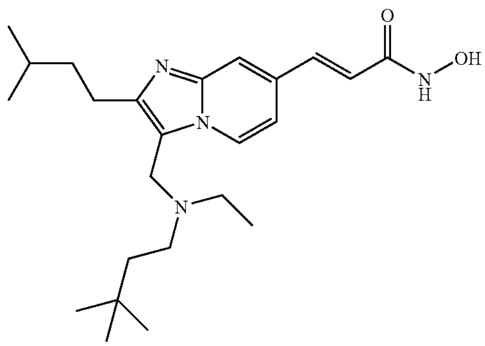 [SMILES: CCN(CCC(C)(C)C)Cc1c(CCC(C)C)nc2cc(/C=C/C(=O)NO)ccn12] | 415 |
| 144 | 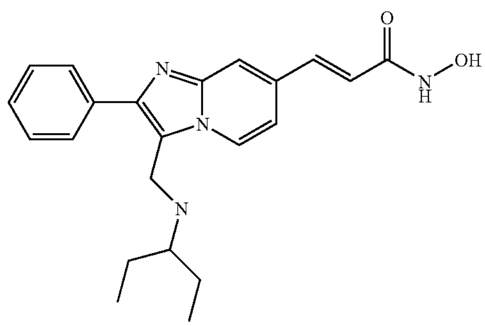 [SMILES: CCC(CC)NCc1c(-c2ccccc2)nc2cc(/C=C/C(=O)NO)ccn12] | 378 |

Biological Testing and Enzyme Assays

Recombinant GST-HDAC1 Protein Expression and Purification

Human cDNA library was prepared using cultured SW620 cells. Amplification of human HDAC1 coding region from this cDNA library was cloned separately into the baculovirus expression pDEST20 vector (GATEWAY Cloning Technology, Invitrogen Pte Ltd). The pDEST20-HDAC1 construct was confirmed by DNA sequencing. Recombinant baculovirus was prepared using the Bac-To-Bac method following the manufacturer's instruction (Invitrogen Pte Ltd). Baculovirus titer was determined by plaque assay to be about $10^8$ PFU/ml.

Expression of GST-HDAC1 was done by infecting SF9 cells (Invitrogen Pte Ltd) with pDEST20-HDAC1 baculovirus at MOI=1 for 48 h. Soluble cell lysate was incubated with pre-equilibrated Glutathione Sepharose 4B beads (Amersham) at 4° C. for 2 h. The beads were washed with PBS buffer for 3 times. The GST-HDAC1 protein was eluted by elution buffer containing 50 mM Tris, pH8.0, 150 mM NaCl, 1% Triton X-100 and 10 mM or 20 mM reduced Glutathione. The purified GST-HDAC1 protein was dialyzed with HDAC storage buffer containing 10 mM Tris, pH7.5, 100 mM NaCl and 3 mM $MgCl_2$. 20% Glycerol was added to purified GST-HDAC1 protein before storage at −80° C.

In Vitro HDAC Assay for Determination of $IC_{50}$ Values

The assay has been carried out in 96 well format and the BIOMOL fluorescent-based HDAC activity assay has been applied. The reaction composed of assay buffer, containing 25 mM Tris pH 7.5, 137 mM NaCl, 2.7 mM KCl, 1 mM $MgCl_2$, 1 mg/ml BSA, tested compounds, an appropriate concentration of HDAC1 enzyme, 500 uM Flur de lys generic substrate for HDAC1 enzyme and subsequently was incubated at room temperature for 2 h. Flur de lys Developer was added and the reaction was incubated for 10 min. Briefly, deacetylation of the substrate sensitizes it to the developer, which then generates a fluorophore. The fluorophore is excited with 360 nm light and the emitted light (460 nm) is detected on a fluorometric plate reader (Tecan Ultra Microplate detection system, Tecan Group Ltd.).

The analytical software, Prism 4.0 (GraphPad Software Inc) has been used to generate $IC_{50}$ from a series of data. $IC_{50}$ is defined as the concentration of compound required for 50% inhibition of HDAC enzyme activity.

The HDAC enzyme inhibition results of representative compounds are shown in Table 3 (unit in the table is micromolar).

TABLE 3

| Compound No. | $IC_{50}$ (μM) (HDAC 1) |
|---|---|
| 1 | 0.15 |
| 2 | 0.72 |
| 3 | 0.79 |
| 4 | 0.64 |
| 5 | 0.35 |
| 6 | 1.4 |
| 7 | 2.7 |
| 8 | 1 |
| 9 | 1.3 |
| 10 | 0.32 |
| 11 | 6 |
| 12 | >10 |
| 13 | 0.72 |
| 14 | 2.7 |
| 15 | 0.76 |
| 16 | >10 |
| 17 | 0.3 |
| 18 | 0.63 |
| 19 | 0.78 |
| 20 | 0.099 |
| 21 | 0.13 |
| 22 | 0.14 |
| 23 | 0.16 |

TABLE 3-continued

| Compound No. | IC$_{50}$ (µM) (HDAC 1) |
|---|---|
| 24 | 0.13 |
| 25 | 0.073 |
| 26 | 0.14 |
| 27 | 0.18 |
| 28 | 0.11 |
| 29 | 0.38 |
| 30 | 0.88 |
| 31 | >10 |
| 32 | 0.24 |
| 33 | 0.83 |
| 34 | 0.87 |
| 35 | 0.14 |
| 36 | 0.39 |
| 37 | 0.59 |
| 38 | 0.36 |
| 39 | 0.16 |
| 40 | 0.24 |
| 41 | 1.3 |
| 42 | 0.16 |
| 43 | 2 |
| 44 | 2.9 |
| 45 | 0.045 |
| 46 | >10 |
| 47 | 0.65 |
| 48 | 1.0 |
| 49 | 0.16 |
| 50 | 0.52 |
| 51 | 0.2 |
| 52 | 0.24 |
| 53 | 0.60 |
| 54 | 1 |
| 55 | 2.4 |
| 56 | 1.6 |
| 57 | 4.6 |
| 58 | 1.5 |
| 59 | 0.23 |
| 60 | 0.084 |
| 61 | 0.08 |
| 62 | 0.31 |
| 63 | 0.063 |
| 64 | 0.051 |
| 65 | >10 |
| 66 | >10 |
| 67 | 0.19 |
| 68 | 0.16 |
| 69 | 0.13 |
| 70 | >10 |
| 71 | 0.12 |
| 72 | 0.02 |
| 73 | 0.02 |
| 74 | 0.20 |
| 75 | 0.18 |
| 76 | 0.07 |
| 77 | 0.06 |
| 78 | 0.09 |
| 79 | >10 |
| 80 | 1.2 |
| 81 | 0.08 |
| 82 | 0.27 |
| 83 | 0.04 |
| 84 | 0.06 |
| 85 | 0.06 |
| 86 | 0.57 |
| 87 | 0.13 |
| 88 | 0.26 |
| 89 | 0.06 |
| 90 | 0.24 |
| 91 | 0.47 |
| 92 | 0.07 |
| 93 | 0.19 |
| 94 | 0.54 |
| 95 | 0.09 |
| 96 | 0.37 |
| 97 | 0.33 |
| 98 | 0.19 |
| 99 | 0.03 |
| 100 | 0.54 |
| 101 | 0.01 |
| 102 | 0.30 |
| 103 | >10 |
| 104 | 0.78 |
| 105 | 7.40 |
| 106 | 0.22 |
| 107 | 0.41 |
| 108 | 0.35 |
| 109 | 0.27 |
| 110 | 0.13 |
| 111 | 0.05 |
| 112 | 0.09 |
| 113 | 0.06 |
| 114 | 0.02 |
| 115 | 0.16 |
| 116 | 0.08 |
| 117 | 0.03 |
| 118 | 0.15 |
| 119 | 0.20 |
| 120 | 0.04 |
| 121 | 0.03 |
| 122 | 0.05 |
| 123 | 0.04 |
| 124 | 0.02 |
| 125 | 0.05 |
| 126 | 0.03 |
| 127 | 0.02 |
| 128 | 0.02 |
| 129 | 0.04 |
| 130 | 0.03 |
| 131 | 0.03 |
| 132 | 0.04 |
| 133 | 0.05 |
| 134 | 0.04 |
| 135 | 0.02 |
| 136 | 0.03 |
| 137 | 0.03 |
| 138 | 0.05 |
| 139 | 0.02 |
| 140 | 0.02 |
| 141 | 0.04 |
| 142 | 0.03 |
| 143 | 0.04 |
| 144 | 0.26 |

Cell-Based Proliferation Assay for Determination of GI$_{50}$ Values

Human cancer cell lines (e.g. Colo205) were obtained from ATCC. Colo205 cells were cultivated in RPMI 1640 containing 2 mM L-Glutamine, 5% FBS, 1.0 mM Na Pyruvate. Colo205 cells were seeded in 96-wells plate at 5000 cells per well. The plates were incubated at 37° C., 5% CO$_2$, for 24 h. Cells were treated with compounds at various concentrations for 96 h. Cell growth was then monitored using CyQUANT® cell proliferation assay (Invitrogen Pte Ltd). Dose response curves were plotted to determine GI$_{50}$ values for the compounds using XL-fit (ID Business Solution, Emeryville, Calif.). GI$_{50}$ is defined as the concentration of compound required for 50% inhibition of cell growth.

The cellular or growth inhibition activity results of representative compounds are shown in Table 4 below (unit in the table is micromolar). The data indicated that the compounds of this invention are active in the inhibition of tumor cell growth.

TABLE 4

| Compound No. | GI$_{50}$ (µM) (Colo205) |
|---|---|
| 1 | 2.1 |
| 2 | 3.9 |

TABLE 4-continued

| Compound No. | GI$_{50}$ (μM) (Colo205) |
|---|---|
| 3 | 1.9 |
| 4 | 2.8 |
| 5 | 27 |
| 6 | 42 |
| 7 | 9.3 |
| 8 | 14 |
| 9 | 5.3 |
| 10 | 39 |
| 11 | >10 |
| 12 | 20 |
| 13 | 8.9 |
| 14 | 9.2 |
| 15 | 16 |
| 16 | 20 |
| 17 | 9.9 |
| 18 | 12 |
| 19 | 24 |
| 20 | 28 |
| 21 | 13 |
| 22 | 19 |
| 23 | 15 |
| 24 | 40 |
| 25 | 2.1 |
| 26 | 7.9 |
| 27 | 8.5 |
| 28 | 7.3 |
| 29 | 2.1 |
| 30 | 3.9 |
| 31 | 1.9 |
| 32 | 2.8 |
| 33 | 27 |
| 34 | 42 |
| 35 | 9.3 |
| 36 | 14 |
| 37 | 5.3 |
| 38 | 3.5 |
| 39 | 0.44 |
| 40 | 0.79 |
| 41 | 2.5 |
| 42 | 1.5 |
| 43 | 34 |
| 44 | 32 |
| 45 | 0.26 |
| 46 | 11 |
| 47 | 30 |
| 48 | 9.2 |
| 49 | 0.59 |
| 50 | 2.4 |
| 51 | 1.1 |
| 52 | 1.2 |
| 53 | 2.9 |
| 54 | 4.7 |
| 55 | 9.3 |
| 56 | 9.0 |
| 57 | 14 |
| 58 | 2.9 |
| 59 | 2.1 |
| 60 | 0.48 |
| 61 | 0.56 |
| 62 | 2.5 |
| 63 | 0.54 |
| 64 | 0.27 |
| 65 | 62 |
| 66 | 55 |
| 67 | 1.5 |
| 68 | 1.5 |
| 69 | 0.74 |
| 70 | >100 |
| 71 | 1.0 |
| 72 | 0.18 |
| 73 | 0.14 |
| 74 | 0.61 |
| 75 | 0.68 |
| 76 | 0.17 |
| 77 | 0.16 |
| 78 | 0.58 |
| 79 | >100 |
| 80 | 4.4 |
| 81 | 0.80 |
| 82 | 1.8 |
| 83 | 0.23 |
| 84 | 0.47 |
| 85 | 0.68 |
| 86 | 3.90 |
| 87 | 0.75 |
| 88 | 2.20 |
| 89 | 0.35 |
| 90 | 2.00 |
| 91 | 2.10 |
| 92 | 0.48 |
| 93 | 0.97 |
| 94 | 2.70 |
| 95 | 0.60 |
| 96 | 3.40 |
| 97 | 2.10 |
| 98 | 1.10 |
| 99 | 0.18 |
| 100 | 4.60 |
| 101 | 0.05 |
| 102 | 2.50 |
| 103 | 41 |
| 104 | 6.30 |
| 105 | 44 |
| 106 | 1.70 |
| 107 | 2.30 |
| 108 | 0.90 |
| 109 | 0.73 |
| 110 | 0.70 |
| 111 | 0.60 |
| 112 | 0.57 |
| 113 | 0.37 |
| 114 | 0.09 |
| 115 | 0.95 |
| 116 | 0.49 |
| 117 | 0.14 |
| 118 | 0.39 |
| 119 | 0.53 |
| 120 | 0.68 |
| 121 | 0.49 |
| 122 | 0.52 |
| 123 | 0.18 |
| 124 | 0.11 |
| 125 | 0.16 |
| 126 | 0.08 |
| 127 | 0.07 |
| 128 | 0.07 |
| 129 | 0.15 |
| 130 | 0.14 |
| 131 | 0.15 |
| 132 | 0.16 |
| 133 | 0.21 |
| 134 | 0.15 |
| 135 | 0.15 |
| 136 | 0.17 |
| 137 | 0.26 |
| 138 | 0.18 |
| 139 | 0.10 |
| 140 | 0.10 |
| 141 | 0.16 |
| 142 | 0.13 |
| 143 | 0.13 |
| 144 | 1.6 |

Histone Acetylation Assay

A hallmark of histone deacetylase (HDAC) inhibition is the increase in the acetylation level of histones. Histone acetylation, including H3, H4 and H2A can be detected by immunoblotting (western-blot). Colo205 cells, approximately 5×10$^5$ cells, were seeded in the previously described medium, cultivated for 24 h and subsequently treated with HDAC inhibitory agents and a positive control at 10 μM final concentration. After 24 h, cells were harvested and lysed according to the instruction from Sigma Mammalian Cell Lysis Kit. The protein concentration was quantified using BCA method (Sigma Pte Ltd). The protein lysate was separated using 4-12% bis-tris SDS-PAGE gel (Invitrogen Pte Ltd) and was transferred onto PVDF membrane (BioRad Pte Ltd). The membrane was probed using primary antibody specific for acetylated histone H3 (Upstate Pte Ltd). The detection antibody, goat anti rabbit antibody conjugated with HRP was used according to the manufacturing instruction (Pierce Pte Ltd). After removing the detection antibody from the membrane, an enhanced chemiluminescent substrate for detection of HRP (Pierce Pte Ltd) was added onto the membrane. After removing the substrate, the membrane was exposed to an X-ray film (Kodak) for 1 sec-20 mins. The X-ray film was developed using the X-ray film processor. The density of each band observed on the developed film could be qualitatively analysed using UVP Bioimaging software (UVP, Inc, Upland, Calif.). The values were then normalized against the density of actin in the corresponding samples to obtain the expression of the protein.

The results of immuno-blotting assay using acetylated histone H3 antibody are shown in Table 5 for representative compounds of this invention.

TABLE 5

| Compound No. | Histone acetylation activities (Histone-3) |
|---|---|
| 39 | active |
| 40 | active |
| 45 | active |
| 49 | active |
| 60 | active |
| 63 | active |
| 64 | active |

These data demonstrate that compounds of this invention inhibit histone deacetylases, thereby resulting in accumulation of acetylated histones.

In Vivo Antineoplastic (or Anti-Tumor) Effect of HDAC Inhibiting Agents:

The efficacy of the compounds of the invention can then be determined using in vivo animal xenograft studies. The animal xenograft model is one of the most commonly used in vivo cancer models.

In these studies Female athymic nude mice (Harlan), 12-14 weeks of age would be implanted subcutaneously in the flank with $5 \times 10^6$ cells of HCT116 human colon tumor cells, or with $5 \times 10^6$ cells of A2780 human ovarian tumor cells, or with $5 \times 10^6$ cells of PC3 prostate cancer cells. When the tumor reaches the size 100 mm$^3$, the xenograft nude mice would be paired-match into various treatment groups. The selected HDAC inhibitors would be dissolved in appropriate vehicles and administered to xenograft nude mice intraperitoneally, intravenously or orally daily for 14-21 days. The dosing volume will be 0.01 ml/g body weight. Paclitaxol, used as positive control, will be prepared for intravenous administration in an appropriate vehicle. The dosing volume for Paclitaxol will be 0.01 ml/g body weight. Tumor volume will be calculated every second day or twice-a-week of post injection using the formula: Volume (mm$^3$)=(W$^2$×l)/2, where w=width and I=length in mm of an HCT116, or A2780, or PC3 tumor. Compounds of this invention that are tested would show significant reduction in tumor volume relative to controls treated with vehicle only. Acetylated histone relative to vehicle treated control group when measured shall be accumulated. The result will therefore indicate that compounds of this invention are efficacious in treating a proliferative disease such as cancer.

The details of specific embodiments described in this invention are not to be construed as limitations. Various equivalents and modifications may be made without departing from the essence and scope of this invention, and it is understood that such equivalent embodiments are part of this invention.

What is claimed is:

1. A method of treatment of cancer in a patient, the method comprising administration of a therapeutically effective amount of a compound of the formula (I):

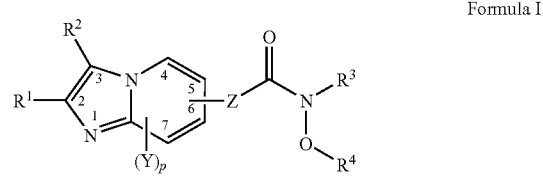

Formula I wherein:

R$^1$ is selected from the group consisting of: H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^5$, —COOR$^5$, —CONHR$^5$, —NHCOR$^5$, —NHCOOR$^5$, —NHCONHR$^5$, C(=NOH)R$^5$, -alkylNCOR$^5$, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may optionally be substituted, or R$^1$=L;

R$^2$ is selected from the group consisting of: H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^5$, —COOR$^5$, —CONHR$^5$, —NHCOR$^5$, —NHCOOR$^5$, —NHCONHR$^5$, C(=NOH)R$^5$, -alkylNCOR$^5$, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may optionally be substituted, or R$^2$=L;

R$^3$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

$R^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each Y is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH —C(O)OR$^6$, —COR$^6$, —SH, —SR$^7$, —OR$^7$, acyl and —NR$^8$R$^9$ each of which may be optionally substituted;

each $R^5$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^6$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^7$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ and $R^9$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

p is an integer selected from the group consisting of 0, 1, 2, and 3;

L is selected from the group consisting of:
a) Cy—L$^1$—W—
b) Cy—L$^1$—W—L$^2$—;
c) Cy—(CH$_2$)$_k$—W—;
d) L$^1$—W—L$^2$—;
e) Cy—L$^1$—;
f) R$^{12}$—W$^1$—L$^1$—W—; and
g) —(CR$^{20}$R$^{21}$)$_m$—(CR$^{22}$R$^{23}$)$_n$—(CR$^{24}$R$^{25}$)$_o$—NR$^{26}$R$^{27}$;

wherein

Cy is selected from the group consisting of C$_1$-C$_{15}$ alkyl, aminoalkyl, heteroalkyl, heterocycloalkyl, cycloalkyl, aryl, aryloxy and heteroaryl, each of which may be optionally substituted;

L$^1$ is selected from the group consisting of a bond, C$_1$-C$_5$ alkyl and C$_2$-C$_5$ alkenyl, each of which may be optionally substituted;

L$^2$ is selected from the group consisting of C$_1$-C$_5$ alkyl and C$_2$-C$_5$ alkenyl, each of which may be optionally substituted;

k is 0, 1, 2, 3, 4 or 5;

W is selected from the group consisting of a bond, —O—, —S—, —S(O)—, —S(O)$_2$—, —N(R$^{10}$)—, —C(O)N(R$^{10}$)—, —SO$_2$N(R$^{10}$)—, —N(R$^{10}$)C(O)—, —N(R$^{10}$)SO$_2$—, —N(R$^{10}$)C(O)N(R$^{11}$)—, —C(O)N(R$^{10}$)C(O)N(R$^{11}$)— and —N(R$^{10}$)C(O)N(R$^{11}$)C(O)—;

W$^1$ is selected from the group consisting of a bond, —O—, —S—, —S(O)—, —S(O)$_2$—, —N(R$^{10}$)—, —C(O)N(R$^{10}$)—, —SO$_2$N(R$^{10}$)—, —N(R$^{10}$)C(O)—, —N(R$^{10}$)SO$_2$—, —N(R$^{10}$)C(O)N(R$^{11}$)—, —C(O)N(R$^{10}$)C(O)N(R$^{11}$)— and —N(R$^{10}$)C(O)N(R$^{11}$)C(O)—;

each R$^{10}$ and R$^{11}$ is independently selected from the group consisting of: H, C$_1$-C$_6$ alkyl, C$_1$-C$_6$ alkenyl, C$_1$-C$_{10}$ heteroalkyl, C$_4$-C$_9$ cycloalkyl, C$_4$-C$_9$ heterocycloalkyl, aryl, heteroaryl, arylalkyl, and heteroarylalkyl and acyl, each of which may be optionally substituted;

each R$^{20}$, R$^{21}$, R$^{22}$, R$^{23}$, R$^{24}$ and R$^{25}$ is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkoxyheteroaryl, alkenyloxy, alkynyloxy, cycloalkyloxy, heterocycloalkyloxy, aryloxy, arylalkyloxy, phenoxy, benzyloxy heteroaryloxy, amino, alkylamino, acylamino, aminoalkyl, arylamino, alkoxycarbonyl, alkylaminocarbonyl, sulfonyl, alkylsulfonyl, aminosulfonyl, arylsulfonyl, arylsulfinyl —COOH, —C(O)OR$^5$, —COR$^5$, —SH, —SR$^6$, —OR$^6$ and acyl, each of which may be optionally substituted; or R$^{20}$ and R$^{21}$ when taken together may form a group of formula =O or =S, and/or R$^{22}$ and R$^{23}$ when taken together may form a group of formula =O or =S, and/or R$^{24}$ and R$^{25}$ when taken together may form a group of formula =O or =S;

each R$^{26}$ and R$^{27}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR$^5$, acyl and G, each of which may be optionally substituted, or R$^{26}$ and R$^{27}$ when taken together with the nitrogen atom to which they are attached form a heterocycloalkyl or heteroaryl group, each of which may be optionally substituted;

m, n and o are each integers that are independently selected from the group consisting of 0, 1, 2, 3 and 4;

G is a group of formula:

—L³W³ wherein

L³ is selected from the group consisting of $C_1$-$C_5$ alkyl and $C_2$-$C_5$ alkenyl, each of which may be optionally substituted;

W³ is selected from the group consisting of —OR¹², —SR¹², —S(O)R¹², —S(O)₂R¹², —N(R¹²)₂, —C(O)N(R¹²)₂, —SO₂N(R¹²)₂, —NR¹²C(O)—, —NR¹²SO₂R¹², —NR¹²C(O)N(R¹²)₂, —C(O)NR¹²C(O)N(R¹²)₂ and —N(R¹²)C(O)N(R¹²)C(O)R¹²;

each R¹² is independently selected from the group consisting H, halogen, —CN, —NO₂, —CF₃, —OCF₃, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR⁵, —COOR⁵, —CONHR⁵, —NHCOR⁵, —NHCOOR⁵, —NHCONHR⁵, C(=NOH)R⁵, -alkylNCOR⁵, alkoxycarbonyl, alkylaminocarbonyl, sulfonyl, alkylsulfonyl, alkylsulfinyl, arylsulfonyl, arylsulfinyl, aminosulfonyl, SR⁶ and acyl, each of which may optionally be substituted;

Z is selected from —CH₂—, —CH₂CH₂—, —CH=CH— and $C_3$-$C_6$ cycloalkyl each of which may be optionally substituted;

or a pharmaceutically acceptable salt thereof to the patient; wherein the cancer is colon cancer, ovarian cancer, prostate cancer, or a hematologic malignancy.

2. The method according to claim 1, wherein in the compound of Formula I, Z is attached at ring position 5 or 6.

3. The method according to claim 1, wherein in the compound of Formula I, Z is —CHH—, and is in the 'E' configuration.

4. The method according to claim 1, wherein in the compound of Formula I, R¹ is selected from the group consisting of: H, hydroxyalkyl, alkyl, arylalkyl, aryl, heteroaryl, heteroarylalkyl, alkoxyalkyl, aminoalkyl, and heterocycloalkyl, each of which may be unsubstituted or substituted.

5. The method according to claim 4, wherein in the compound of Formula I, R¹ is alkyl, aryl or heteroaryl, each of which may be optionally substituted.

6. The method according to claim 5, wherein in the compound of Formula I, R¹ is selected from the group consisting of methyl, ethyl, propyl, isopropyl, 2-methyl-propyl, 2,2-dimethyl-propyl, butyl, isobutyl, tert-butyl, 3-methyl-butyl, pentyl, 2,4,4-trimethyl-pentyl, hexyl and phenyl, each of which may be optionally substituted.

7. The method according to claim 1, wherein in the compound of Formula I, R² is selected from the group consisting of H, alkyl, arylalkyl, aryl, heteroaryl, heteroalkyl, cycloalkyl, each of which may be optionally substituted, or R² is L which is a group of the formula:

(a) Cy-L¹-W—;
(b) R¹²—W¹-L₁W—; or
(c) —(CR²⁰R²¹)ₘ—(CR²²R²³)ₙ—(CR²⁴R²⁵)ₒ—NR²⁶R²⁷;

wherein Cy, L¹, W, W¹, R¹², R²⁰, R²¹, R²², R²³, R²⁴, R²⁵, R²⁶, R²⁷, m, n and o are as defined in claim 1.

8. The method according to claim 1, wherein in the compound of Formula I, R² is selected from the group consisting of:

(a) Cy-L¹-W—;
(b) R¹²—W¹-L¹-W—; and
(c) —(CR²⁰R²¹)ₘ—(CR²²R²³)ₙ—(CR²⁴R²⁵)ₒ—NR²⁶R²⁷;

wherein Cy, L¹, W, W¹, R²⁰, R²¹, R22, R23, R²⁴, R²⁵, R²⁶, R²⁷, m, n and o are as defined in claim 1.

9. The method according to claim 1, wherein in the compound of Formula I, R² is a group of formula:

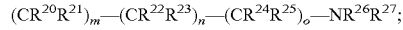

wherein R²⁰, R²¹, R²², R²³, R²⁴, R²⁵, R²⁶, R²⁷, m, n and o are as defined in claim 1.

10. The method according to claim 9, wherein the compound of Formula I is selected from the group consisting of:

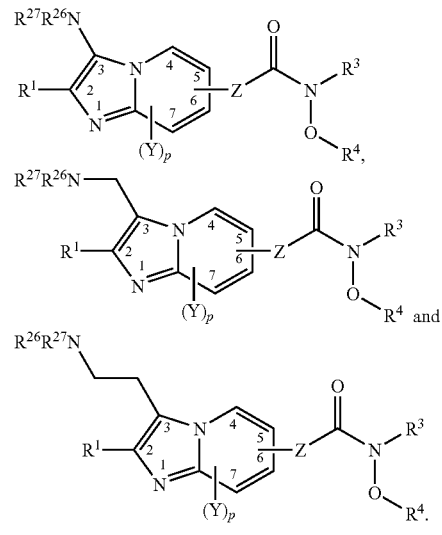

11. The method according to claim 10, wherein the compound of Formula I has the formula

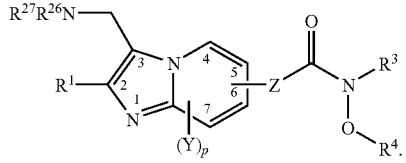

12. The method according to claim 11, wherein in the compound of Formula I, R²⁶ and R²⁷ are each independently selected from the group consisting of H, alkyl, heteroalkyl, cycloalkyl, aryl, arylalkyl, cycloalkylalkyl and G, each of which may be optionally substituted.

13. The method according to claim 12, wherein in the compound of Formula I, R²⁶ and R²⁷ are independently selected from the group consisting of: H, methyl, cyclopropyl-methyl, cyclohexyl-methyl, ethyl, 2-methoxy-ethyl, 2-hydroxy-ethyl, 2-cyclopropyl-ethyl, 2,2,2-trifluoroethyl, 2-(dimethylamino)-ethyl, 2-(diethylamino)-ethyl, propyl, isopropyl, cyclopropyl, 1-methyl-propyl, 2-methyl-propyl, 2,2-dimethyl-propyl, butyl, t-butyl, sec-butyl, 2-ethyl-butyl, 2-methyl-butyl, 3-methyl-butyl, 3,3-dimethyl-butyl, pentyl, 2-methyl-pentyl, hexyl, 3,5,5-tromethyl-hexyl, heptyl, 3,4,5- trimethoxyphenyl, 3,4-methylenedioxybenzyl, 4-piperidin-1-yl-phenyl, and 3,4-methylenedioxyphenyl.
14. The method according to claim 7, wherein in the compound of Formula I, R² is selected from the group consisting of:
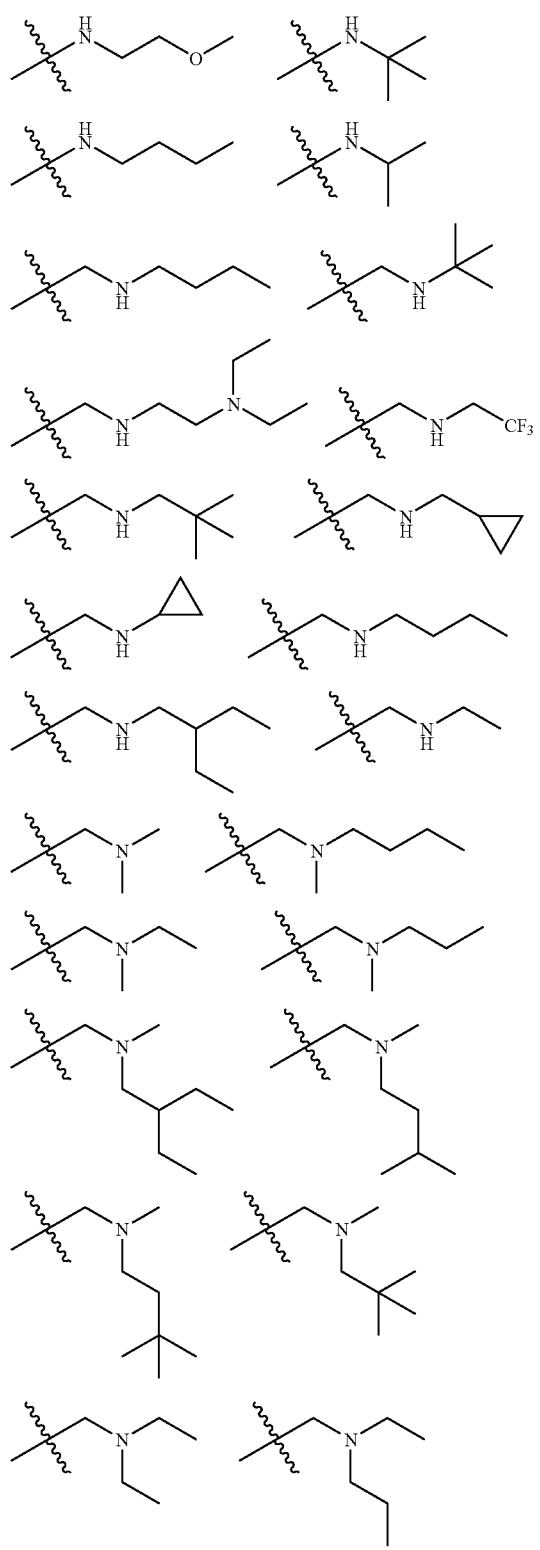
-continued
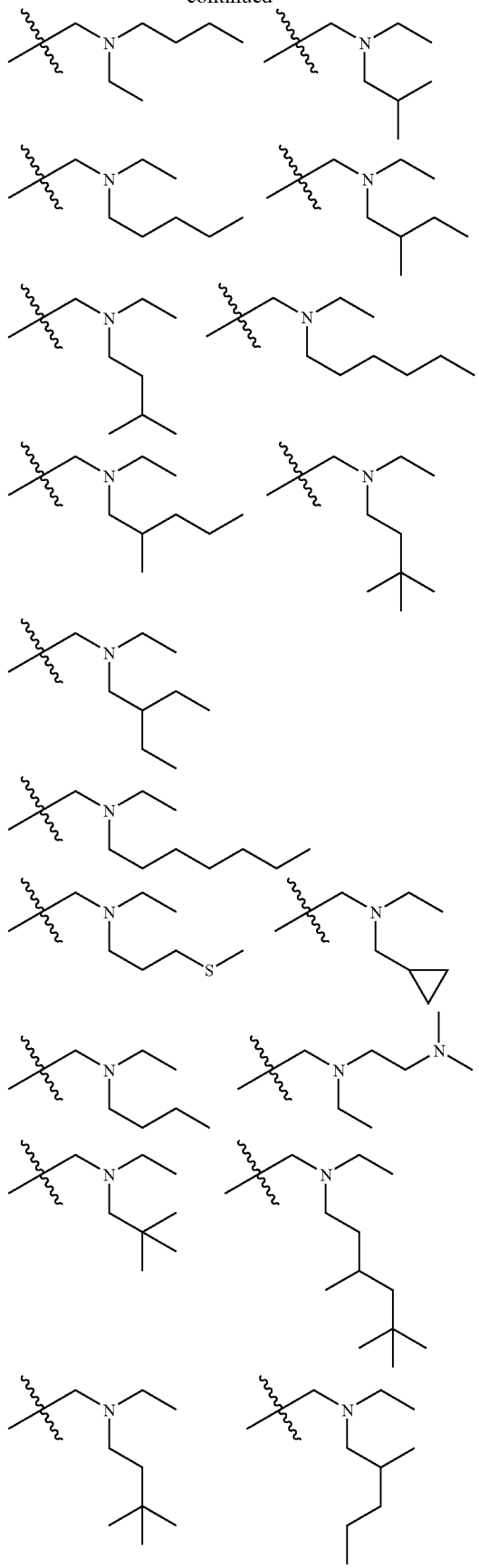

-continued

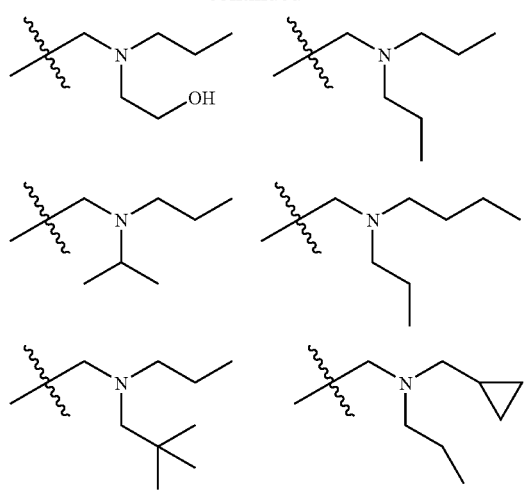

-continued

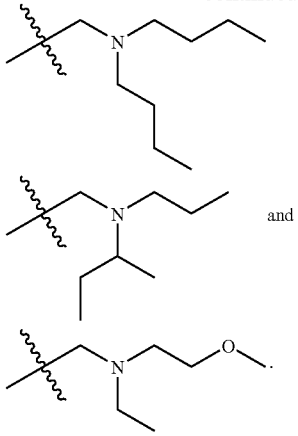

and

15. The method of claim 1, wherein the compound of Formula I is selected from compounds, and their pharmaceutically acceptable salts, selected from the group consisting of

| Structure | Name |
| --- | --- |
| 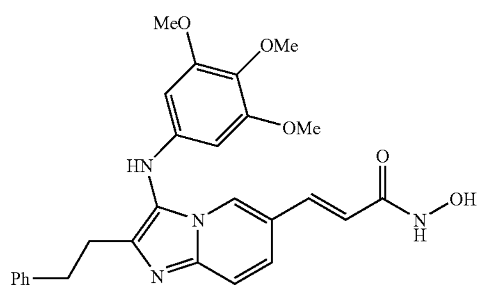 [SMILES: COc1cc(Nc2c(CCc3ccccc3)nc3ccc(/C=C/C(=O)NO)cn23)cc(OC)c1OC] | (E)-N-hydroxy-3-(2-phenethyl-3-(3,4,5-trimethoxyphenylamino)imidazo[1,2-a]pyridin-6-yl)acrylamide |
| 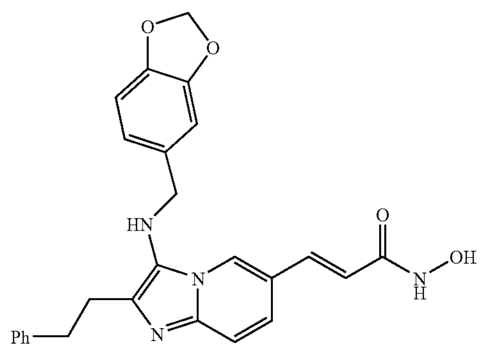 [SMILES: O=C(/C=C/c1ccc2nc(CCc3ccccc3)c(NCc3ccc4c(c3)OCO4)n2c1)NO] | (E)-3-(3-(benzo[d][1,3]dioxol-5-ylmethylamino)-2-phenethylimidazo[1,2-a]pyridin-6-yl)-N-hydroxyacrylamide |
| 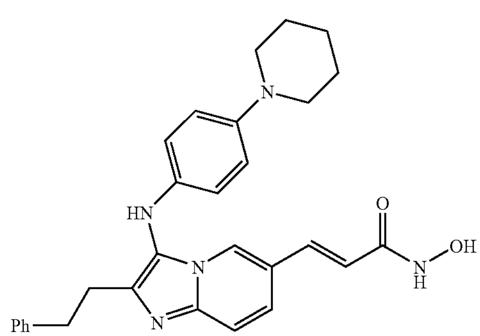 [SMILES: O=C(/C=C/c1ccc2nc(CCc3ccccc3)c(Nc3ccc(N4CCCCC4)cc3)n2c1)NO] | N-Hydroxy-3-[2-phenethyl-3-(4-piperidin-1-yl-phenylamino)-imidazo[1,2-a]pyridin-6-yl]-acrylamide |

-continued

| Structure | Name |
|---|---|
| 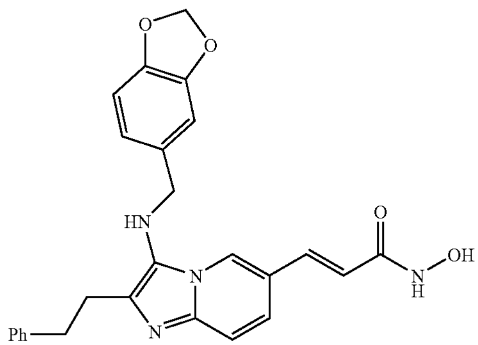 [SMILES: O=C(/C=C/c1ccc2nc(CCc3ccccc3)c(NCc3ccc4c(c3)OCO4)n2c1)NO] | (E)-3-(3-(benzo[d][1,3]dioxol-5-ylamino)-2-phenethylimidazo[1,2-a]pyridin-6-yl)-N-hydroxyacrylamide |
| 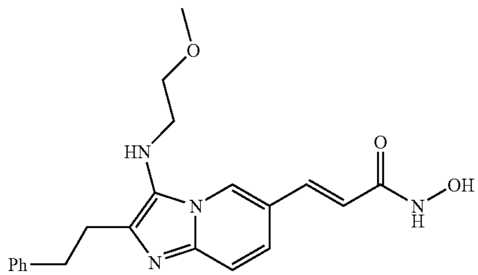 [SMILES: COCCNc1c(CCc2ccccc2)nc2ccc(/C=C/C(=O)NO)cn12] | (E)-N-hydroxy-3-(3-(2-methoxyethylamino)-2-phenethylimidazo[1,2-a]pyridin-6-yl)acrylamide |
| 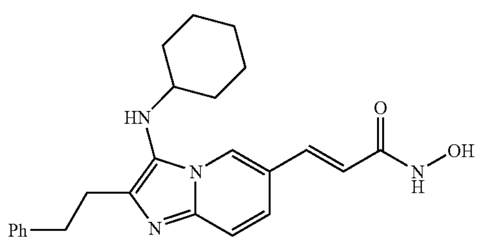 [SMILES: O=C(/C=C/c1ccc2nc(CCc3ccccc3)c(NC3CCCCC3)n2c1)NO] | (E)-3-(3-(cyclohexylamino)-2-phenethylimidazo[1,2-a]pyridin-6-yl)-N-hydroxyacrylamide |
| 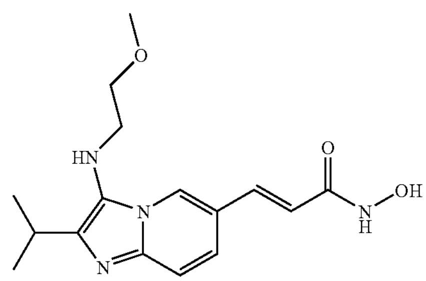 [SMILES: COCCNc1c(C(C)C)nc2ccc(/C=C/C(=O)NO)cn12] | (E)-N-hydroxy-3-(2-isopropyl-3-(2-methoxyethylamino)imidazo[1,2-a]pyridin-6-yl)acrylamide |
| 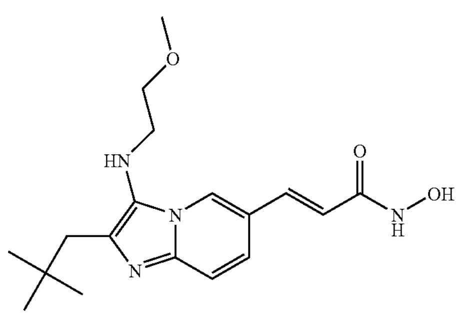 [SMILES: COCCNc1c(CC(C)(C)C)nc2ccc(/C=C/C(=O)NO)cn12] | 3-[2-(2,2-Dimethyl-propyl)-3-(2-methoxy-ethylamino)-imidazo[1,2-a]pyridin-6-yl]-N-hydroxy-acrylamide |

| Structure | Name |
|---|---|
| 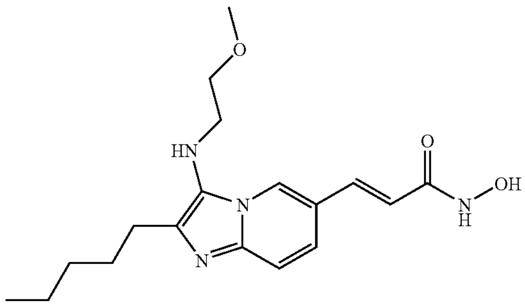 [SMILES: CCCCCc1nc2ccc(/C=C/C(=O)NO)cn2c1NCCOC] | (E)-N-hydroxy-3-(3-(2-methoxyethylamino)-2-pentylimidazo[1,2-a]pyridin-6-yl)acrylamide |
| 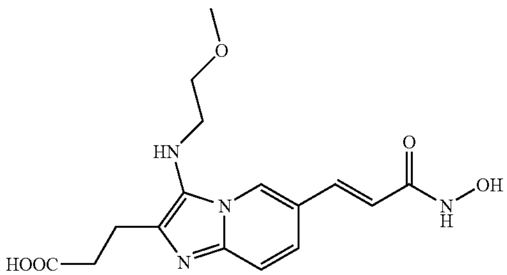 [SMILES: COCCNc1c(CCC(=O)O)nc2ccc(/C=C/C(=O)NO)cn12] | 3-[6-(2-Hydroxycarbamoyl-vinyl)-3-(2-methoxy-ethylamino)-imidazo[1,2-a]pyridin-2-yl]-propionic acid |
| 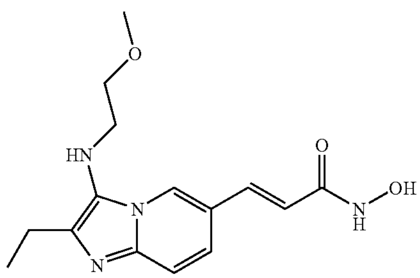 [SMILES: CCc1nc2ccc(/C=C/C(=O)NO)cn2c1NCCOC] | 3-[2-Ethyl-3-(2-methoxy-ethylamino)-imidazo[1,2-a]pyridin-6-yl]-N-hydroxy-acrylamide |
| 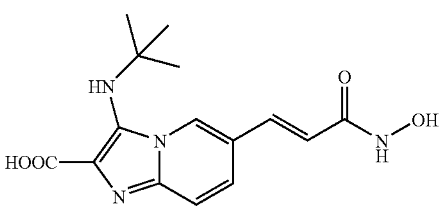 [SMILES: CC(C)(C)Nc1c(C(=O)O)nc2ccc(/C=C/C(=O)NO)cn12] | (E)-3-(tert-butylamino)-6-(3-(hydroxyamino)-3-oxoprop-1-enyl)imidazo[1,2-a]pyridine-2-carboxylic acid |
| 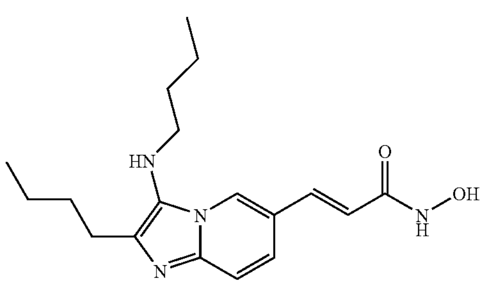 [SMILES: CCCCNc1c(CCCC)nc2ccc(/C=C/C(=O)NO)cn12] | (E)-3-(2-butyl-3-(butylamino)imidazo[1,2-a]pyridin-6-yl)-N-hydroxyacrylamide |
| 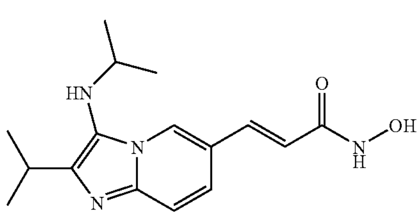 [SMILES: CC(C)Nc1c(C(C)C)nc2ccc(/C=C/C(=O)NO)cn12] | (E)-N-hydroxy-3-(2-isopropyl-3-(isopropylamino)imidazo[1,2-a]pyridin-6-yl)acrylamide |

| Structure | Name |
|---|---|
| 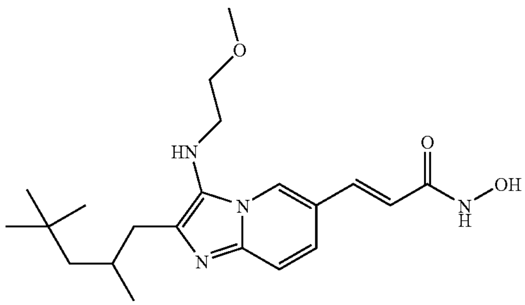 [SMILES: COCCNc1c(CC(C)CC(C)(C)C)nc2ccc(/C=C/C(=O)NO)cn12] | (E)-N-hydroxy-3-(3-(2-methoxyethylamino)-2-(2,4,4-trimethylpentyl)imidazo[1,2-a]pyridin-6-yl)acrylamide |
| 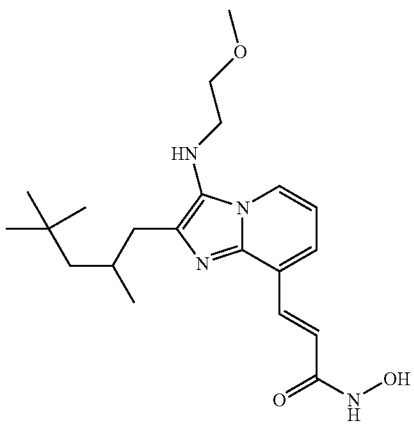 [SMILES: COCCNc1c(CC(C)CC(C)(C)C)nc2c(/C=C/C(=O)NO)cccn12] | (E)-N-hydroxy-3-(3-(2-methoxyethylamino)-2-(2,4,4-trimethylpentyl)imidazo[1,2-a]pyridin-8-yl)acrylamide |
| 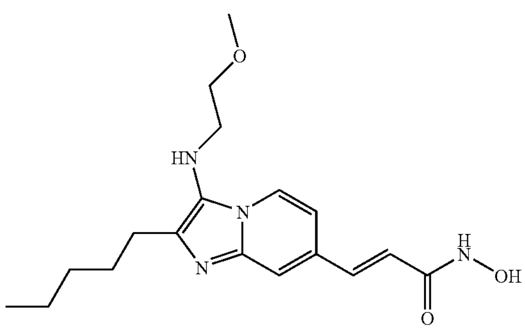 [SMILES: CCCCCc1nc2cc(/C=C/C(=O)NO)ccn2c1NCCOC] | (E)-N-hydroxy-3-(3-(2-methoxyethylamino)-2-pentylimidazo[1,2-a]pyridin-7-yl)acrylamide |
| 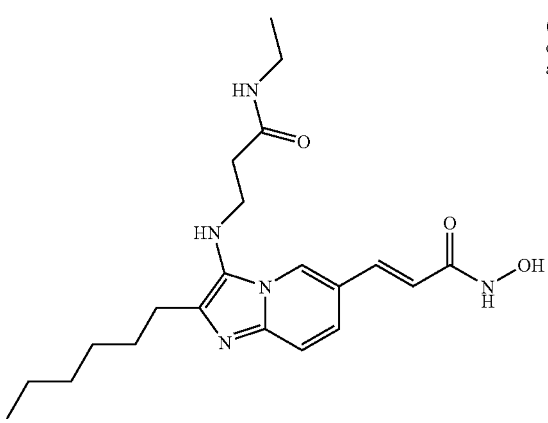 | (E)-3-(3-(3-(ethylamino)-3-oxopropylamino)-2-hexylimidazo[1,2-a]pyridin-6-yl)-N-hydroxyacrylamide |

| Structure | Name |
|---|---|
| 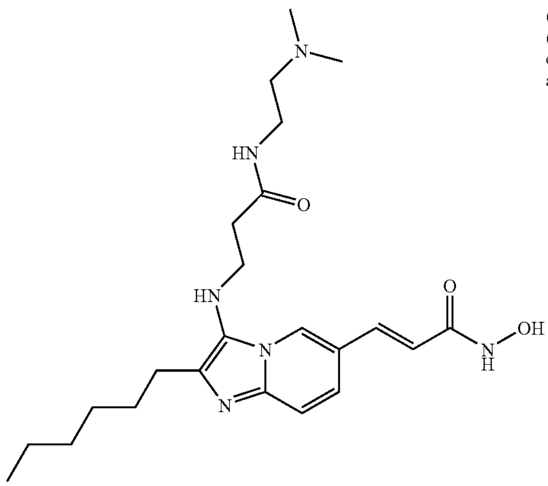 | (E)-3-(3-(3-(2-(dimethylamino)ethylamino)-3-oxopropylamino)-2-hexylimidazo[1,2-a]pyridin-6-yl)-N-hydroxyacrylamide |
| 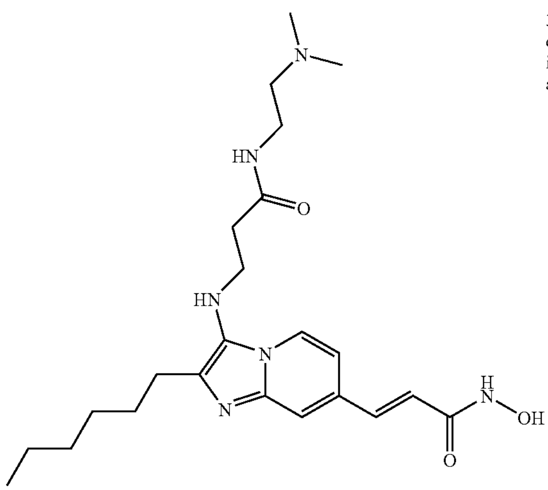 | 3-{3-[2-(2-Dimethylamino-ethylcarbamoyl)-ethylamino]-2-hexyl-imidazo[1,2-a]pyridin-7-yl}-N-hydroxy-acrylamide |
| 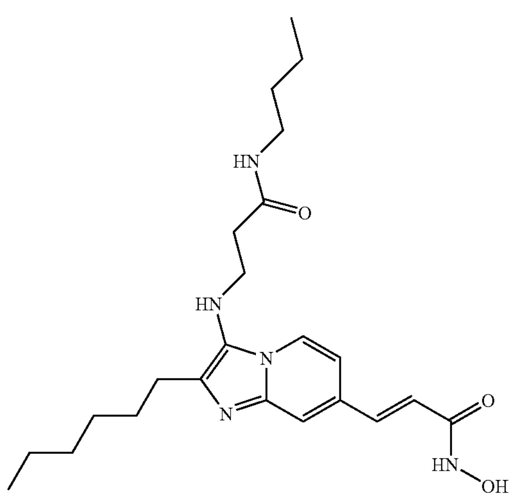 [SMILES: CCCCCCc1nc2cc(/C=C/C(=O)NO)ccn2c1NCCC(=O)NCCCC] | 3-[3-(2-Butylcarbamoyl-ethylamino)-2-hexyl-imidazo[1,2-a]pyridin-7-yl]-N-hydroxy-acrylamide |

| Structure | Name |
|---|---|
| 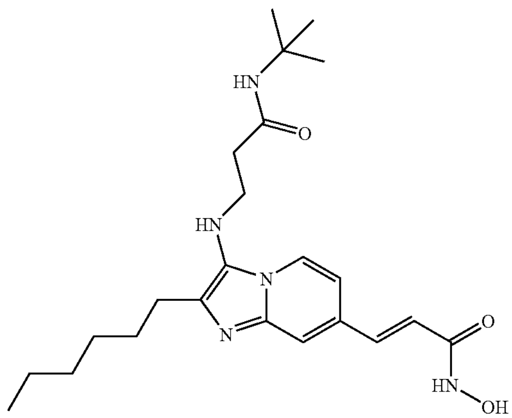 [SMILES: CCCCCCc1nc2cc(/C=C/C(=O)NO)ccn2c1NCCC(=O)NC(C)(C)C] | 3-[3-(2-tert-Butylcarbamoyl-ethylamino)-2-hexyl-imidazo[1,2-a]pyridin-7-yl]-N-hydroxy-acrylamide |
| 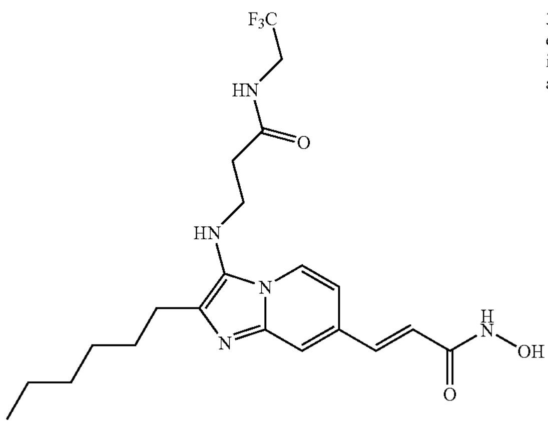 | 3-{2-Hexyl-3-[2-(2,2,2-trifluoro-ethylcarbamoyl)-ethylamino]-imidazo[1,2-a]pyridin-7-yl}-N-hydroxy-acrylamide |
| 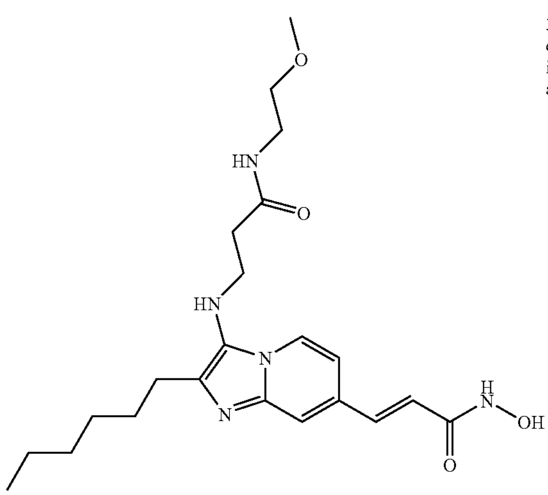 | 3-{2-Hexyl-3-[2-(2-methoxy-ethylcarbamoyl)-ethylamino]-imidazo[1,2-a]pyridin-7-yl}-N-hydroxy-acrylamide |

| Structure | Name |
|---|---|
| 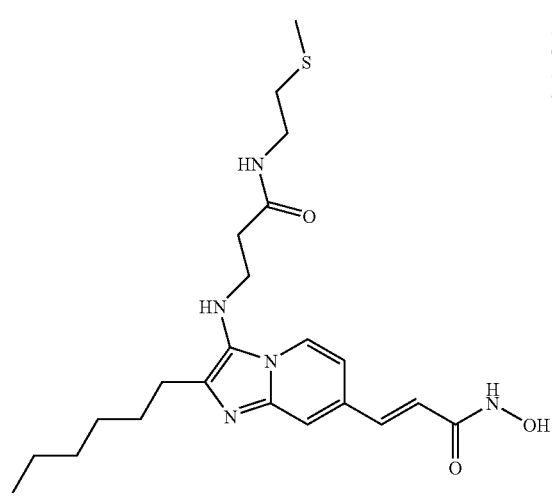 | 3-{2-Hexyl-3-[2-(2-methylsulfanyl-ethylcarbamoyl)-ethylamino]-imidazo[1,2-a]pyridin-7-yl}-N-hydroxy-acrylamide |
| 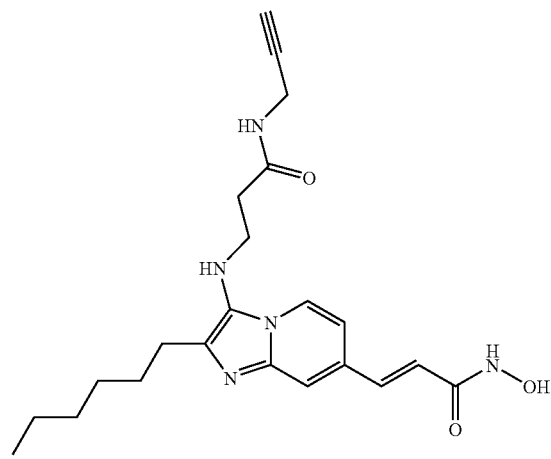 [SMILES: C#CCNC(=O)CCNc1c(CCCCCC)nc2cc(/C=C/C(=O)NO)ccn12] | 3-[2-Hexyl-3-(2-prop-2-ynylcarbamoyl-ethylamino)-imidazo[1,2-a]pyridin-7-yl]-N-hydroxy-acrylamide |
| 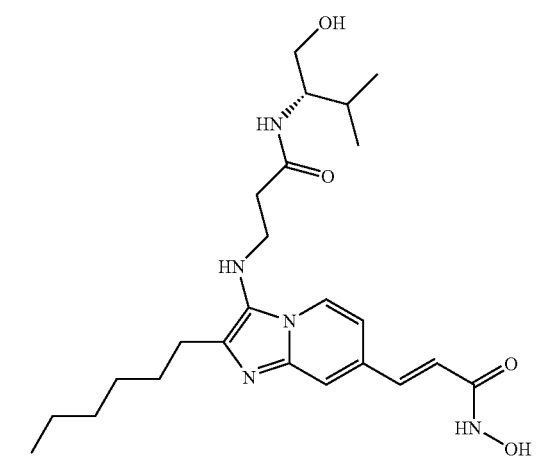 | 3-{2-Hexyl-3-[2-(1-hydroxymethyl-2-methyl-propylcarbamoyl)-ethylamino]-imidazo[1,2-a]pyridin-7-yl}-N-hydroxy-acrylamide |

| Structure | Name |
|---|---|
| 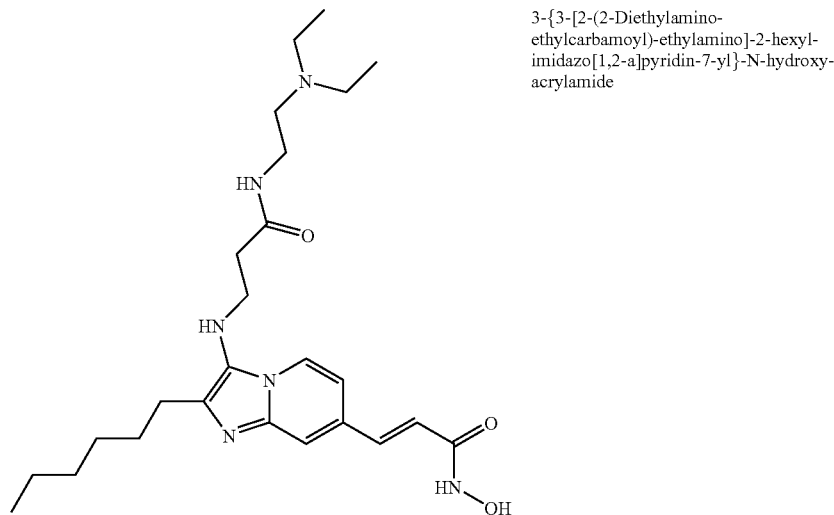 | 3-{3-[2-(2-Diethylamino-ethylcarbamoyl)-ethylamino]-2-hexyl-imidazo[1,2-a]pyridin-7-yl}-N-hydroxy-acrylamide |
| 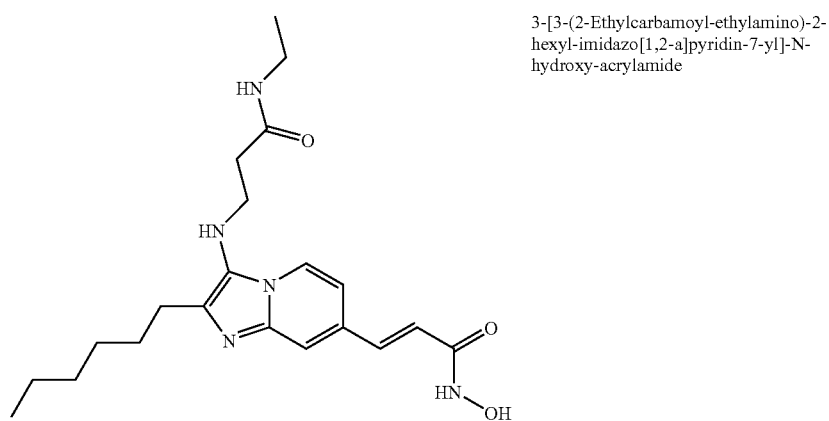 | 3-[3-(2-Ethylcarbamoyl-ethylamino)-2-hexyl-imidazo[1,2-a]pyridin-7-yl]-N-hydroxy-acrylamide |
| 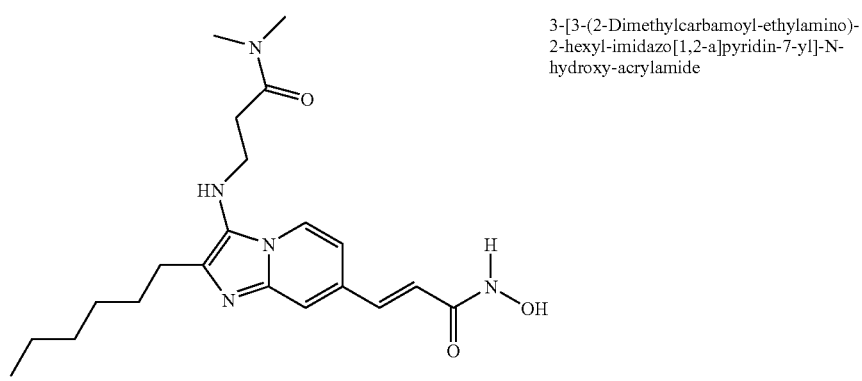 | 3-[3-(2-Dimethylcarbamoyl-ethylamino)-2-hexyl-imidazo[1,2-a]pyridin-7-yl]-N-hydroxy-acrylamide |

| Structure | Name |
|---|---|
| 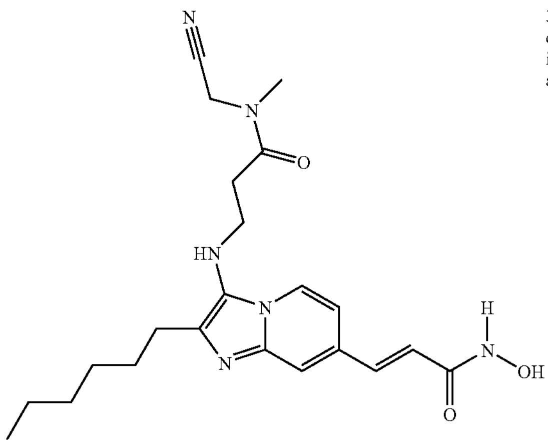 | 3-{3-[2-(Cyanomethyl-methyl-carbamoyl)-ethylamino]-2-hexyl-imidazo[1,2-a]pyridin-7-yl}-N-hydroxy-acrylamide |
| 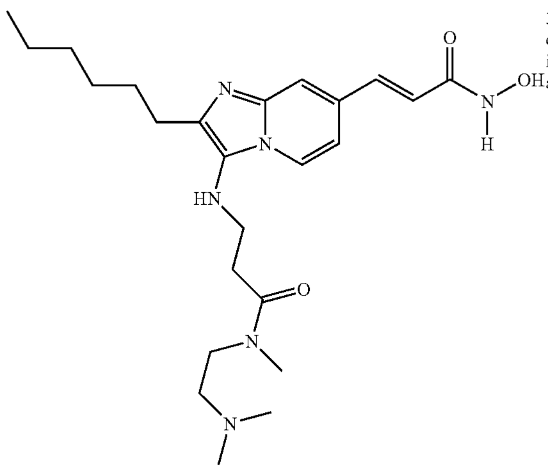 | 3-(3-{2-[(2-Dimethylamino-ethyl)-methyl-carbamoyl]-ethylamino}-2-hexyl-imidazo[1,2-a]pyridin-7-yl)-N-hydroxy-acrylamide |
| 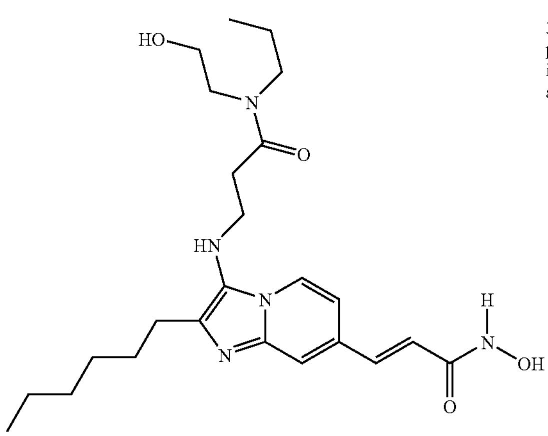 | 3-(2-Hexyl-3-{2-[(2-hydroxy-ethyl)-propyl-carbamoyl]-ethylamino}-imidazo[1,2-a]pyridin-7-yl)-N-hydroxy-acrylamide |
| 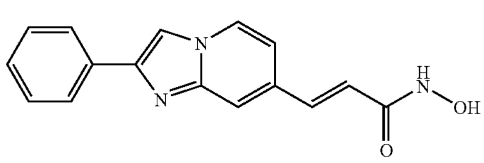 [SMILES: O=C(/C=C/c1ccn2cc(-c3ccccc3)nc2c1)NO] | N-Hydroxy-3-(2-phenyl-imidazo[1,2-a]pyridin-7-yl)-acrylamide |

-continued
| Structure | Name |
|---|---|
| 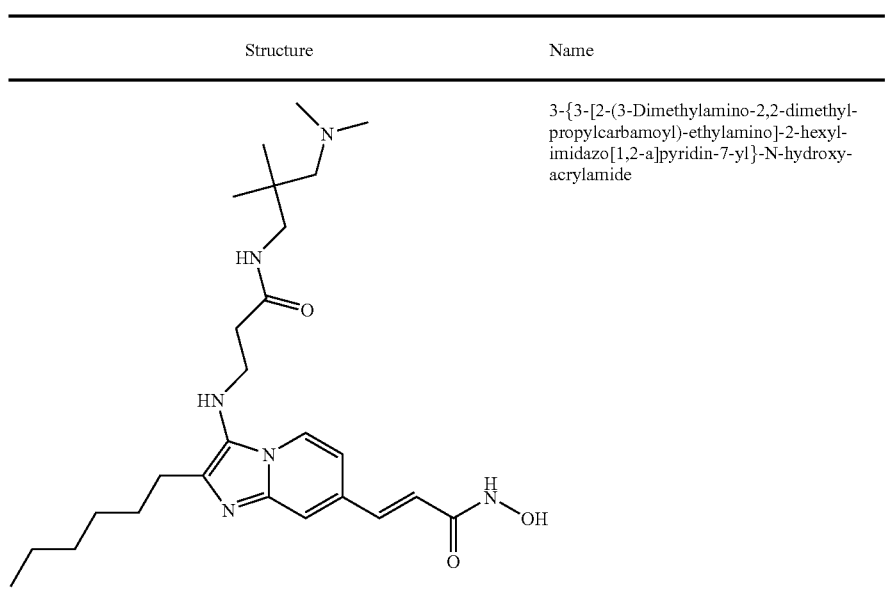 | 3-{3-[2-(3-Dimethylamino-2,2-dimethyl-propylcarbamoyl)-ethylamino]-2-hexyl-imidazo[1,2-a]pyridin-7-yl}-N-hydroxy-acrylamide |
| 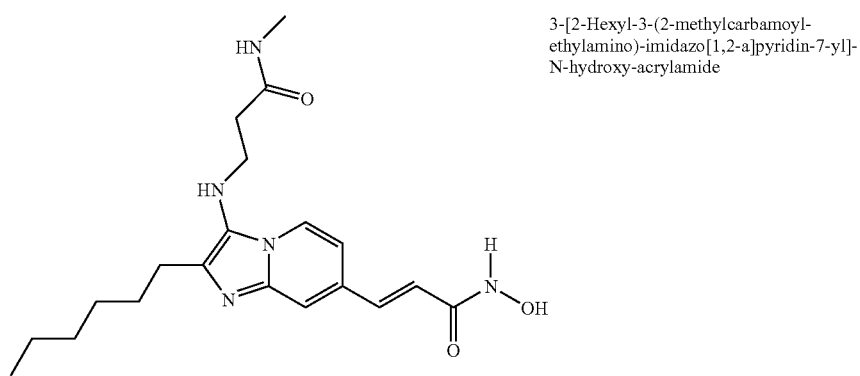 | 3-[2-Hexyl-3-(2-methylcarbamoyl-ethylamino)-imidazo[1,2-a]pyridin-7-yl]-N-hydroxy-acrylamide |
| 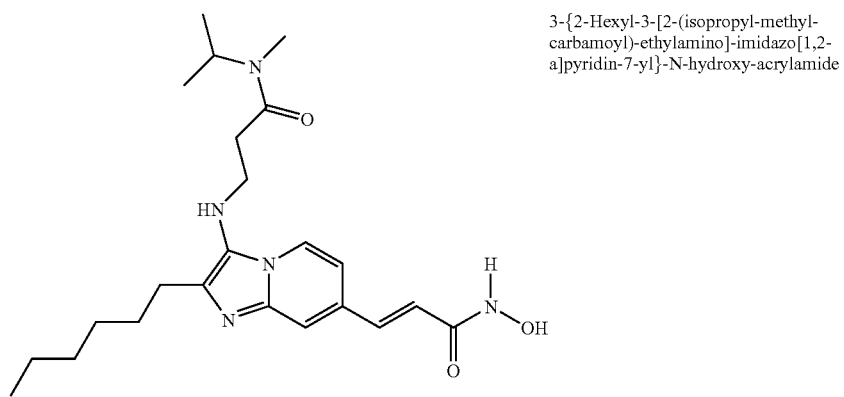 | 3-{2-Hexyl-3-[2-(isopropyl-methyl-carbamoyl)-ethylamino]-imidazo[1,2-a]pyridin-7-yl}-N-hydroxy-acrylamide |

| Structure | Name |
|---|---|
| 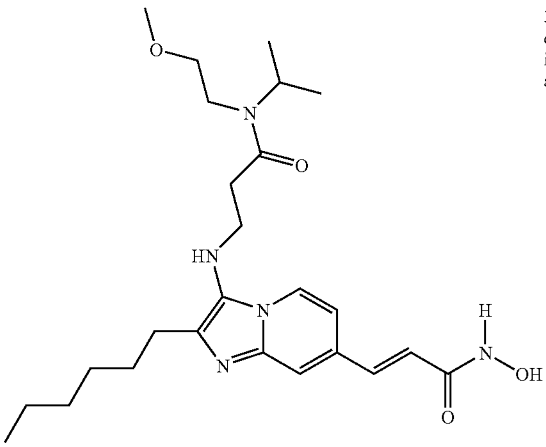 | 3-(2-Hexyl-3-{2-[isopropyl-(2-methoxy-ethyl)-carbamoyl]-ethylamino}-imidazo[1,2-a]pyridin-7-yl)-N-hydroxy-acrylamide |
| 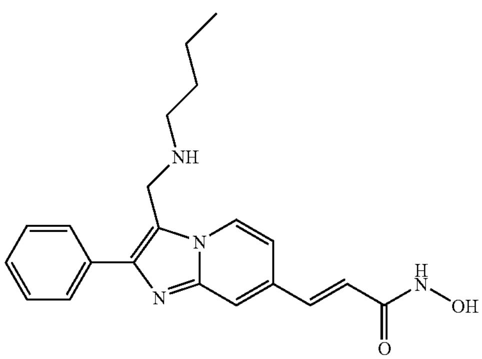 [SMILES: CCCCNCc1c(-c2ccccc2)nc2cc(/C=C/C(=O)NO)ccn12] | 3-(3-Butylaminomethyl-2-phenyl-imidazo[1,2-a]pyridin-7-yl)-N-hydroxy-acrylamide |
| 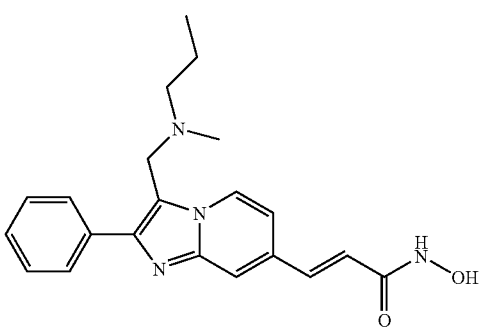 [SMILES: CCCN(C)Cc1c(-c2ccccc2)nc2cc(/C=C/C(=O)NO)ccn12] | N-Hydroxy-3-{3-[(methyl-propyl-amino)-methyl]-2-phenyl-imidazo[1,2-a]pyridin-7-yl}-acrylamide. |
| 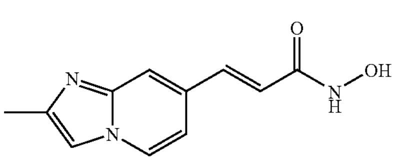 [SMILES: Cc1cn2ccc(/C=C/C(=O)NO)cc2n1] | N-Hydroxy-3-(2-methyl-imidazo[1,2-a]pyridin-7-yl)-acrylamide |

| Structure | Name |
|---|---|
| 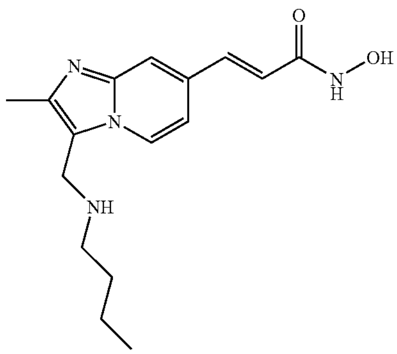 [SMILES: CCCCNCc1c(C)nc2cc(/C=C/C(=O)NO)ccn12] | 3-(3-Butylaminomethyl-2-methyl-imidazo[1,2-a]pyridin-7-yl)-N-hydroxy-acrylamide |
| 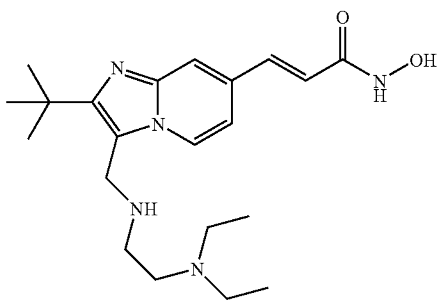 [SMILES: CCN(CC)CCNCc1c(C(C)(C)C)nc2cc(/C=C/C(=O)NO)ccn12] | 3-{2-tert-Butyl-3-[(2-diethylamino-ethylamino)-methyl]-imidazo[1,2-a]pyridin-7-yl}-N-hydroxy-acrylamide |
| 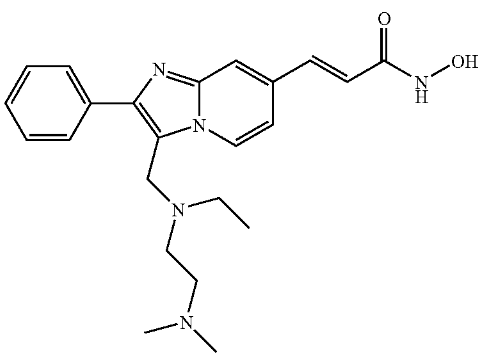 [SMILES: CCN(CCN(C)C)Cc1c(-c2ccccc2)nc2cc(/C=C/C(=O)NO)ccn12] | 3-(3-{[(2-Dimethylamino-ethyl)-ethyl-amino]-methyl}-2-phenyl-imidazo[1,2-a]pyridin-7-yl)-N-hydroxy-acrylamide |
| 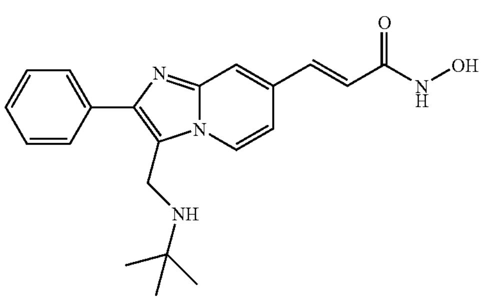 [SMILES: CC(C)(C)NCc1c(-c2ccccc2)nc2cc(/C=C/C(=O)NO)ccn12] | 3-[3-(tert-Butylamino-methyl)-2-phenyl-imidazo[1,2-a]pyridin-7-yl]-N-hydroxy-acrylamide |
| 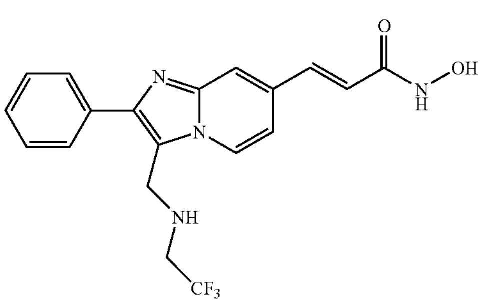 [SMILES: O=C(/C=C/c1ccn2c(CNCC(F)(F)F)c(-c3ccccc3)nc2c1)NO] | N-Hydroxy-3-{2-phenyl-3-[(2,2,2-trifluoro-ethylamino)-methyl]-imidazo[1,2-a]pyridin-7-yl}-acrylamide |

| Structure | Name |
|---|---|
| 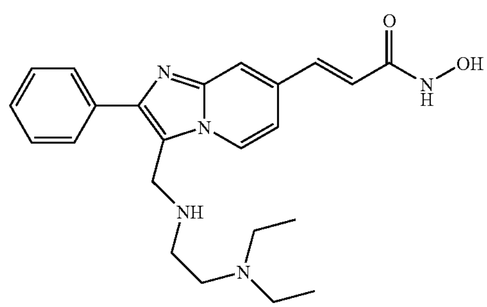 [SMILES: CCN(CC)CCNCc1c(-c2ccccc2)nc2cc(/C=C/C(=O)NO)ccn12] | 3-{3-[(2-Diethylamino-ethylamino)-methyl]-2-phenyl-imidazo[1,2-a]pyridin-7-yl}-N-hydroxy-acrylamide |
| 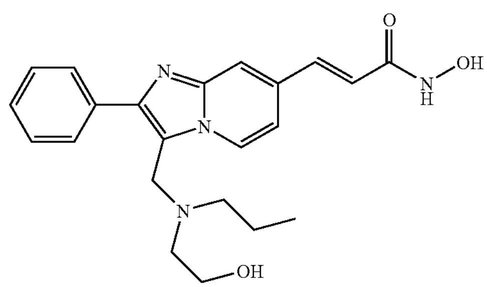 [SMILES: CCCN(CCO)Cc1c(-c2ccccc2)nc2cc(/C=C/C(=O)NO)ccn12] | N-Hydroxy-3-(3-{[(2-hydroxy-ethyl)-propyl-amino]-methyl}-2-phenyl-imidazo[1,2-a]pyridin-7-yl)-acrylamide |
| 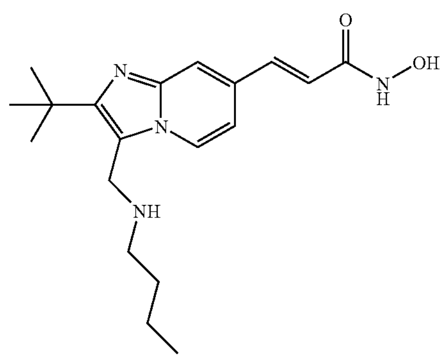 [SMILES: CCCCNCc1c(C(C)(C)C)nc2cc(/C=C/C(=O)NO)ccn12] | 3-(2-tert-Butyl-3-butylaminomethyl-imidazo[1,2-a]pyridin-7-yl)-N-hydroxy-acrylamide |
| 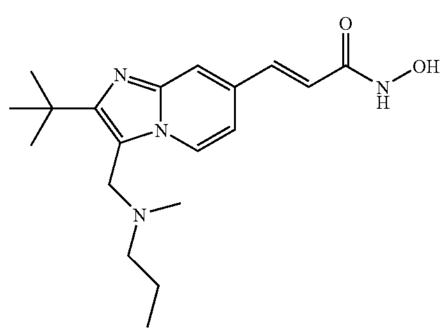 [SMILES: CCCN(C)Cc1c(C(C)(C)C)nc2cc(/C=C/C(=O)NO)ccn12] | 3-{2-tert-Butyl-3-[(methyl-propyl-amino)-methyl]-imidazo[1,2-a]pyridin-7-yl}-N-hydroxy-acrylamide |
| 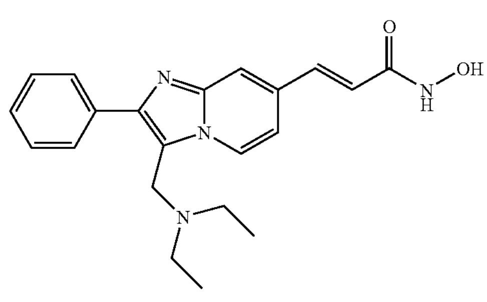 [SMILES: CCN(CC)Cc1c(-c2ccccc2)nc2cc(/C=C/C(=O)NO)ccn12] | 3-(3-Diethylaminomethyl-2-phenyl-imidazo[1,2-a]pyridin-7-yl)-N-hydroxy-acrylamide |

| Structure | Name |
|---|---|
| 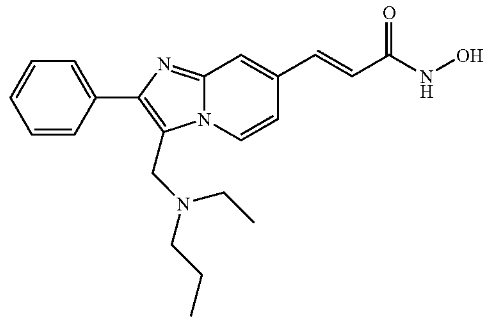 [SMILES: CCCN(CC)Cc1c(-c2ccccc2)nc2cc(/C=C/C(=O)NO)ccn12] | 3-{3-[(Ethyl-propyl-amino)-methyl]-2-phenyl-imidazo[1,2-a]pyridin-7-yl}-N-hydroxy-acrylamide |
| 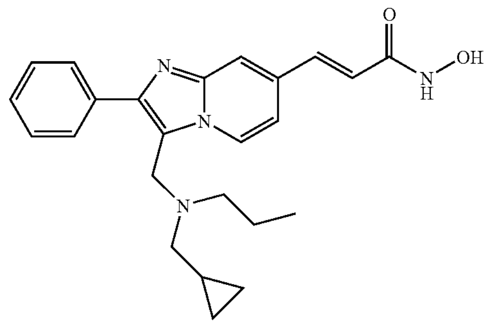 [SMILES: CCCN(Cc1c(-c2ccccc2)nc2cc(/C=C/C(=O)NO)ccn12)CC1CC1] | 3-{3-[(Cyclopropylmethyl-propyl-amino)-methyl]-2-phenyl-imidazo[1,2-a]pyridin-7-yl}-N-hydroxy-acrylamide |
| 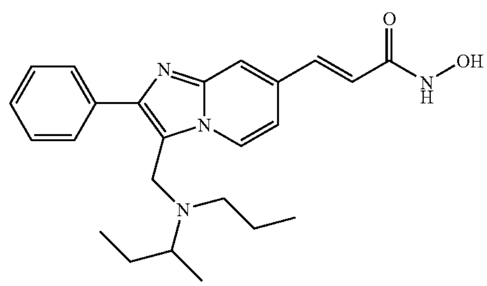 [SMILES: CCCN(Cc1c(-c2ccccc2)nc2cc(/C=C/C(=O)NO)ccn12)C(C)CC] | 3-{3-[(sec-Butyl-propyl-amino)-methyl]-2-phenyl-imidazo[1,2-a]pyridin-7-yl}-N-hydroxy-acrylamide |
| 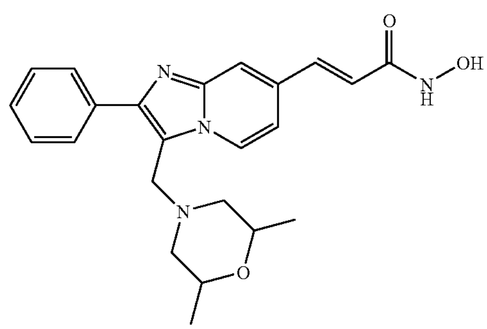 [SMILES: CC1CN(Cc2c(-c3ccccc3)nc3cc(/C=C/C(=O)NO)ccn23)CC(C)O1] | 3-[3-(2,6-Dimethyl-morpholin-4-ylmethyl)-2-phenyl-imidazo[1,2-a]pyridin-7-yl]-N-hydroxy-acrylamide |
| 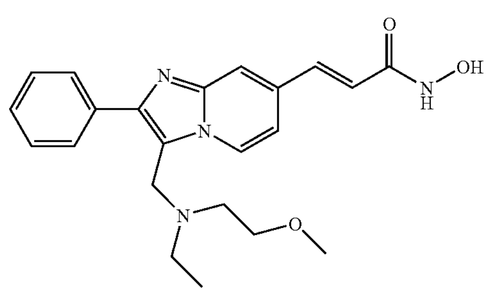 [SMILES: CCN(CCOC)Cc1c(-c2ccccc2)nc2cc(/C=C/C(=O)NO)ccn12] | 3-(3-{[Ethyl-(2-methoxy-ethyl)-amino]-methyl}-2-phenyl-imidazo[1,2-a]pyridin-7-yl)-N-hydroxy-acrylamide |

| Structure | Name |
|---|---|
| 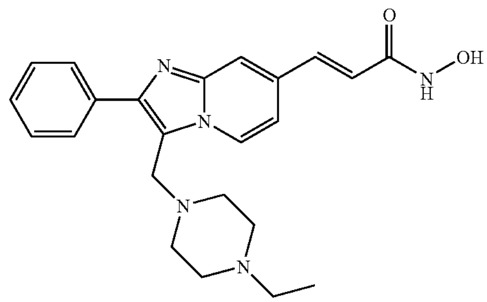 [SMILES: CCN1CCN(Cc2c(-c3ccccc3)nc3cc(/C=C/C(=O)NO)ccn23)CC1] | 3-[3-(4-Ethyl-piperazin-1-ylmethyl)-2-phenyl-imidazo[1,2-a]pyridin-7-yl]-N-hydroxy-acrylamide |
| 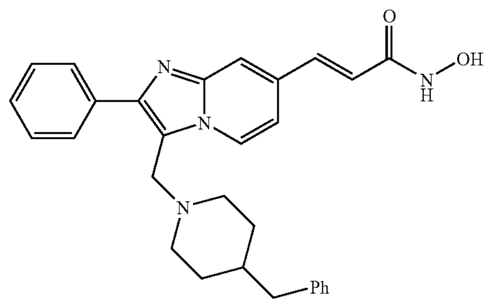 [SMILES: O=C(/C=C/c1ccn2c(CN3CCC(Cc4ccccc4)CC3)c(-c3ccccc3)nc2c1)NO] | 3-[3-(4-Benzyl-piperidin-1-ylmethyl)-2-phenyl-imidazo[1,2-a]pyridin-7-yl]-N-hydroxy-acrylamide |
| 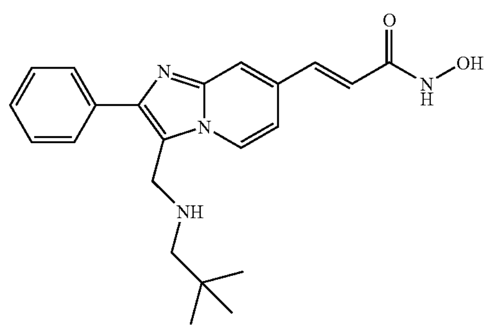 [SMILES: CC(C)(C)CNCc1c(-c2ccccc2)nc2cc(/C=C/C(=O)NO)ccn12] | 3-{3-[(2,2-Dimethyl-propylamino)-methyl]-2-phenyl-imidazo[1,2-a]pyridin-7-yl}-N-hydroxy-acrylamide |
| 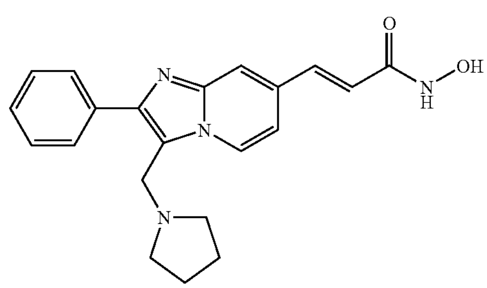 [SMILES: O=C(/C=C/c1ccn2c(CN3CCCC3)c(-c3ccccc3)nc2c1)NO] | N-Hydroxy-3-(2-phenyl-3-pyrrolidin-1-ylmethyl-imidazo[1,2-a]pyridin-7-yl)-acrylamide |
| 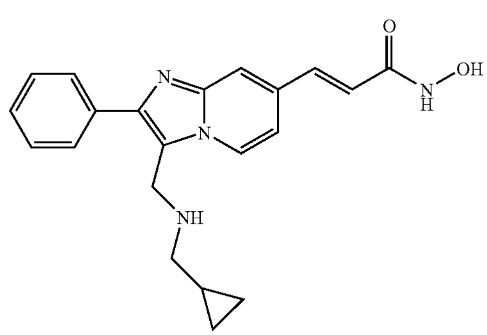 [SMILES: O=C(/C=C/c1ccn2c(CNCC3CC3)c(-c3ccccc3)nc2c1)NO] | 3-{3-[(Cyclopropylmethyl-amino)-methyl]-2-phenyl-imidazo[1,2-a]pyridin-7-yl}-N-hydroxy-acrylamide |

| Structure | Name |
|---|---|
| 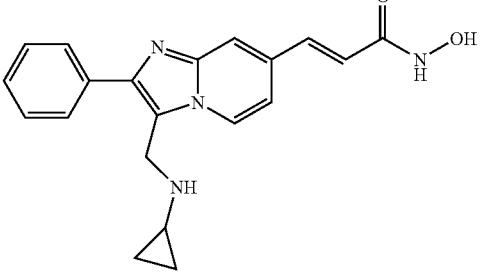 | 3-(3-Cyclopropylaminomethyl-2-phenyl-imidazo[1,2-a]pyridin-7-yl)-N-hydroxy-acrylamide |
| 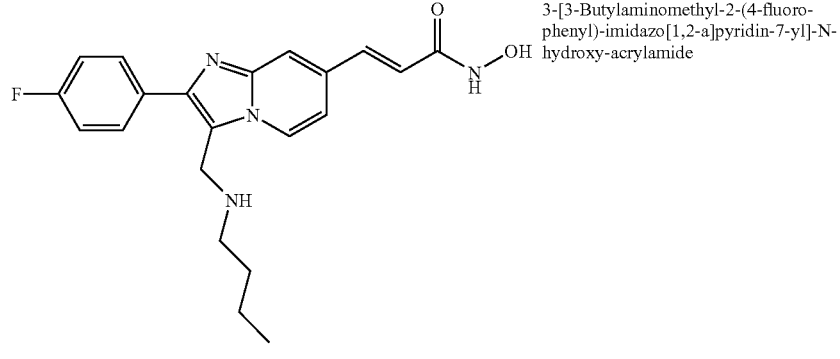 | 3-[3-Butylaminomethyl-2-(4-fluoro-phenyl)-imidazo[1,2-a]pyridin-7-yl]-N-hydroxy-acrylamide |
| 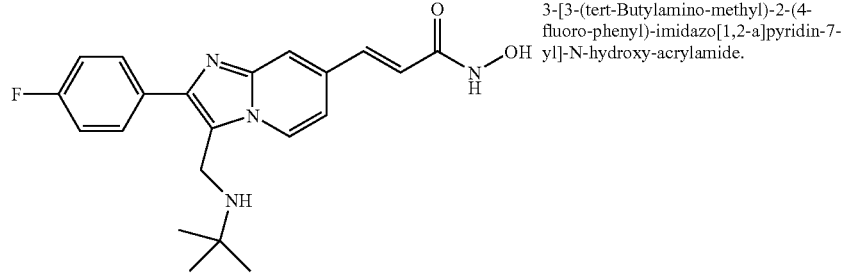 | 3-[3-(tert-Butylamino-methyl)-2-(4-fluoro-phenyl)-imidazo[1,2-a]pyridin-7-yl]-N-hydroxy-acrylamide. |
| 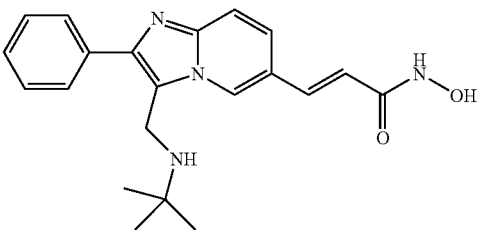 [SMILES: CC(C)(C)NCc1c(-c2ccccc2)nc2ccc(/C=C/C(=O)NO)cn12] | 3-[3-(tert-Butylamino-methyl)-2-phenyl-imidazo[1,2-a]pyridin-6-yl]-N-hydroxy-acrylamide |
| 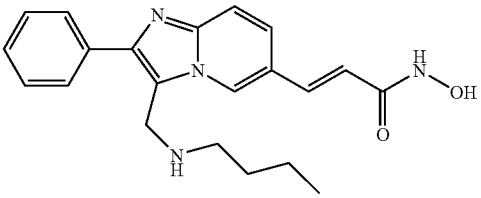 [SMILES: CCCCNCc1c(-c2ccccc2)nc2ccc(/C=C/C(=O)NO)cn12] | 3-(3-Butylaminomethyl-2-phenyl-imidazo[1,2-a]pyridin-6-yl)-N-hydroxy-acrylamide |

| Structure | Name |
|---|---|
| 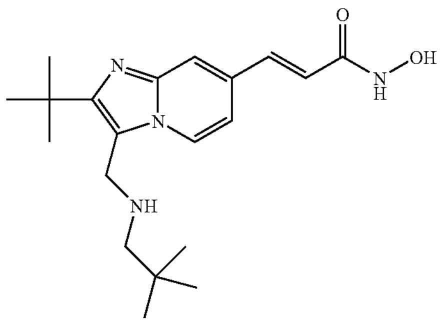 [SMILES: CC(C)(C)CNCc1c(C(C)(C)C)nc2cc(/C=C/C(=O)NO)ccn12] | 3-{2-tert-Butyl-3-[(2,2-dimethyl-propylamino)-methyl]-imidazo[1,2-a]pyridin-7-yl}-N-hydroxy-acrylamide |
| 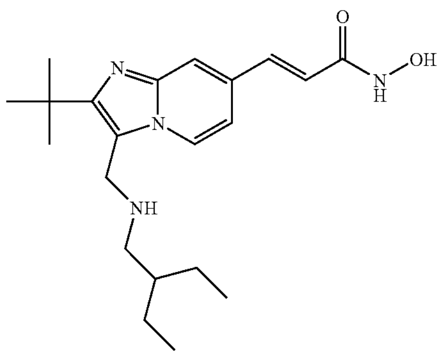 [SMILES: CCC(CC)CNCc1c(C(C)(C)C)nc2cc(/C=C/C(=O)NO)ccn12] | 3-{2-tert-Butyl-3-[(2-ethyl-butylamino)-methyl]-imidazo[1,2-a]pyridin-7-yl}-N-hydroxy-acrylamide |
| 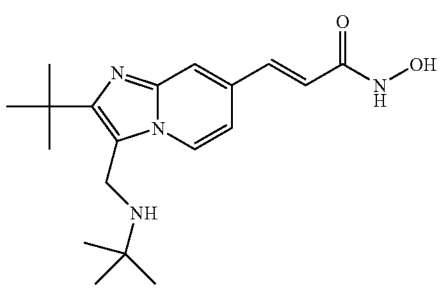 [SMILES: CC(C)(C)NCc1c(C(C)(C)C)nc2cc(/C=C/C(=O)NO)ccn12] | 3-[2-tert-Butyl-3-(tert-butylamino-methyl)-imidazo[1,2-a]pyridin-7-yl]-N-hydroxy-acrylamide |
| 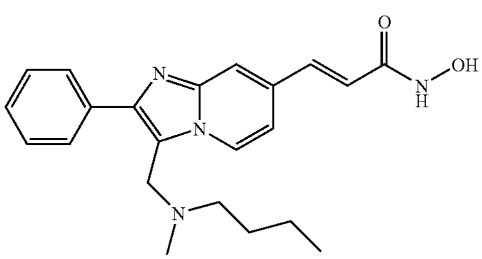 [SMILES: CCCCN(C)Cc1c(-c2ccccc2)nc2cc(/C=C/C(=O)NO)ccn12] | 3-{3-[(Butyl-methyl-amino)-methyl]-2-phenyl-imidazo[1,2-a]pyridin-7-yl}-N-hydroxy-acrylamide |
| 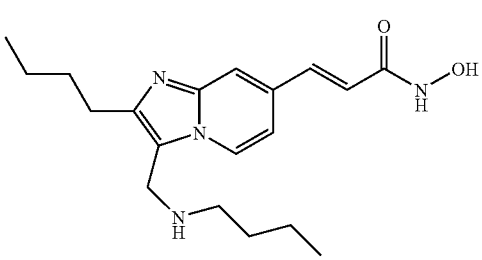 [SMILES: CCCCNCc1c(CCCC)nc2cc(/C=C/C(=O)NO)ccn12] | 3-(2-Butyl-3-butylaminomethyl-imidazo[1,2-a]pyridin-7-yl)-N-hydroxy-acrylamide |

-continued

| Structure | Name |
|---|---|
| 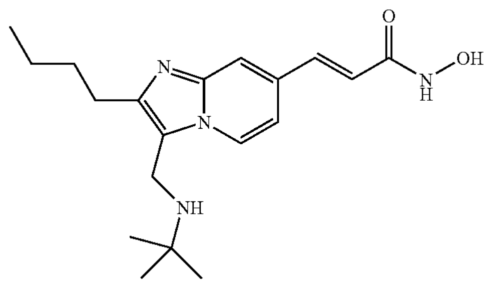 [SMILES: CCCCc1nc2cc(/C=C/C(=O)NO)ccn2c1CNC(C)(C)C] | 3-[2-Butyl-3-(tert-butylamino-methyl)-imidazo[1,2-a]pyridin-7-yl]-N-hydroxy-acrylamide |
| 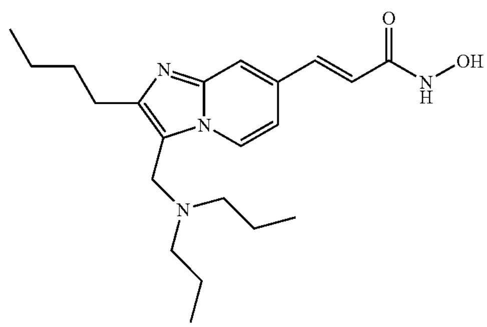 [SMILES: CCCCc1nc2cc(/C=C/C(=O)NO)ccn2c1CN(CCC)CCC] | 3-(2-Butyl-3-dipropylaminomethyl-imidazo[1,2-a]pyridin-7-yl)-N-hydroxy-acrylamide |
| 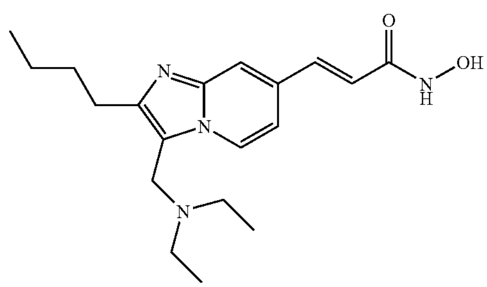 [SMILES: CCCCc1nc2cc(/C=C/C(=O)NO)ccn2c1CN(CC)CC] | 3-(2-Butyl-3-diethylaminomethyl-imidazo[1,2-a]pyridin-7-yl)-N-hydroxy-acrylamide |
| 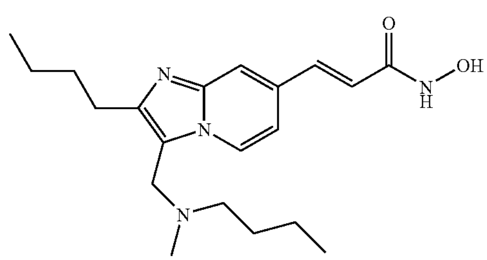 [SMILES: CCCCc1nc2cc(/C=C/C(=O)NO)ccn2c1CN(C)CCCC] | 3-{2-Butyl-3-[(butyl-methyl-amino)-methyl]-imidazo[1,2-a]pyridin-7-yl}-N-hydroxy-acrylamide |
| 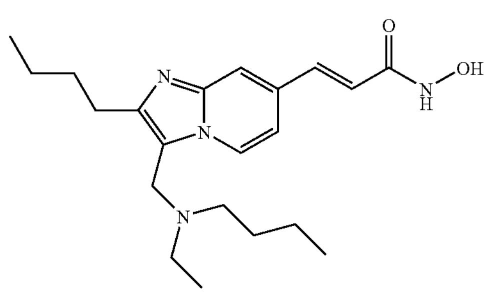 | 3-{2-Butyl-3-[(butyl-ethyl-amino)-methyl]-imidazo[1,2-a]pyridin-7-yl}-N-hydroxy-acrylamide |

| Structure | Name |
|---|---|
| 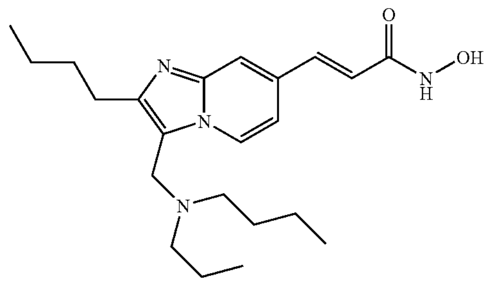 [SMILES: CCCCc1nc2cc(/C=C/C(=O)NO)ccn2c1CN(CCC)CCCC] | 3-{2-Butyl-3-[(butyl-propyl-amino)-methyl]-imidazo[1,2-a]pyridin-7-yl}-N-hydroxy-acrylamide |
| 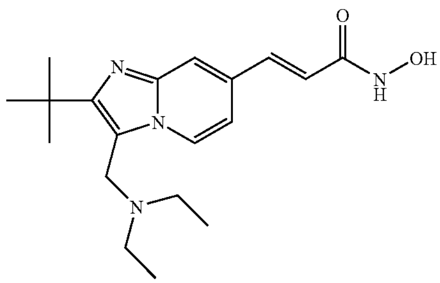 [SMILES: CCN(CC)Cc1c(C(C)(C)C)nc2cc(/C=C/C(=O)NO)ccn12] | 3-(2-tert-Butyl-3-diethylaminomethyl-imidazo[1,2-a]pyridin-7-yl)-N-hydroxy-acrylamide |
| 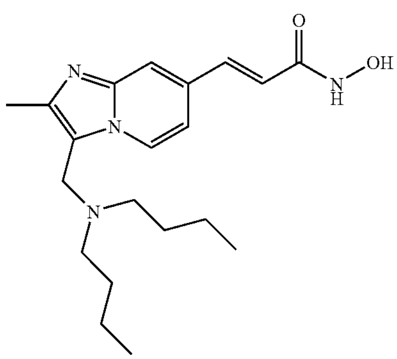 [SMILES: CCCCN(CCCC)Cc1c(C)nc2cc(/C=C/C(=O)NO)ccn12] | 3-(3-Dibutylaminomethyl-2-methyl-imidazo[1,2-a]pyridin-7-yl)-N-hydroxy-acrylamide |
| 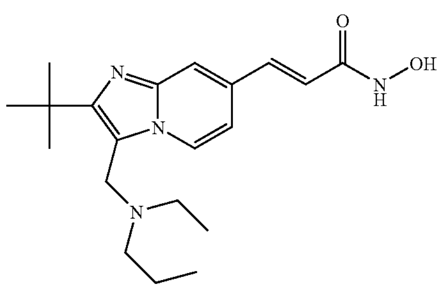 [SMILES: CCCN(CC)Cc1c(C(C)(C)C)nc2cc(/C=C/C(=O)NO)ccn12] | 3-{2-tert-Butyl-3-[(ethyl-propyl-amino)-methyl]-imidazo[1,2-a]pyridin-7-yl}-N-hydroxy-acrylamide |
| 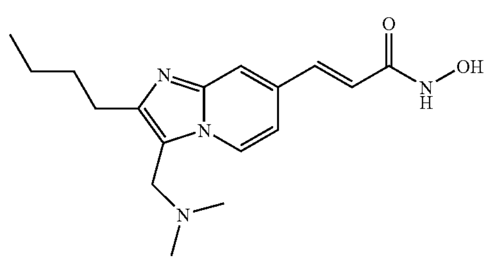 [SMILES: CCCCc1nc2cc(/C=C/C(=O)NO)ccn2c1CN(C)C] | 3-(2-Butyl-3-dimethylaminomethyl-imidazo[1,2-a]pyridin-7-yl)-N-hydroxy-acrylamide |

| Structure | Name |
|---|---|
| 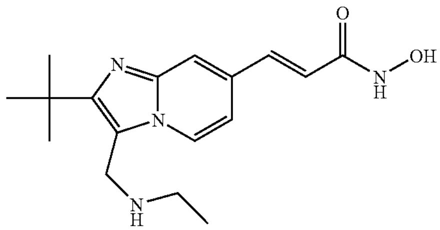 [SMILES: CCNCc1c(C(C)(C)C)nc2cc(/C=C/C(=O)NO)ccn12] | 3-(2-tert-Butyl-3-ethylaminomethyl-imidazo[1,2-a]pyridin-7-yl)-N-hydroxy-acrylamide |
| 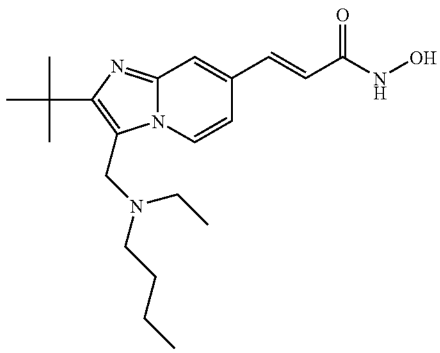 [SMILES: CCCCN(CC)Cc1c(C(C)(C)C)nc2cc(/C=C/C(=O)NO)ccn12] | 3-{2-tert-Butyl-3-[(butyl-ethyl-amino)-methyl]-imidazo[1,2-a]pyridin-7-yl}-N-hydroxy-acrylamide |
| 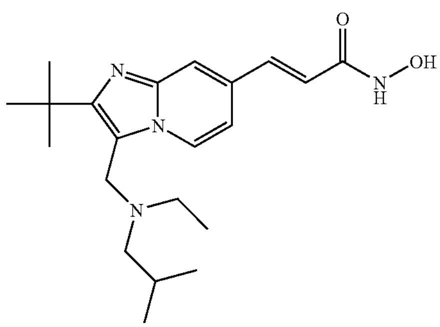 [SMILES: CCN(Cc1c(C(C)(C)C)nc2cc(/C=C/C(=O)NO)ccn12)CC(C)C] | 3-{2-tert-Butyl-3-[(ethyl-isobutyl-amino)-methyl]-imidazo[1,2-a]pyridin-7-yl}-N-hydroxy-acrylamide |
| 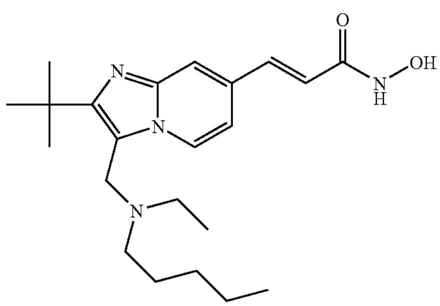 [SMILES: CCCCCN(CC)Cc1c(C(C)(C)C)nc2cc(/C=C/C(=O)NO)ccn12] | 3-{2-tert-Butyl-3-[(ethyl-pentyl-amino)-methyl]-imidazo[1,2-a]pyridin-7-yl}-N-hydroxy-acrylamide |
| 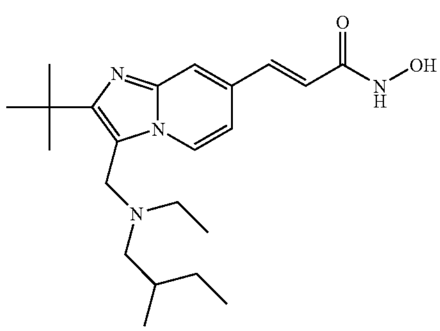 [SMILES: CCC(C)CN(CC)Cc1c(C(C)(C)C)nc2cc(/C=C/C(=O)NO)ccn12] | 3-(2-tert-Butyl-3-{[ethyl-(2-methyl-butyl)-amino]-methyl}-imidazo[1,2-a]pyridin-7-yl)-N-hydroxy-acrylamide |

| Structure | Name |
|---|---|
| 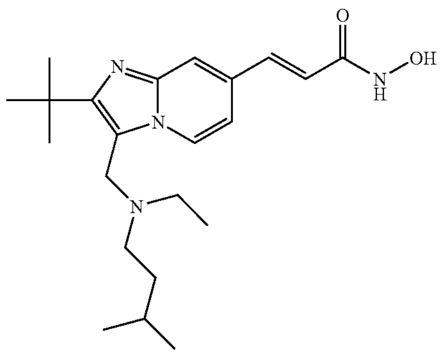 [SMILES: CCN(CCC(C)C)Cc1c(C(C)(C)C)nc2cc(/C=C/C(=O)NO)ccn12] | 3-(2-tert-Butyl-3-{[ethyl-(3-methyl-butyl)-amino]-methyl}-imidazo[1,2-a]pyridin-7-yl)-N-hydroxy-acrylamide |
| 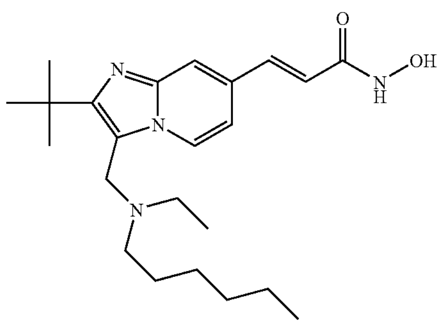 [SMILES: CCCCCCN(CC)Cc1c(C(C)(C)C)nc2cc(/C=C/C(=O)NO)ccn12] | 3-{2-tert-Butyl-3-[(ethyl-hexyl-amino)-methyl]-imidazo[1,2-a]pyridin-7-yl}-N-hydroxy-acrylamide |
| 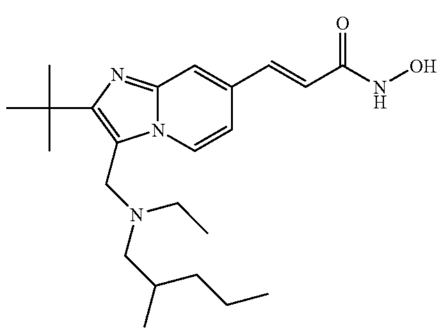 [SMILES: CCCC(C)CN(CC)Cc1c(C(C)(C)C)nc2cc(/C=C/C(=O)NO)ccn12] | 3-(2-tert-Butyl-3-{[ethyl-(2-methyl-pentyl)-amino]-methyl}-imidazo[1,2-a]pyridin-7-yl)-N-hydroxy-acrylamide |
| 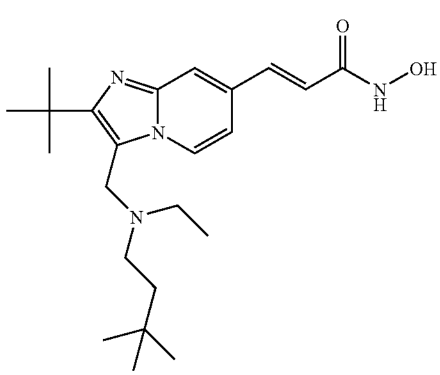 [SMILES: CCN(CCC(C)(C)C)Cc1c(C(C)(C)C)nc2cc(/C=C/C(=O)NO)ccn12] | 3-(2-tert-Butyl-3-{[(3,3-dimethyl-butyl)-ethyl-amino]-methyl}-imidazo[1,2-a]pyridin-7-yl)-N-hydroxy-acrylamide |

| Structure | Name |
|---|---|
| 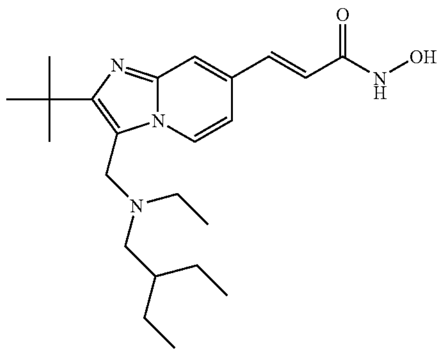 [SMILES: CCC(CC)CN(CC)Cc1c(C(C)(C)C)nc2cc(/C=C/C(=O)NO)ccn12] | 3-(2-tert-Butyl-3-{[ethyl-(2-ethyl-butyl)-amino]-methyl}-imidazo[1,2-a]pyridin-7-yl)-N-hydroxy-acrylamide |
| 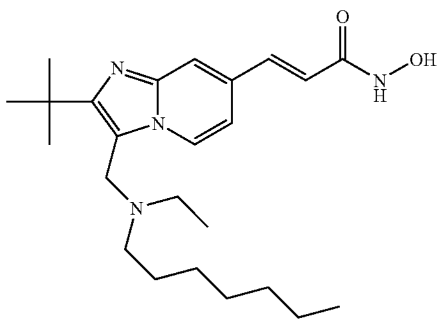 [SMILES: CCCCCCCN(CC)Cc1c(C(C)(C)C)nc2cc(/C=C/C(=O)NO)ccn12] | 3-{2-tert-Butyl-3-[(ethyl-heptyl-amino)-methyl]-imidazo[1,2-a]pyridin-7-yl}-N-hydroxy-acrylamide |
| 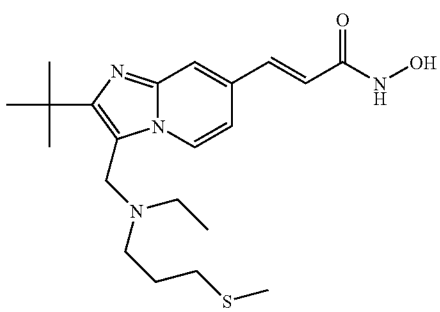 [SMILES: CCN(CCCSC)Cc1c(C(C)(C)C)nc2cc(/C=C/C(=O)NO)ccn12] | 3-(2-tert-Butyl-3-{[ethyl-(3-methylsulfanyl-propyl)-amino]-methyl}-imidazo[1,2-a]pyridin-7-yl)-N-hydroxy-acrylamide |
| 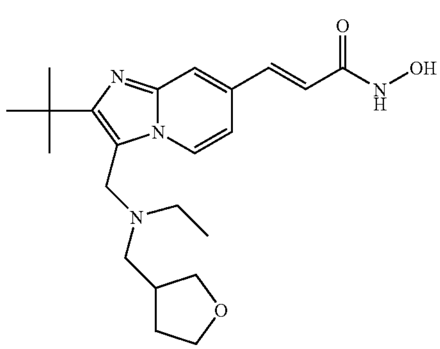 [SMILES: CCN(Cc1c(C(C)(C)C)nc2cc(/C=C/C(=O)NO)ccn12)CC1CCOC1] | 3-(2-tert-Butyl-3-{[ethyl-(tetrahydro-furan-3-yl methyl)-amino]-methyl}-imidazo[1,2-a]pyridin-7-yl)-N-hydroxy-acrylamide |

| Structure | Name |
|---|---|
| 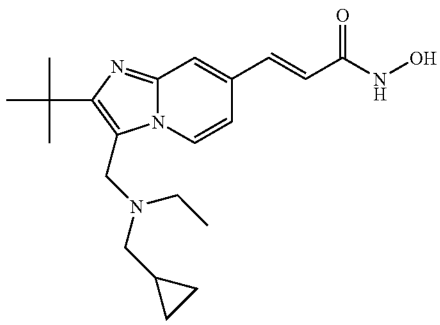 [SMILES: CCN(Cc1c(C(C)(C)C)nc2cc(/C=C/C(=O)NO)ccn12)CC1CC1] | 3-{2-tert-Butyl-3-[(cyclopropylmethyl-ethyl-amino)-methyl]-imidazo[1,2-a]pyridin-7-yl}-N-hydroxy-acrylamide |
| 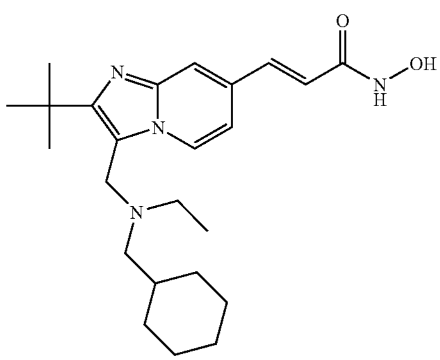 [SMILES: CCN(Cc1c(C(C)(C)C)nc2cc(/C=C/C(=O)NO)ccn12)CC1CCCCC1] | 3-{2-tert-Butyl-3-[(cyclohexylmethyl-ethyl-amino)-methyl]-imidazo[1,2-a]pyridin-7-yl}-N-hydroxy-acrylamide |
| 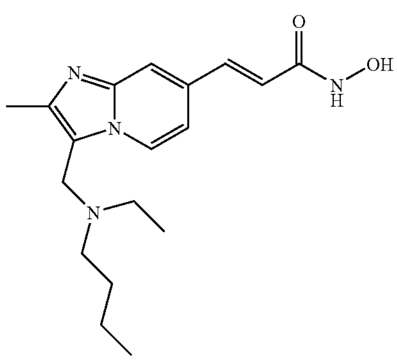 [SMILES: CCCCN(CC)Cc1c(C)nc2cc(/C=C/C(=O)NO)ccn12] | 3-{3-[(Butyl-ethyl-amino)-methyl]-2-methyl-imidazo[1,2-a]pyridin-7-yl}-N-hydroxy-acrylamide |
| 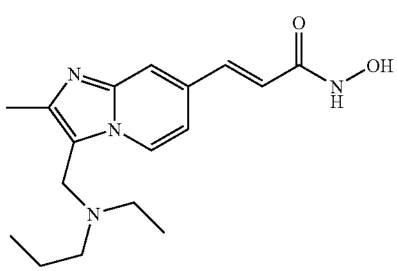 [SMILES: CCCN(CC)Cc1c(C)nc2cc(/C=C/C(=O)NO)ccn12] | 3-{3-[(Ethyl-propyl-amino)-methyl]-2-methyl-imidazo[1,2-a]pyridin-7-yl}-N-hydroxy-acrylamide |

| Structure | Name |
|---|---|
| 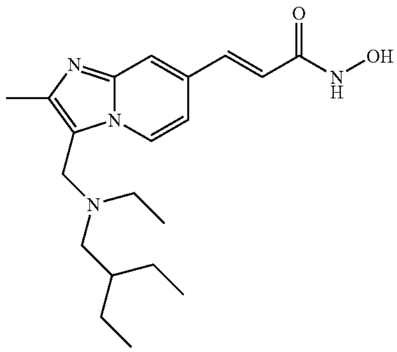 [SMILES: CCC(CC)CN(CC)Cc1c(C)nc2cc(/C=C/C(=O)NO)ccn12] | 3-(3-{[Ethyl-(2-ethyl-butyl)-amino]-methyl}-2-methyl-imidazo[1,2-a]pyridin-7-yl)-N-hydroxy-acrylamide |
| 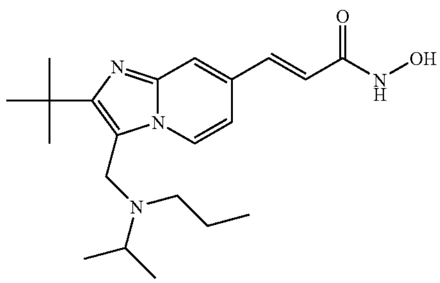 [SMILES: CCCN(Cc1c(C(C)(C)C)nc2cc(/C=C/C(=O)NO)ccn12)C(C)C] | 3-{2-tert-Butyl-3-[(isopropyl-propyl-amino)-methyl]-imidazo[1,2-a]pyridin-7-yl}-N-hydroxy-acrylamide |
| 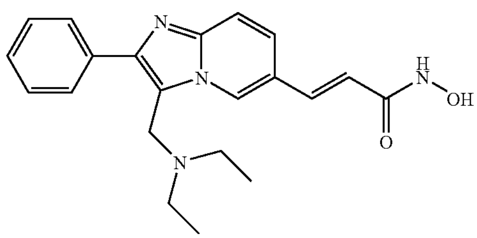 [SMILES: CCN(CC)Cc1c(-c2ccccc2)nc2ccc(/C=C/C(=O)NO)cn12] | 3-(3-Diethylaminomethyl-2-phenyl-imidazo[1,2-a]pyridin-6-yl)-N-hydroxy-acrylamide |
| 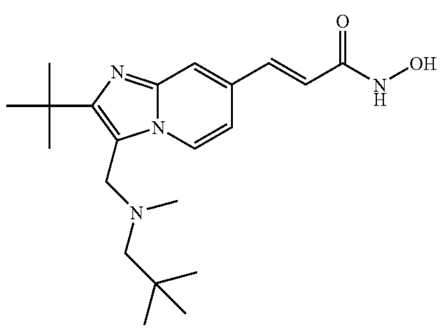 [SMILES: CN(Cc1c(C(C)(C)C)nc2cc(/C=C/C(=O)NO)ccn12)CC(C)(C)C] | 3-(2-tert-Butyl-3-{[(2,2-dimethyl-propyl)-methyl-amino]-methyl}-imidazo[1,2-a]pyridin-7-yl)-N-hydroxy-acrylamide |
| 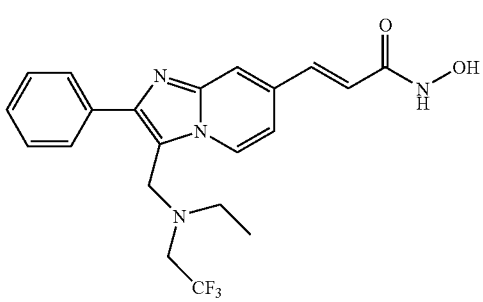 [SMILES: CCN(Cc1c(-c2ccccc2)nc2cc(/C=C/C(=O)NO)ccn12)CC(F)(F)F] | 3-(3-{[Ethyl-(2,2,2-trifluoro-ethyl)-amino]-methyl}-2-phenyl-imidazo[1,2-a]pyridin-7-yl)-N-hydroxy-acrylamide |

| Structure | Name |
|---|---|
| 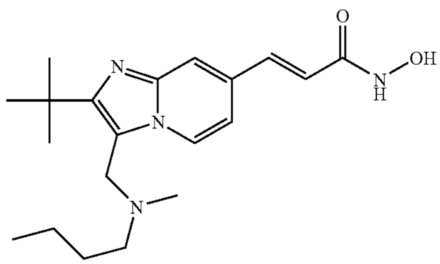 [SMILES: CCCCN(C)Cc1c(C(C)(C)C)nc2cc(/C=C/C(=O)NO)ccn12] | 3-{2-tert-Butyl-3-[(butyl-methyl-amino)-methyl]-imidazo[1,2-a]pyridin-7-yl}-N-hydroxy-acrylamide |
| 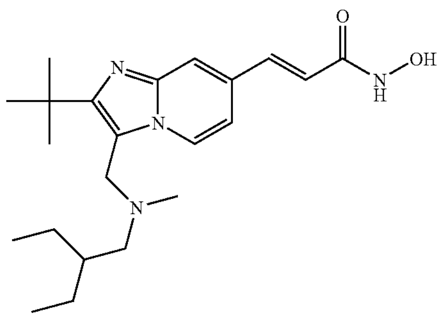 [SMILES: CCC(CC)CN(C)Cc1c(C(C)(C)C)nc2cc(/C=C/C(=O)NO)ccn12] | 3-(2-tert-Butyl-3-{[(2-ethyl-butyl)-methyl-amino]-methyl}-imidazo[1,2-a]pyridin-7-yl)-N-hydroxy-acrylamide |
| 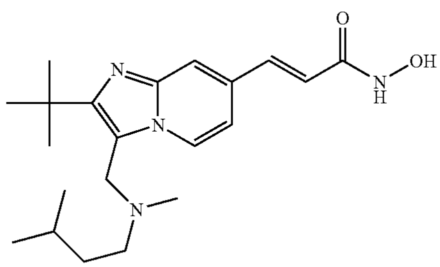 [SMILES: CC(C)CCN(C)Cc1c(C(C)(C)C)nc2cc(/C=C/C(=O)NO)ccn12] | 3-(2-tert-Butyl-3-{[methyl-(3-methyl-butyl)-amino]-methyl}-imidazo[1,2-a]pyridin-7-yl)-N-hydroxy-acrylamide |
| 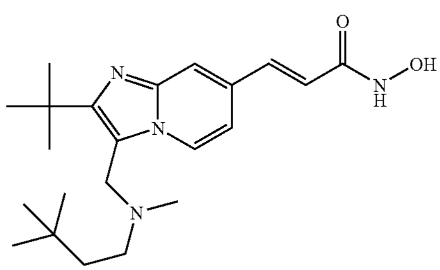 [SMILES: CN(CCC(C)(C)C)Cc1c(C(C)(C)C)nc2cc(/C=C/C(=O)NO)ccn12] | 3-(2-tert-Butyl-3-{[(3,3-dimethyl-butyl)-methyl-amino]-methyl}-imidazo[1,2-a]pyridin-7-yl)-N-hydroxy-acrylamide |
| 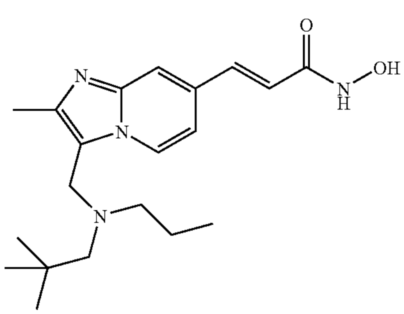 [SMILES: CCCN(Cc1c(C)nc2cc(/C=C/C(=O)NO)ccn12)CC(C)(C)C] | 3-(3-{[(2,2-Dimethyl-propyl)-propyl-amino]-methyl}-2-methyl-imidazo[1,2-a]pyridin-7-yl)-N-hydroxy-acrylamide |

| Structure | Name |
|---|---|
| 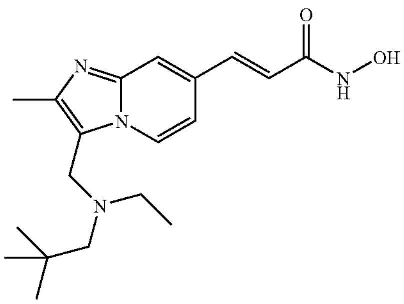 [SMILES: CCN(Cc1c(C)nc2cc(/C=C/C(=O)NO)ccn12)CC(C)(C)C] | 3-(3-{[(2,2-Dimethyl-propyl)-ethyl-amino]-methyl}-2-methyl-imidazo[1,2-a]pyridin-7-yl)-N-hydroxy-acrylamide |
| 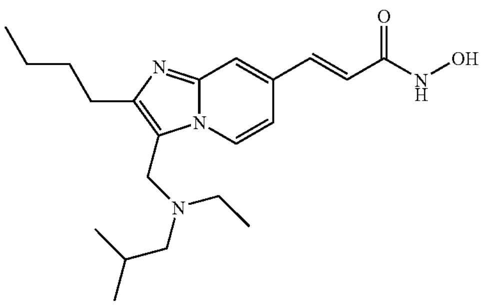 [SMILES: CCCCc1nc2cc(/C=C/C(=O)NO)ccn2c1CN(CC)CC(C)C] | 3-{2-Butyl-3-[(ethyl-isobutyl-amino)-methyl]-imidazo[1,2-a]pyridin-7-yl}-N-hydroxy-acrylamide |
| 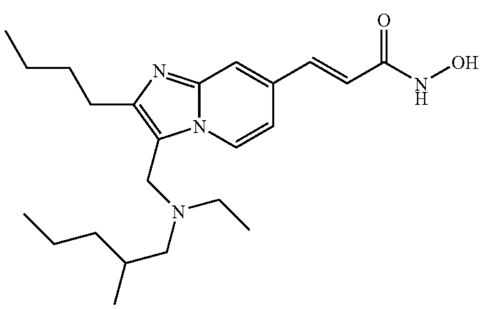 [SMILES: CCCCc1nc2cc(/C=C/C(=O)NO)ccn2c1CN(CC)CC(C)CCC] | 3-(2-Butyl-3-{[ethyl-(2-methyl-pentyl)-amino]-methyl}-imidazo[1,2-a]pyridin-7-yl)-N-hydroxy-acrylamide |
| 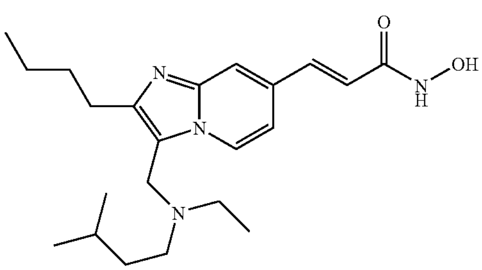 [SMILES: CCCCc1nc2cc(/C=C/C(=O)NO)ccn2c1CN(CC)CCC(C)C] | 3-(2-Butyl-3-{[ethyl-(3-methyl-butyl)-amino]-methyl}-imidazo[1,2-a]pyridin-7-yl)-N-hydroxy-acrylamide |
| 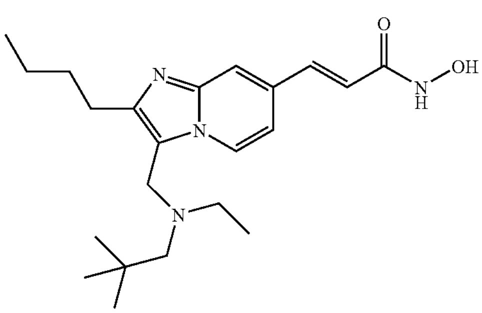 [SMILES: CCCCc1nc2cc(/C=C/C(=O)NO)ccn2c1CN(CC)CC(C)(C)C] | 3-(2-Butyl-3-{[(2,2-dimethyl-propyl)-ethyl-amino]-methyl}-imidazo[1,2-a]pyridin-7-yl)-N-hydroxy-acrylamide |

| Structure | Name |
|---|---|
| 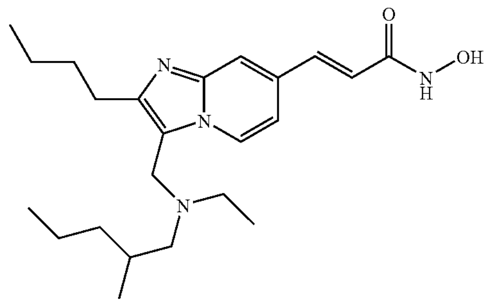 [SMILES: CCCCc1nc2cc(/C=C/C(=O)NO)ccn2c1CN(CC)CC(C)CCC] | 3-(2-Butyl-3-{[ethyl-(2-methyl-pentyl)-amino]-methyl}-imidazo[1,2-a]pyridin-7-yl)-N-hydroxy-acrylamide |
| 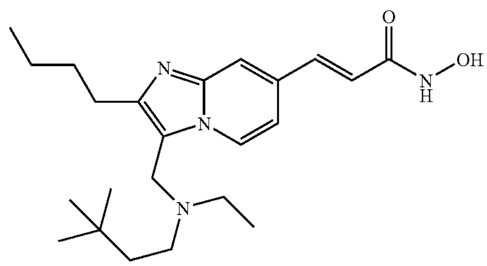 [SMILES: CCCCc1nc2cc(/C=C/C(=O)NO)ccn2c1CN(CC)CCC(C)(C)C] | 3-(2-Butyl-3-{[(3,3-dimethyl-butyl)-ethyl-amino]-methyl}-imidazo[1,2-a]pyridin-7-yl)-N-hydroxy-acrylamide |
| 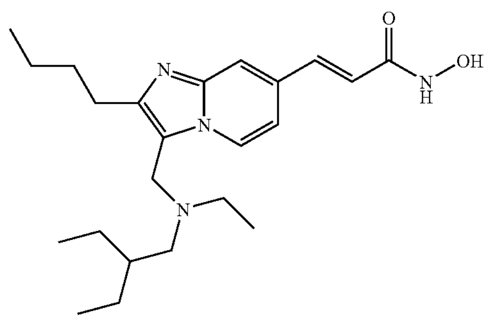 [SMILES: CCCCc1nc2cc(/C=C/C(=O)NO)ccn2c1CN(CC)CC(CC)CC] | 3-(2-Butyl-3-{[ethyl-(2-ethyl-butyl)-amino]-methyl}-imidazo[1,2-a]pyridin-7-yl)-N-hydroxy-acrylamide |
| 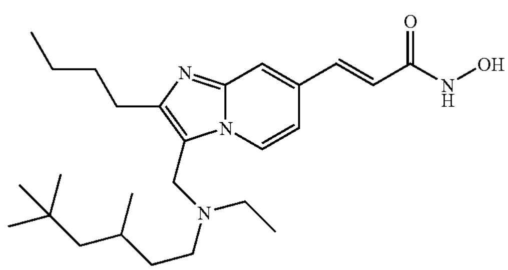 [SMILES: CCCCc1nc2cc(/C=C/C(=O)NO)ccn2c1CN(CC)CCC(C)CC(C)(C)C] | 3-(2-Butyl-3-{[ethyl-(3,5,5-trimethyl-hexyl)-amino]-methyl}-imidazo[1,2-a]pyridin-7-yl)-N-hydroxy-acrylamide |
| 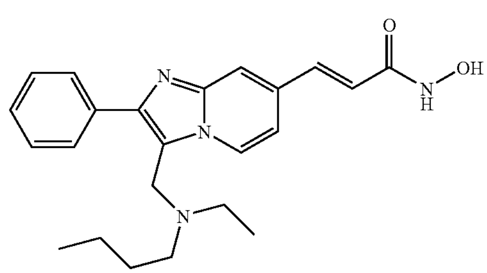 [SMILES: CCCCN(CC)Cc1c(-c2ccccc2)nc2cc(/C=C/C(=O)NO)ccn12] | 3-{3-[(Butyl-ethyl-amino)-methyl]-2-phenyl-imidazo[1,2-a]pyridin-7-yl}-N-hydroxy-acrylamide |

| Structure | Name |
|---|---|
| 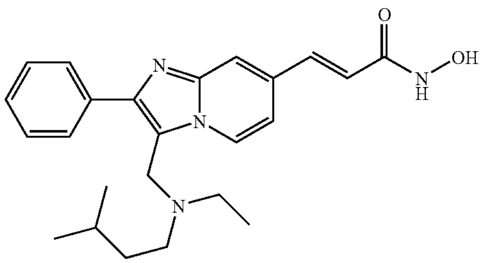 [SMILES: CCN(CCC(C)C)Cc1c(-c2ccccc2)nc2cc(/C=C/C(=O)NO)ccn12] | 3-(3-{[Ethyl-(3-methyl-butyl)-amino]-methyl}-2-phenyl-imidazo[1,2-a]pyridin-7-yl)-N-hydroxy-acrylamide |
| 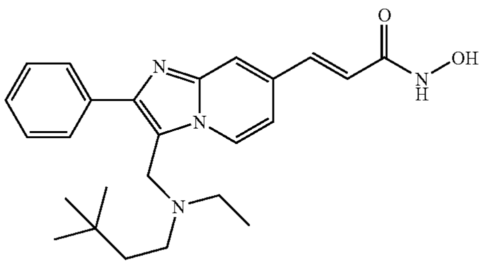 [SMILES: CCN(CCC(C)(C)C)Cc1c(-c2ccccc2)nc2cc(/C=C/C(=O)NO)ccn12] | 3-(3-{[(3,3-Dimethyl-butyl)-ethyl-amino]-methyl}-2-phenyl-imidazo[1,2-a]pyridin-7-yl)-N-hydroxy-acrylamide |
| 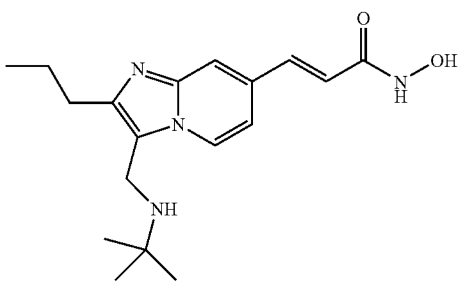 [SMILES: CCCc1nc2cc(/C=C/C(=O)NO)ccn2c1CNC(C)(C)C] | 3-[3-(tert-Butylamino-methyl)-2-propyl-imidazo[1,2-a]pyridin-7-yl]-N-hydroxy-acrylamide |
| 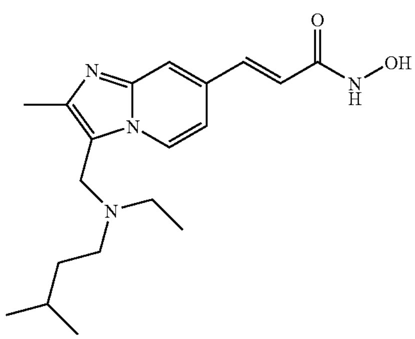 [SMILES: CCN(CCC(C)C)Cc1c(C)nc2cc(/C=C/C(=O)NO)ccn12] | 3-(3-{[Ethyl-(3-methyl-butyl)-amino]-methyl}-2-methyl-imidazo[1,2-a]pyridin-7-yl)-N-hydroxy-acrylamide |
| 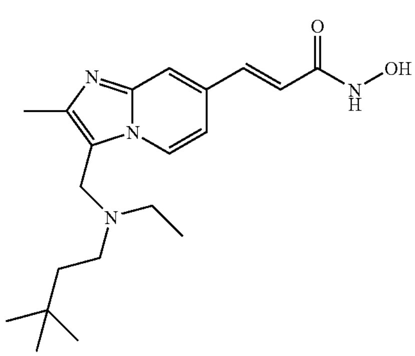 [SMILES: CCN(CCC(C)(C)C)Cc1c(C)nc2cc(/C=C/C(=O)NO)ccn12] | 3-(3-{[(3,3-Dimethyl-butyl)-ethyl-amino]-methyl}-2-methyl-imidazo[1,2-a]pyridin-7-yl)-N-hydroxy-acrylamide |

| Structure | Name |
|---|---|
| 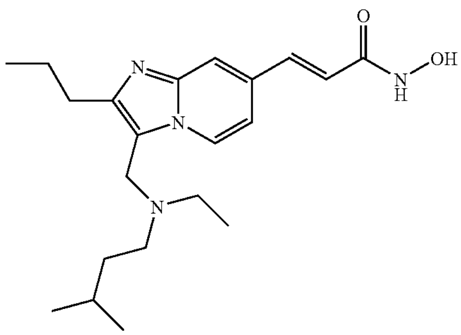 [SMILES: CCCc1nc2cc(/C=C/C(=O)NO)ccn2c1CN(CC)CCC(C)C] | 3-(3-{[Ethyl-(3-methyl-butyl)-amino]-methyl}-2-propyl-imidazo[1,2-a]pyridin-7-yl)-N-hydroxy-acrylamide |
| 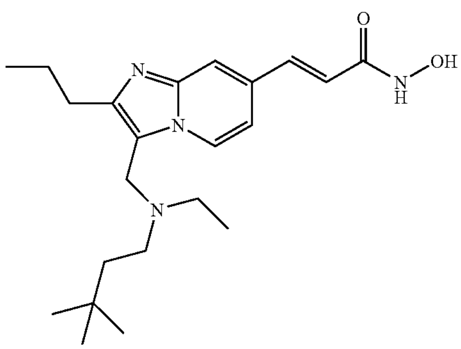 [SMILES: CCCc1nc2cc(/C=C/C(=O)NO)ccn2c1CN(CC)CCC(C)(C)C] | 3-(3-{[(3,3-Dimethyl-butyl)-ethyl-amino]-methyl}-2-propyl-imidazo[1,2-a]pyridin-7-yl)-N-hydroxy-acrylamide |
| 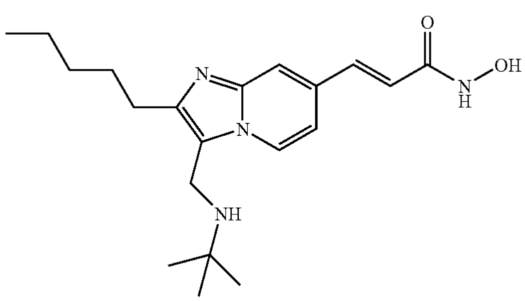 [SMILES: CCCCCc1nc2cc(/C=C/C(=O)NO)ccn2c1CNC(C)(C)C] | 3-[3-(tert-Butylamino-methyl)-2-pentyl-imidazo[1,2-a]pyridin-7-yl]-N-hydroxy-acrylamide |
| 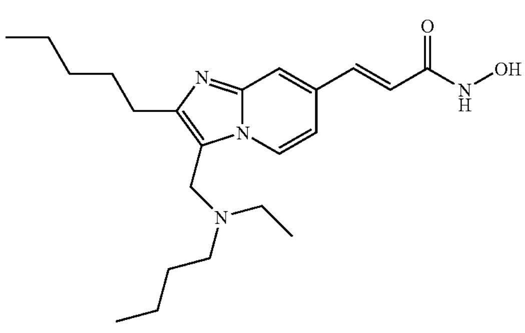 [SMILES: CCCCCc1nc2cc(/C=C/C(=O)NO)ccn2c1CN(CC)CCCC] | 3-{3-[(Butyl-ethyl-amino)-methyl]-2-pentyl-imidazo[1,2-a]pyridin-7-yl}-N-hydroxy-acrylamide |

| Structure | Name |
|---|---|
| 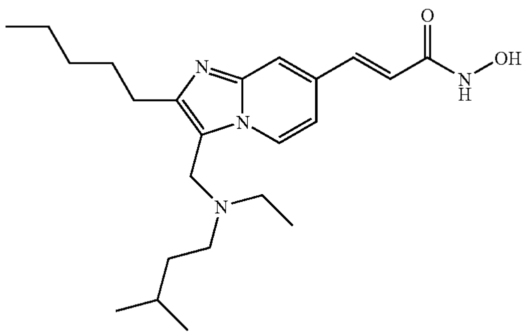 [SMILES: CCCCCc1nc2cc(/C=C/C(=O)NO)ccn2c1CN(CC)CCC(C)C] | 3-(3-{[Ethyl-(3-methyl-butyl)-amino]-methyl}-2-pentyl-imidazo[1,2-a]pyridin-7-yl)-N-hydroxy-acrylamide |
| 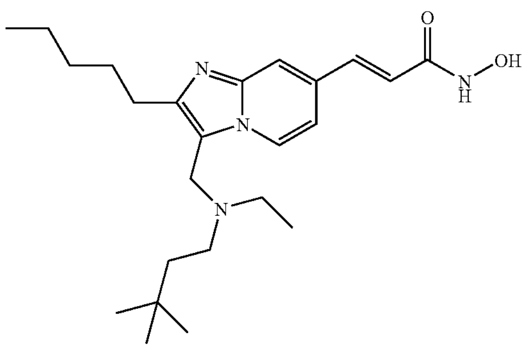 [SMILES: CCCCCc1nc2cc(/C=C/C(=O)NO)ccn2c1CN(CC)CCC(C)(C)C] | 3-(3-{[(3,3-Dimethyl-butyl)-ethyl-amino]-methyl}-2-pentyl-imidazo[1,2-a]pyridin-7-yl)-N-hydroxy-acrylamide |
| 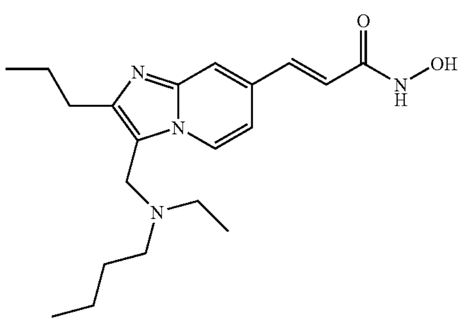 [SMILES: CCCCN(CC)Cc1c(CCC)nc2cc(/C=C/C(=O)NO)ccn12] | 3-{3-[(Butyl-ethyl-amino)-methyl]-2-propyl-imidazo[1,2-a]pyridin-7-yl}-N-hydroxy-acrylamide |
| 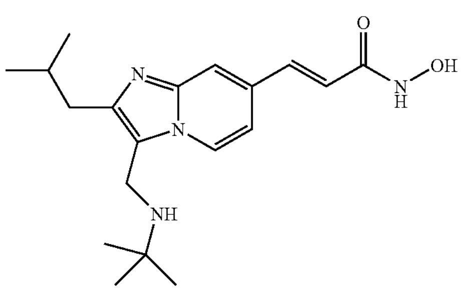 [SMILES: CC(C)Cc1nc2cc(/C=C/C(=O)NO)ccn2c1CNC(C)(C)C] | 3-[3-(tert-Butylamino-methyl)-2-isobutyl-imidazo[1,2-a]pyridin-7-yl]-N-hydroxy-acrylamide |
| 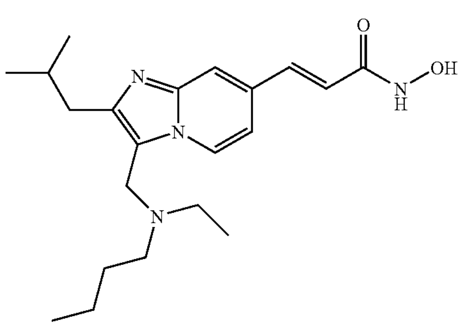 [SMILES: CCCCN(CC)Cc1c(CC(C)C)nc2cc(/C=C/C(=O)NO)ccn12] | 3-{3-[(Butyl-ethyl-amino)-methyl]-2-isobutyl-imidazo[1,2-a]pyridin-7-yl}-N-hydroxy-acrylamide |

-continued
| Structure | Name |
|---|---|
| 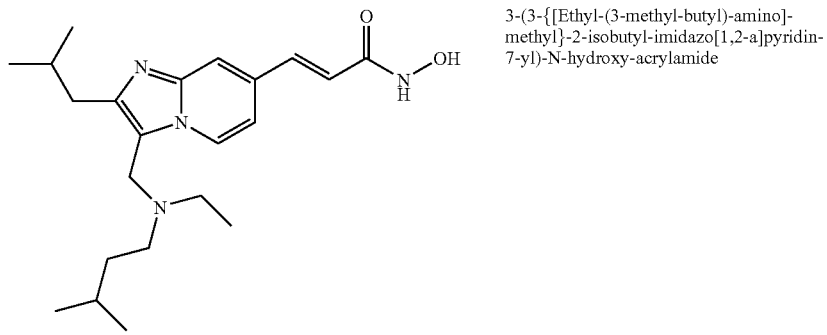 | 3-(3-{[Ethyl-(3-methyl-butyl)-amino]-methyl}-2-isobutyl-imidazo[1,2-a]pyridin-7-yl)-N-hydroxy-acrylamide |
| 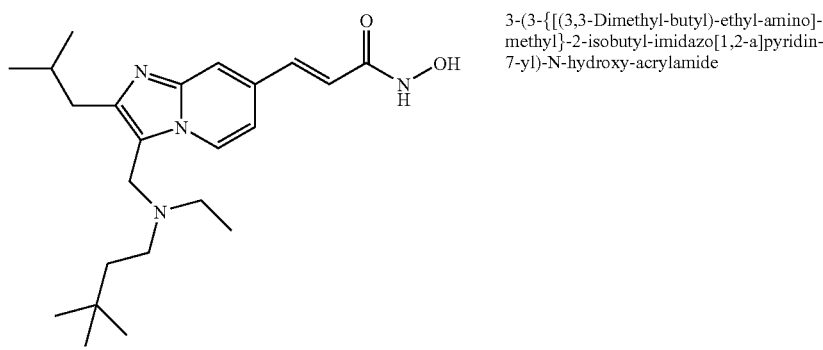 | 3-(3-{[(3,3-Dimethyl-butyl)-ethyl-amino]-methyl}-2-isobutyl-imidazo[1,2-a]pyridin-7-yl)-N-hydroxy-acrylamide |
| 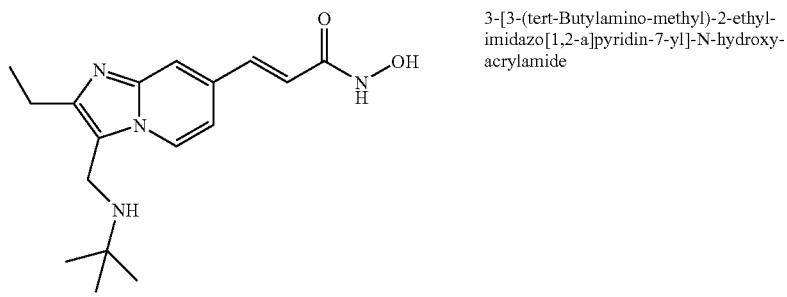 | 3-[3-(tert-Butylamino-methyl)-2-ethyl-imidazo[1,2-a]pyridin-7-yl]-N-hydroxy-acrylamide |
| 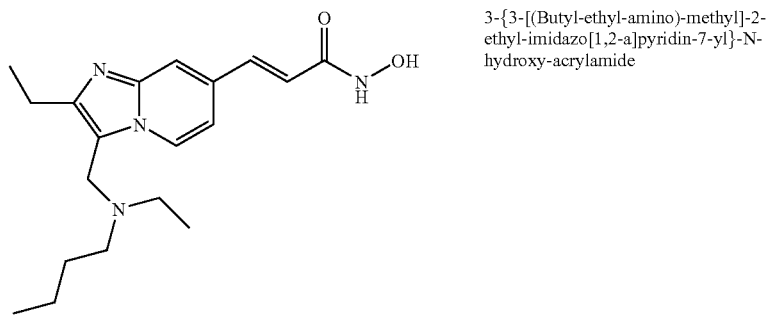 | 3-{3-[(Butyl-ethyl-amino)-methyl]-2-ethyl-imidazo[1,2-a]pyridin-7-yl}-N-hydroxy-acrylamide |

| Structure | Name |
|---|---|
| 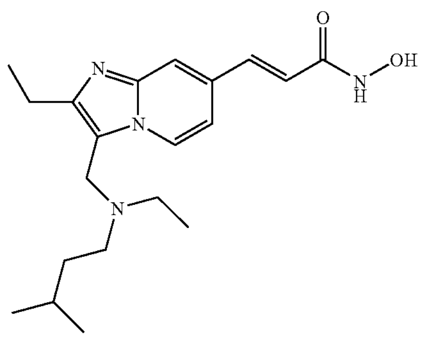 [SMILES: CCc1nc2cc(/C=C/C(=O)NO)ccn2c1CN(CC)CCC(C)C] | 3-(2-Ethyl-3-{[ethyl-(3-methyl-butyl)-amino]-methyl}-imidazo[1,2-a]pyridin-7-yl)-N-hydroxy-acrylamide |
| 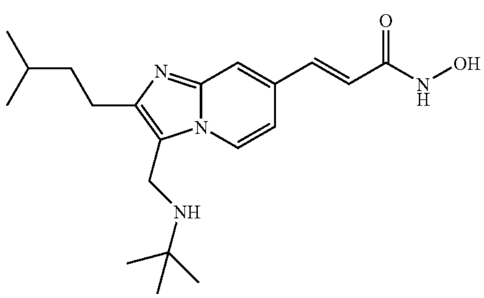 [SMILES: CC(C)CCc1nc2cc(/C=C/C(=O)NO)ccn2c1CNC(C)(C)C] | 3-[3-(tert-Butylamino-methyl)-2-(3-methyl-butyl)-imidazo[1,2-a]pyridin-7-yl]-N-hydroxy-acrylamide |
| 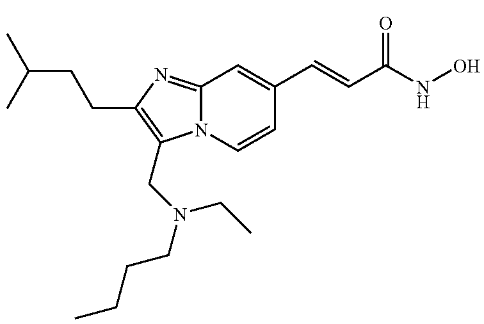 [SMILES: CCCCN(CC)Cc1c(CCC(C)C)nc2cc(/C=C/C(=O)NO)ccn12] | 3-[3-[(Butyl-ethyl-amino)-methyl]-2-(3-methyl-butyl)-imidazo[1,2-a]pyridin-7-yl]-N-hydroxy-acrylamide |
| 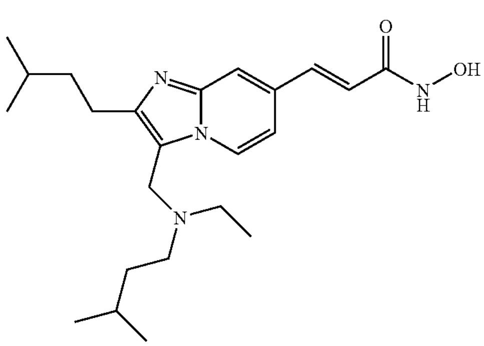 [SMILES: CCN(CCC(C)C)Cc1c(CCC(C)C)nc2cc(/C=C/C(=O)NO)ccn12] | 3-[3-{[Ethyl-(3-methyl-butyl)-amino]-methyl}-2-(3-methyl-butyl)-imidazo[1,2-a]pyridin-7-yl]-N-hydroxy-acrylamide |

| Structure | Name |
|---|---|
| 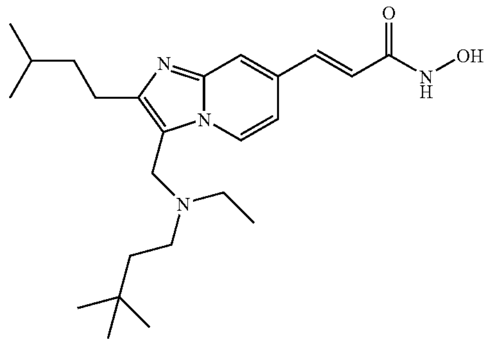 [SMILES: CCN(CCC(C)(C)C)Cc1c(CCC(C)C)nc2cc(/C=C/C(=O)NO)ccn12] | 3-[3-{[(3,3-Dimethyl-butyl)-ethyl-amino]-methyl}-2-(3-methyl-butyl)-imidazo[1,2-a]pyridin-7-yl]-N-hydroxy-acrylamide |
| | 3-[3-(2-Diethylamino-ethyl)-2-phenyl-imidazo[1,2-a]pyridin-7-yl]-N-hydroxy-acrylamide. | and

16. The method according to claim 15, wherein the cancer is prostate cancer or colon cancer.

17. The method according to claim 15, wherein the cancer is a hematologic malignancy.

18. A method of inhibiting tumor cell growth, the method including administration of a therapeutic effective amount of a compound of the formula:

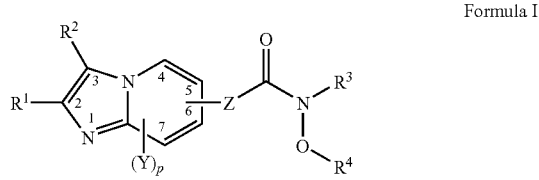

Formula I wherein:

$R^1$ is selected from the group consisting of: H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —$COR^5$, —$COOR^5$, —$CONHR^5$, —$NHCOR^5$, —$NHCOOR^5$, —$NHCONHR^5$, C(=NOH)$R^5$, -alkyl$NCOR^5$, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may optionally be substituted, or $R^1$=L;

$R^2$ is selected from the group consisting of: H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —$COR^5$, —$COOR^5$, —$CONHR^5$, —$NHCOR^5$, —$NHCOOR^5$, —$NHCONHR^5$, C(=NOH)$R^5$, -alkyl$NCOR^5$, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may optionally be substituted, or $R^2$=L;

$R^3$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

$R^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each Y is independently selected from the group consisting of: H, halogen, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH—C(O)$OR^6$, —$COR^E$, —SH, —$SR^7$, —$OR^7$, acyl and —$NR^8R^9$ each of which may be optionally substituted;

each $R^5$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^6$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^7$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ and $R^9$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

p is an integer selected from the group consisting of 0, 1, 2, and 3;

L is selected from the group consisting of:
a) Cy-$L^1$-W—
b) Cy-$L^1$-W-$L^2$-;
c) Cy-$(CH_2)_k$—W—;
d) $L^1$-W-$L^2$-;
e) Cy-$L^1$-;
f) $R^{12}$—$W^1$-$L^1$-W—; and
g) —$(CR^{20}R^{21})_m$—$(CR^{22}R^{23})_n$—$(CR^{24}R^{25})_o$—$NR^{26}R^{27}$;

wherein

Cy is selected from the group consisting of $C_1$-$C_{15}$ alkyl, aminoalkyl, heteroalkyl, heterocycloalkyl, cycloalkyl, aryl, aryloxy and heteroaryl, each of which may be optionally substituted;

$L^1$ is selected from the group consisting of a bond, $C_1$-$C_5$ alkyl and $C_2$-$C_5$ alkenyl, each of which may be optionally substituted;

$L^2$ is selected from the group consisting of $C_1$-$C_5$ alkyl and $C_2$-$C_5$ alkenyl, each of which may be optionally substituted;

k is 0, 1, 2, 3, 4 or 5;

W is selected from the group consisting of a bond, —O—, —S—, —S(O)—, —S(O)$_2$—, —N($R^{10}$)—, —C(O)N($R^{10}$)—, —$SO_2$N($R^{10}$)—, —N($R^{10}$)C(O)—, —N($R^{10}$)$SO_2$—, —N($R^{10}$)C(O)N($R^{11}$)—, —C(O)N($R^{10}$)C(O)N($R^{11}$)— and —N($R^{10}$)C(O)N($R^{11}$)C(O)—;

$W^1$ is selected from the group consisting of a bond, —O—, —S—, —S(O)—, —S(O)$_2$—, —N($R^{10}$)—, —C(O)N($R^{10}$)—, —$SO_2$N($R^{10}$)—, —N($R^{10}$)C(O)—, —N($R^{10}$)$SO_2$—, —N($R^{10}$)C(O)N($R^{11}$)—, —C(O)N($R^{10}$)C(O)N($R^{11}$)— and —N($R^{10}$)C(O)N($R^{11}$)C(O)—;

each $R^{10}$ and $R^{11}$ is independently selected from the group consisting of: H, $C_1$-$C_6$ alkyl, $C_1$-$C_6$ alkenyl, $C_1$-$C_{10}$ heteroalkyl, $C_4$-$C_9$ cycloalkyl, $C_4$-$C_9$ heterocycloalkyl, aryl, heteroaryl, arylalkyl, and heteroarylalkyl and acyl, each of which may be optionally substituted;

each $R^{20}$, $R^{21}$, $R^{22}$, $R^{23}$, $R^{24}$ and $R^{25}$ is independently selected from the group consisting of: H, halogen, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkoxyheteroaryl, alkenyloxy, alkynyloxy, cycloalkyloxy, heterocycloalkyloxy, aryloxy, arylalkyloxy, phenoxy, benzyloxy heteroaryloxy, amino, alkylamino, acylamino, aminoalkyl, arylamino, alkoxycarbonyl, alkylaminocarbonyl, sulfonyl, alkylsulfonyl, aminosulfonyl, arylsulfonyl, arylsulfinyl —COOH, —C(O)$OR^5$, —$COR^5$, —SH, —$SR^6$, —$OR^6$ and acyl, each of which may be optionally substituted; or $R^{20}$ and $R^{21}$ when taken together may form a group of formula =O or =S, and/or $R^{22}$ and $R^{23}$ when taken together may form a group of formula =O or =S, and/or $R^{24}$ and $R^{25}$ when taken together may form a group of formula =O or =S;

each $R^{26}$ and $R^{27}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^5$, acyl and G, each of which may be optionally substituted, or $R^{26}$ and $R^{27}$ when taken together with the nitrogen atom to which they are attached form a heterocycloalkyl or heteroaryl group, each of which may be optionally substituted;

m, n and o are each integers that are independently selected from the group consisting of 0, 1, 2, 3 and 4;

G is a group of formula:

-$L^3W^3$ wherein $L^3$ is selected from the group consisting of $C_1$-$C_5$ alkyl and $C_2$-$C_5$ alkenyl, each of which may be optionally substituted;

$W^3$ is selected from the group consisting of —$OR^{12}$, —$SR^{12}$, —S(O)$R^{12}$, —S(O)$_2R^{12}$, —N($R^{12}$)$_2$, —C(O)N $(R^{12})_2$, —SO$_2$N(R$^{12}$)$_2$, —NR$^{12}$C(O)—, —NR$^{12}$SO$_2$R$^{12}$, —NR$^{12}$C(O)N(R$^{12}$)$_2$, —C(O)NR$^{12}$C(O)N(R$^{12}$)$_2$ and —N(R$^{12}$)C(O)N(R$^{12}$)C(O)R$^{12}$;

each R$^{12}$ is independently selected from the group consisting H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^5$, —COOR$^5$, —CONHR$^5$, —NHCOR$^5$, —NHCOOR$^5$, —NHCONHR$^5$, C(=NOH)R$^5$, -alkylNCOR$^5$, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may optionally be substituted;

Z is selected from —CH$_2$—, —CH$_2$CH$_2$—, —CH=H— and C$_3$-C$_6$ cycloalkyl each of which may be optionally substituted;

or a pharmaceutically acceptable salt thereof to a patient; wherein the tumor cell growth is colon cancer, ovarian cancer, prostate cancer, or a hematologic malignancy.

19. The method according to claim 18, wherein in the compound of Formula I, Z is attached at ring position 5 or 6.

20. The method according to claim 18, wherein in the compound of Formula I, Z is —CH=CH—, and is in the 'E' configuration.

21. The method according to claim 18, wherein in the compound of Formula I, R$^1$ is selected from the group consisting of: H, hydroxyalkyl, alkyl, arylalkyl, aryl, heteroaryl, heteroarylalkyl, alkoxyalkyl, aminoalkyl, and heterocycloalkyl, each of which may be unsubstituted or substituted.

22. The method according to claim 21, wherein in the compound of Formula I, R$^1$ is alkyl, aryl or heteroaryl, each of which may be optionally substituted.

23. The method according to claim 22, wherein in the compound of Formula I, R$^1$ is selected from the group consisting of methyl, ethyl, propyl, isopropyl, 2-methyl-propyl, 2,2-dimethyl-propyl, butyl, isobutyl, tert-butyl, 3-methyl-butyl, pentyl, 2,4,4-trimethyl-pentyl, hexyl and phenyl, each of which may optionally be substituted.

24. The method according to claim 18, wherein in the compound of Formula I, R$^2$ is selected from the group consisting of H, alkyl, arylalkyl, aryl, heteroaryl, heteroalkyl, cycloalkyl, each of which may be optionally substituted, or R$^2$ is L which is a group of the formula:
(a) Cy-L$^1$-W—;
(b) R$^{12}$—W$^1$-L$^1$W—; or
(c) —(CR$^{20}$R$^{21}$)$_m$—(CR$^{22}_R$$^{23}$)$_n$—(CR$^{24}$R$^{25}$)$_o$—NR$^{26}$R$^{27}$;
wherein Cy, L$^1$, W, W$^1$, R$^{12}$, R$^{20}$, R$^{21}$, R$^{22}$, R$^{23}$, R$^{24}$, R$^{25}$, R$^{26}$, R$^{27}$, m, n and o are as defined in claim 18.

25. The method according to claim 18, wherein in the compound of Formula I, R$^2$ is selected from the group consisting of:
(a) Cy-L$^1$-W—;
(b) R$^{12}$—W$^1$-L$^1$-W—; or
(c) —(CR$^{20}$R$^{21}$)$_m$—(CR$^{22}_R$$^{23}$)$_n$—(CR$^{24}$R$^{25}$)$_o$—NR$^{26}$R$^{27}$;
wherein Cy, L$^1$, W, W$^1$, R$^{12}$, R$^{20}$, R$^{21}$, R$^{22}$, R$^{23}$, R$^{24}$, R$^{25}$, R$^{26}$, R$^{27}$, m, n and o are as defined in claim 18.

26. The method according to claim 18, wherein in the compound of Formula I, R$^2$ is a group of formula:

$(CR^{20}R^{21})_m$—$(CR^{22}_R{}^{23})_n$—$(CR^{24}R^{25})_o$—NR$^{26}$R$^{27}$;

wherein R$^{20}$, R$^{21}$, R$^{22}$, R$^{23}$, R$^{24}$, R$^{25}$, R$^{26}$, R$^{27}$, m, n and o are as defined in claim 18.

27. The method according to claim 26, wherein the compound of Formula I is selected from the group consisting of:

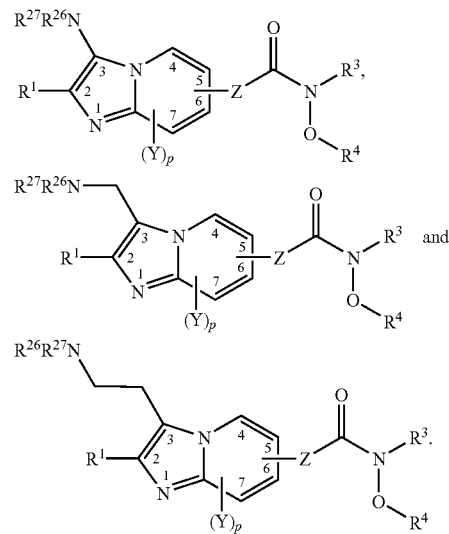

28. The method according to claim 27, wherein the compound has the formula

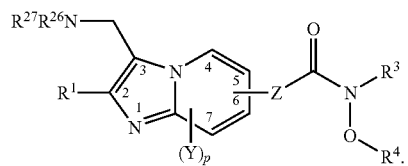

29. The method according to claim 26, wherein in the compound of Formula I, R$^{26}$ and R$^{27}$ are each independently selected from the group consisting of H, alkyl, heteroalkyl, cycloalkyl, aryl, arylalkyl, cycloalkylalkyl and G, each of which may be optionally substituted.

30. The method according to claim 29, wherein R$^{26}$ and R$^{27}$ are independently selected from the group consisting of: H, methyl, cyclopropyl-methyl, cyclohexyl-methyl, ethyl, 2-methoxy-ethyl, 2-hydroxy-ethyl, 2-cyclopropyl-ethyl, 2,2,2-trifluoroethyl, 2-(dimethylamino)-ethyl, 2-(diethylamino)-ethyl, propyl, isopropyl, cyclopropyl, 1-methyl-propyl, 2-methyl-propyl, 2,2-dimethyl-propyl, butyl, t-butyl, sec-butyl, 2-ethyl-butyl, 2-methyl-butyl, 3-methyl-butyl, 3,3-dimethyl-butyl, pentyl, 2-methyl-pentyl, hexyl, 3,5,5-tromethyl-hexyl, heptyl, 3,4,5-trimethoxyphenyl, 3,4-methylenedioxybenzyl, 4-piperidin-1-yl-phenyl, and 3,4-methylenedioxyphenyl.

31. The method according to claim 18, wherein in the compound of Formula I, R$^2$ is selected from the group consisting of:

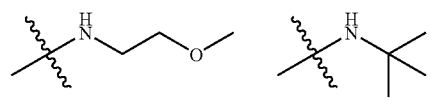

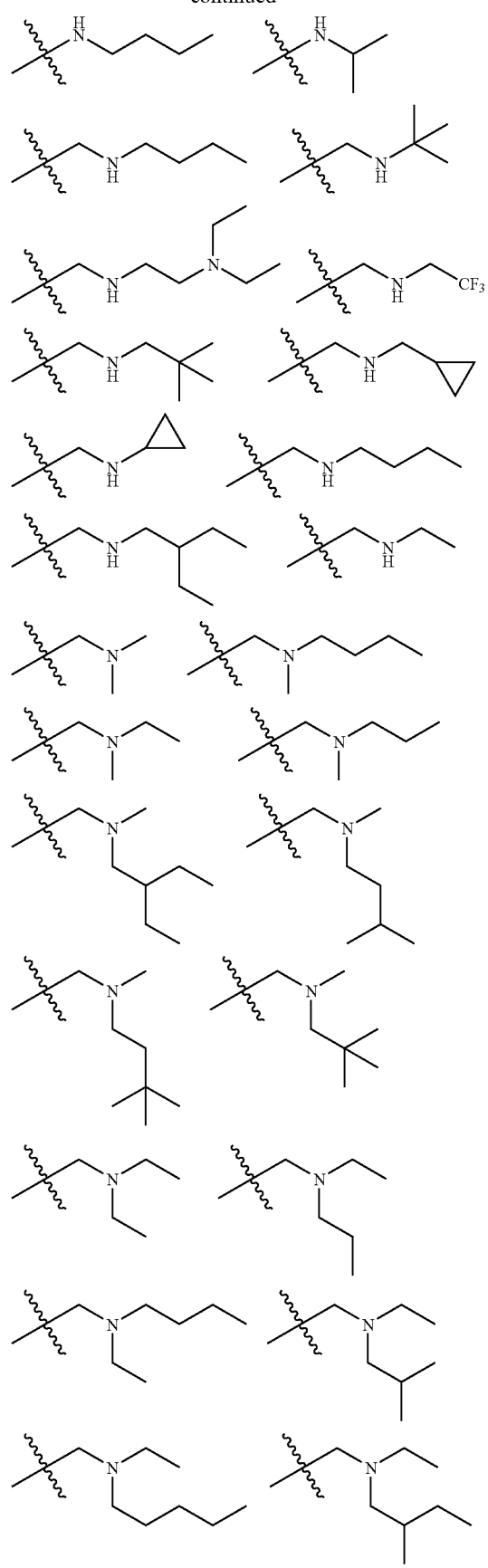
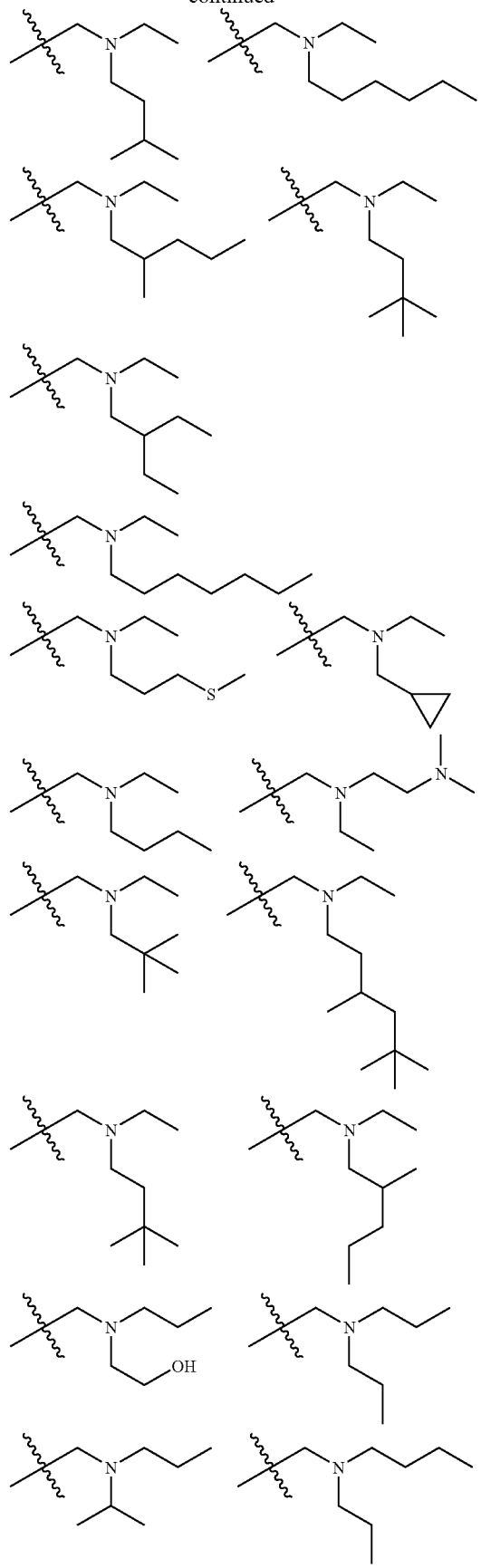

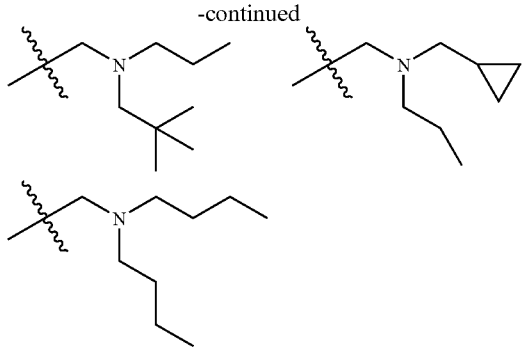
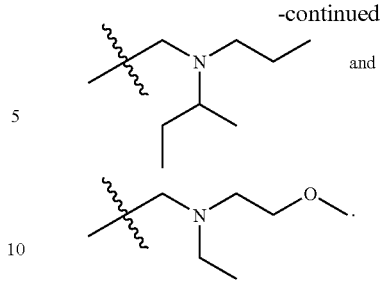

32. The method of claim 18, wherein the compound is selected from compounds, and their pharmaceutically acceptable salts, selected from the group consisting of

| Structure | Name |
|---|---|
| 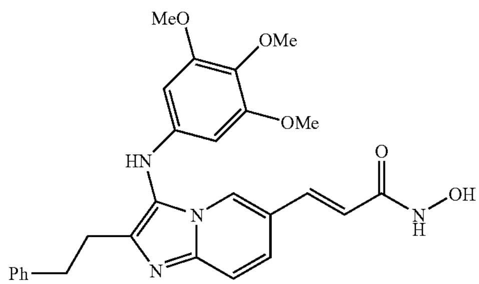 [SMILES: COc1cc(Nc2c(CCc3ccccc3)nc3ccc(/C=C/C(=O)NO)cn23)cc(OC)c1OC] | (E)-N-hydroxy-3-(2-phenethyl-3-(3,4,5-trimethoxyphenylamino)imidazo[1,2-a]pyridin-6-yl)acrylamide |
| 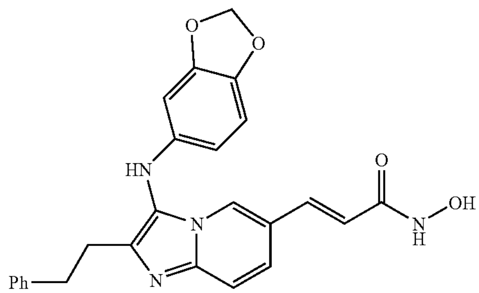 [SMILES: O=C(/C=C/c1ccc2nc(CCc3ccccc3)c(Nc3ccc4c(c3)OCO4)n2c1)NO] | (E)-3-(3-(benzo[d][1,3]dioxol-5-ylmethylamino)-2-phenethylimidazo[1,2-a]pyridin-6-yl)-N-hydroxyacrylamide |
| 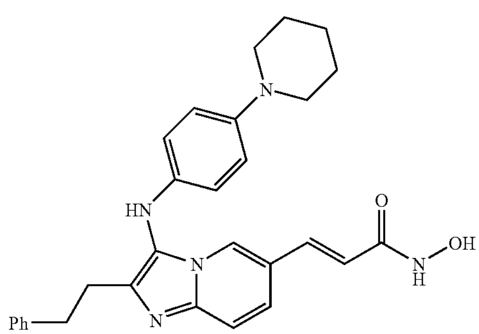 [SMILES: O=C(/C=C/c1ccc2nc(CCc3ccccc3)c(Nc3ccc(N4CCCCC4)cc3)n2c1)NO] | N-Hydroxy-3-[2-phenethyl-3-(4-piperidin-1-yl-phenylamino)-imidazo[1,2-a]pyridin-6-yl]-acrylamide |
| 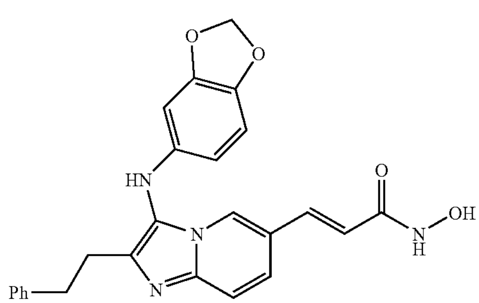 [SMILES: O=C(/C=C/c1ccc2nc(CCc3ccccc3)c(Nc3ccc4c(c3)OCO4)n2c1)NO] | (E)-3-(3-(benzo[d][1,3]dioxol-5-ylamino)-2-phenethylimidazo[1,2-a]pyridin-5-yl)-N-hydroxyacrylamide |

-continued

| Structure | Name |
|---|---|
| 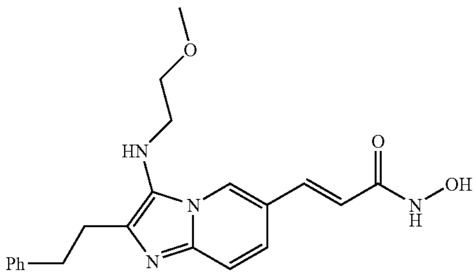 [SMILES: COCCNc1c(CCc2ccccc2)nc2ccc(/C=C/C(=O)NO)cn12] | (E)-N-hydroxy-3-(3-(2-methoxyethylamino)-2-phenethylimidazo[1,2-a]pyridin-6-yl)acrylamide |
| 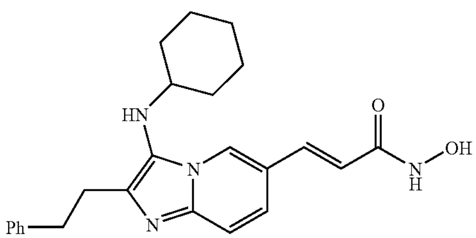 [SMILES: O=C(/C=C/c1ccc2nc(CCc3ccccc3)c(NC3CCCCC3)n2c1)NO] | (E)-3-(3-(cyclohexylamino)-2-phenethylimidazo[1,2-a]pyridin-6-yl)-N-hydroxyacrylamide |
| 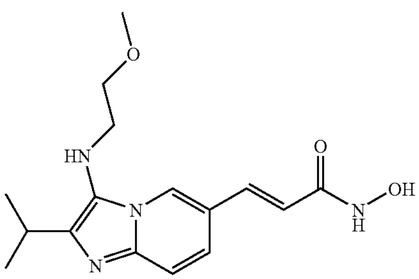 | (E)-N-hydroxy-3-(2-isopropyl-3-(2-methoxyethylamino)imidazo[1,2-a]pyridin-6-yl)acrylamide |
| 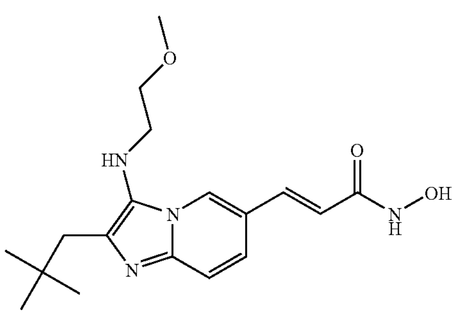 [SMILES: COCCNc1c(CC(C)(C)C)nc2ccc(/C=C/C(=O)NO)cn12] | 3-[2-(2,2-Dimethyl-propyl)-3-(2-methoxy-ethylamino)-imidazo[1,2-a]pyridin-6-yl]-N-hydroxy-acrylamide |
| 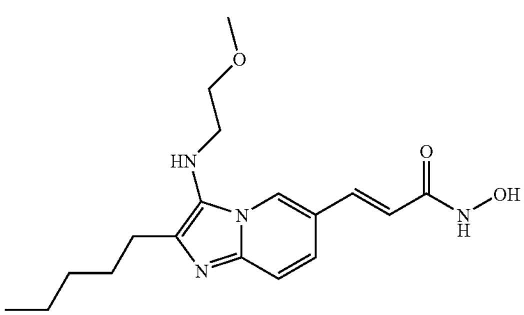 [SMILES: CCCCCc1nc2ccc(/C=C/C(=O)NO)cn2c1NCCOC] | (E)-N-hydroxy-3-(3-(2-methoxyethylamino)-2-pentylimidazo[1,2-a]pyridin-6-yl)acrylamide |

| Structure | Name |
|---|---|
| 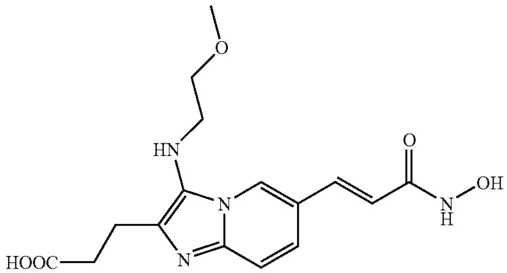 [SMILES: COCCNc1c(CCC(=O)O)nc2ccc(/C=C/C(=O)NO)cn12] | 3-[6-(2-Hydroxycarbamoyl-vinyl)-3-(2-methoxy-ethylamino)-imidazo[1,2-a]pyridin-2-yl]-propionic acid |
| 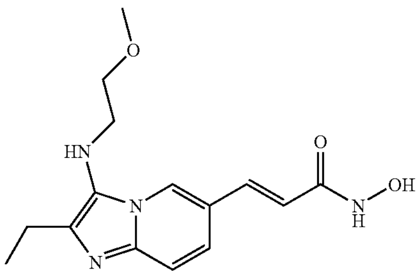 [SMILES: CCc1nc2ccc(/C=C/C(=O)NO)cn2c1NCCOC] | 3-[2-Ethyl-3-(2-methoxy-ethylamino)-imidazo[1,2-a]pyridin-6-yl]-N-hydroxy-acrylamide |
| 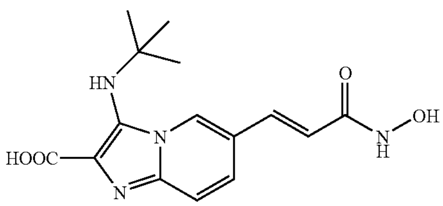 [SMILES: CC(C)(C)Nc1c(C(=O)O)nc2ccc(/C=C/C(=O)NO)cn12] | (E)-3-(tert-butylamino)-6-(3-(hydroxyamino)-3-oxoprop-1-enyl)imidazo[1,2-a]pyridine-2-carboxylic acid |
| 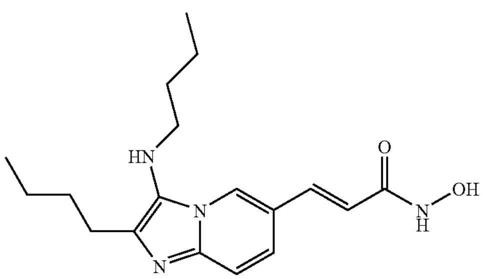 [SMILES: CCCCNc1c(CCCC)nc2ccc(/C=C/C(=O)NO)cn12] | (E)-3-(2-butyl-3-(butylamino)imidazo[1,2-a]pyridin-6-yl)-N-hydroxyacrylamide |
| 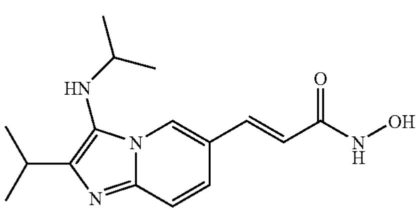 [SMILES: CC(C)Nc1c(C(C)C)nc2ccc(/C=C/C(=O)NO)cn12] | (E)-N-hydroxy-3-(2-isopropyl-3-(isopropylamino)imidazo[1,2-a]pyridin-6-yl)acrylamide |
| 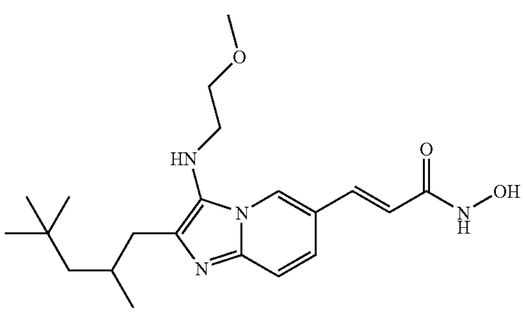 [SMILES: COCCNc1c(CC(C)CC(C)(C)C)nc2ccc(/C=C/C(=O)NO)cn12] | (E)-N-hydroxy-3-(3-(2-methoxyethylamino)-2-(2,4,4-trimethylpentyl)imidazo[1,2-a]pyridin-6-yl)acrylamide |

| Structure | Name |
|---|---|
| 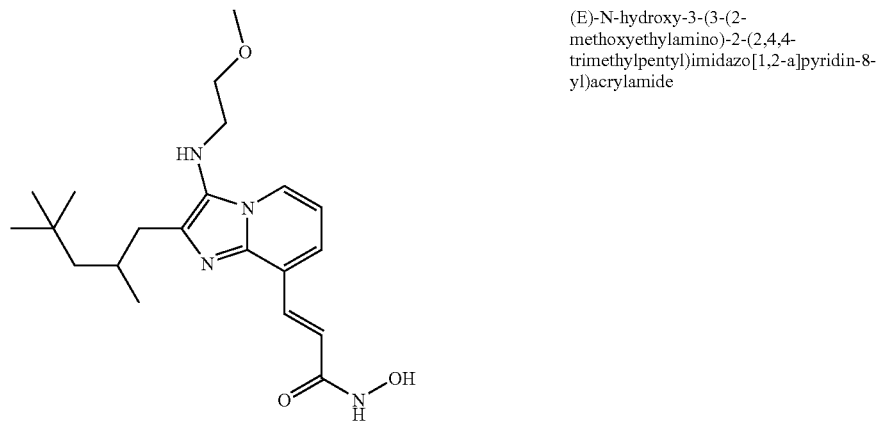 | (E)-N-hydroxy-3-(3-(2-methoxyethylamino)-2-(2,4,4-trimethylpentyl)imidazo[1,2-a]pyridin-8-yl)acrylamide |
| 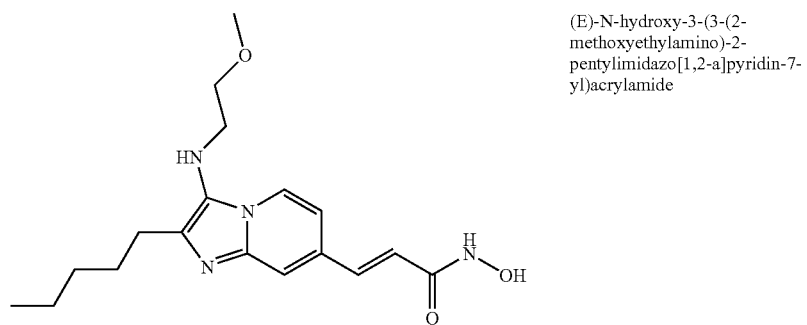 | (E)-N-hydroxy-3-(3-(2-methoxyethylamino)-2-pentylimidazo[1,2-a]pyridin-7-yl)acrylamide |
| 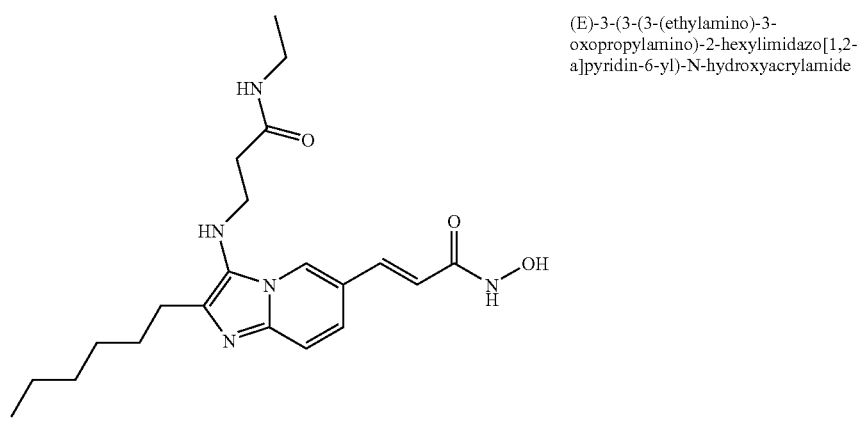 | (E)-3-(3-(3-(ethylamino)-3-oxopropylamino)-2-hexylimidazo[1,2-a]pyridin-6-yl)-N-hydroxyacrylamide |

| Structure | Name |
|---|---|
| 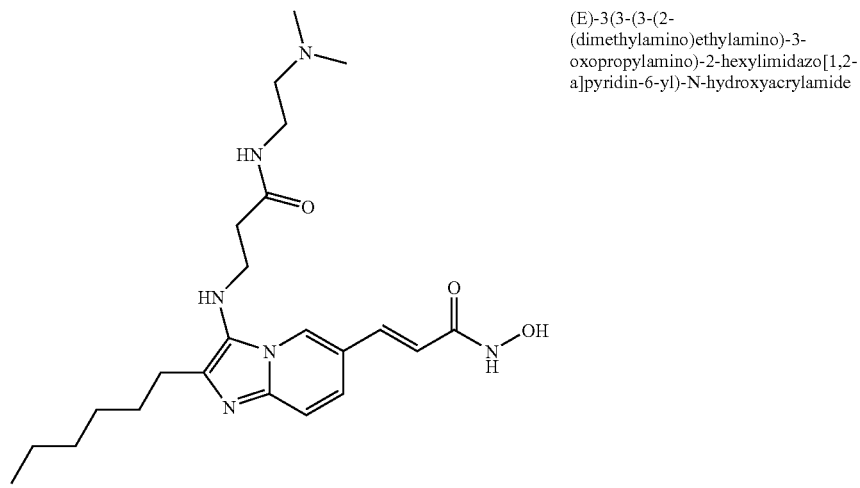 | (E)-3(3-(3-(2-(dimethylamino)ethylamino)-3-oxopropylamino)-2-hexylimidazo[1,2-a]pyridin-6-yl)-N-hydroxyacrylamide |
| 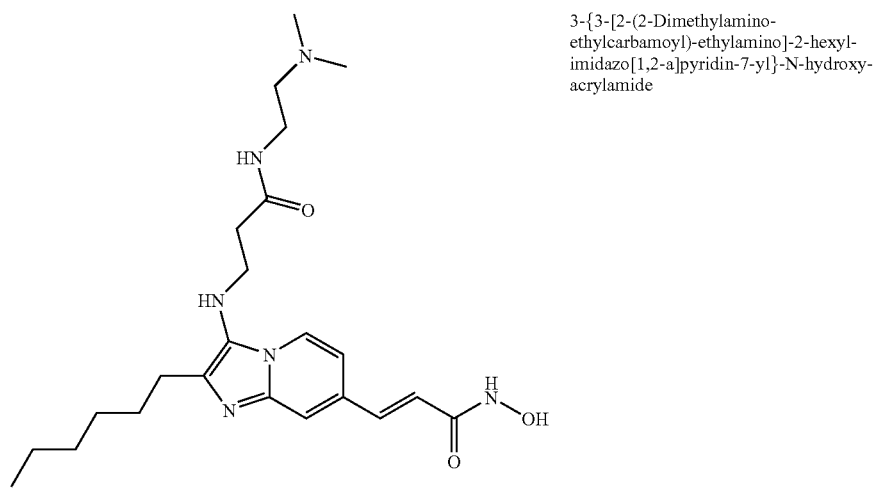 | 3-{3-[2-(2-Dimethylamino-ethylcarbamoyl)-ethylamino]-2-hexyl-imidazo[1,2-a]pyridin-7-yl}-N-hydroxy-acrylamide |
| 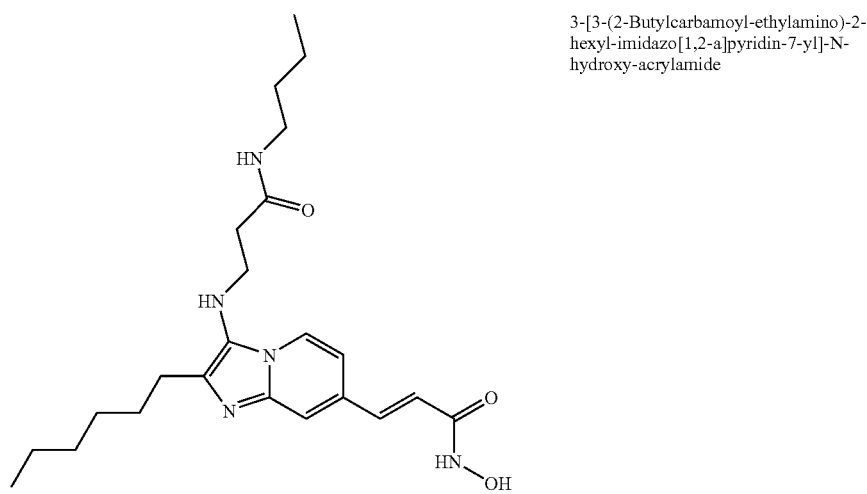 | 3-[3-(2-Butylcarbamoyl-ethylamino)-2-hexyl-imidazo[1,2-a]pyridin-7-yl]-N-hydroxy-acrylamide |

| Structure | Name |
|---|---|
| 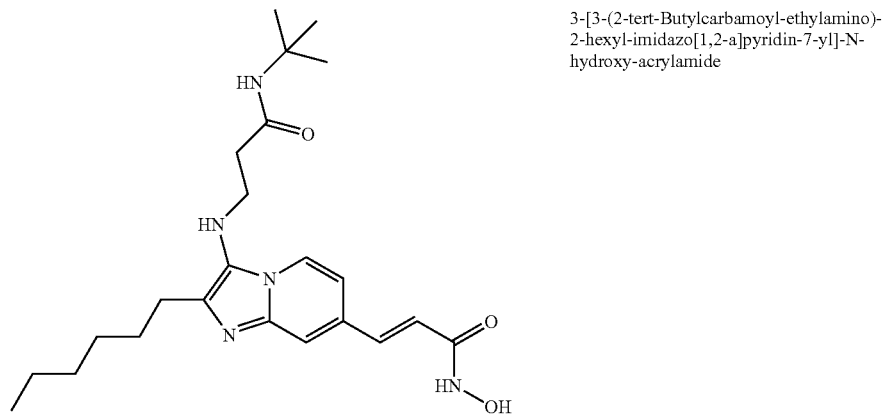 | 3-[3-(2-tert-Butylcarbamoyl-ethylamino)-2-hexyl-imidazo[1,2-a]pyridin-7-yl]-N-hydroxy-acrylamide |
| 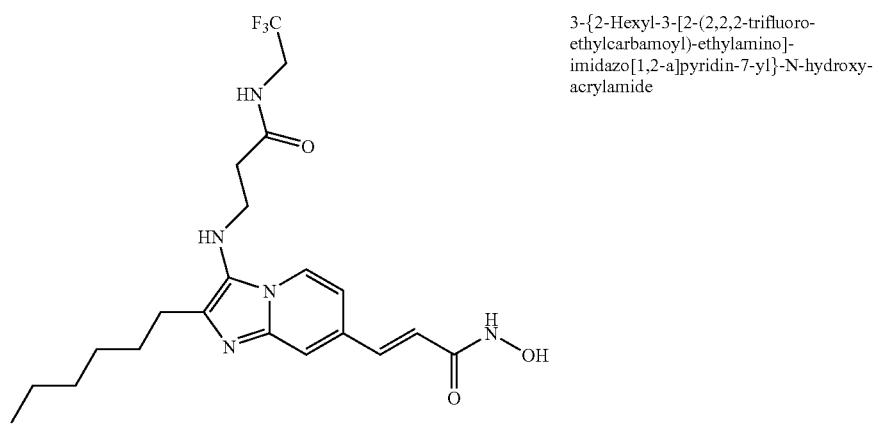 | 3-{2-Hexyl-3-[2-(2,2,2-trifluoro-ethylcarbamoyl)-ethylamino]-imidazo[1,2-a]pyridin-7-yl}-N-hydroxy-acrylamide |
| 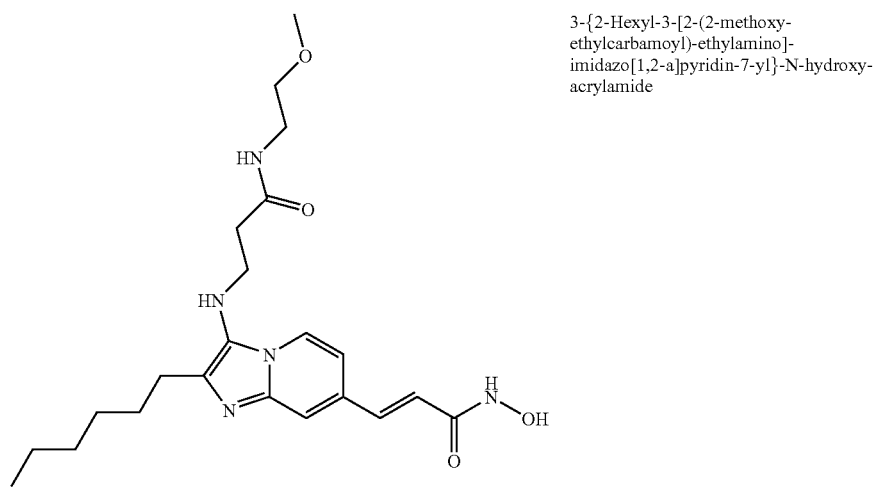 | 3-{2-Hexyl-3-[2-(2-methoxy-ethylcarbamoyl)-ethylamino]-imidazo[1,2-a]pyridin-7-yl}-N-hydroxy-acrylamide |

| Structure | Name |
|---|---|
| 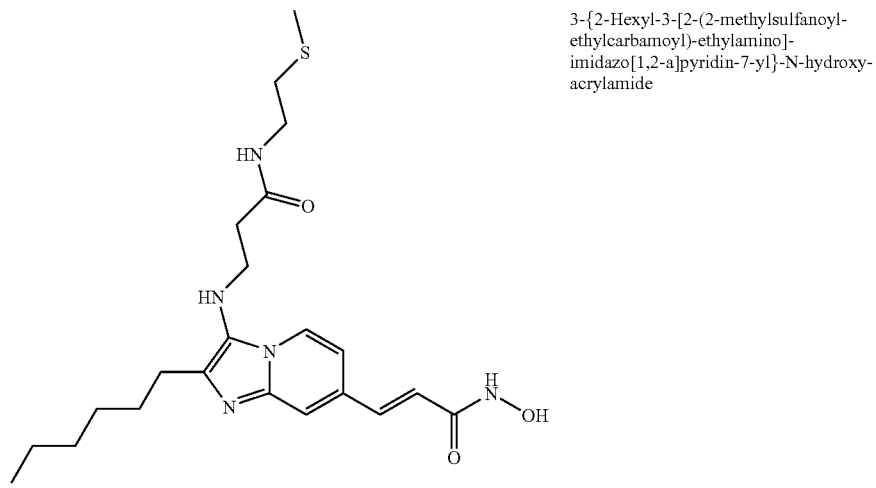 | 3-{2-Hexyl-3-[2-(2-methylsulfanoyl-ethylcarbamoyl)-ethylamino]-imidazo[1,2-a]pyridin-7-yl}-N-hydroxy-acrylamide |
| 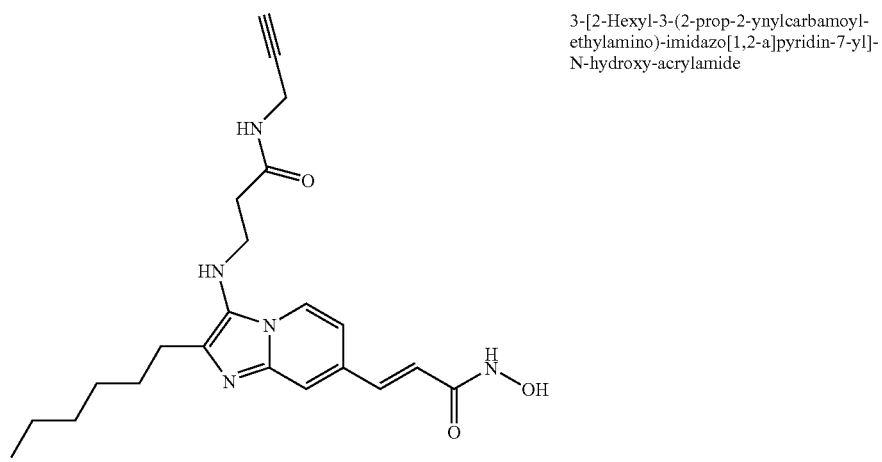 | 3-[2-Hexyl-3-(2-prop-2-ynylcarbamoyl-ethylamino)-imidazo[1,2-a]pyridin-7-yl]-N-hydroxy-acrylamide |
| 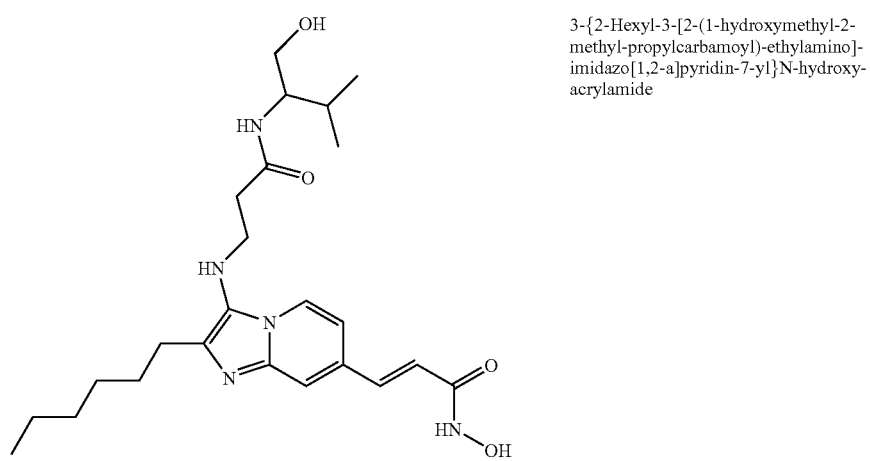 | 3-{2-Hexyl-3-[2-(1-hydroxymethyl-2-methyl-propylcarbamoyl)-ethylamino]-imidazo[1,2-a]pyridin-7-yl}N-hydroxy-acrylamide |

| Structure | Name |
|---|---|
| 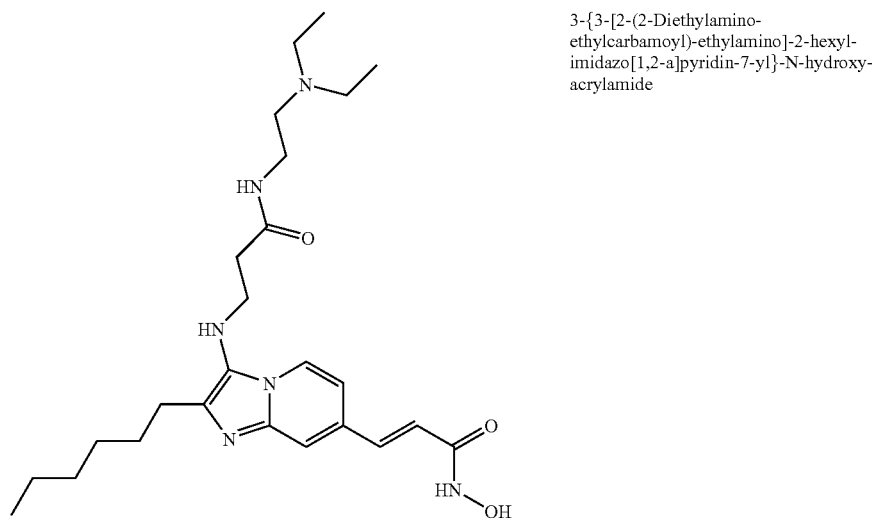 | 3-{3-[2-(2-Diethylamino-ethylcarbamoyl)-ethylamino]-2-hexyl-imidazo[1,2-a]pyridin-7-yl}-N-hydroxy-acrylamide |
| 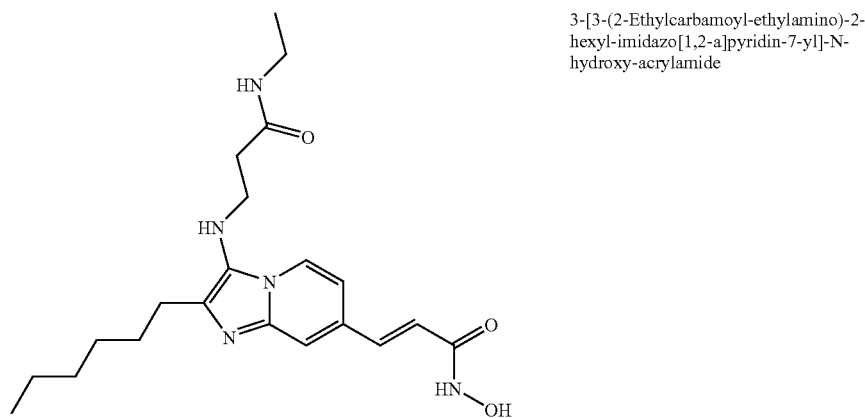 | 3-[3-(2-Ethylcarbamoyl-ethylamino)-2-hexyl-imidazo[1,2-a]pyridin-7-yl]-N-hydroxy-acrylamide |
| 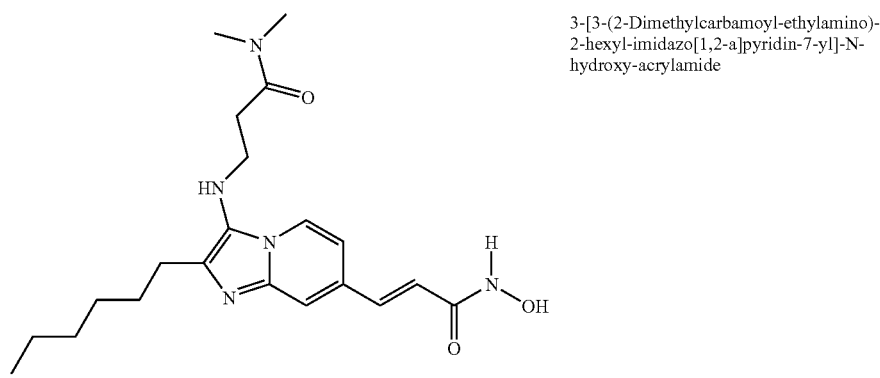 | 3-[3-(2-Dimethylcarbamoyl-ethylamino)-2-hexyl-imidazo[1,2-a]pyridin-7-yl]-N-hydroxy-acrylamide |

-continued
| Structure | Name |
|---|---|
| 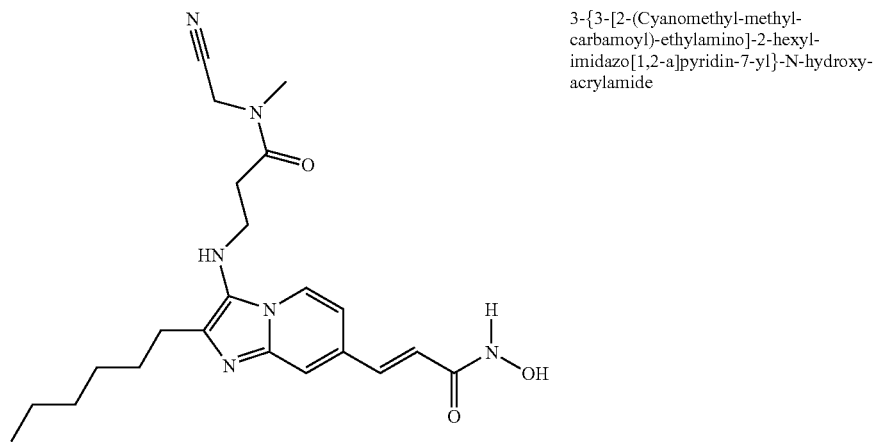 | 3-{3-[2-(Cyanomethyl-methyl-carbamoyl)-ethylamino]-2-hexyl-imidazo[1,2-a]pyridin-7-yl}-N-hydroxy-acrylamide |
| 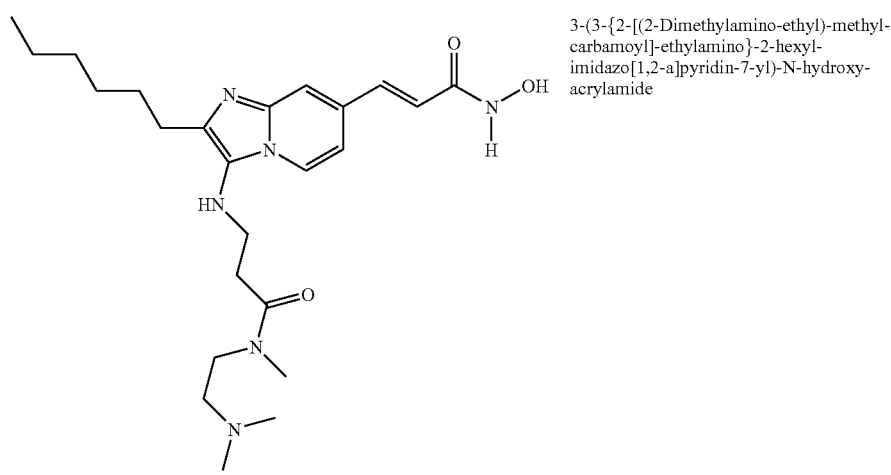 | 3-(3-{2-[(2-Dimethylamino-ethyl)-methyl-carbamoyl]-ethylamino}-2-hexyl-imidazo[1,2-a]pyridin-7-yl)-N-hydroxy-acrylamide |
| 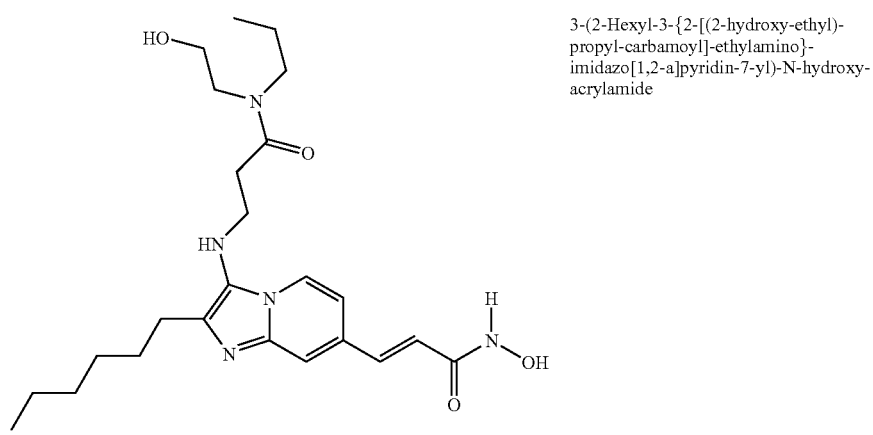 | 3-(2-Hexyl-3-{2-[(2-hydroxy-ethyl)-propyl-carbamoyl]-ethylamino}-imidazo[1,2-a]pyridin-7-yl)-N-hydroxy-acrylamide |
| 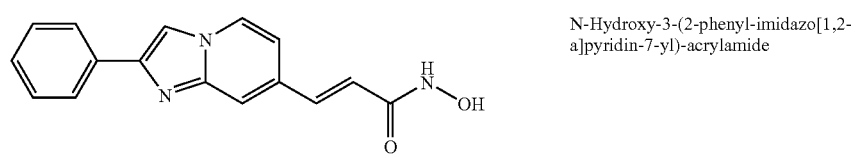 | N-Hydroxy-3-(2-phenyl-imidazo[1,2-a]pyridin-7-yl)-acrylamide |

| Structure | Name |
|---|---|
| 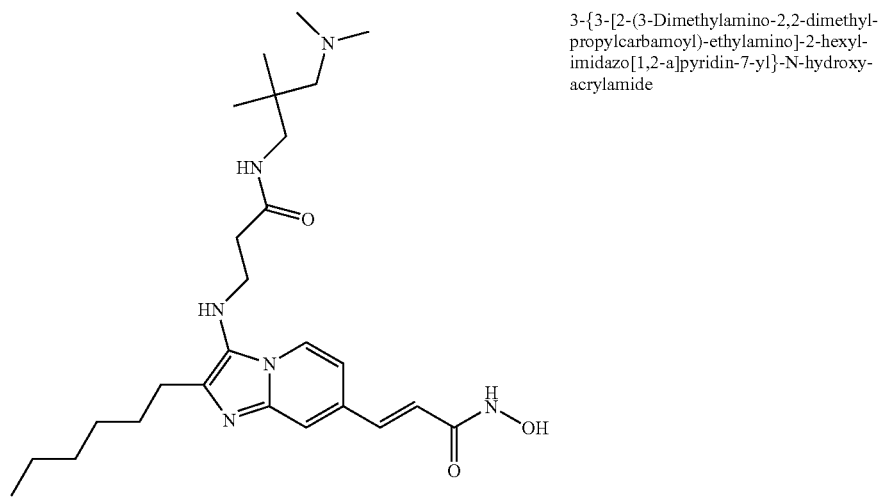 | 3-{3-[2-(3-Dimethylamino-2,2-dimethyl-propylcarbamoyl)-ethylamino]-2-hexyl-imidazo[1,2-a]pyridin-7-yl}-N-hydroxy-acrylamide |
| 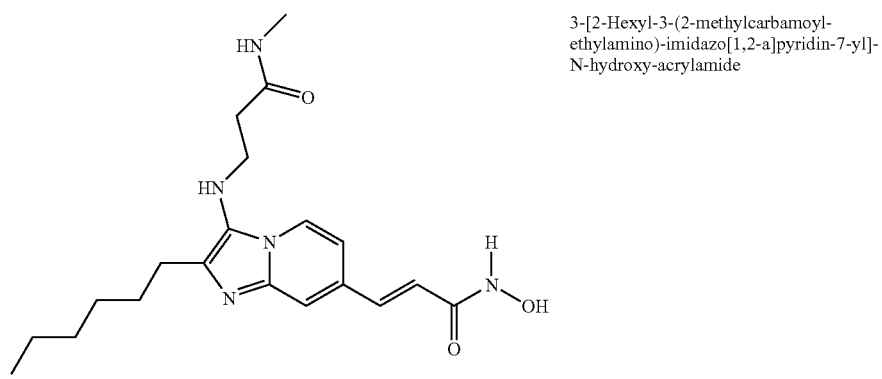 | 3-[2-Hexyl-3-(2-methylcarbamoyl-ethylamino)-imidazo[1,2-a]pyridin-7-yl]-N-hydroxy-acrylamide |
| 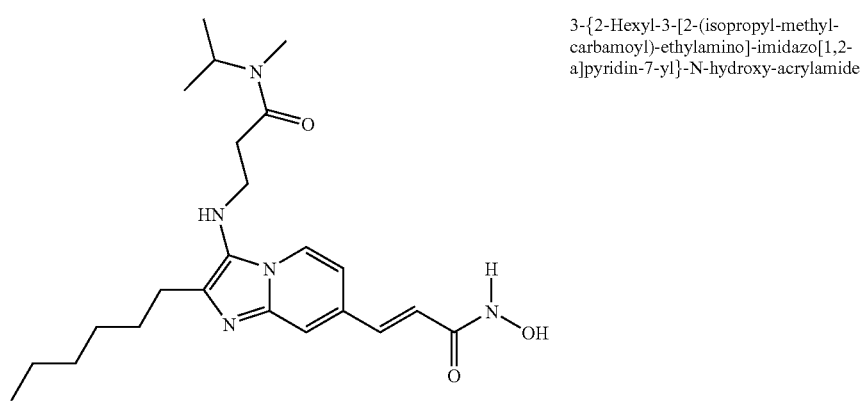 | 3-{2-Hexyl-3-[2-(isopropyl-methyl-carbamoyl)-ethylamino]-imidazo[1,2-a]pyridin-7-yl}-N-hydroxy-acrylamide |

| Structure | Name |
|---|---|
| 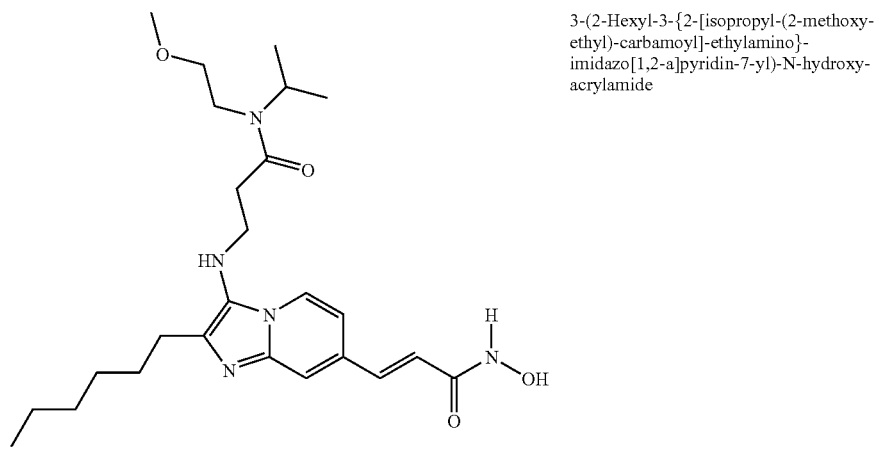 | 3-(2-Hexyl-3-{2-[isopropyl-(2-methoxy-ethyl)-carbamoyl]-ethylamino}-imidazo[1,2-a]pyridin-7-yl)-N-hydroxy-acrylamide |
| 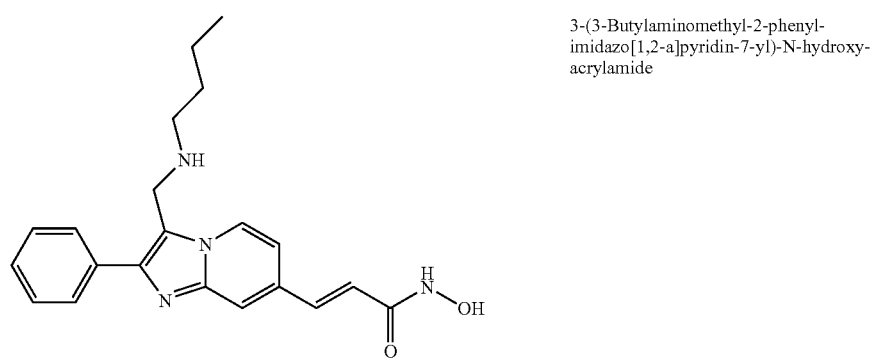 | 3-(3-Butylaminomethyl-2-phenyl-imidazo[1,2-a]pyridin-7-yl)-N-hydroxy-acrylamide |
| 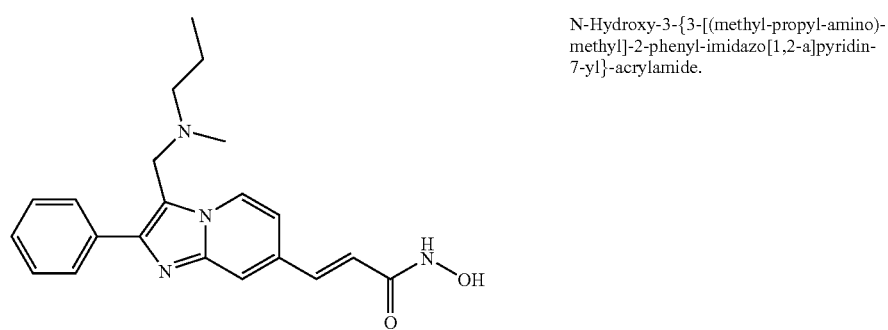 | N-Hydroxy-3-{3-[(methyl-propyl-amino)-methyl]-2-phenyl-imidazo[1,2-a]pyridin-7-yl}-acrylamide. |
| 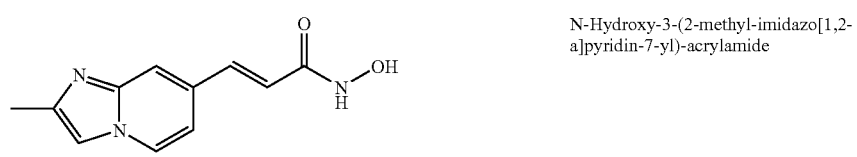 | N-Hydroxy-3-(2-methyl-imidazo[1,2-a]pyridin-7-yl)-acrylamide |

-continued

| Structure | Name |
|---|---|
| 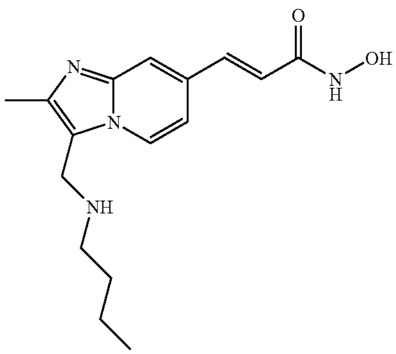 [SMILES: CCCCNCc1c(C)nc2cc(/C=C/C(=O)NO)ccn12] | 3-(3-Butylaminomethyl-2-methyl-imidazo[1,2-a]pyridin-7-yl)-N-hydroxy-acrylamide |
| 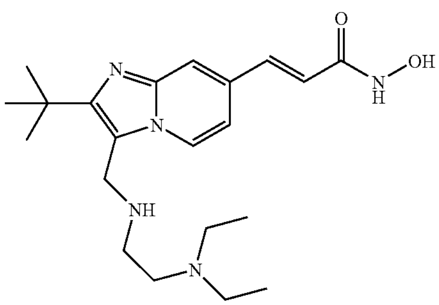 [SMILES: CCN(CC)CCNCc1c(C(C)(C)C)nc2cc(/C=C/C(=O)NO)ccn12] | 3-{2-tert-Butyl-3-[(2-diethylamino-ethylamino)-methyl]-imidazo[1,2-a]pyridin-7-yl}-N-hydroxy-acrylamide |
| 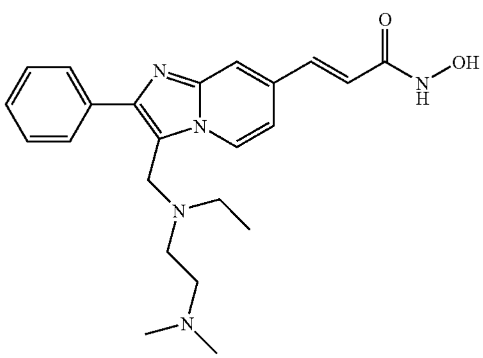 [SMILES: CCN(CCN(C)C)Cc1c(-c2ccccc2)nc2cc(/C=C/C(=O)NO)ccn12] | 3-(3-{[(2-Dimethylamino-ethyl)-ethyl-amino]-methyl}-2-phenyl-imidazo[1,2-a]pyridin-7-yl)-N-hydroxy-acrylamide |
| 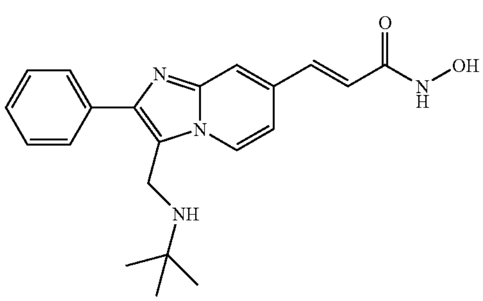 [SMILES: CC(C)(C)NCc1c(-c2ccccc2)nc2cc(/C=C/C(=O)NO)ccn12] | 3-[3-(tert-Butylamino-methyl)-2-phenyl-imidazo[1,2-a]pyridin-7-yl]-N-hydroxy-acrylamide |
| 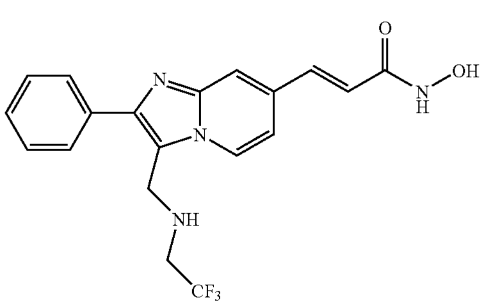 [SMILES: O=C(/C=C/c1ccn2c(CNCC(F)(F)F)c(-c3ccccc3)nc2c1)NO] | N-Hydroxy-3-{2-phenyl-3-[(2,2,2-trifluoro-ethylamino)-methyl]-imidazo[1,2-a]pyridin-7-yl}-acrylamide |

-continued

| Structure | Name |
|---|---|
| 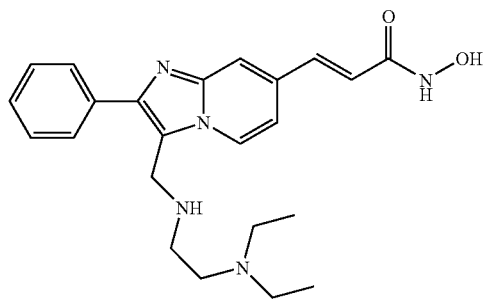 [SMILES: CCN(CC)CCNCc1c(-c2ccccc2)nc2cc(/C=C/C(=O)NO)ccn12] | 3-{3-[(2-Diethylamino-ethylamino)-methyl]-2-phenyl-imidazo[1,2-a]pyridin-7-yl}-N-hydroxy-acrylamide |
| 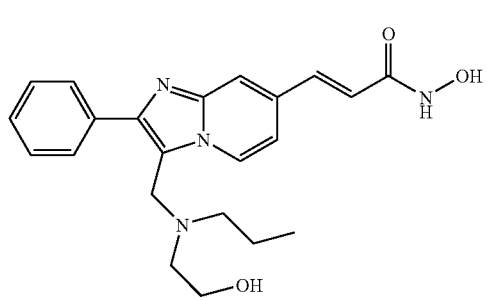 [SMILES: CCCN(CCO)Cc1c(-c2ccccc2)nc2cc(/C=C/C(=O)NO)ccn12] | N-Hydroxy-3-(3-{[(2-hydroxy-ethyl)-propyl-amino]-methyl}-2-phenyl-imidazo[1,2-a]pyridin-7-yl)-acrylamide |
| 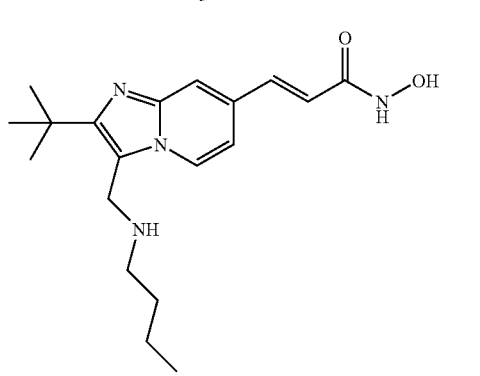 | 3-(2-tert-Butyl-3-butylaminomethyl-imidazo[1,2-a]pyridin-7-yl)-N-hydroxy-acrylamide |
| 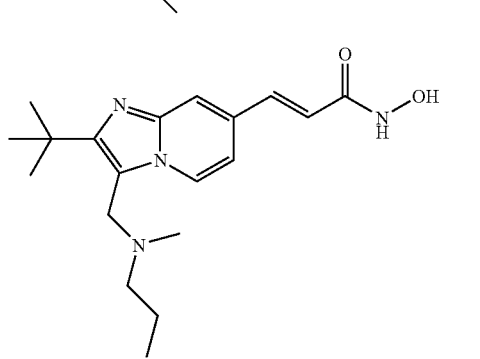 | 3-{2-tert-Butyl-3-[(methyl-propyl-amino)-methyl]-imidazo[1,2-a]pyridin-7-yl}-N-hydroxy-acrylamide |
| 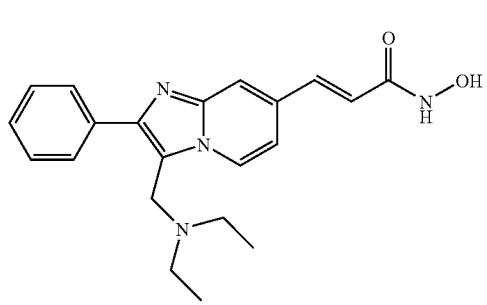 [SMILES: CCN(CC)Cc1c(-c2ccccc2)nc2cc(/C=C/C(=O)NO)ccn12] | 3-(3-Diethylaminomethyl-2-phenyl-imidazo[1,2-a]pyridin-7-yl)-N-hydroxy-acrylamide |

| Structure | Name |
|---|---|
| 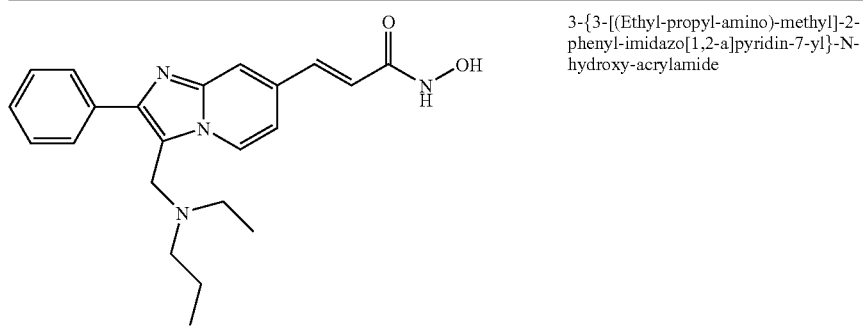 | 3-{3-[(Ethyl-propyl-amino)-methyl]-2-phenyl-imidazo[1,2-a]pyridin-7-yl}-N-hydroxy-acrylamide |
| 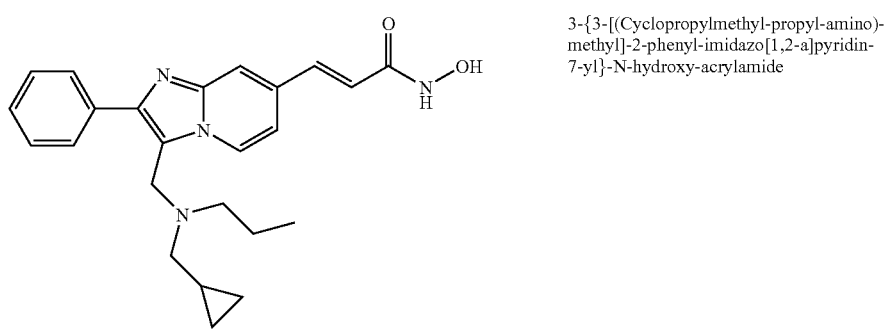 | 3-{3-[(Cyclopropylmethyl-propyl-amino)-methyl]-2-phenyl-imidazo[1,2-a]pyridin-7-yl}-N-hydroxy-acrylamide |
| 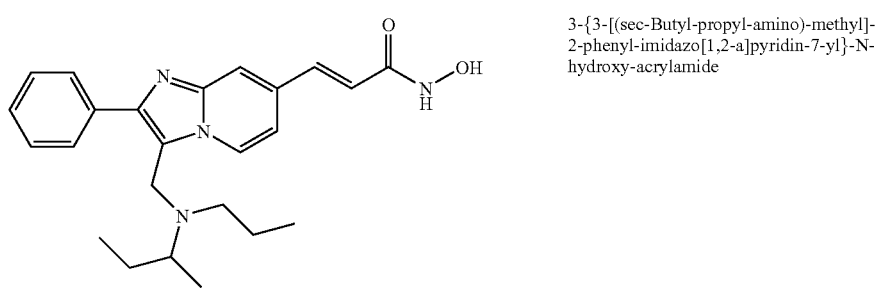 | 3-{3-[(sec-Butyl-propyl-amino)-methyl]-2-phenyl-imidazo[1,2-a]pyridin-7-yl}-N-hydroxy-acrylamide |
| 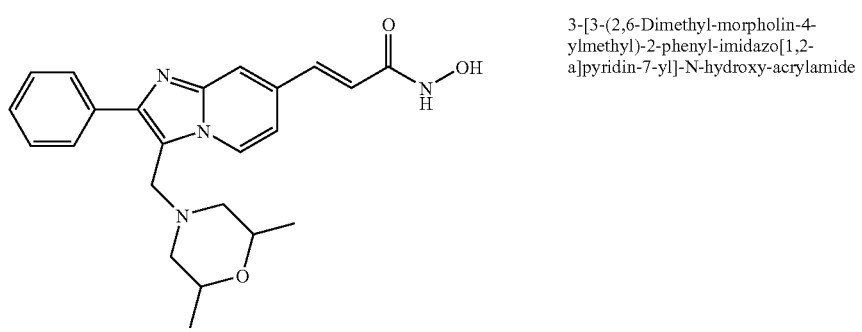 | 3-[3-(2,6-Dimethyl-morpholin-4-ylmethyl)-2-phenyl-imidazo[1,2-a]pyridin-7-yl]-N-hydroxy-acrylamide |
| 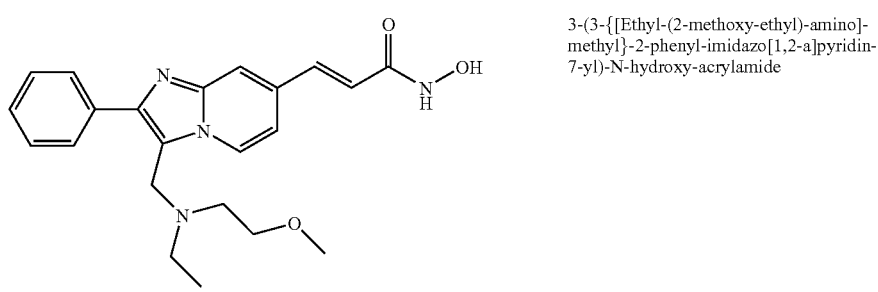 | 3-(3-{[Ethyl-(2-methoxy-ethyl)-amino]-methyl}-2-phenyl-imidazo[1,2-a]pyridin-7-yl)-N-hydroxy-acrylamide |

| Structure | Name |
|---|---|
| 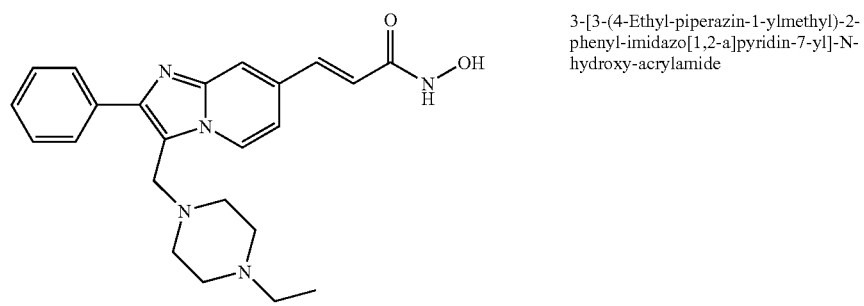 | 3-[3-(4-Ethyl-piperazin-1-ylmethyl)-2-phenyl-imidazo[1,2-a]pyridin-7-yl]-N-hydroxy-acrylamide |
| 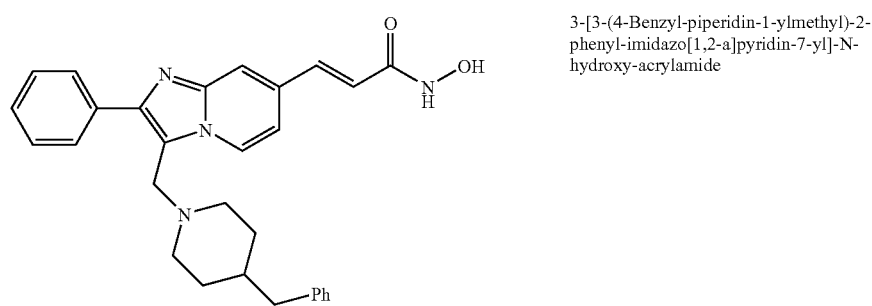 | 3-[3-(4-Benzyl-piperidin-1-ylmethyl)-2-phenyl-imidazo[1,2-a]pyridin-7-yl]-N-hydroxy-acrylamide |
| 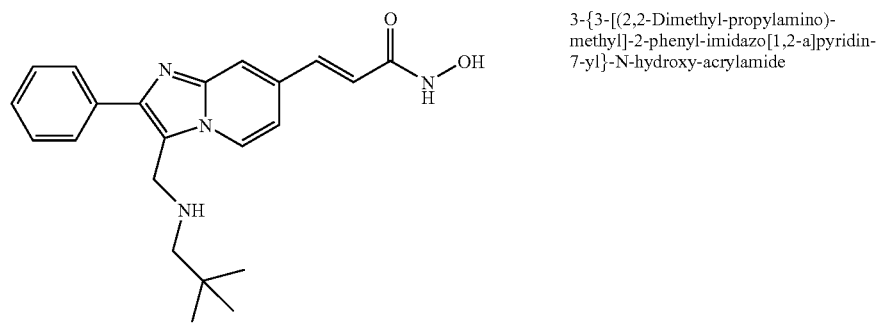 | 3-{3-[(2,2-Dimethyl-propylamino)-methyl]-2-phenyl-imidazo[1,2-a]pyridin-7-yl}-N-hydroxy-acrylamide |
| 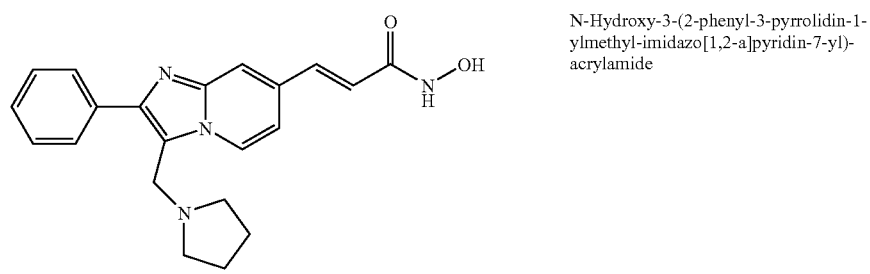 | N-Hydroxy-3-(2-phenyl-3-pyrrolidin-1-ylmethyl-imidazo[1,2-a]pyridin-7-yl)-acrylamide |
| 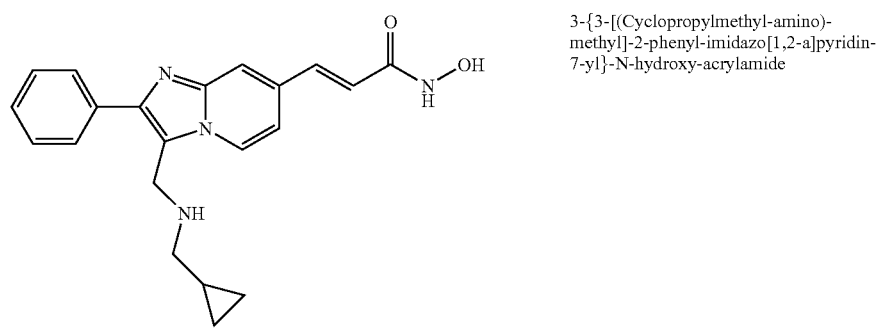 | 3-{3-[(Cyclopropylmethyl-amino)-methyl]-2-phenyl-imidazo[1,2-a]pyridin-7-yl}-N-hydroxy-acrylamide |

-continued

| Structure | Name |
|---|---|
| 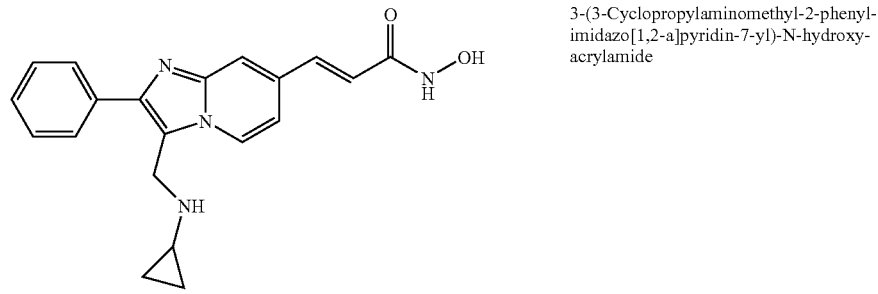 | 3-(3-Cyclopropylaminomethyl-2-phenyl-imidazo[1,2-a]pyridin-7-yl)-N-hydroxy-acrylamide |
| 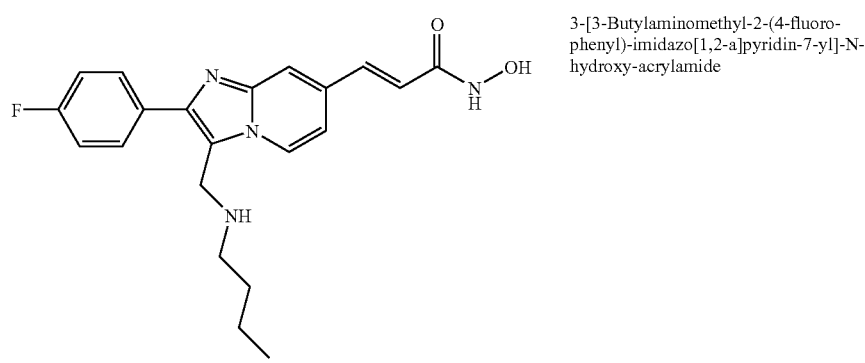 | 3-[3-Butylaminomethyl-2-(4-fluoro-phenyl)-imidazo[1,2-a]pyridin-7-yl]-N-hydroxy-acrylamide |
| 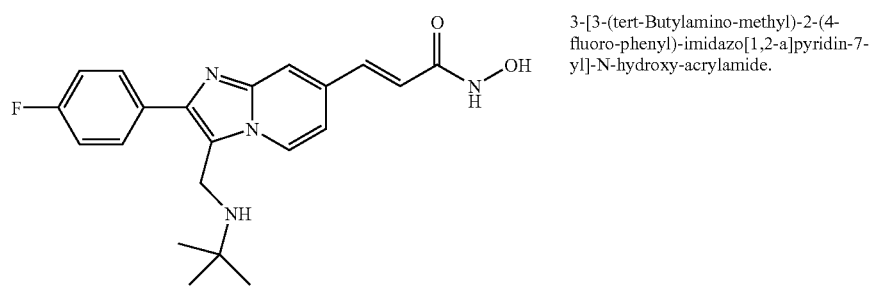 | 3-[3-(tert-Butylamino-methyl)-2-(4-fluoro-phenyl)-imidazo[1,2-a]pyridin-7-yl]-N-hydroxy-acrylamide. |
| 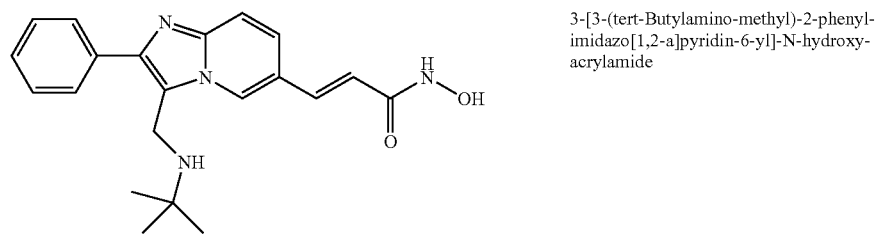 | 3-[3-(tert-Butylamino-methyl)-2-phenyl-imidazo[1,2-a]pyridin-6-yl]-N-hydroxy-acrylamide |
| 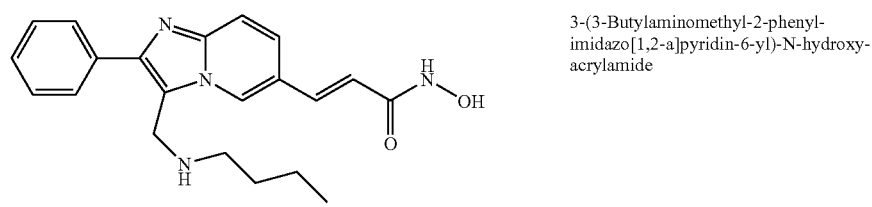 | 3-(3-Butylaminomethyl-2-phenyl-imidazo[1,2-a]pyridin-6-yl)-N-hydroxy-acrylamide |

| Structure | Name |
|---|---|
| 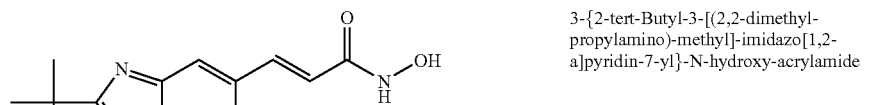 | 3-{2-tert-Butyl-3-[(2,2-dimethyl-propylamino)-methyl]-imidazo[1,2-a]pyridin-7-yl}-N-hydroxy-acrylamide |
| 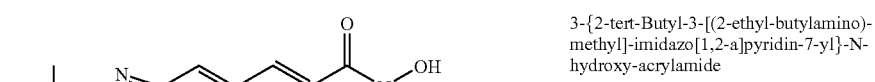 | 3-{2-tert-Butyl-3-[(2-ethyl-butylamino)-methyl]-imidazo[1,2-a]pyridin-7-yl}-N-hydroxy-acrylamide |
| 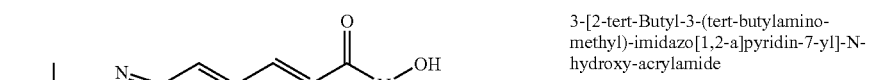 | 3-[2-tert-Butyl-3-(tert-butylamino-methyl)-imidazo[1,2-a]pyridin-7-yl]-N-hydroxy-acrylamide |
| 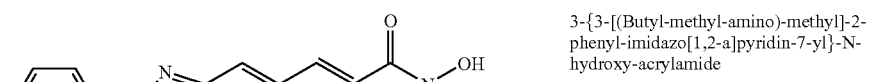 | 3-{3-[(Butyl-methyl-amino)-methyl]-2-phenyl-imidazo[1,2-a]pyridin-7-yl}-N-hydroxy-acrylamide |
| 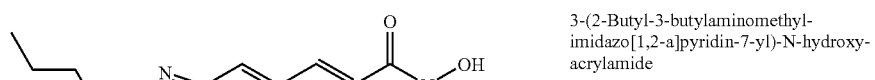 | 3-(2-Butyl-3-butylaminomethyl-imidazo[1,2-a]pyridin-7-yl)-N-hydroxy-acrylamide |

| Structure | Name |
|---|---|
| 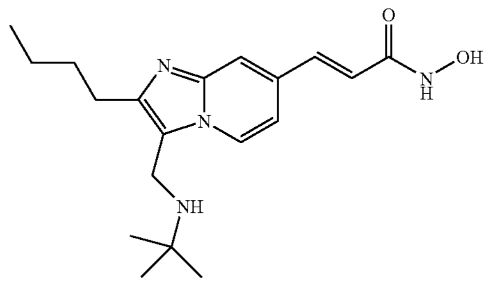 [SMILES: CCCCc1nc2cc(/C=C/C(=O)NO)ccn2c1CNC(C)(C)C] | 3-[2-Butyl-3-(tert-butylamino-methyl)-imidazo[1,2-a]pyridin-7-yl]-N-hydroxy-acrylamide |
| 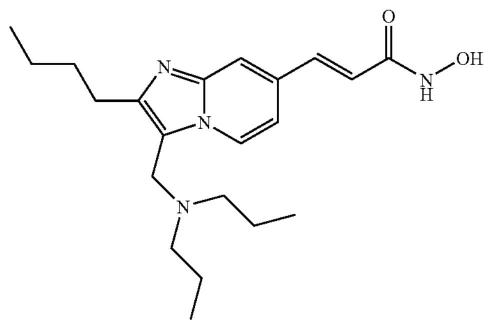 [SMILES: CCCCc1nc2cc(/C=C/C(=O)NO)ccn2c1CN(CCC)CCC] | 3-(2-Butyl-3-dipropylaminomethyl-imidazo[1,2-a]pyridin-7-yl)-N-hydroxy-acrylamide |
| 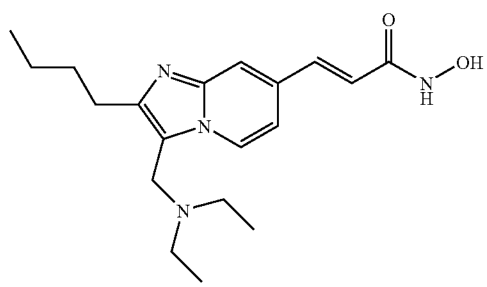 [SMILES: CCCCc1nc2cc(/C=C/C(=O)NO)ccn2c1CN(CC)CC] | 3-(2-Butyl-3-diethyaminomethyl-imidazo[1,2-a]pyridin-7-yl)-N-hydroxy-acrylamide |
| 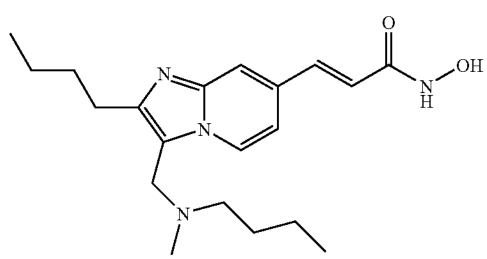 [SMILES: CCCCc1nc2cc(/C=C/C(=O)NO)ccn2c1CN(C)CCCC] | 3-{2-Butyl-3-[(butyl-methyl-amino)-methyl]-imidazo[1,2-a]pyridin-7-yl}-N-hydroxy-acrylamide |
| 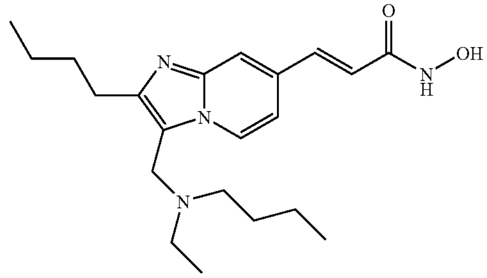 [SMILES: CCCCc1nc2cc(/C=C/C(=O)NO)ccn2c1CN(CC)CCCC] | 3-{2-Butyl-3-[(butyl-ethyl-amino)-methyl]-imidazo[1,2-a]pyridin-7-yl}-N-hydroxy-acrylamide |

| Structure | Name |
|---|---|
| 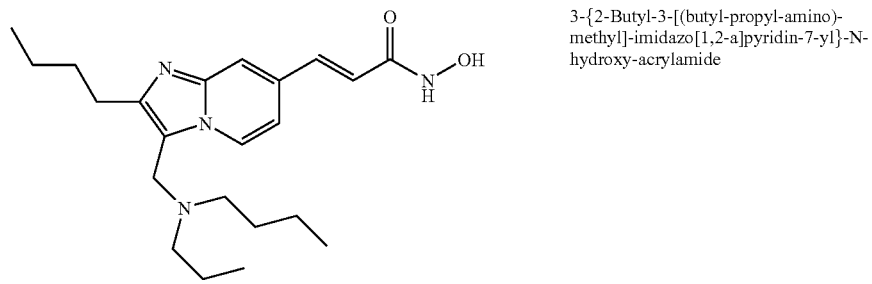 | 3-{2-Butyl-3-[(butyl-propyl-amino)-methyl]-imidazo[1,2-a]pyridin-7-yl}-N-hydroxy-acrylamide |
| 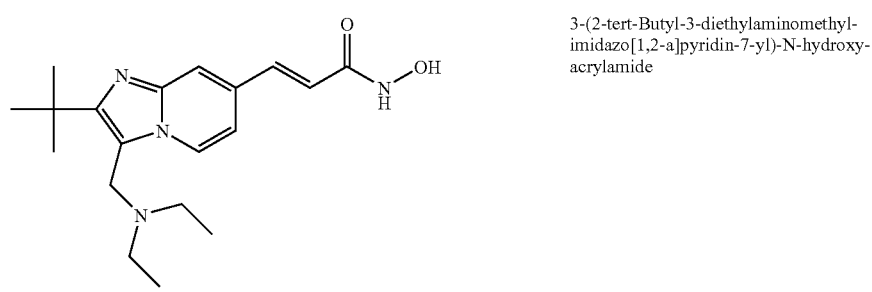 | 3-(2-tert-Butyl-3-diethylaminomethyl-imidazo[1,2-a]pyridin-7-yl)-N-hydroxy-acrylamide |
| 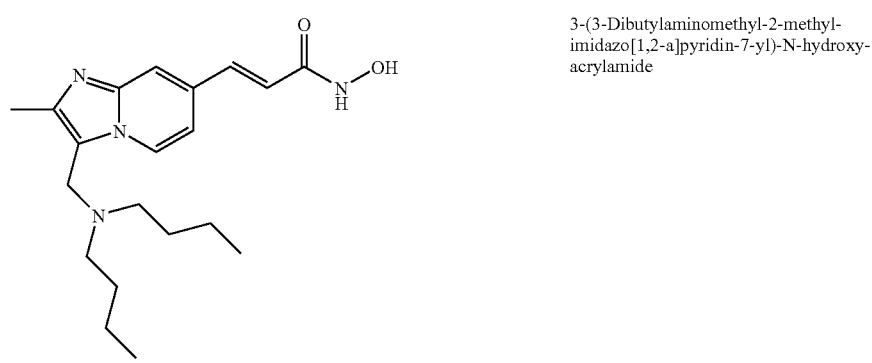 | 3-(3-Dibutylaminomethyl-2-methyl-imidazo[1,2-a]pyridin-7-yl)-N-hydroxy-acrylamide |
| 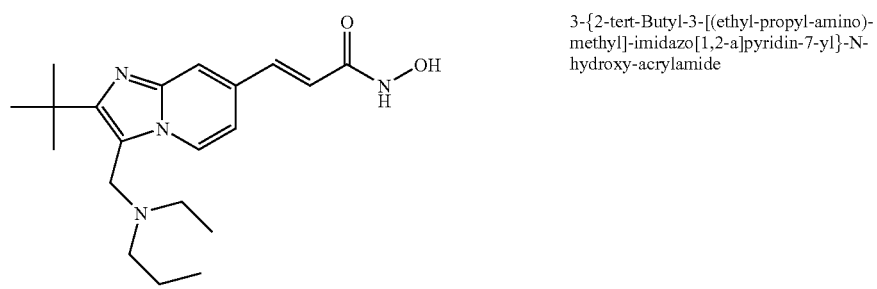 | 3-{2-tert-Butyl-3-[(ethyl-propyl-amino)-methyl]-imidazo[1,2-a]pyridin-7-yl}-N-hydroxy-acrylamide |
| 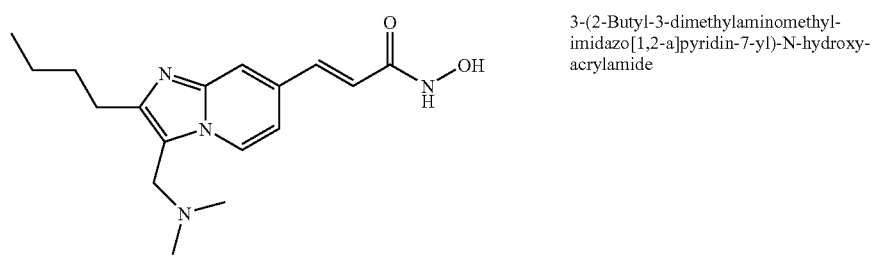 | 3-(2-Butyl-3-dimethylaminomethyl-imidazo[1,2-a]pyridin-7-yl)-N-hydroxy-acrylamide |

-continued

| Structure | Name |
|---|---|
| 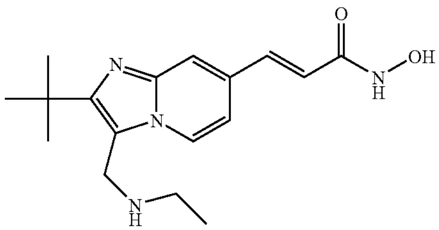 [SMILES: CCNCc1c(C(C)(C)C)nc2cc(/C=C/C(=O)NO)ccn12] | 3-(2-tert-Butyl-3-ethylaminomethyl-imidazo[1,2-a]pyridin-7-yl)-N-hydroxy-acrylamide |
| 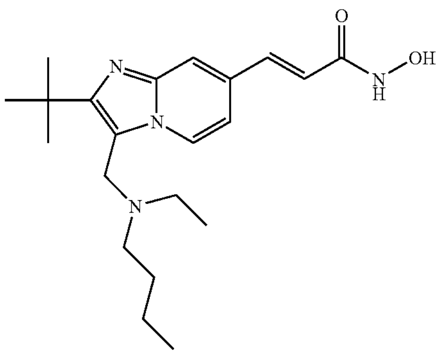 [SMILES: CCCCN(CC)Cc1c(C(C)(C)C)nc2cc(/C=C/C(=O)NO)ccn12] | 3-{2-tert-Butyl-3-[(butyl-ethyl-amino)-methyl]-imidazo[1,2-a]pyridin-7-yl}-N-hydroxy-acrylamide |
| 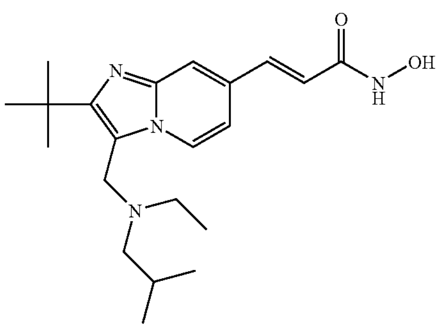 [SMILES: CCN(Cc1c(C(C)(C)C)nc2cc(/C=C/C(=O)NO)ccn12)CC(C)C] | 3-{2-tert-Butyl-3-[(ethyl-isobutyl-amino)-methyl]-imidazo[1,2-a]pyridin-7-yl}-N-hydroxy-acrylamide |
| 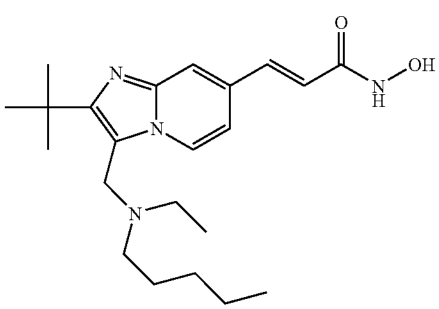 [SMILES: CCCCCN(CC)Cc1c(C(C)(C)C)nc2cc(/C=C/C(=O)NO)ccn12] | 3-{2-tert-Butyl-3-[(ethyl-pentyl-amino)-methyl]-imidazo[1,2-a]pyridin-7-yl}-N-hydroxy-acrylamide |
| 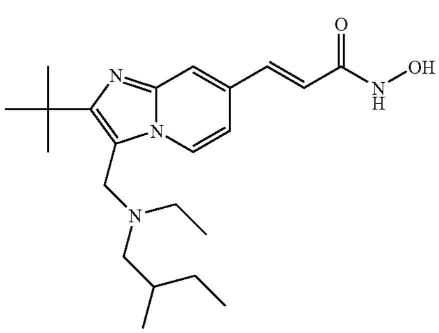 [SMILES: CCC(C)CN(CC)Cc1c(C(C)(C)C)nc2cc(/C=C/C(=O)NO)ccn12] | 3-(2-tert-Butyl-3-{[ethyl-(2-methyl-butyl)-amino]-methyl}-imidazo[1,2-a]pyridin-7-yl)-N-hydroxy-acrylamide |

| Structure | Name |
|---|---|
| 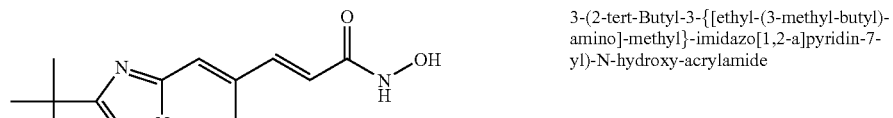 | 3-(2-tert-Butyl-3-{[ethyl-(3-methyl-butyl)-amino]-methyl}-imidazo[1,2-a]pyridin-7-yl)-N-hydroxy-acrylamide |
| 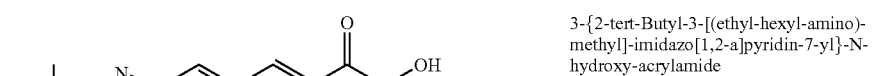 | 3-{2-tert-Butyl-3-[(ethyl-hexyl-amino)-methyl]-imidazo[1,2-a]pyridin-7-yl}-N-hydroxy-acrylamide |
| 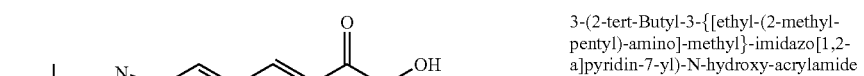 | 3-(2-tert-Butyl-3-{[ethyl-(2-methyl-pentyl)-amino]-methyl}-imidazo[1,2-a]pyridin-7-yl)-N-hydroxy-acrylamide |
| 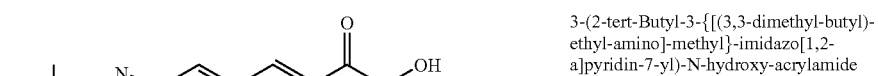 | 3-(2-tert-Butyl-3-{[(3,3-dimethyl-butyl)-ethyl-amino]-methyl}-imidazo[1,2-a]pyridin-7-yl)-N-hydroxy-acrylamide |

| Structure | Name |
|---|---|
| 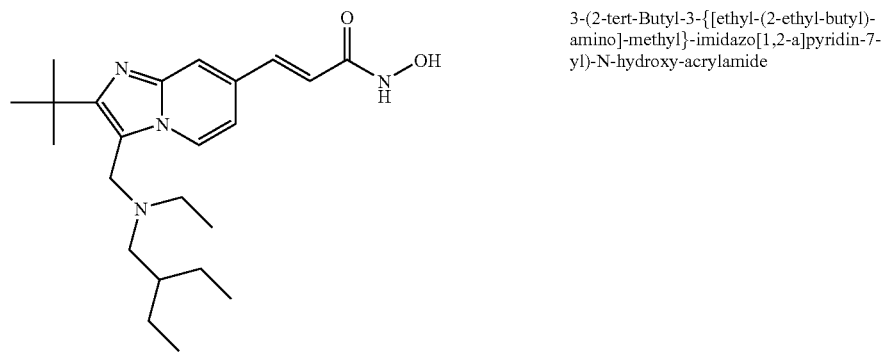 | 3-(2-tert-Butyl-3-{[ethyl-(2-ethyl-butyl)-amino]-methyl}-imidazo[1,2-a]pyridin-7-yl)-N-hydroxy-acrylamide |
| 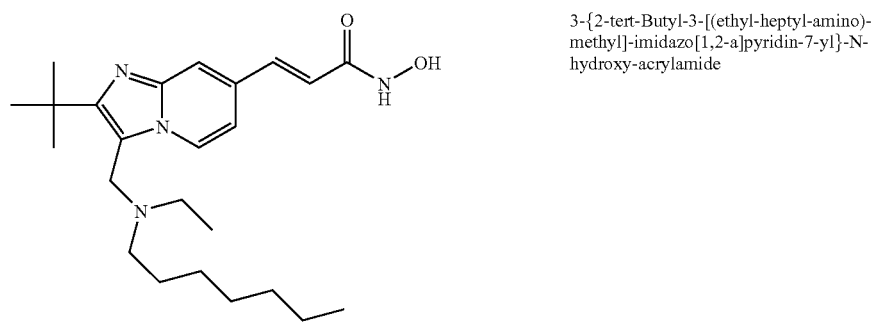 | 3-{2-tert-Butyl-3-[(ethyl-heptyl-amino)-methyl]-imidazo[1,2-a]pyridin-7-yl}-N-hydroxy-acrylamide |
| 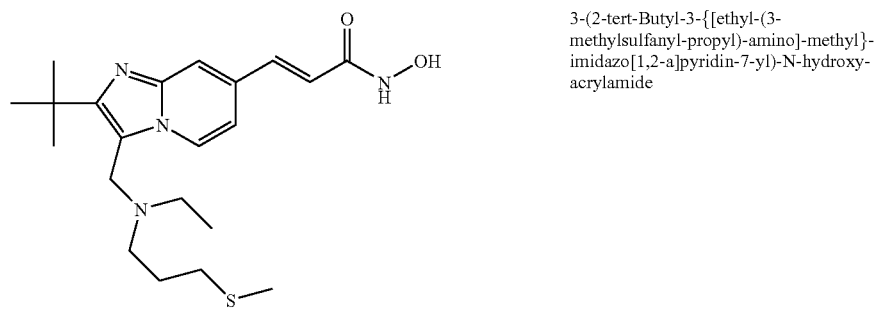 | 3-(2-tert-Butyl-3-{[ethyl-(3-methylsulfanyl-propyl)-amino]-methyl}-imidazo[1,2-a]pyridin-7-yl)-N-hydroxy-acrylamide |
| 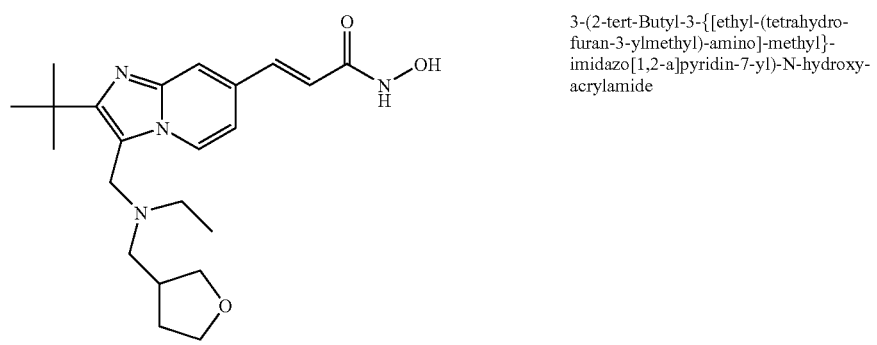 | 3-(2-tert-Butyl-3-{[ethyl-(tetrahydro-furan-3-ylmethyl)-amino]-methyl}-imidazo[1,2-a]pyridin-7-yl)-N-hydroxy-acrylamide |

| Structure | Name |
|---|---|
| 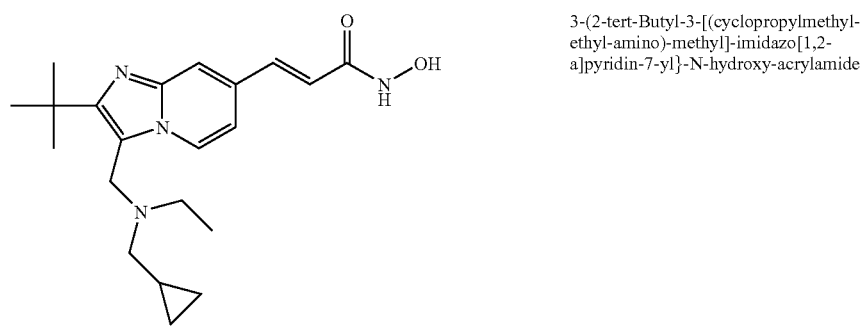 | 3-(2-tert-Butyl-3-[(cyclopropylmethyl-ethyl-amino)-methyl]-imidazo[1,2-a]pyridin-7-yl}-N-hydroxy-acrylamide |
| 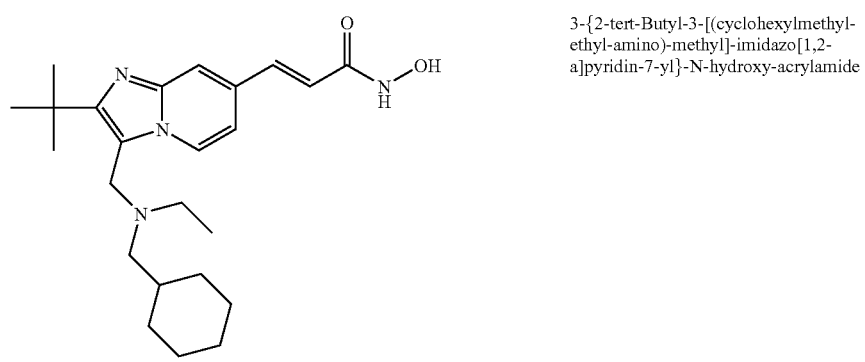 | 3-{2-tert-Butyl-3-[(cyclohexylmethyl-ethyl-amino)-methyl]-imidazo[1,2-a]pyridin-7-yl}-N-hydroxy-acrylamide |
| 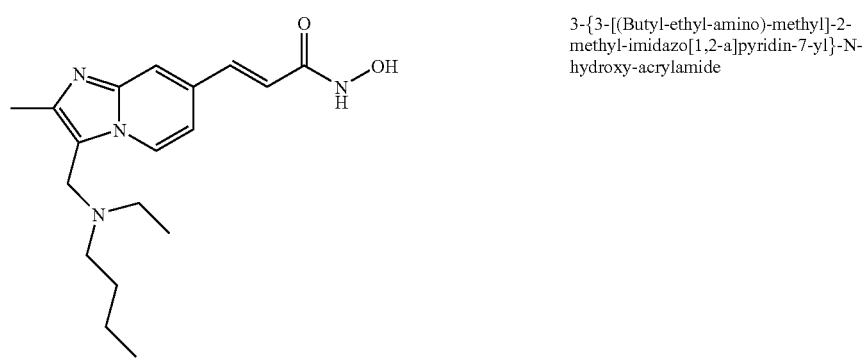 | 3-{3-[(Butyl-ethyl-amino)-methyl]-2-methyl-imidazo[1,2-a]pyridin-7-yl}-N-hydroxy-acrylamide |
| 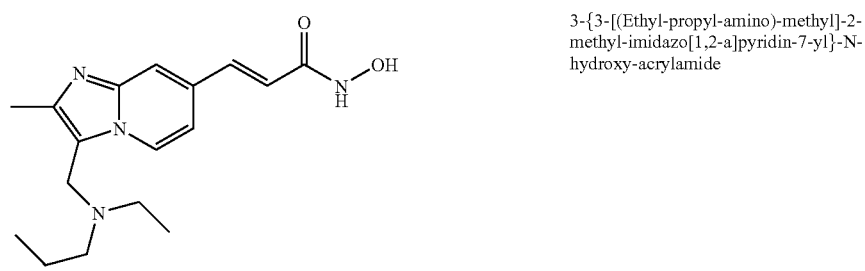 | 3-{3-[(Ethyl-propyl-amino)-methyl]-2-methyl-imidazo[1,2-a]pyridin-7-yl}-N-hydroxy-acrylamide |

| Structure | Name |
|---|---|
| 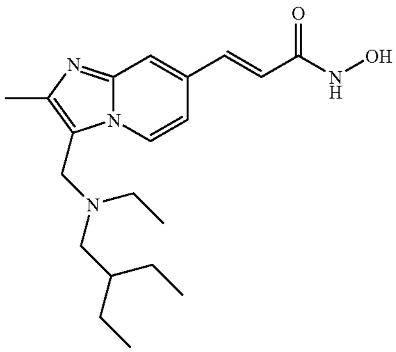 [SMILES: CCC(CC)CN(CC)Cc1c(C)nc2cc(/C=C/C(=O)NO)ccn12] | 3-(3-{[Ethyl-(2-ethyl-butyl)-amino]-methyl}-2-methyl-imidazo[1,2-a]pyridin-7-yl)-N-hydroxy-acrylamide |
| 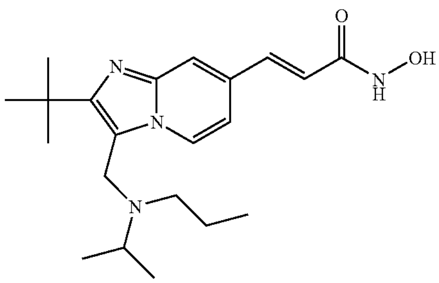 [SMILES: CCCN(Cc1c(C(C)(C)C)nc2cc(/C=C/C(=O)NO)ccn12)C(C)C] | 3-{2-tert-Butyl-3-[(isopropyl-propyl-amino)-methyl]-imidazo[1,2-a]pyridin-7-yl}-N-hydroxy-acrylamide |
| 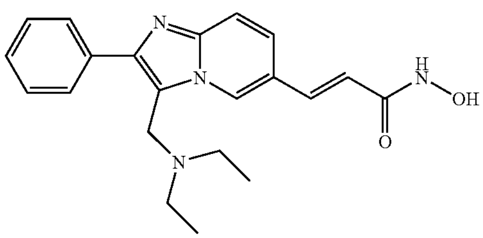 [SMILES: CCN(CC)Cc1c(-c2ccccc2)nc2ccc(/C=C/C(=O)NO)cn12] | 3-(3-Diethylaminomethyl-2-phenyl-imidazo[1,2-a]pyridin-6-yl)-N-hydroxy-acrylamide |
| 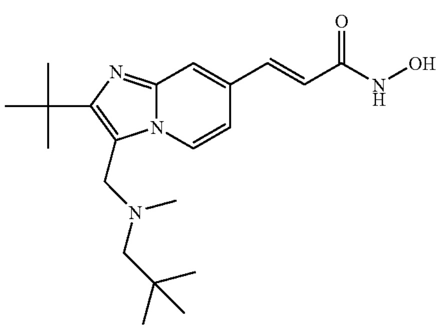 [SMILES: CN(Cc1c(C(C)(C)C)nc2cc(/C=C/C(=O)NO)ccn12)CC(C)(C)C] | 3-(2-tert-Butyl-3-{[(2,2-dimethyl-propyl)-methyl-amino]-methyl}-imidazo[1,2-a]pyridin-7-yl)-N-hydroxy-acrylamide |
| 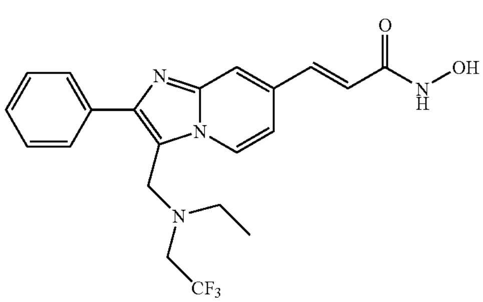 [SMILES: CCN(Cc1c(-c2ccccc2)nc2cc(/C=C/C(=O)NO)ccn12)CC(F)(F)F] | 3-(3-{[Ethyl-(2,2,2-trifluoro-ethyl)-amino]-methyl}-2-phenyl-imidazo[1,2-a]pyridin-7-yl)-N-hydroxy-acrylamide |

| Structure | Name |
|---|---|
| 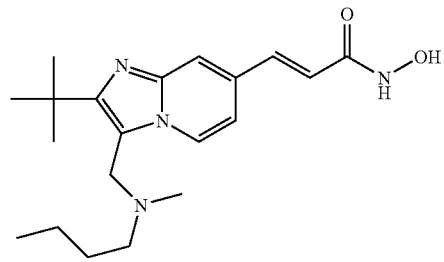 [SMILES: CCCCN(C)Cc1c(C(C)(C)C)nc2cc(/C=C/C(=O)NO)ccn12] | 3-{2-tert-Butyl-3-[(butyl-methyl-amino)-methyl]-imidazo[1,2-a]pyridin-7-yl}-N-hydroxy-acrylamide |
| 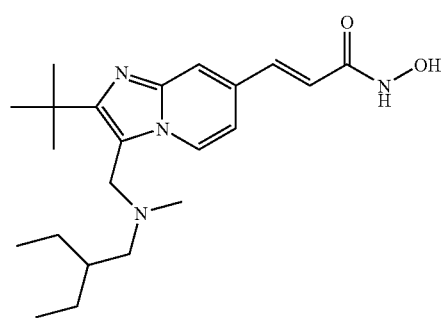 [SMILES: CCC(CC)CN(C)Cc1c(C(C)(C)C)nc2cc(/C=C/C(=O)NO)ccn12] | 3-(2-tert-Butyl-3-{[(2-ethyl-butyl)-methyl-amino]-methyl}-imidazo[1,2-a]pyridin-7-yl)-N-hydroxy-acrylamide |
| 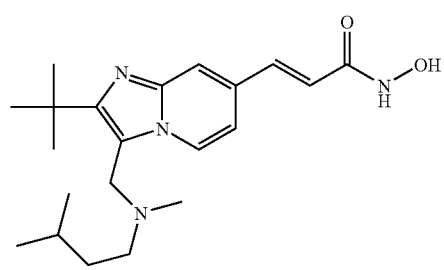 [SMILES: CC(C)CCN(C)Cc1c(C(C)(C)C)nc2cc(/C=C/C(=O)NO)ccn12] | 3-(2-tert-Butyl-3-{[methyl-(3-methyl-butyl)-amino]-methyl}-imidazo[1,2-a]pyridin-7-yl)-N-hydroxy-acrylamide |
| 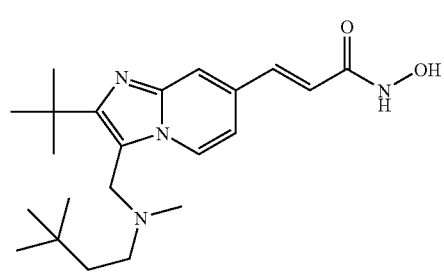 [SMILES: CN(CCC(C)(C)C)Cc1c(C(C)(C)C)nc2cc(/C=C/C(=O)NO)ccn12] | 3-(2-tert-Butyl-3-{[(3,3-dimethyl-butyl)-methyl-amino]-methyl}-imidazo[1,2-a]pyridin-7-yl)-N-hydroxy-acrylamide |
| 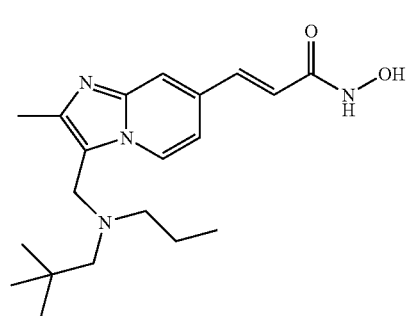 [SMILES: CCCN(Cc1c(C)nc2cc(/C=C/C(=O)NO)ccn12)CC(C)(C)C] | 3-(3-{[(2,2-Dimethyl-propyl)-propyl-amino]-methyl}-2-methyl-imidazo[1,2-a]pyridin-7-yl)-N-hydroxy-acrylamide |

| Structure | Name |
|---|---|
| 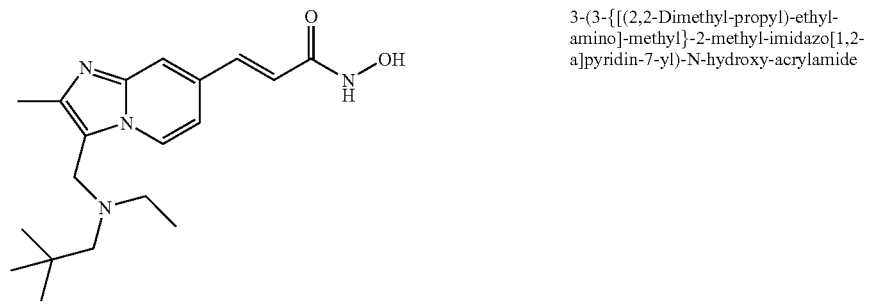 | 3-(3-{[(2,2-Dimethyl-propyl)-ethyl-amino]-methyl}-2-methyl-imidazo[1,2-a]pyridin-7-yl)-N-hydroxy-acrylamide |
| 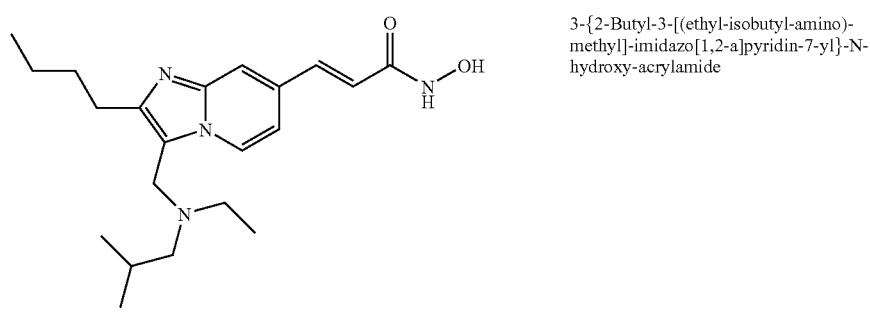 | 3-{2-Butyl-3-[(ethyl-isobutyl-amino)-methyl]-imidazo[1,2-a]pyridin-7-yl}-N-hydroxy-acrylamide |
| 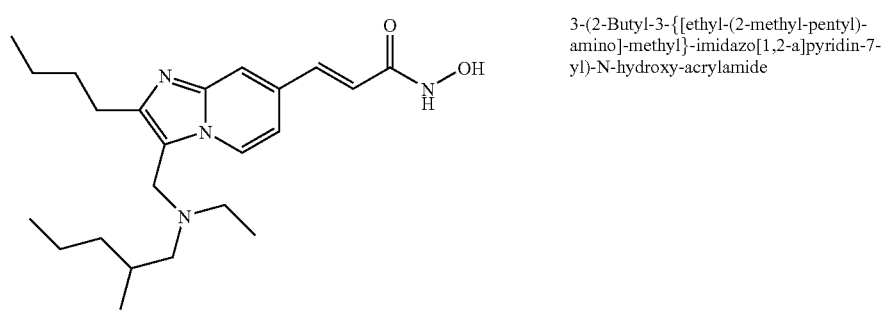 | 3-(2-Butyl-3-{[ethyl-(2-methyl-pentyl)-amino]-methyl}-imidazo[1,2-a]pyridin-7-yl)-N-hydroxy-acrylamide |
| 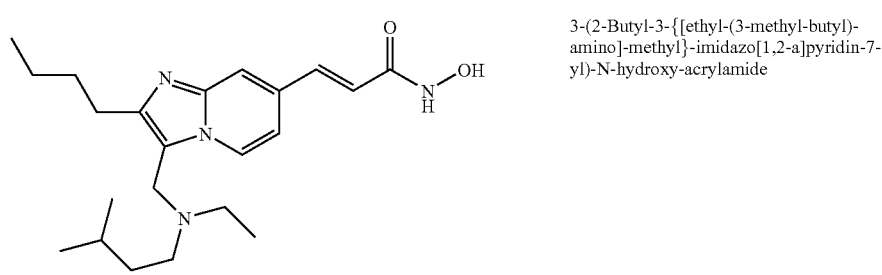 | 3-(2-Butyl-3-{[ethyl-(3-methyl-butyl)-amino]-methyl}-imidazo[1,2-a]pyridin-7-yl)-N-hydroxy-acrylamide |
| 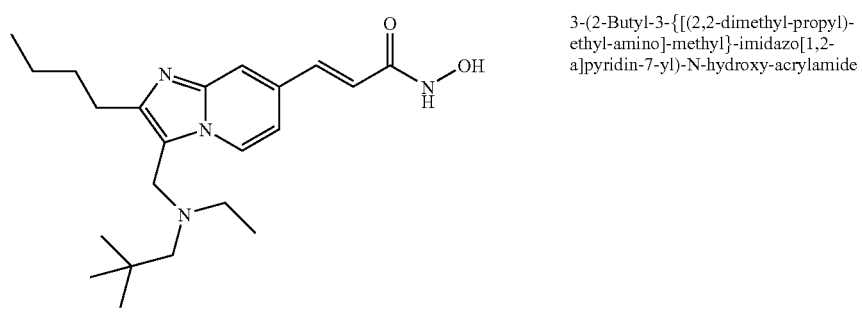 | 3-(2-Butyl-3-{[(2,2-dimethyl-propyl)-ethyl-amino]-methyl}-imidazo[1,2-a]pyridin-7-yl)-N-hydroxy-acrylamide |

| Structure | Name |
|---|---|
| 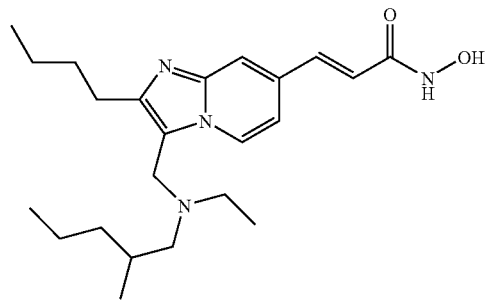 [SMILES: CCCCc1nc2cc(/C=C/C(=O)NO)ccn2c1CN(CC)CC(C)CCC] | 3-(2-Butyl-3-{[ethyl-(2-methyl-pentyl)-amino]-methyl}-imidazo[1,2-a]pyridin-7-yl)-N-hydroxy-acrylamide |
| 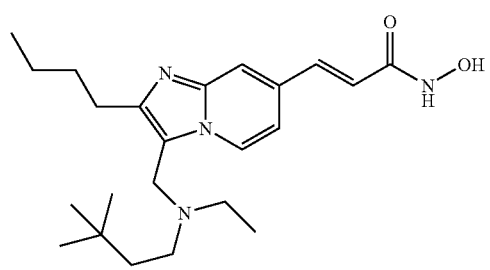 [SMILES: CCCCc1nc2cc(/C=C/C(=O)NO)ccn2c1CN(CC)CCC(C)(C)C] | 3-(2-Butyl-3-{[(3,3-dimethyl-butyl)-ethyl-amino]-methyl}-imidazo[1,2-a]pyridin-7-yl)-N-hydroxy-acrylamide |
| 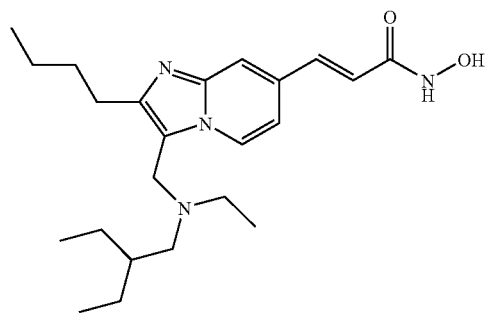 [SMILES: CCCCc1nc2cc(/C=C/C(=O)NO)ccn2c1CN(CC)CC(CC)CC] | 3-(2-Butyl-3-{[ethyl-(2-ethyl-butyl)-amino]-methyl}-imidazo[1,2-a]pyridin-7-yl)-N-hydroxy-acrylamide |
| 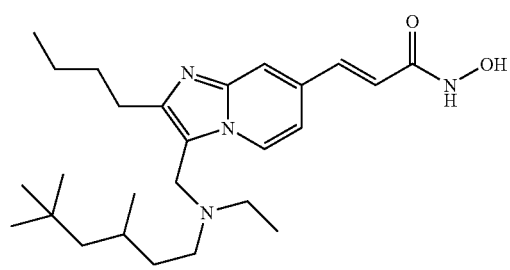 [SMILES: CCCCc1nc2cc(/C=C/C(=O)NO)ccn2c1CN(CC)CCC(C)CC(C)(C)C] | 3-(2-Butyl-3-{[ethyl-(3,5,5-trimethyl-hexyl)-amino]-methyl}-imidazo[1,2-a]pyridin-7-yl)-N-hydroxy-acrylamide |
| 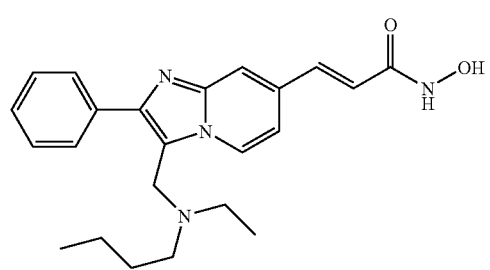 [SMILES: CCCCN(CC)Cc1c(-c2ccccc2)nc2cc(/C=C/C(=O)NO)ccn12] | 3-{3-[(Butyl-ethyl-amino)-methyl]-2-phenyl-imidazo[1,2-a]pyridin-7-yl}-N-hydroxy-acrylamide |

-continued

| Structure | Name |
|---|---|
| 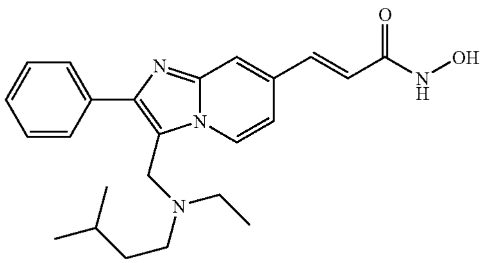 [SMILES: CCN(CCC(C)C)Cc1c(-c2ccccc2)nc2cc(/C=C/C(=O)NO)ccn12] | 3-(3-{[Ethyl-(3-methyl-butyl)-amino]-methyl}-2-phenyl-imidazo[1,2-a]pyridin-7-yl)-N-hydroxy-acrylamide |
| 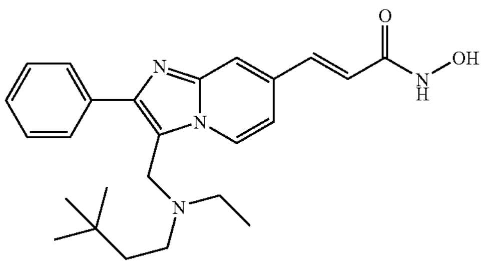 [SMILES: CCN(CCC(C)(C)C)Cc1c(-c2ccccc2)nc2cc(/C=C/C(=O)NO)ccn12] | 3-(3-{[(3,3-Dimethyl-butyl)-ethyl-amino]-methyl}-2-phenyl-imidazo[1,2-a]pyridin-7-yl)-N-hydroxy-acrylamide |
| 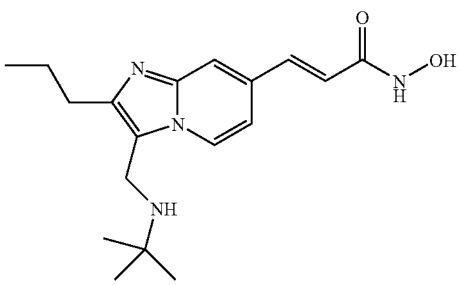 | 3-[3-(tert-Butylamino-methyl)-2-propyl-imidazo[1,2-a]pyridin-7-yl]-N-hydroxy-acrylamide |
| 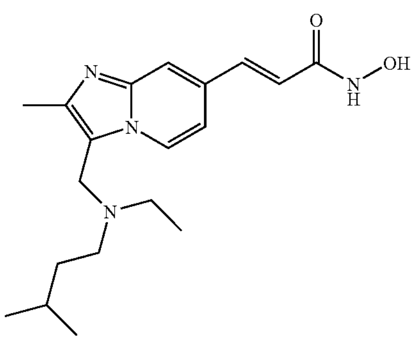 [SMILES: CCN(CCC(C)C)Cc1c(C)nc2cc(/C=C/C(=O)NO)ccn12] | 3-(3-{[Ethyl-(3-methyl-butyl)-amino]-methyl}-2-methyl-imidazo[1,2-a]pyridin-7-yl)-N-hydroxy-acrylamide |
| 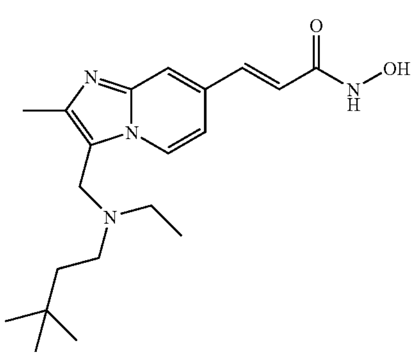 [SMILES: CCN(CCC(C)(C)C)Cc1c(C)nc2cc(/C=C/C(=O)NO)ccn12] | 3-(3-{[(3,3-Dimethyl-butyl)-ethyl-amino]-methyl}-2-methyl-imidazo[1,2-a]pyridin-7-yl)-N-hydroxy-acrylamide |

| Structure | Name |
|---|---|
| 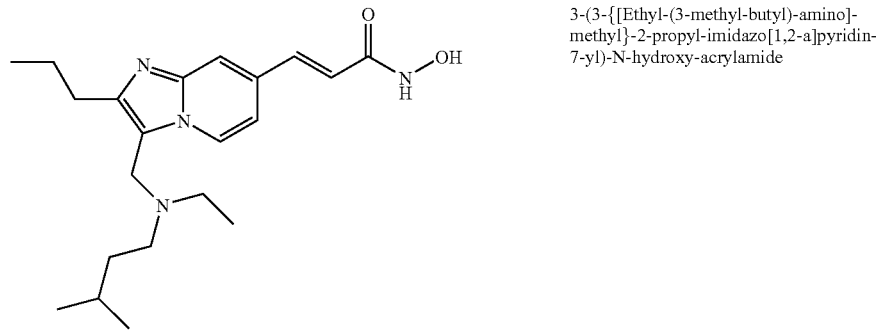 | 3-(3-{[Ethyl-(3-methyl-butyl)-amino]-methyl}-2-propyl-imidazo[1,2-a]pyridin-7-yl)-N-hydroxy-acrylamide |
| 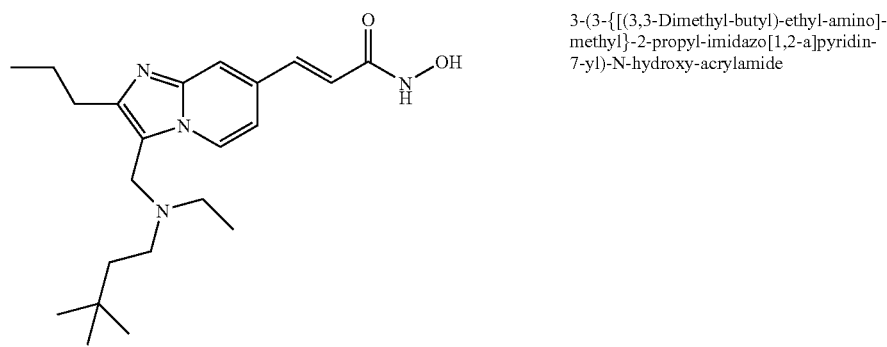 | 3-(3-{[(3,3-Dimethyl-butyl)-ethyl-amino]-methyl}-2-propyl-imidazo[1,2-a]pyridin-7-yl)-N-hydroxy-acrylamide |
| 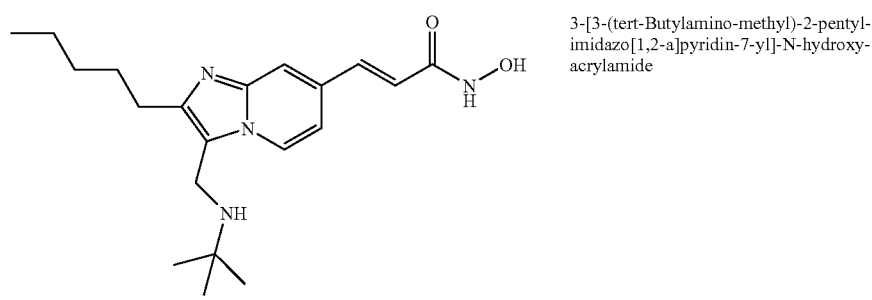 | 3-[3-(tert-Butylamino-methyl)-2-pentyl-imidazo[1,2-a]pyridin-7-yl]-N-hydroxy-acrylamide |
| 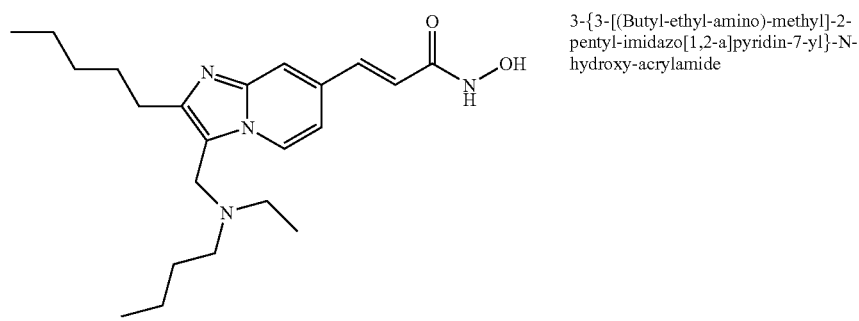 | 3-{3-[(Butyl-ethyl-amino)-methyl]-2-pentyl-imidazo[1,2-a]pyridin-7-yl}-N-hydroxy-acrylamide |

| Structure | Name |
|---|---|
| 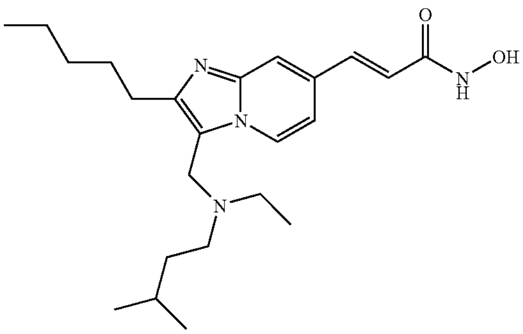 [SMILES: CCCCCc1nc2cc(/C=C/C(=O)NO)ccn2c1CN(CC)CCC(C)C] | 3-(3-{[Ethyl-(3-methyl-butyl)-amino]-methyl}-2-pentyl-imidazo[1,2-a]pyridin-7-yl)-N-hydroxy-acrylamide |
| 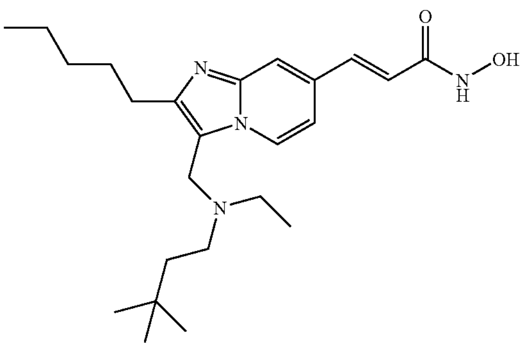 [SMILES: CCCCCc1nc2cc(/C=C/C(=O)NO)ccn2c1CN(CC)CCC(C)(C)C] | 3-(3-{[(3,3-Dimethyl-butyl)-ethyl-amino]-methyl}-2-pentyl-imidazo[1,2-a]pyridin-7-yl)-N-hydroxy-acrylamide |
| 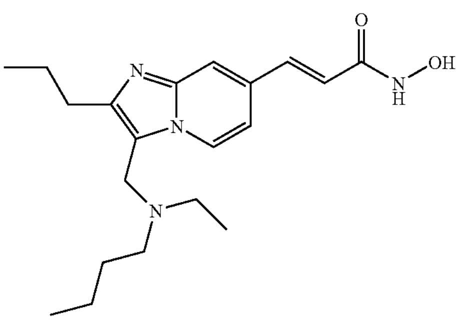 [SMILES: CCCCN(CC)Cc1c(CCC)nc2cc(/C=C/C(=O)NO)ccn12] | 3-{3-[(Butyl-ethyl-amino)-methyl]-2-propyl-imidazo[1,2-a]pyridin-7-yl}-N-hydroxy-acrylamide |
| 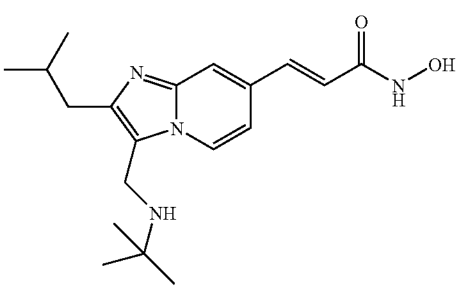 [SMILES: CC(C)Cc1nc2cc(/C=C/C(=O)NO)ccn2c1CNC(C)(C)C] | 3-[3-(tert-Butylamino-methyl)-2-isobutyl-imidazo[1,2-a]pyridin-7-yl]-N-hydroxy-acrylamide |
| 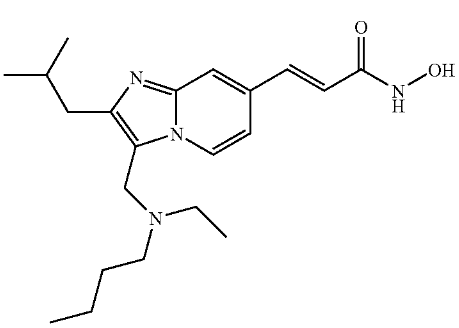 [SMILES: CCCCN(CC)Cc1c(CC(C)C)nc2cc(/C=C/C(=O)NO)ccn12] | 3-{3-[(Butyl-ethyl-amino)-methyl]-2-isobutyl-imidazo[1,2-a]pyridin-7-yl}-N-hydroxy-acrylamide |

| Structure | Name |
|---|---|
| 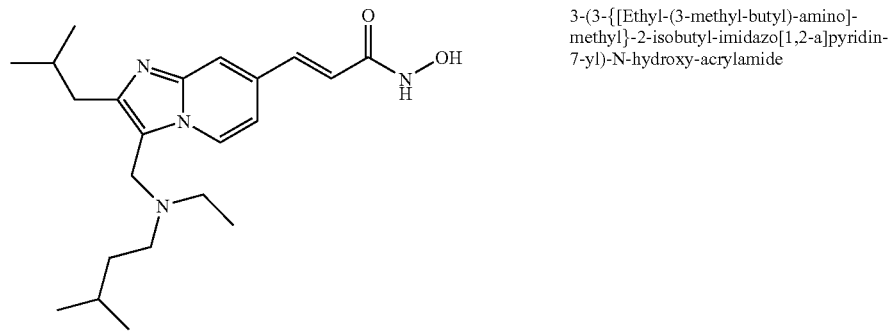 | 3-(3-{[Ethyl-(3-methyl-butyl)-amino]-methyl}-2-isobutyl-imidazo[1,2-a]pyridin-7-yl)-N-hydroxy-acrylamide |
| 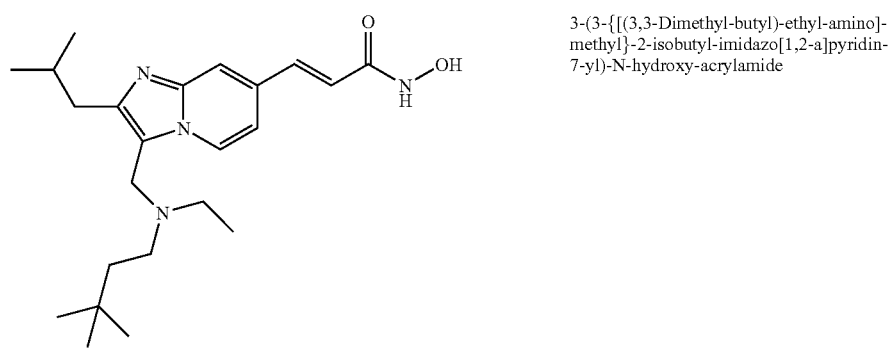 | 3-(3-{[(3,3-Dimethyl-butyl)-ethyl-amino]-methyl}-2-isobutyl-imidazo[1,2-a]pyridin-7-yl)-N-hydroxy-acrylamide |
| 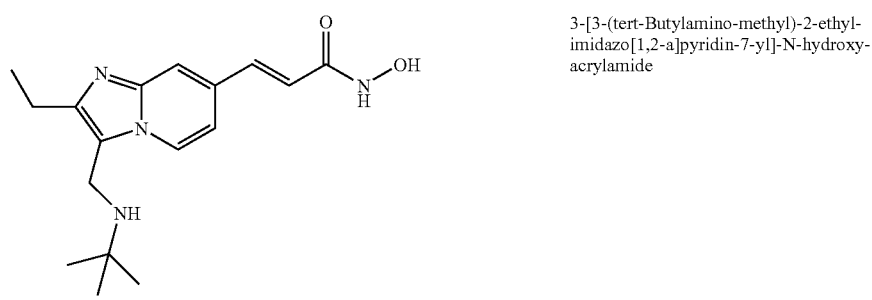 | 3-[3-(tert-Butylamino-methyl)-2-ethyl-imidazo[1,2-a]pyridin-7-yl]-N-hydroxy-acrylamide |
| 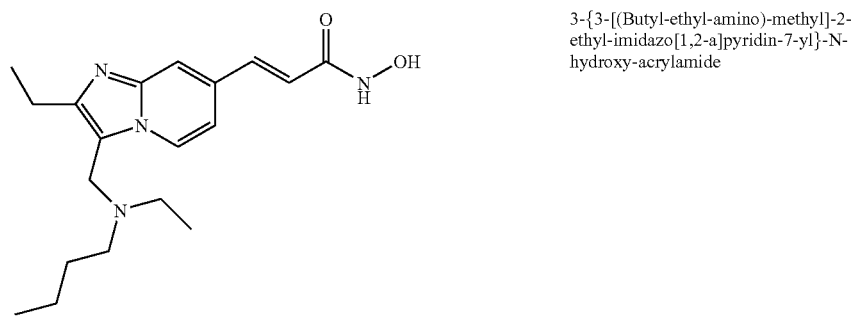 | 3-{3-[(Butyl-ethyl-amino)-methyl]-2-ethyl-imidazo[1,2-a]pyridin-7-yl}-N-hydroxy-acrylamide |

| Structure | Name |
|---|---|
| 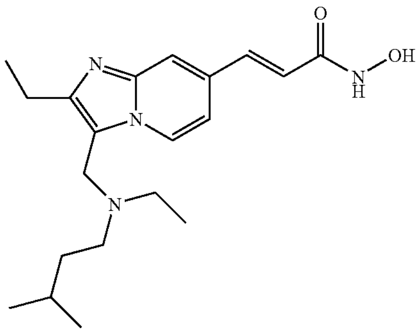 [SMILES: CCc1nc2cc(/C=C/C(=O)NO)ccn2c1CN(CC)CCC(C)C] | 3-(2-Ethyl-3-{[ethyl-(3-methyl-butyl)-amino]-methyl}-imidazo[1,2-a]pyridin-7-yl)-N-hydroxy-acrylamide |
| 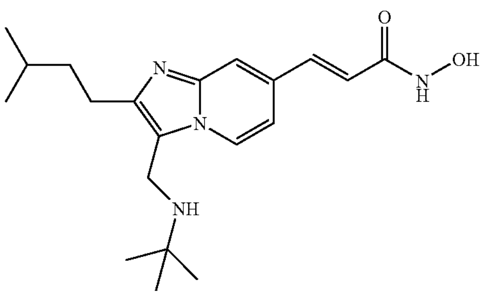 [SMILES: CC(C)CCc1nc2cc(/C=C/C(=O)NO)ccn2c1CNC(C)(C)C] | 3-[3-(tert-Butylamino-methyl)-2-(3-methyl-butyl)-imidazo[1,2-a]pyridin-7-yl]-N-hydroxy-acrylamide |
| 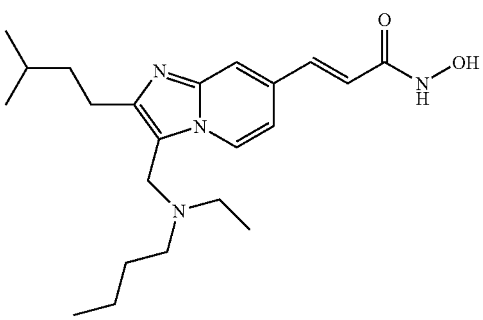 [SMILES: CCCCN(CC)Cc1c(CCC(C)C)nc2cc(/C=C/C(=O)NO)ccn12] | 3-[3-[(Butyl-ethyl-amino)-methyl]-2-(3-methyl-butyl)-imidazo[1,2-a]pyridin-7-yl]-N-hydroxy-acrylamide |
| 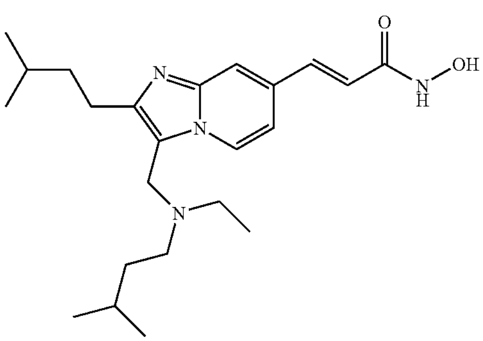 [SMILES: CCN(CCC(C)C)Cc1c(CCC(C)C)nc2cc(/C=C/C(=O)NO)ccn12] | 3-[3-{[Ethyl-(3-methyl-butyl)-amino]-methyl}-2-(3-methyl-butyl)-imidazo[1,2-a]pyridin-7-yl]-N-hydroxy-acrylamide |

-continued

| Structure | Name |
|---|---|
| 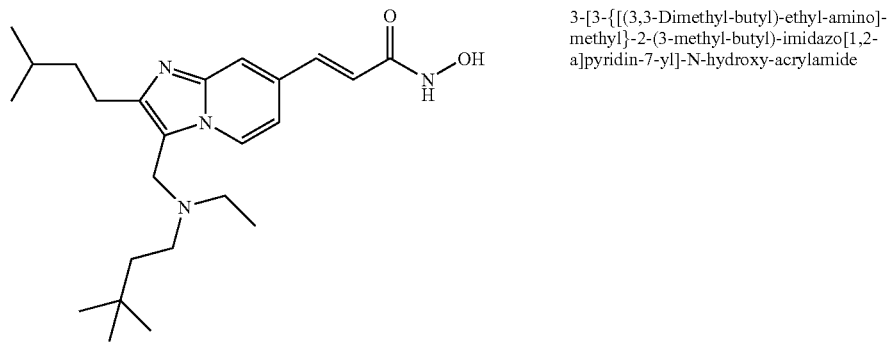 | 3-[3-{[(3,3-Dimethyl-butyl)-ethyl-amino]-methyl}-2-(3-methyl-butyl)-imidazo[1,2-a]pyridin-7-yl]-N-hydroxy-acrylamide |
| and | |
| 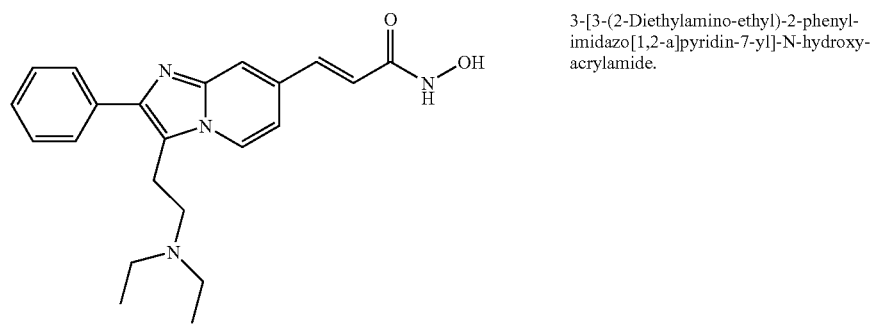 | 3-[3-(2-Diethylamino-ethyl)-2-phenyl-imidazo[1,2-a]pyridin-7-yl]-N-hydroxy-acrylamide. |

33. The method according to claim 32, wherein the tumor is ovarian cancer, colon cancer, or prostate cancer.

34. The method according to claim 32, wherein the tumor cell growth is a hematologic malignancy.

35. The method according to claim 34, wherein the hematologic malignancy is selected from the group consisting of B-cell lymphoma, T-cell lymphoma and leukemia.

* * * * *

UNITED STATES PATENT AND TRADEMARK OFFICE
CERTIFICATE OF CORRECTION

| | | |
|---|---|---|
| PATENT NO. | : 8,648,092 B2 | Page 1 of 1 |
| APPLICATION NO. | : 12/651052 | |
| DATED | : February 11, 2014 | |
| INVENTOR(S) | : Lee et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this
Seventh Day of July, 2015

Michelle K. Lee
*Director of the United States Patent and Trademark Office*